(12) United States Patent
Burlew et al.

(10) Patent No.: US 8,865,443 B2
(45) Date of Patent: Oct. 21, 2014

(54) EXTRACTION SOLVENTS DERIVED FROM OIL FOR ALCOHOL REMOVAL IN EXTRACTIVE FERMENTATION

(71) Applicant: Butamax(TM) Advanced Biofuels LLC, Wilmington, DE (US)

(72) Inventors: Keith H. Burlew, Middletown, DE (US); Robert Dicosimo, Chadds Ford, PA (US); Michael Charles Grady, Oaklyn, NJ (US)

(73) Assignee: Butamax Advanced Biofuels LLC, Wilmington, DE (US)

( * ) Notice: Subject to any disclaimer, the term of this patent is extended or adjusted under 35 U.S.C. 154(b) by 0 days.

(21) Appl. No.: 13/894,894

(22) Filed: May 15, 2013

(65) Prior Publication Data

US 2013/0236935 A1 Sep. 12, 2013

Related U.S. Application Data

(63) Continuation of application No. 13/692,254, filed on Dec. 3, 2012, now Pat. No. 8,476,047, which is a continuation of application No. 13/162,643, filed on Jun. 17, 2011, now Pat. No. 8,409,834.

(60) Provisional application No. 61/356,290, filed on Jun. 18, 2010, provisional application No. 61/368,451, filed on Jul. 28, 2010, provisional application No. 61/368,436, filed on Jul. 28, 2010, provisional application No. 61/368,444, filed on Jul. 28, 2010, provisional application No. 61/368,429, filed on Jul. 28, 2010, provisional application No. 61/379,546, filed on Sep. 2, 2010, provisional application No. 61/440,034, filed on Feb. 7, 2011.

(51) Int. Cl.
| | |
|---|---|
| C12N 9/16 | (2006.01) |
| C12N 1/00 | (2006.01) |
| C07C 29/86 | (2006.01) |
| C11B 13/00 | (2006.01) |
| C12P 7/16 | (2006.01) |
| C12M 1/00 | (2006.01) |
| B01D 21/26 | (2006.01) |
| C11B 1/02 | (2006.01) |
| B01D 3/00 | (2006.01) |
| C12P 7/64 | (2006.01) |

(52) U.S. Cl.
CPC ............... *C12M 45/04* (2013.01); *C07C 29/86* (2013.01); *C11B 13/00* (2013.01); *Y02E 50/17* (2013.01); *C12P 7/16* (2013.01); *C12M 1/00* (2013.01); *B01D 21/26* (2013.01); *Y02E 50/16* (2013.01); *C11B 1/025* (2013.01); *B01D 3/002* (2013.01); *B01D 21/262* (2013.01); *C12P 7/6418* (2013.01); *Y02E 50/10* (2013.01)
USPC ....................... 435/183; 435/197; 435/254.21

(58) Field of Classification Search
None
See application file for complete search history.

(56) References Cited

U.S. PATENT DOCUMENTS

| | | | |
|---|---|---|---|
| 6,646,146 B1 | 11/2003 | Sinnema et al. | |
| 7,851,188 B2 | 12/2010 | Donaldson et al. | |
| 7,932,063 B2 | 4/2011 | Dunson et al. | |
| 2007/0077635 A1 | 4/2007 | Brunner et al. | |
| 2008/0182308 A1 | 7/2008 | Donaldson et al. | |
| 2009/0163376 A1 | 6/2009 | Li et al. | |
| 2009/0171129 A1 | 7/2009 | Evanko et al. | |
| 2009/0269823 A1 | 10/2009 | Bramucci et al. | |
| 2009/0305363 A1 | 12/2009 | Anthony et al. | |
| 2009/0305370 A1 | 12/2009 | Grady et al. | |
| 2010/0081154 A1 | 4/2010 | Flint et al. | |
| 2010/0124773 A1 | 5/2010 | Yang | |
| 2011/0124060 A1 | 5/2011 | Anthony et al. | |
| 2011/0244536 A1 | 10/2011 | Nagarajan et al. | |
| 2011/0312044 A1 | 12/2011 | Anton et al. | |
| 2011/0312053 A1 | 12/2011 | Burlew et al. | |
| 2012/0015416 A1 | 1/2012 | Anthony et al. | |
| 2012/0156738 A1 | 6/2012 | Anton et al. | |
| 2012/0164302 A1 | 6/2012 | Roesch et al. | |

FOREIGN PATENT DOCUMENTS

| | | |
|---|---|---|
| GB | 2146638 | 4/1985 |
| JP | 1986192291 | 8/1986 |
| WO | WO2009149270 | 12/2009 |
| WO | WO2010049491 | 5/2010 |
| WO | WO2011063402 | 5/2011 |

OTHER PUBLICATIONS

Ban et al., Whole cell biocatalyst for biodiesel fuel production utilizing *Rhizopus oryzae* cells immobilized within biomass support particles, Biochem. Eng. J. 8:39-43, 2001.

(Continued)

*Primary Examiner* — Nashaat Nashed

(57) ABSTRACT

In an alcohol fermentation process, oil derived from biomass is hydrolyzed into an extractant available for in situ removal of a product alcohol such as butanol from a fermentation broth. The glycerides in the oil can be catalytically (e.g., enzymatically) hydrolyzed into free fatty acids, which form a fermentation product extractant having a partition coefficient for a product alcohol greater than a partition coefficient of the oil of the biomass for the product alcohol. Oil derived from a feedstock of an alcohol fermentation process can be hydrolyzed by contacting the feedstock including the oil with one or more enzymes whereby at least a portion of the oil is hydrolyzed into free fatty acids forming a fermentation product extractant, or the oil can be separated from the feedstock prior to the feedstock being fed to a fermentation vessel, and the separated oil can be contacted with the enzymes to form the fermentation product extractant. The fermentation product extractant can be contacted with a fermentation broth for in situ removal of a product alcohol.

15 Claims, 9 Drawing Sheets

(56) References Cited

OTHER PUBLICATIONS

Barros et al., Integration of Enzyme Catalysis in an Extraction Fermentation Process, Studies in Organic Chemistry 29, 1986.

Bellion et al., Microb. Growth C1 Compd., [Int. Symp.], 7th (1993), 415 32, Editor(s): Murrell, J. Collin; Kelly, Don P. Publisher: Intercept, Andover, UK.

Bligh et al., A Rapid Method of Total Lipid Extraction and Purification, Can J Biochem Physiol 37:911-917, 1959.

Gupta et al., Bacterial lipases: an overview of production, purification and biochemical properties, Appl Microbiol Biotechnol 64:763-781, 2004.

Horton et al., Engineering hybrid genes without the use of restriction enzymes: gene splicing by overlap extension, Gene, 77:61-68, 1989.

Kim et al., Extractive Recovery of Products from Fermentation Broths, Biotechnol Bioprocess Eng 4:1-11, 1999.

Kohlhase et al., Catalytic Effects in the Ammonclysis of Vegetable Oils, The Journal of the American Oil Chemists' Society 48:265-270, 1971.

Lynd et al., Microbial Cellulose Utilization: Fundamentals of Biotechnology, Microbiology and Molecular Biology Reviews 66:506-577, 2002.

Ma et al., Plasmid construction by homologous recombination in yeast, Gene, 58:201-216, 1987.

Malinowski, Two-phase partitioning bioreactors in fermentation technology, Biotechnology Advances 19:525-538, 2001.

Oliveira et al., Production and Extractive Biocatalysis of Ethanol Using Microencapsulated Yeast Cells and Lipase System, J Chem Technol Biotechnol 52:219-225, 1991.

Oliveira et al., Immobilization of *Saccharomyces cerevisiae* Cells and *Rhizomucor miehi* Lipase for the Production and Extractive . . . , Bioprocess Eng 16:349-353, 1997.

Oliveira et al., Improvement of Alcoholic Fermentations by Simultaneous Extraction and Enzymatic Esterification of Ethanol, J Mol Catal B: Enzym 5:29-33, 1998.

Oliveira, et al., Effect of extraction and Enzymatic Esterification of Ethanol on Glucose Consumption by Two *Saccharomyces* . . . , J Chem Technol Biotechnol 78:285-290, 2001.

Oudshoorn et al., Assessment of Options for Selectiye 1-Butanol Recovery from Aqueous Solution, Industrial and Engineering Chemistry Research 48:7325-7336, 2009.

Roe et al., Fatty Acid Amides. IV. Reaction of Fats With Ammonia and Amines, The Journal of the American Oil Chemists' Society 29:18-22, 1952.

Roffler, Steve Ronald: Extractive fermentation—lactic acid and acetone/butanol production, 1986, pp. 1-289, PhD. Dissertation in Chemical Engineering, UC Berkeley.

Sulter et al., Proliferation and metabolic significance of peroxisomes in *Candida boidinii* during growth on D-alanine or oleic acid . . . , Arch Microbial 153:485-489, 1990.

Yoo et al., Enzymatic Synthesis of Sugar Fatty Acid Esters, Journal of Industrial Engineering Chemistry 13:1-5, 2007.

International Search Report and Written Opinion dated Oct. 14, 2011, International Application No, PCT/US2011/040806.

U.S. Appl. No. 13/193,147, filed Jul. 28, 2011.

U.S. Appl. No. 61/440,034, filed Feb. 7, 2011.

EXTRACTION SOLVENTS DERIVED FROM OIL FOR ALCOHOL REMOVAL IN EXTRACTIVE FERMENTATION

This application is a continuation of U.S. patent application Ser. No. 13/692,254, filed on Dec. 3, 2012, now U.S. Pat. No. 8,476,047, which is a continuation of U.S. patent application Ser. No. 13/162,643, filed on Jun. 17, 2011, now U.S. Pat. No. 8,409,034, which claims the benefit of U.S. Provisional Application No. 61/356,290, filed on Jun. 18, 2010; U.S. Provisional Application No. 61/368,451, filed on Jul. 28, 2010; U.S. Provisional Application No. 61/368,436, filed on Jul. 28, 2010; U.S. Provisional Application No. 61/368,444, filed on Jul. 28, 2010; U.S. Provisional Application No. 61/368,429, filed on Jul. 28, 2010; U.S. Provisional Application No. 61/379,546, filed on Sep. 2, 2010; and U.S. Provisional Application No. 61/440,034, filed on Feb. 7, 2011; the entire contents of which are all herein incorporated by reference.

The Sequence Listing associated with this application is filed in electronic form via EFS-Web and hereby incorporated by reference into the specification in its entirety.

FIELD OF THE INVENTION

The present invention relates the production of fermentative alcohols such as butanol, and in particular to extraction solvents for extractive fermentation and processes for converting oil derived from biomass into the extraction solvents.

BACKGROUND OF THE INVENTION

Alcohols have a variety of applications in industry and science such as a beverage (i.e., ethanol), fuel, reagents, solvents, and antiseptics. For example, butanol is an alcohol that is an important industrial chemical with a variety of applications including use as a fuel additive, as a feedstock chemical in the plastics industry, and as a food-grade extractant in the food and flavor industry. Accordingly, there is a high demand for alcohols such as butanol, as well as for efficient and environmentally-friendly production methods.

Production of alcohol utilizing fermentation by microorganisms is one such environmentally-friendly production method. In the production of butanol, in particular, some microorganisms that produce butanol in high yields also have low butanol toxicity thresholds. Removal of butanol from the fermentation vessel as it is being produced is a means to manage these low butanol toxicity thresholds.

In situ product removal (ISPR) (also referred to as extractive fermentation) can be used to remove butanol (or other fermentative alcohol) from the fermentation vessel as it is produced, thereby allowing the microorganism to produce butanol at high yields. One ISPR method for removing fermentative alcohol that has been described in the art is liquid-liquid extraction (U.S. Patent Application Publication No. 2009/0305370). In order to be technically and economically viable, liquid-liquid extraction calls for good contact between the extractant and the fermentation broth for efficient mass transfer of the product alcohol into the extractant; good phase separation of the extractant from the fermentation broth (during and/or after fermentation); efficient recovery and recycle of the extractant; minimal degradation of the ability of the extractant to extract the product alcohol (e.g., by preventing the lowering of the partition coefficient for the product alcohol into the extractant); and minimal contamination of the extractant by lipids that lower the partition coefficient over a long-term operation.

The partition coefficient of the extractant can be degraded over time with each recycle, for example, by the build-up of lipids present in the biomass that is fed to the fermentation vessel as feedstock of hydrolysable starch. As an example, a liquefied corn mash loaded to a fermentation vessel at 30 wt % dry corn solids can result in a fermentation broth that contains about 1.2 wt % corn oil during conversion of glucose to butanol by simultaneous saccharification and fermentation (SSF) (with saccharification of the liquefied mash occurring during fermentation by the addition of glucoamylase to produce glucose). The dissolution of the corn oil lipids in oleyl alcohol (OA) serving as an extractant during ISPR can result in build-up of lipid concentration with each OA recycle, decreasing the partition coefficient for the product alcohol in OA as the lipid concentration in OA increases with each recycle of OA.

In addition, the presence of the undissolved solids during extractive fermentation can negatively affect the efficiency of alcohol production. For example, the presence of the undissolved solids may lower the mass transfer coefficient inside the fermentation vessel, impede phase separation in the fermentation vessel, result in the accumulation of corn oil from the undissolved solids in the extractant leading to reduced extraction efficiency over time, increase the loss of solvent because it becomes trapped in solids and ultimately removed as Dried Distillers' Grains with Solubles (DDGS), slow the disengagement of extractant drops from the fermentation broth, and/or result in a lower fermentation vessel volume efficiency.

Several approaches for reducing the degradation of the extractant used in extractive fermentation with lipid have included biomass wet milling, fractionation, and removal of solids. Wet milling is an expensive, multi-step process that separates a biomass (e.g., corn) into its key components (germ, pericarp fiber, starch, and gluten) in order to capture value from each co-product separately. This process gives a purified starch stream; however, it is costly and includes the separation of the biomass into its non-starch components which is unnecessary for fermentative alcohol production. Fractionation removes fiber and germ which contains a majority of the lipids present in ground whole grain such as corn, resulting in corn that has a higher starch (endosperm) content. Dry fractionation does not separate the germ and fiber and therefore, it is less expensive than wet milling. However, fractionation does not remove the entirety of the fiber or germ, and does not result in total elimination of solids. Furthermore, there is some loss of starch in fractionation. Wet milling of corn is more expensive than dry fractionation, but dry fractionation is more expensive than dry grinding of unfractionated corn. Removal of solids including germ containing lipids, from liquefied mash prior to use in fermentation can substantially eliminate undissolved solids as described, for example, in commonly owned U.S. Provisional Application Ser. No. 61/356,290, filed Jun. 18, 2010. However, it would be advantageous if the degradation of the partition coefficient of the extractant can be reduced even without fractionation or removal of undissolved solids. Thus, there is a continuing need to develop more efficient methods and systems for producing product alcohols, such as butanol, through extractive fermentation in which the degradation of the partition coefficient of the extractant is reduced.

Moreover, the extractant (e.g., oleyl alcohol) is typically added to the fermentation process, rather than produced at a step in the process and therefore, the extractant is a raw material expense. Since extractant can be lost by adsorption on non-fermentable solids and/or diluted by lipids introduced into the fermentation process, the economics of an alcohol production process can be affected by the efficiency of the extractant recovery and recycle. Thus, there exists a continuing need for alternative extractants for ISPR that can result in a more economical process by reducing capital and/or operating costs.

BRIEF SUMMARY OF THE INVENTION

The present invention satisfies the above needs by providing methods for producing product alcohols such as butanol, in which the lipids in a biomass are converted into an extractant that can be used in ISPR, and in which the amount of lipids that are fed to the fermentation vessel with the feedstock and/or upon extractant recycle, are decreased. The present invention offers a solution to the degradation of the ability of the extractant to extract a product alcohol (e.g., butanol) by preventing the lowering of the partition coefficient for the product alcohol into the extractant. The application offers a solution to the contamination of the extractant by triglycerides that lower the partition coefficient of the extractant for a product alcohol. The present invention provides further related advantages as will be made apparent by the description of the embodiments that follow.

Catalytic (e.g., enzymatic) hydrolysis of lipids derived from biomass into fatty acids can decrease the rate of undesirable build-up of lipids in the ISPR extractant. The fatty acids can be obtained from hydrolysis of lipids found in the biomass which supplies the fermentable carbon for fermentation. Fatty acids would not be expected to decrease the partition coefficient of the product alcohol such as a butanol into the extractant phase as much as the lipids, as the partition coefficient for butanol from water to fatty acids has been determined to be significantly greater than the partition coefficient for butanol from water to fatty acid esters or triglycerides. Moreover, the fatty acids can be used as an ISPR extractant which can be produced at a step in the alcohol production process and can be used in place of, or in addition to, a supplied, exogenous ISPR extractant that is not produced in the process (such as, but not limited to, oleyl alcohol or oleic acid), thereby reducing the raw material expense for the ISPR extractant.

In one embodiment, the present invention is directed to a method comprising contacting biomass comprising water, fermentable carbon source, and oil with one or more catalyst whereby at least a portion of the oil is hydrolyzed by one or more catalyst to form an extractant, wherein the fermentable carbon source and the oil are both derived from the biomass. The biomass may comprises corn grain, corn cobs, crop residues, corn husks, corn stover, grasses, wheat, rye, wheat straw, barley, barley straw, hay, rice straw, switchgrass, waste paper, sugar cane bagasse, sorghum, sugar cane, soy, grains, cellulosic material, lignocellulosic material, trees, branches, roots, leaves, wood chips, sawdust, shrubs and bushes, vegetables, fruits, flowers, animal manure, and mixtures thereof. In a further embodiment, the oil may comprise glycerides and one or more catalysts may hydrolyze the glycerides to form fatty acids. In another embodiment, the one or more catalysts may be selected from esterase, lipase, phospholipase, and lysophospholipase.

In another embodiment, the extractant may comprise fatty acids, fatty amides, fatty alcohols, fatty esters, triglycerides, or mixtures thereof. In a further embodiment, the extractant may comprise a mixture of fatty acids or a mixture of fatty acids and fatty amides. In a further embodiment, a partition coefficient of the extractant for the product alcohol may be greater than a partition coefficient of the oil of the biomass for the product alcohol.

The method of the present invention may further comprise the step of inactivating the catalyst after at least a portion of the oil is hydrolyzed. In another embodiment, the method may further comprise the step of separating the oil from the biomass prior to hydrolysis by one or more catalyst. The claimed method may also further comprise the steps of contacting the biomass with a fermentation broth in a fermentation vessel; fermenting the carbon source of the biomass to produce a product alcohol; and removing in situ the product alcohol from the fermentation broth by contacting the broth with the extractant. The product alcohol may be butanol.

In another embodiment, the present invention is directed to a method for producing an alcohol comprising (a) providing biomass comprising water, fermentable carbon source, and oil; (b) liquefying the biomass to produce a liquefied biomass; (c) contacting the liquefied biomass with one or more catalysts whereby at least a portion of the oil is hydrolyzed to form an extractant; (d) contacting the liquefied biomass with a saccharification enzyme capable of converting oligosaccharides into fermentable sugar; (e) contacting the liquefied biomass with a fermentation broth in a fermentation vessel; (f) fermenting the carbon source of the liquefied biomass to produce a product alcohol; (g) removing in situ the product alcohol from the fermentation broth by contacting the broth with the extractant; and optionally steps (c) and (d) occur concurrently. The biomass may comprises corn grain, corn cobs, crop residues, corn husks, corn stover, grasses, wheat, rye, wheat straw, barley, barley straw, hay, rice straw, switchgrass, waste paper, sugar cane bagasse, sorghum, sugar cane, soy, grains, cellulosic material, lignocellulosic material, trees, branches, roots, leaves, wood chips, sawdust, shrubs and bushes, vegetables, fruits, flowers, animal manure, and mixtures thereof. In a further embodiment, the oil may comprise glycerides and one or more catalysts may hydrolyze the glycerides to form fatty acids. In another embodiment, the one or more catalysts may be selected from esterase, lipase, phospholipase, and lysophospholipase. In another embodiment, the extractant may comprise fatty acids, fatty amides, fatty alcohols, fatty esters, triglycerides, or mixtures thereof. In a further embodiment, the extractant may comprise a mixture of fatty acids or a mixture of fatty acids or fatty amides. In a further embodiment, a partition coefficient of the extractant for the product alcohol may be greater than a partition coefficient of the oil of the biomass for the product alcohol. The method of the present invention may further comprise the step of inactivating the catalyst after at least a portion of the oil is hydrolyzed. The product alcohol may be butanol.

The present invention is also directed to a composition comprising a recombinant microorganism capable of producing an alcohol; fermentable carbon source; one or more catalysts capable of hydrolyzing glycerides into fatty acids; oil comprising glycerides; and fatty acids. The one or more catalysts may be selected from esterase, lipase, phospholipase, and lysophospholipase, and the oil may be corn, tallow, canola, capric/caprylic triglycerides, castor, coconut, cottonseed, fish, jojoba, lard, linseed, neetsfoot, oiticica, palm, peanut, rapeseed, rice, safflower, soya, sunflower, tung, jatropha and vegetable oil blends. In a further embodiment, the fermentable carbon source and the oil are derived from biomass. The biomass may comprise corn grain, corn cobs, crop residues, corn husks, corn stover, grasses, wheat, rye, wheat straw, barley, barley straw, hay, rice straw, switchgrass, waste paper, sugar cane bagasse, sorghum, sugar cane, soy, grains, cellulosic material, lignocellulosic material, trees, branches, roots, leaves, wood chips, sawdust, shrubs and bushes, vegetables, fruits, flowers, animal manure, and mixtures thereof. The composition may further comprise a saccharification enzyme and/or undissolved solids. The composition may also comprise at least one or more of monoglycerides, diglycerides, triglycerides, glycerol, monosaccharides, oligosaccharides, or alcohol. In addition, the alcohol may be butanol.

In some embodiments, a method of removing oil derived from biomass from a fermentation process includes contacting an aqueous biomass feedstream with a catalyst. The feedstream includes water, fermentable carbon and an amount of oil, and the fermentable carbon and the oil are both derived from the biomass. At least a portion of the oil is hydrolyzed according to methods described in the present invention into fatty acids to form a catalyst-treated biomass feedstream including the fatty acids.

In some embodiments, a method of producing an extractant for in situ removal of a product alcohol includes providing biomass which includes sugar and oil, the oil having an amount of triglycerides, and contacting the oil with a composition including one or more enzymes capable of hydrolyzing the triglycerides into fatty acids. The triglycerides in the oil are hydrolyzed to form a fermentation product extractant having a partition coefficient for the product alcohol greater than a partition coefficient of the oil of the biomass for the product alcohol.

In some embodiments, a method for producing butanol includes (a) providing biomass having starch and oil, the oil including an amount of glycerides; (b) liquefying the biomass to produce a liquefied biomass, the liquefied biomass including oligosaccharides hydrolyzed from the starch; (c) contacting the biomass of step (a) or the liquefied biomass of step (b) with a composition having one or more enzymes capable of converting the glycerides into free fatty acids whereby the free fatty acids form a fermentation product extractant; (d) contacting the liquefied biomass with a saccharification enzyme capable of converting oligosaccharides into fermentable sugar including monomeric glucose; (e) contacting the liquefied biomass with a biocatalyst capable of converting the fermentable sugar to butanol whereby a fermentation product comprising butanol is produced; and (f) contacting the fermentation product with the fermentation product extractant whereby the butanol is separated from the fermentation product, the fermentation product extractant having a partition coefficient for the butanol greater than a partition coefficient of the oil of the biomass for the butanol.

In some embodiments, a method includes, at a step during a process to produce a product alcohol from a feedstock, contacting the product alcohol with an extractant comprising free fatty acids obtained from enzymatic hydrolysis of a native oil wherein the oil comprises glycerides. The extractant has a partition coefficient for the product alcohol greater than a partition coefficient of the native oil for the product alcohol.

In some embodiments, the process to produce a product alcohol from a feedstock includes (a) liquefying the feedstock to create a feedstock slurry; (b) centrifuging the feedstock slurry of (a) to produce a centrifuge product including (i) an aqueous layer comprising sugar, (ii) a plant-derived oil layer, and (iii) a solids layer; (c) feeding the aqueous layer of (b) to a fermentation vessel; and (d) fermenting the sugar of the aqueous layer to produce the product alcohol.

In some embodiments, the process to produce a product alcohol from a feedstock further includes adding the extractant to the fermentation vessel to form a two-phase mixture comprising an aqueous phase and a product alcohol-containing organic phase.

In some embodiments, the native oil is a plant-derived oil, and in some embodiments, the process to produce a product alcohol from a feedstock further includes obtaining the plant-derived oil from the plant-derived oil layer; and converting the plant-derived oil into the extractant by contacting the oil with one or more enzymes that hydrolyze the glycerides into free fatty acids.

In some embodiments, the process to produce a product alcohol from a feedstock further includes inactivating the one or more enzymes after at least a portion of the glycerides have been hydrolyzed into free fatty acids.

In some embodiments, the process to produce a product alcohol from a feedstock further includes feeding the plant-derived oil to the fermentation vessel prior to the step of converting the plant-derived oil into the extractant.

In some embodiments, the process to produce a product alcohol from a feedstock further includes adding a second extractant to the fermentation vessel to form a two-phase mixture comprising an aqueous phase and a product alcohol-containing organic phase.

In some embodiments, the plant-derived oil is converted to the extractant after the step of adding a second extractant.

In some embodiments, a method of removing oil derived from biomass from a fermentation process, includes (a) providing a fermentation broth comprising a product alcohol and oil derived from biomass, the oil including glycerides; (b) contacting the fermentation broth with a first extractant to form a two-phase mixture comprising an aqueous phase and an organic phase, wherein the product alcohol and the oil partition into the organic phase to form a product alcohol-containing organic phase; (c) separating the product alcohol-containing organic phase from the aqueous phase; (d) separating the product alcohol from the organic phase to produce a lean organic phase; and (e) contacting the lean organic phase with a composition comprising one or more catalysts capable of hydrolyzing the glycerides into free fatty acids to produce a second extractant comprising at least a portion of the first extractant and free fatty acids.

In some embodiments, the method further includes repeating step (b) by contacting the fermentation broth with the second extractant of step (e).

In some embodiments, an in situ fermentation extractant-forming composition includes (a) mash formed from biomass and including water, starch and oil, (b) a catalyst capable of hydrolyzing at least a portion of the triglycerides into free fatty acids, and (c) free fatty acids. The starch and the oil are both derived from the biomass, and the oil includes an amount of triglycerides.

In some embodiments, a fermentation broth includes (a) a recombinant microorganism capable of producing butanol, (b) oligosaccharides, (c) a catalyst for hydrolyzing glycerides into free fatty acids, (d) glycerides, and (e) free fatty acids.

BRIEF DESCRIPTION OF THE DRAWINGS/FIGURES

The accompanying drawings, which are incorporated herein and form a part of the specification, illustrate the present invention and, together with the description, further serve to explain the principles of the invention and to enable a person skilled in the pertinent art to make and use the invention.

FIG. 1 schematically illustrates an exemplary method and system of the present invention, in which a liquefied biomass is contacted with a catalyst for lipid hydrolysis before fermentation.

FIG. 2 schematically illustrates an exemplary method and system of the present invention, in which a liquefied and saccharified biomass is contacted with a catalyst for lipid hydrolysis before fermentation.

FIG. 3 schematically illustrates an exemplary method and system of the present invention, in which lipids in a biomass feedstream are contacted with a catalyst for lipid hydrolysis before or during liquefaction.

FIG. 4 schematically illustrates an exemplary method and system of the present invention, in which undissolved solids and lipids are removed from a liquefied biomass before fermentation, and in which the removed lipids are hydrolyzed into free fatty acids using a catalyst, and the free fatty acids are supplied to the fermentation vessel.

FIG. 5 schematically illustrates an exemplary method and system of the present invention, in which lipids derived from native oil are hydrolyzed into free fatty acids using a catalyst, and the free fatty acids are supplied to the fermentation vessel.

FIG. 6 schematically illustrates an exemplary method and system of the present invention, in which biomass lipids present in a first extractant exiting a fermentation vessel are converted into free fatty acids that are supplied to a fermentation vessel as a second extractant.

DETAILED DESCRIPTION OF THE INVENTION

Figure 1:
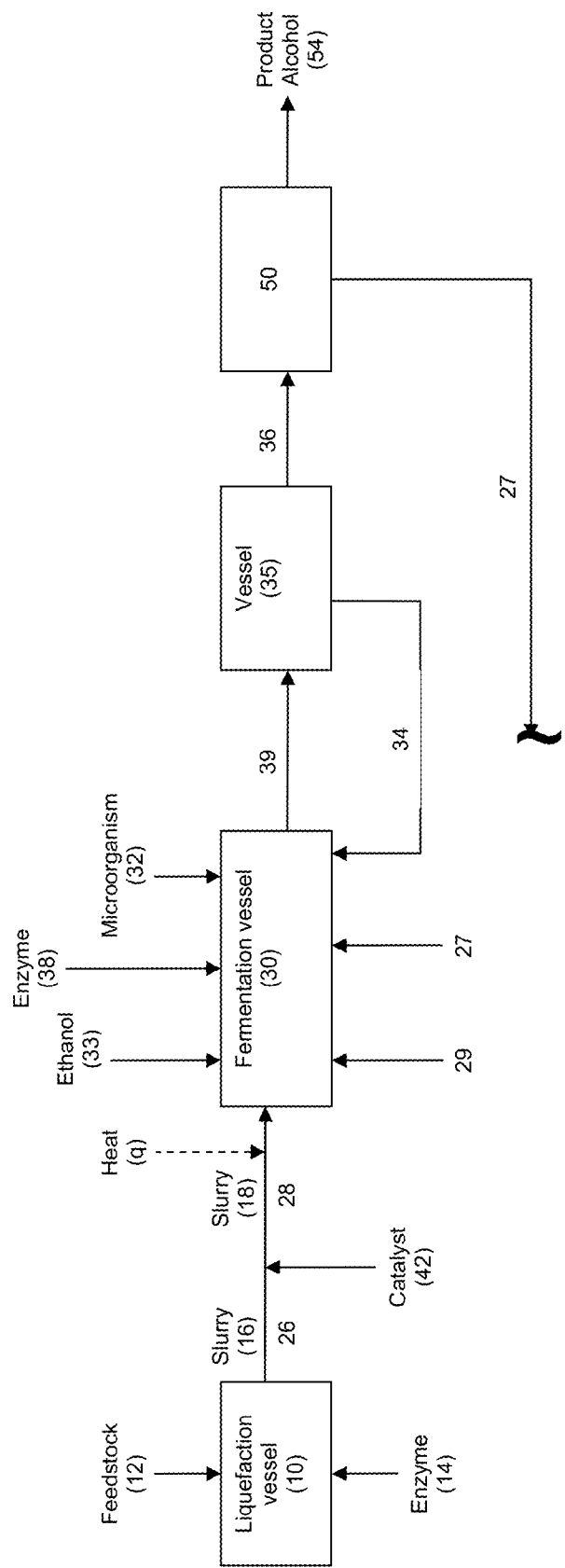

Unless defined otherwise, all technical and scientific terms used herein have the same meaning as commonly understood by one of ordinary skill in the art to which this invention belongs. In case of conflict, the present application including the definitions will control. Also, unless otherwise required by context, singular terms shall include pluralities and plural terms shall include the singular. All publications, patents and other references mentioned herein are incorporated by reference in their entireties for all purposes.

In order to further define this invention, the following terms and definitions are herein provided.

As used herein, the terms "comprises," "comprising," "includes," "including," "has," "having," "contains," or "containing," or any other variation thereof, will be understood to imply the inclusion of a stated integer or group of integers but not the exclusion of any other integer or group of integers. For example, a composition, a mixture, a process, a method, an article, or an apparatus that comprises a list of elements is not necessarily limited to only those elements but can include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances, that is, occurrences of the element or component. Therefore "a" or "an" should be read to include one or at least one, and the singular word form of the element or component also includes the plural unless the number is obviously meant to be singular.

The term "invention" or "present invention" as used herein is a non-limiting term and is not intended to refer to any single embodiment of the particular invention but encompasses all possible embodiments as described in the application.

As used herein, the term "about" modifying the quantity of an ingredient or reactant of the invention employed refers to variation in the numerical quantity that can occur, for example, through typical measuring and liquid handling procedures used for making concentrates or solutions in the real world; through inadvertent error in these procedures; through differences in the manufacture, source, or purity of the ingredients employed to make the compositions or to carry out the methods; and the like. The term "about" also encompasses amounts that differ due to different equilibrium conditions for a composition resulting from a particular initial mixture. Whether or not modified by the term "about," the claims include equivalents to the quantities. In one embodiment, the term "about" means within 10% of the reported numerical value, alternatively within 5% of the reported numerical value.

"Biomass" as used herein refers to a natural product containing hydrolyzable polysaccharides that provide fermentable sugars including any sugars and starch derived from natural resources such as corn, cane, wheat, cellulosic or lignocellulosic material and materials comprising cellulose, hemicellulose, lignin, starch, oligosaccharides, disaccharides and/or monosaccharides, and mixtures thereof. Biomass may also comprise additional components such as protein and/or lipids. Biomass may be derived from a single source or biomass can comprise a mixture derived from more than one source. For example, biomass may comprise a mixture of corn cobs and corn stover, or a mixture of grass and leaves. Biomass includes, but is not limited to, bioenergy crops, agricultural residues, municipal solid waste, industrial solid waste, sludge from paper manufacture, yard waste, wood and forestry waste. Examples of biomass include, but are not limited to, corn grain, corn cobs, crop residues such as corn husks, corn stover, grasses, wheat, rye, wheat straw, barley, barley straw, hay, rice straw, switchgrass, waste paper, sugar cane bagasse, sorghum, sugar cane, soy, components obtained from milling of grains, trees, branches, roots, leaves, wood chips, sawdust, shrubs and bushes, vegetables, fruits, flowers, animal manure, and mixtures thereof. For example, mash, juice, molasses, or hydrolysate may be formed from biomass by any processing known in the art for processing the biomass for purposes of fermentation such as by milling, treating, and/or liquefying and comprises fermentable sugar and may comprise water. For example, cellulosic and/or lignocellulosic biomass may be processed to obtain a hydrolysate containing fermentable sugars by any method known to one skilled in the art. A low ammonia pretreatment is disclosed in U.S. Patent Application Publication No. 2007/0031918A1, which is herein incorporated by reference. Enzymatic saccharification of cellulosic and/or lignocellulosic biomass typically makes use of an enzyme consortium for breaking down cellulose and hemicellulose to produce a hydrolysate containing sugars including glucose, xylose, and arabinose. (Saccharification enzymes suitable for cellulosic and/or lignocellulosic biomass are reviewed in Lynd, et al. (Microbiol. Mol. Biol. Rev. 66:506-577, 2002).

Mash, juice, molasses, or hydrolysate may include feedstock 12 and feedstock slurry 16 as described herein. An aqueous feedstream may be derived or formed from biomass by any processing known in the art for processing the biomass for purposes of fermentation such as by milling, treating, and/or liquefying and comprises fermentable carbon substrate (e.g., sugar) and may comprise water. An aqueous feedstream may include feedstock 12 and feedstock slurry 16 as described herein.

"Feedstock" as used herein means a feed in a fermentation process, the feed containing a fermentable carbon source with or without undissolved solids, and where applicable, the feed containing the fermentable carbon source before or after the fermentable carbon source has been liberated from starch or obtained from the break down of complex sugars by further processing such as by liquefaction, saccharification, or other process. Feedstock includes or is derived from a biomass. Suitable feedstocks include, but are not limited to, rye, wheat, corn, cane, barley, cellulosic material, lignocellulosic material, or mixtures thereof.

"Fermentation broth" as used herein means the mixture of water, sugars, dissolved solids, optionally microorganisms producing alcohol, product alcohol, and all other constituents of the material held in the fermentation vessel in which product alcohol is being made by the reaction of sugars to alcohol, water, and carbon dioxide ($CO_2$) by the microorganisms present. From time to time, as used herein the term "fermentation medium" and "fermented mixture" can be used synonymously with "fermentation broth."

"Fermentable carbon source" or "fermentable carbon substrate" as used herein means a carbon source capable of being metabolized by the microorganisms disclosed herein for the production of fermentative alcohol. Suitable fermentable carbon sources include, but are not limited to, monosaccharides such as glucose or fructose; disaccharides such as lactose or sucrose; oligosaccharides; polysaccharides such as starch or cellulose; C5 sugars such as xylose and arabinose; one carbon substrates including methane; and mixtures thereof.

"Fermentable sugar" as used herein refers to one or more sugars capable of being metabolized by the microorganisms disclosed herein for the production of fermentative alcohol.

"Fermentation vessel" as used herein means the vessel in which the fermentation reaction is carried out whereby product alcohol such as butanol is made from sugars.

"Liquefaction vessel" as used herein means the vessel in which liquefaction is carried out. Liquefaction is the process in which oligosaccharides are liberated from the feedstock. In some embodiments where the feedstock is corn, oligosaccharides are liberated from the corn starch content during liquefaction.

"Saccharification vessel" as used herein means the vessel in which saccharification (i.e., the break down of oligosaccharides into monosaccharides) is carried out. Where fermentation and saccharification occur simultaneously, the saccharification vessel and the fermentation vessel may be one in the same vessel.

"Sugar" as used herein refers to oligosaccharides, disaccharides, monosaccharides, and/or mixtures thereof. The term "saccharide" also includes carbohydrates including starches, dextrans, glycogens, cellulose, pentosans, as well as sugars.

As used herein, "saccharification enzyme" means one or more enzymes that are capable of hydrolyzing polysaccharides and/or oligosaccharides, for example, alpha-1,4-glucosidic bonds of glycogen, or starch. Saccharification enzymes may include enzymes capable of hydrolyzing cellulosic or lignocellulosic materials as well.

"Undissolved solids" as used herein means non-fermentable portions of feedstock, for example, germ, fiber, and gluten.

"Product alcohol" as used herein refers to any alcohol that can be produced by a microorganism in a fermentation process that utilizes biomass as a source of fermentable carbon substrate. Product alcohols include, but are not limited to, $C_1$ to $C_8$ alkyl alcohols. In some embodiments, the product alcohols are $C_2$ to $C_8$ alkyl alcohols. In other embodiments, the product alcohols are $C_2$ to $C_5$ alkyl alcohols. It will be appreciated that $C_1$ to $C_8$ alkyl alcohols include, but are not limited to, methanol, ethanol, propanol, butanol, and pentanol. Likewise $C_2$ to $C_8$ alkyl alcohols include, but are not limited to, ethanol, propanol, butanol, and pentanol. "Alcohol" is also used herein with reference to a product alcohol.

"Butanol" as used herein refers with specificity to the butanol isomers 1-butanol (1-BuOH), 2-butanol (2-BuOH), tert-butanol, and/or isobutanol (iBuOH or i-BuOH or I-BUOH, also known as 2-methyl-1-propanol), either individually or as mixtures thereof. From time to time, when referring to esters of butanol, the terms "butyl esters" and "butanol esters" may be used interchangeably.

"Propanol" as used herein refers to the propanol isomers isopropanol or 1-propanol.

"Pentanol" as used herein refers to the pentanol isomers 1-pentanol, 3-methyl-1-butanol, 2-methyl-1-butanol, 2,2-dimethyl-1-propanol, 3-pentanol, 2-pentanol, 3-methyl-2-butanol, or 2-methyl-2-butanol.

The term "alcohol equivalent" as used herein refers to the weight of alcohol that would be obtained by a perfect hydrolysis of an alcohol ester and the subsequent recovery of the alcohol from an amount of alcohol ester.

The term "aqueous phase titer" as used herein refers to the concentration of a particular alcohol (e.g., butanol) in the fermentation broth.

The term "effective titer" as used herein refers to the total amount of a particular alcohol (e.g., butanol) produced by fermentation or alcohol equivalent of the alcohol ester produced by alcohol esterification per liter of fermentation medium. For example, the effective titer of butanol in a unit volume of a fermentation includes: (i) the amount of butanol in the fermentation medium; (ii) the amount of butanol recovered from the organic extractant; (iii) the amount of butanol recovered from the gas phase, if gas stripping is used; and (iv) the alcohol equivalent of the butanol ester in either the organic or aqueous phase.

"In Situ Product Removal (ISPR)" as used herein means the selective removal of a specific fermentation product from a biological process such as fermentation, to control the product concentration in the biological process as the product is produced.

"Extractant" or "ISPR extractant" as used herein means an organic solvent used to extract any product alcohol such as butanol or used to extract any product alcohol ester produced by a catalyst from a product alcohol and a carboxylic acid or lipid. From time to time, as used herein the term "solvent" may be used synonymously with "extractant." For the processes described herein, extractants are water-immiscible.

The terms "water-immiscible" or "insoluble" refer to a chemical component such as an extractant or solvent, which is incapable of mixing with an aqueous solution such as a fermentation broth, in such a manner as to form one liquid phase.

The term "aqueous phase" as used herein refers to the aqueous phase of a biphasic mixture obtained by contacting a fermentation broth with a water-immiscible organic extractant. In an embodiment of a process described herein that includes fermentative extraction, the term "fermentation broth" then specifically refers to the aqueous phase in biphasic fermentative extraction.

The term "organic phase" as used herein refers to the non-aqueous phase of a biphasic mixture obtained by contacting a fermentation broth with a water-immiscible organic extractant.

The term "carboxylic acid" as used herein refers to any organic compound with the general chemical formula —COOH in which a carbon atom is bonded to an oxygen atom by a double bond to make a carbonyl group (—C=O) and to a hydroxyl group (—OH) by a single bond. A carboxylic acid may be in the form of the protonated carboxylic acid, in the form of a salt of a carboxylic acid (e.g., an ammonium, sodium, or potassium salt), or as a mixture of protonated carboxylic acid and salt of a carboxylic acid. The term carboxylic acid may describe a single chemical species (e.g., oleic acid) or a mixture of carboxylic acids as can be produced, for example, by the hydrolysis of biomass-derived fatty acid esters or triglycerides, diglycerides, monoglycerides, and phospholipids.

The term "fatty acid" as used herein refers to a carboxylic acid (e.g., aliphatic monocarboxylic acid) having $C_4$ to $C_{28}$ carbon atoms (most commonly $C_{12}$ to $C_{24}$ carbon atoms), which is either saturated or unsaturated. Fatty acids may also be branched or unbranched. Fatty acids may be derived from, or contained in esterified form, in an animal or vegetable fat, oil, or wax. Fatty acids may occur naturally in the form of glycerides in fats and fatty oils or may be obtained by hydrolysis of fats or by synthesis. The term fatty acid may describe a single chemical species or a mixture of fatty acids. In addition, the term fatty acid also encompasses free fatty acids.

The term "fatty alcohol" as used herein refers to an alcohol having an aliphatic chain of $C_4$ to $C_{22}$ carbon atoms, which is either saturated or unsaturated.

The term "fatty aldehyde" as used herein refers to an aldehyde having an aliphatic chain of $C_4$ to $C_{22}$ carbon atoms, which is either saturated or unsaturated.

The term "fatty amide" as used herein refers to an amide having a long, aliphatic chain of $C_4$ to $C_{22}$ carbon atoms, which is either saturated or unsaturated.

The term "fatty ester" as used herein refers to an ester having a long aliphatic chain of $C_4$ to $C_{22}$ carbon atoms, which is either saturated or unsaturated.

"Native oil" as used herein refers to lipids obtained from plants (e.g., biomass) or animals. "Plant-derived oil" as used herein refers to lipids obtain from plants in particular. From time to time, "lipids" may be used synonymously with "oil" and "acyl glycerides." Native oils include, but are not limited to, tallow, corn, canola, capric/caprylic triglycerides, castor, coconut, cottonseed, fish, jojoba, lard, linseed, neetsfoot, oiticica, palm, peanut, rapeseed, rice, safflower, soya, sunflower, tung, jatropha, and vegetable oil blends.

The term "separation" as used herein is synonymous with "recovery" and refers to removing a chemical compound from an initial mixture to obtain the compound in greater purity or at a higher concentration than the purity or concentration of the compound in the initial mixture.

As used herein, "recombinant microorganism" refers to microorganisms such as bacteria or yeast, that are modified by use of recombinant DNA techniques, for example, by engineering a host cell to comprise a biosynthetic pathway such as a biosynthetic pathway to produce an alcohol such as butanol.

The present invention provides extractants obtained by catalytic hydrolysis of oil glycerides derived from biomass and methods of producing the extractants. In particular, the glycerides in biomass oil can be catalytically hydrolyzed into fatty acids using a catalyst such as an enzyme. The fatty acids can serve as extractants for in situ removal of a product alcohol such as butanol from a fermentation broth. Thus, the present invention also provides methods for producing a product alcohol such as butanol through extractive fermentation using the extractants that were produced from the biomass oil. The present invention also provides methods for catalytically hydrolyzing the oil present in a feedstock slurry into fatty acids prior to fermentation, whereby the oil is converted to fatty acids and the degradation of the partition coefficient of the ISPR extractant over time that is attributable to the presence of the oil in the fermentation vessel can be reduced. Moreover, the fatty acids obtained by hydrolysis of the feedstock oil can serve as an ISPR extractant having a partition coefficient for a fermentative alcohol greater than a partition coefficient of the feedstock oil for the fermentative alcohol. The feedstock oil can be separated from the feedstock slurry prior to hydrolysis and used as an ISPR extractant, or the oil can be hydrolyzed into fatty acids while in the feedstock slurry. Further, fatty acids as ISPR extractant can be used in place of or in addition to a conventional exogenous extractant, such as oleyl alcohol or oleic acid, thereby reducing the raw material expense associated with the exogenous extractant.

The present invention will be described with reference to the Figures. FIG. 1 illustrates an exemplary process flow diagram for production of fermentative alcohol according to an embodiment of the present invention. As shown, a feedstock 12 can be introduced to an inlet in a liquefaction vessel 10 and liquefied to produce a feedstock slurry 16. Feedstock 12 contains hydrolysable starch that supplies a fermentable carbon source (e.g., fermentable sugar such as glucose), and can be a biomass such as, but not limited to, rye, wheat, corn, cane, barley, cellulosic material, lignocellulosic material, or mixtures thereof, or can otherwise be derived from a biomass. In some embodiments, feedstock 12 can be one or more components of a fractionated biomass and in other embodiments, feedstock 12 can be a milled, unfractionated biomass. In some embodiments, feedstock 12 can be corn such as dry milled, unfractionated corn kernels, and the undissolved solids can include germ, fiber, and gluten. The undissolved solids are non-fermentable portions of feedstock 12. For purposes of the discussion herein with reference to the embodiments shown in the Figures, feedstock 12 will often be described as constituting milled, unfractionated corn in which the undissolved solids have not been separated therefrom. However, it should be understood that the exemplary methods and systems described herein can be modified for different feedstocks whether fractionated or not, as apparent to one of skill in the art. In some embodiments, feedstock 12 can be high-oleic corn, such that corn oil derived therefrom is a high-oleic corn oil having an oleic acid content of at least about 55 wt % oleic acid. In some embodiments, the oleic acid content in high-oleic corn oil can be up to about 65 wt %, as compared with the oleic acid content in normal corn oil which is about 24 wt %. High-oleic oil can provide some advantages for use in the methods of the present invention, as hydrolysis of the oil provides fatty acids having a high oleic acid content for contacting with a fermentation broth. In some embodiments, the fatty acids or mixtures thereof comprise unsaturated fatty acids. The presence of unsaturated fatty acids decreases the melting point, providing advantages for handling. Of the unsaturated fatty acids, those which are monounsaturated, that is, possessing a single carbon-carbon double bond, may provide advantages with respect to melting point without sacrificing suitable thermal and oxidative stability for process considerations.

The process of liquefying feedstock 12 involves hydrolysis of starch in feedstock 12 into sugars including, for example, dextrins and oligosaccharides, and is a conventional process. Any known liquefying processes, as well as the corresponding liquefaction vessel, normally utilized by the industry can be used including, but not limited to, the acid process, the acid-enzyme process, or the enzyme process. Such processes can be used alone or in combination. In some embodiments, the enzyme process can be utilized and an appropriate enzyme 14, for example, alpha-amylase, is introduced to an inlet in liquefaction vessel 10. Water can also be introduced to liquefaction vessel 10. In some embodiments, a saccharification enzyme, for example, glucoamylase, may also be introduced to liquefaction vessel 10. In additional embodiments, a lipase may also be introduced to liquefaction vessel 10 to catalyze the conversion of one or more components of the oil to fatty acids.

Feedstock slurry 16 produced from liquefying feedstock 12 includes sugar, oil 26, and undissolved solids derived from the biomass from which feedstock 12 was formed. In some embodiments, the oil is in an amount of about 0 wt % to at least about 2 wt % of the fermentation broth composition. In some embodiments, the oil is in an amount of at least about 0.5 wt % of the feedstock. Feedstock slurry 16 can be discharged from an outlet of liquefaction vessel 10. In some embodiments, feedstock 12 is corn or corn kernels and therefore, feedstock slurry 16 is a corn mash slurry.

A catalyst 42 can be added to feedstock slurry 16. Catalyst 42 is capable of hydrolyzing glycerides in oil 26 to free fatty acids (FFA) 28. For example, when feedstock 12 is corn, then oil 26 is the feedstock's constituent corn oil, and the free fatty acids 28 are corn oil fatty acids (COFA). Thus, after introduction of catalyst 42 to feedstock slurry 16, at least a portion of the glycerides in oil 26 are hydrolyzed to FFA 28, resulting in a feedstock slurry 18 having FFA 28 and catalyst 42. The resulting acid/oil composition from hydrolyzing oil 26 is typically at least about 17 wt % FFA. In some embodiments, the resulting acid/oil composition from hydrolyzing oil 26 is at least about 20 wt % FFA, at least about 25 wt % FFA, at least about 30 wt % FFA, at least about 35 wt % FFA, at least about 40 wt % FFA, at least about 45 wt % FFA, at least about 50 wt % FFA, at least about 55 wt % FFA, at least about 60 wt % FFA, at least about 65 wt % FFA, at least about 70 wt % FFA, at least about 75 wt % FFA, at least about 80 wt % FFA, at least about 85 wt % FFA, at least about 90 wt % FFA, at least about 95 wt % FFA, or at least about 99 wt % FFA. In some embodiments, the concentration of the fatty acid (such as carboxylic acid) in the fermentation vessel exceeds the solubility limit in the aqueous phase and results in the production a two-phase fermentation mixture comprising an organic phase and an aqueous phase. In some embodiments, the concentration of carboxylic acid (or fatty acid) in the fermentation broth is typically not greater than about 0.8 g/L and is limited by the solubility of the carboxylic acid (or fatty acid) in the broth.

In some embodiments, catalyst 42 can be one or more enzymes, for example, hydrolase enzymes such as lipase enzymes. Lipase enzymes used may be derived from any source including, for example, *Absidia, Achromobacter, Aeromonas, Alcaligenes, Alternaria, Aspergillus, Achromobacter, Aureobasidium, Bacillus, Beauveria, Brochothrix, Candida, Chromobacter, Coprinus, Fusarium, Geotricum, Hansenula, Humicola, Hyphozyma, Lactobacillus, Metarhizium, Mucor, Nectria, Neurospora, Paecilomyces, Penicillium, Pseudomonas, Rhizoctonia, Rhizomucor, Rhizopus, Rhodosporidium, Rhodotorula, Saccharomyces, Sus, Sporobolomyces, Thermomyces, Thiarosporella, Trichoderma, Verticillium*, and/or a strain of *Yarrowia*. In a preferred aspect, the source of the lipase is selected from the group consisting of *Absidia blakesleena, Absidia corymbifera, Achromobacter iophagus, Alcaligenes* sp., *Alternaria brassiciola, Aspergillus flavus, Aspergillus niger, Aspergillus tubingensis, Aureobasidium pullulans, Bacillus pumilus, Bacillus strearothermophilus, Bacillus subtilis, Brochothrix thermosohata, Candida cylindracea (Candida rugosa), Candida paralipolytica, Candida Antarctica* lipase A, *Candida antartica* lipase B, *Candida emobii, Candida deformans, Chromobacter viscosum, Coprinus cinerius, Fusarium oxysporum, Fusarium solani, Fusarium solani pisi, Fusarium roseum culmorum, Geotricum penicillatum, Hansenula anomala, Humicola brevispora, Humicola brevis* var. *thermoidea, Humicola insolens, Lactobacillus curvatus, Rhizopus oryzae, Penicillium cyclopium, Penicillium crustosum, Penicillium expansum, Penicillium* sp. I, *Penicillium* sp. II, *Pseudomonas aeruginosa, Pseudomonas alcaligenes, Pseudomonas cepacia* (syn. *Burkholderia cepacia*), *Pseudomonas fluorescens, Pseudomonas fragi, Pseudomonas maltophilia, Pseudomonas mendocina, Pseudomonas mephitica lipolytica, Pseudomonas alcaligenes, Pseudomonas plantari, Pseudomonas pseudoalcaligenes, Pseudomonas putida, Pseudomonas stutzeri,* and *Pseudomonas wisconsinensis, Rhizoctonia solani, Rhizomucor miehei, Rhizopus japonicus, Rhizopus microsporus, Rhizopus nodosus, Rhodosporidium toruloides, Rhodotorula glutinis, Saccharomyces cerevisiae, Sporobolomyces shibatanus, Sus scrofa, Thermomyces lanuginosus* (formerly *Humicola lanuginose*), *Thiarosporella phaseolina, Trichoderma harzianum, Trichoderma reesei,* and *Yarrowia lipolytica*. In a further preferred aspect, the lipase is selected from the group consisting of *Thermomcyces lanuginosus* lipase, *Aspergillus* sp. lipase, *Aspergillus niger* lipase, *Aspergillus tubingensis* lipase, *Candida antartica* lipase B, *Pseudomonas* sp. lipase, *Penicillium roqueforti* lipase, *Penicillium camembertii* lipase, *Mucor javanicus* lipase, *Burkholderia cepacia* lipase, *Alcaligenes* sp. lipase, *Candida rugosa* lipase, *Candida parapsilosis* lipase, *Candida deformans* lipase, lipases A and B from *Geotrichum candidum, Neurospora crassa* lipase, *Nectria haematococca* lipase, *Fusarium heterosporum* lipase *Rhizopus delemar* lipase, *Rhizomucor miehei* lipase, *Rhizopus arrhizus* lipase, and *Rhizopus oryzae* lipase. Suitable commercial lipase preparations suitable as enzyme catalyst 42 include, but are not limited to Lipolase® 100 L, Lipex® 100L, Lipoclean® 2000T, Lipozyme® CALB L, Novozyme® CALA L, and Palatase 20000L, available from Novozymes, or from *Pseudomonas fluorescens, Pseudomonas cepacia, Mucor miehei*, hog pancreas, *Candida cylindracea, Rhizopus niveus, Candida antarctica, Rhizopus arrhizus* or *Aspergillus* available from SigmaAldrich.

Phospholipases are enzymes that hydrolyze the ester bonds of phospholipids, but many phospholipases also can hydrolyze triglycerides, diglycerides, and monoglycerides (lipid acyl hydrolase (LAH) activity). As used herein, the term "phospholipase" encompasses enzymes having any phospholipase activity, for example, cleaving a glycerolphosphate ester linkage (catalyzing hydrolysis of a glycerolphosphate ester linkage), for example, in an oil, such as a crude oil or a vegetable oil. The phospholipase activity of the invention can generate a water extractable phosphorylated base and a diglyceride. The phospholipase activity can comprise a phospholipase C (PLC) activity; a PI-PLC activity, a phospholipase A (PLA) activity such as a phospholipase A1 or phospholipase A2 activity; a phospholipase B (PLB) activity such as a phospholipase B1 or phospholipase B2 activity, including lysophospholipase (LPL) activity and/or lysophospholipase-transacylase (LPT A) activity; a phospholipase D (PLD) activity such as a phospholipase DI or a phospholipase D2 activity; and/or a patatin activity or any combination thereof. The term "phospholipase" also encompasses enzymes having lysophospholipase activity, where the two substrates of this enzyme are 2-lysophosphatidylcholine and $H_2O$, and where its two products are glycerophosphocholine and carboxylate. Phospholipase Al (PLA1) enzymes remove the 1-position fatty acid to produce free fatty acid and 1-lyso-2-acylphospholipid. Phospholipase A2 (PLA2) enzymes remove the 2-position fatty acid to produce free fatty acid and l-acyl-2-lysophospholipid. PLA1 and PLA2 enzymes can be intra- or extra-cellular, membrane-bound or soluble. Phospholipase C (PLC) enzymes remove the phosphate moiety to produce 1,2 diacylglycerol and a phosphate ester. Phospholipase D (PLD) enzymes produce 1,2-diacylglycerophosphate and base group. A phospholipase useful in the present invention may be obtained from a variety of biological sources, for example, but not limited to, filamentous fungal species within the genus *Fusarium*, such as a strain of *F. culmorum, F. heterosporum, F. solani*, or *F. oxysporum*; or a filamentous fungal species within the genus *Aspergillus*, such as a strain of *Aspergillus awamori, Aspergillus foetidus, Aspergillus japonicus, Aspergillus niger* or *Aspergillus oryzae*. Also useful in the present invention are *Thermomyces lanuginosus* phospholipase variants such as the commercial product Lecitase® Ultra (Novozymes A'S, Denmark). One or more phospholipases may be applied as lyophilized powder, immobilized or in aqueous solution.

After at least a portion of the glycerides are hydrolyzed, in some embodiments, catalyst 42 can be inactivated. Any method known in the art can be used to render catalyst 42 inactive. For example, in some embodiments, catalyst 42 can be inactivated by the application of heat, by adjusting the pH of the reaction mass to a pH where catalyst 42 is irreversibly inactivated, and/or by adding a chemical or biochemical species capable of selectively inactivating the catalyst activity. As shown, for example, in the embodiment of FIG. 1, heat q is applied to feedstock slurry 18, whereby catalyst 42 becomes inactive. The application of heat q can be applied to feedstock slurry 18 before feedstock slurry 18 is fed to a fermentation vessel 30. Heat-treated feedstock slurry 18 (with inactive catalyst 42) is then introduced into a fermentation vessel 30 along with a microorganism 32 to be included in a fermentation broth held in fermentation vessel 30. Alternatively, feedstock slurry 18 can be fed to fermentation vessel 30 and subjected to heat q while in the fermentation vessel, before fermentation vessel inoculation of microorganism 32. For example, in some embodiments, catalyst inactivation treatment can be achieved by heating feedstock slurry 18 with heat q to temperature of at least about 75° C. for at least about 5 minutes, at least about 75° C. for at least about 10 minutes, at least about 75° C. for at least about 15 minutes, at least about 80° C. for at least about 5 minutes, at least about 80° C. for at least about 10 minutes, at least about 80° C. for at least about 15 minutes, at least about 85° C. for at least about 5 minutes, at least about 85° C. for at least about 10 minutes, or at least about 85° C. for at least about 15 minutes. In some embodiments, after being subject to heat q, feedstock slurry 18 is cooled to an appropriate temperature for fermentation prior to introduction to fermentation vessel 30 (or prior to fermentation vessel inoculation in the case that the application of heat q is conducted in the fermentation vessel). For example, in some embodiments, the temperature of feedstock slurry 18 is about 30° C. prior to contacting with a fermentation broth.

Inactivation of catalyst 42 is preferred when it is desirable to prevent catalyst 42 from esterifying alcohol with fatty acids 28 in the fermentation vessel. In some embodiments, production of an alcohol ester by esterification of product alcohol in a fermentation medium with an organic acid (e.g., fatty acid) and a catalyst (e.g., lipase) is desirable, as further described in co-pending, commonly owned U.S. Provisional Application Ser. No. 61/368,429, filed on Jul. 28, 2010; U.S. Provisional Application Ser. No. 61/379,546, filed on Sep. 2, 2010; and U.S. Provisional Application Ser. No. 61/440,034, filed on Feb. 7, 2011, all incorporated herein in its entirety by reference thereto. For example, for butanol production, active catalyst 42 in fermentation vessel (introduced via slurry 18) can catalyze the esterification of the butanol with fatty acids 28 (introduced via slurry 18) to form fatty acid butyl esters (FABE) in situ.

Fermentation vessel 30 is configured to ferment slurry 18 to produce a product alcohol such as butanol. In particular, microorganism 32 metabolizes the fermentable sugar in slurry 18 and excretes a product alcohol. Microorganism 32 is selected from the group of bacteria, cyanobacteria, filamentous fungi, and yeasts. In some embodiments, microorganism 32 can be a bacteria such as *E. coli*. In some embodiments, microorganism 32 can be a fermentative recombinant microorganism. The slurry can include sugar, for example, in the form of oligosaccharides, and water, and can comprise less than about 20 g/L of monomeric glucose, more preferably less than about 10 g/L or less than about 5 g/L of monomeric glucose. Suitable methodology to determine the amount of monomeric glucose is well known in the art. Such suitable methods known in the art include HPLC.

In some embodiments, slurry 18 is subjected to a saccharification process in order to break the complex sugars (e.g., oligosaccharides) in slurry 18 into monosaccharides that can be readily metabolized by microorganism 32. Any known saccharification process that is routinely utilized by the industry can be used including, but not limited to, the acid process, the acid-enzyme process, or the enzyme process. In some embodiments, simultaneous saccharification and fermentation (SSF) can occur inside fermentation vessel 30, as shown in FIG. 1. In some embodiments, an enzyme 38, such as glucoamylase, can be introduced to an inlet in fermentation vessel 30 in order to breakdown the starch or oligosaccharides to glucose capable of being metabolized by microorganism 32.

Optionally, ethanol 33 may be supplied to fermentation vessel 30 to be included in the fermentation broth. In some embodiments, when a recombinant microorganism having a butanol biosynthetic pathway is used as microorganism 32 for butanol production, microorganism 32 may require supplementation of a 2-carbon substrate (e.g., ethanol) to survive and grow. Thus, in some embodiments, ethanol 33 may be supplied to fermentation vessel 30.

However, it has been surprisingly found that methods of the present invention, in which free fatty acid (e.g., FFA 28) is present in the fermentation vessel, can allow reduction of the amount of ethanol 33 typically supplied for a given recombinant microorganism without detriment to the vitality of the recombinant microorganism. Further, in some embodiments, the methods of the present invention provide that the alcohol (e.g., butanol) production rate without ethanol supplementation to be comparable with the production rate that can be realized when ethanol 33 is supplemented. As further demonstrated by the comparative examples presented in Examples 1-14 below, the butanol production rate when fatty acid but not ethanol is in the fermentation vessel can be greater than the butanol production rate when neither fatty acid nor ethanol is in the fermentation vessel. Thus, in some embodiments, the amount of ethanol 33 supplementation is reduced compared to conventional processes. For example, a typical amount of ethanol added to a fermentation vessel for microorganisms requiring supplementation of a 2-carbon substrate is about 5 g/L anhydrous ethanol (i.e., 5 g anhydrous ethanol per liter of fermentation medium). In some embodiments, the butanol fermentation is not supplemented with any ethanol 33. In the latter case, the stream of ethanol 33 is entirely omitted from the fermentation vessel. Thus, in some embodiments of the present invention, it is possible to reduce or eliminate the cost associated with supplemental ethanol 33, as well as the inconvenience associated with storing vats of ethanol 33 and supplying it to the fermentation vessel during butanol fermentation.

Moreover, regardless of ethanol supplementation, in some embodiments, the methods of the present invention can provide a higher rate of glucose uptake by microorganism 32 by virtue of the presence of fatty acids during the fermentation. The fatty acids can be introduced into fermentation vessel 30 as carboxylic acid 28, hydrolyzed from supplied oil 26, and/or derived from hydrolysis of constituent biomass oil of slurry 16. Methods for producing a product alcohol from a fermentation process in which fatty acids are produced at a step in the process and are contacted with microorganism cultures in a fermentation vessel for improving microorganism growth rate and glucose consumption are described in commonly owned U.S. Provisional Application Ser. No. 61/368,451, filed on Jul. 28, 2010, which is incorporated herein in its entirety by reference thereto.

In fermentation vessel 30, alcohol is produced by microorganism 32. In situ product removal (ISPR) can be utilized to remove the product alcohol from the fermentation broth. In some embodiments, ISPR includes liquid-liquid extraction. Liquid-liquid extraction can be performed according to the processes described in U.S. Patent Application Publication No. 2009/0305370, the disclosure of which is hereby incorporated in its entirety. U.S. Patent Application Publication No. 2009/0305370 describes methods for producing and recovering butanol from a fermentation broth using liquid-liquid extraction, the methods comprising the step of contacting the fermentation broth with a water-immiscible extractant to form a two-phase mixture comprising an aqueous phase and an organic phase. Typically, the extractant can be an organic extractant selected from the group consisting of saturated, mono-unsaturated, poly-unsaturated (and mixtures thereof) $C_{12}$ to $C_{22}$ fatty alcohols, $C_{12}$ to $C_{22}$ fatty acids, esters of $C_{12}$ to $C_{22}$ fatty acids, $C_{12}$ to $C_{22}$ fatty aldehydes, $C_{12}$ to $C_{22}$ fatty amides, triglycerides, and mixtures thereof, which contacts a fermentation broth and to form a two-phase mixture comprising an aqueous phase and an organic phase. The extractant may also be an organic extractant selected from the group consisting of saturated, mono-unsaturated, poly-unsaturated (and mixtures thereof) $C_4$ to $C_{22}$ fatty alcohols, $C_4$ to $C_{28}$ fatty acids, esters of $C_4$ to $C_{28}$ fatty acids, $C_4$ to $C_{22}$ fatty aldehydes, $C_4$ to $C_{22}$ fatty amides, and mixtures thereof, which contacts a fermentation broth and to form a two-phase mixture comprising an aqueous phase and an organic phase. Free fatty acids 28 from slurry 18 can also serve as an ISPR extractant 28. For example, when free fatty acids 28 are corn oil fatty acids (COFA), ISPR extractant 28 is COFA. ISPR extractant (FFA) 28 contacts the fermentation broth and forms a two-phase mixture comprising an aqueous phase 34 and an organic phase. The product alcohol present in the fermentation broth preferentially partitions into the organic phase to form an alcohol-containing organic phase 36. In some embodiments, fermentation vessel 30 has one or more inlets for receiving one or more additional ISPR extractants 29 which form a two-phase mixture comprising an aqueous phase and an organic phase, with the product alcohol partitioning into the organic phase.

The biphasic mixture can be removed from fermentation vessel 30 as stream 39 and introduced into a vessel 35, in which the alcohol-containing organic phase 36 is separated from the aqueous phase 34. The alcohol-containing organic phase 36 is separated from the aqueous phase 34 of the biphasic mixture stream 39 using methods known in the art including, but not limited to, siphoning, aspiration, decantation, centrifugation, using a gravity settler, membrane-assisted phase splitting, and the like. All or part of the aqueous phase 34 can be recycled into fermentation vessel 30 as fermentation medium (as shown), or otherwise discarded and replaced with fresh medium, or treated for the removal of any remaining product alcohol and then recycled to fermentation vessel 30. Then, the alcohol-containing organic phase 36 is treated in a separator 50 to recover product alcohol 54, and the resulting alcohol-lean extractant 27 can then be recycled back into fermentation vessel 30, usually in combination with fresh FFA 28 from slurry 18 and/or with fresh extractant 29 for further extraction of the product alcohol. Alternatively, fresh FFA 28 (from slurry 18) and/or extractant 29 can be continuously added to the fermentation vessel to replace the ISPR extractant(s) removed in biphasic mixture stream 39.

In some embodiments, any additional ISPR extractant 29 can be an exogenous organic extractant such as oleyl alcohol, behenyl alcohol, cetyl alcohol, lauryl alcohol, myristyl alcohol, stearyl alcohol, 1-undecanol, oleic acid, lauric acid, myristic acid, stearic acid, methyl myristate, methyl oleate, undecanal, lauric aldehyde, 20-methylundecanal, and mixtures thereof. In some embodiments, ISPR extractant 29 can be a carboxylic acid and in some embodiments, ISPR extractant 29 can be a fatty acid. In some embodiments, the carboxylic acid or fatty acid can have 4 to 28 carbons, 4 to 22 carbons in other embodiments, 8 to 22 carbons in other embodiments, 10 to 28 carbons in other embodiments, 7 to 22 carbons in other embodiments, 12 to 22 carbons in other embodiments, 4 to 18 carbons in other embodiments, 12 to 22 carbons in other embodiments, and 12 to 18 carbons in still other embodiments. In some embodiments, ISPR extractant 29 is one or more of the following fatty acids: azaleic, capric, caprylic, castor, coconut (i.e., as a naturally-occurring combination of fatty acids, including lauric, myrisitic, palmitic, caprylic, capric, stearic, caproic, arachidic, oleic, and linoleic, for example), dimer, isostearic, lauric, linseed, myristic, oleic, olive, palm oil, palmitic, palm kernel, peanut, pelargonic, ricinoleic, sebacic, soya, stearic acid, tall oil, tallow, #12 hydroxy stearic, or any seed oil. In some embodiments, ISPR extractant 29 is one or more of diacids, azelaic, dimer and sebacic acid. Thus, in some embodiments, ISPR extractant 29 can be a mixture of two or more different fatty acids. In some embodiments, ISPR extractant 29 can be a fatty acid derived from chemical or enzymatic hydrolysis of glycerides derived from native oil. For example, in some embodiments, ISPR extractant 29 can be free fatty acids 28' obtained by enzymatic hydrolysis of native oil such as biomass lipids as later described with reference to the embodiment of FIG. 5. In some embodiments, ISPR extractant 29 can be a fatty acid extractant selected from the group consisting of fatty acids, fatty alcohols, fatty amides, fatty acid methyl esters, lower alcohol esters of fatty acids, fatty acid glycol esters, hydroxylated triglycerides, and mixtures thereof, obtained from chemical conversion of native oil such as biomass lipids as described for example in commonly owned U.S. Provisional Application Ser. No. 61/368,436, filed on Jul. 28, 2010. In such embodiments, the biomass lipids for producing extractant 29 can be from a same or different biomass source from which feedstock 12 is obtained. For example, in some embodiments, the biomass lipids for producing extractant 29 can be derived from soya, whereas the biomass source of feedstock 12 is corn. Any possible combination of different biomass sources for extractant 29 versus feedstock 12 can be used, as should be apparent to one of skill in the art. In some embodiments, additional ISPR extractant 29 includes COFA.

In situ extractive fermentation can be carried out in a batch mode or a continuous mode in fermentation vessel 30. For in situ extractive fermentation, the organic extractant can contact the fermentation medium at the start of the fermentation forming a biphasic fermentation medium. Alternatively, the organic extractant can contact the fermentation medium after the microorganism has achieved a desired amount of growth, which can be determined by measuring the optical density of the culture. Further, the organic extractant can contact the fermentation medium at a time at which the product alcohol level in the fermentation medium reaches a preselected level. In the case of butanol production, for example, the ISPR extractant can contact the fermentation medium at a time before the butanol concentration reaches a level which would be toxic to the microorganism. After contacting the fermentation medium with the ISPR extractant, the butanol product partitions into the extractant, decreasing the concentration in the aqueous phase containing the microorganism, thereby limiting the exposure of the production microorganism to the inhibitory butanol product.

The volume of the ISPR extractant to be used depends on a number of factors including the volume of the fermentation medium, the size of the fermentation vessel, the partition coefficient of the extractant for the butanol product, and the fermentation mode chosen, as described below. The volume of the extractant can be about 3% to about 60% of the fermentation vessel working volume. Depending on the efficiency of the extraction, the aqueous phase titer of butanol in the fermentation medium can be, for example, from about 1 g/L to about 85 g/L, from about 10 g/L to about 40 g/L, from about 10 g/L to about 20 g/L, from about 15 g/L to about 50 g/L or from about 20 g/L to about 60 g/L. In some embodiments, the resulting fermentation broth after alcohol esterification can comprise free (i.e., unesterified) alcohol and in some embodiments, the concentration of free alcohol in the fermentation broth after alcohol esterification is not greater than 1, 3, 6, 10, 15, 20, 25, 30 25, 40, 45, 50, 55, or 60 g/L when the product alcohol is butanol, or when the product alcohol is ethanol, the concentration of free alcohol in the fermentation broth after alcohol esterification is not greater than 15, 20, 25, 30 25, 40, 45, 50, 55, 60, 65, 70, 75, 80, 85, 90, 95, or 100 g/L. Without being held to theory, it is believed that higher butanol titer may obtained with the extractive fermentation method, in part, from the removal of the toxic butanol product from the fermentation medium, thereby keeping the level below that which is toxic to the microorganism.

In a batchwise mode of in situ extractive fermentation, a volume of organic extractant is added to the fermentation vessel and the extractant is not removed during the process. This mode requires a larger volume of organic extractant to minimize the concentration of the inhibitory butanol product in the fermentation medium. Consequently, the volume of the fermentation medium is less and the amount of product produced is less than that obtained using the continuous mode. For example, the volume of the extractant in the batchwise mode can be 20% to about 60% of the fermentation vessel working volume in one embodiment, and about 30% to about 60% in another embodiment.

Gas stripping (not shown) can be used concurrently with the ISPR extractant to remove the product alcohol from the fermentation medium.

In the embodiment of FIG. 1, the product alcohol is extracted from the fermentation broth in situ, with the separation of the biphasic mixture 39 occurring in a separate vessel 35. In some embodiments, separation of the biphasic mixture 39 can occur in the fermentation vessel, as shown in the embodiments of later described FIGS. 2 and 3 in which the alcohol-containing organic phase stream 36 exits directly from fermentation vessel 30. Aqueous phase stream 34 can also exit directly from fermentation vessel 30, be treated for the removal of any remaining product alcohol and recycled, or discarded and replaced with fresh fermentation medium. The extraction of the product alcohol by the organic extractant(s) can be done with or without the removal of the microorganism from the fermentation broth. The microorganism can be removed from the fermentation broth by means known in the art including, but not limited to, filtration or centrifugation. For example, aqueous phase stream 34 can include microorganism 32 such as yeast. Microorganism 32 can be easily separated from the aqueous phase stream, for example, in a centrifuge (not shown). Microorganism 32 can then be recycled to fermentation vessel 30 which over time can increase the production rate of alcohol production, thereby resulting in an increase in the efficiency of the alcohol production.

In a continuous mode of in situ extractive fermentation, the volume of the extractant can be about 3% to about 50% of the fermentation vessel working volume in one embodiment, about 3% to about 30% in another embodiment, 3% to about 20% in another embodiment; and 3% to about 10% in another embodiment. Because the product is continually removed from the reactor, a smaller volume of extractant is required enabling a larger volume of the fermentation medium to be used.

As an alternative to in situ extractive fermentation, the product alcohol can be extracted from the fermentation broth downstream of fermentation vessel 30. In such an instance, the fermentation broth can be removed from fermentation vessel 30 and introduced into vessel 35. Extractant 28 can then be introduced into vessel 35 and contacted with the fermentation broth to obtain biphasic mixture 39 in vessel 35, which is then separated into the organic and aqueous phases 36 and 34. Alternatively, extractant 28 can be added to the fermentation broth in a separate vessel (not shown) prior to introduction to vessel 35.

As a non-limiting prophetic example, with reference to the embodiment of FIG. 1, an aqueous suspension of ground whole corn (as feedstock 12), which can nominally contain about 4 wt % corn oil, can be treated with amylase (as liquefaction enzyme 14) at about 85° C. to 120° C. for 30 minutes to 2 hours, and the resulting liquefied mash 16 cooled to between 65° C. and 30° C. and treated with 0.1 ppm to 10 ppm (in some embodiments, 0.5 ppm to 1.0 ppm) of lipase (as catalyst 42) at pH 4.5 to 7.5 (in some embodiments, between pH 5.5 and 6.5) for sufficient time to produce from at least 30% to as high as at least 99% conversion of the available fatty acid content in lipids to free fatty acids. Optionally, the liquefied and lipase-treated mash 18 can be heated to inactivate lipase 42 prior to fermentation. Mash 18 can be cooled to about 30° C. (e.g., using a heat-exchanger) and loaded to fermentation vessel 30 at about 25% to 30 wt % dry corn solids. Saccharification of the liquefied mash 18 during fermentation by the addition of glucoamylase (as saccharification enzyme 38) can result in the production of glucose. The resulting fermentation broth can contain significantly less than the amount of corn oil (e.g., about 1.2 wt % corn oil) that can be present in a fermentation broth using a liquefied mash that has not been treated with lipase 42. In particular, the lipase 42 treatment can result in the conversion of corn oil lipids 26 (triglycerides (TG)) into COFA as FFA 28 (and some diglycerides (DG) or monoglycerides (MG)), decreasing the rate of build-up of lipids 26 in any ISPR extractant 29 (e.g., oleyl alcohol), and dissolution of COFA 28 into organic phase 36 during ISPR should not decrease the partition coefficient of butanol in organic phase 36 as much as would the dissolution of lipids (TG) into the organic phase 36.

In some embodiments, the system and processes of FIG. 1 can be modified such that feedstock slurry 16 (having oil 26) and catalyst 42 are introduced and contacted in fermentation vessel 30 so as to produce slurry 18 (having FFA 28). The fermentation vessel temperature can then be raised to heat inactivate catalyst 42. The fermentation vessel temperature can then be reduced, and the fermentation vessel can be inoculated with microorganism 32, whereby the sugars of slurry 18 can be fermented to produce a product alcohol.

In some embodiments, the system and processes of FIG. 1 can be modified such that simultaneous saccharification and fermentation (SSF) in fermentation vessel 30 is replaced with a separate saccharification vessel 60 (see FIG. 2) prior to fermentation vessel 30, as should be apparent to one of skill in the art. Thus, slurry 18 can be saccharified either before fermentation or during fermentation in an SSF process. It should also be apparent that catalyst 42 for hydrolysis of feedstock oil 26 can be introduced before, after, or contemporaneously with saccharification enzyme 38. Thus, in some embodiments, addition of enzyme 38 and catalyst 42 can be stepwise (e.g., catalyst 42, then enzyme 38, or vice versa), or substantially simultaneous (i.e., at exactly the same time as in the time it takes for a person or a machine to perform the addition in one stroke, or one enzyme/catalyst immediately following the other catalyst/enzyme as in the time it takes for a person or a machine to perform the addition in two strokes).

Figure 2:
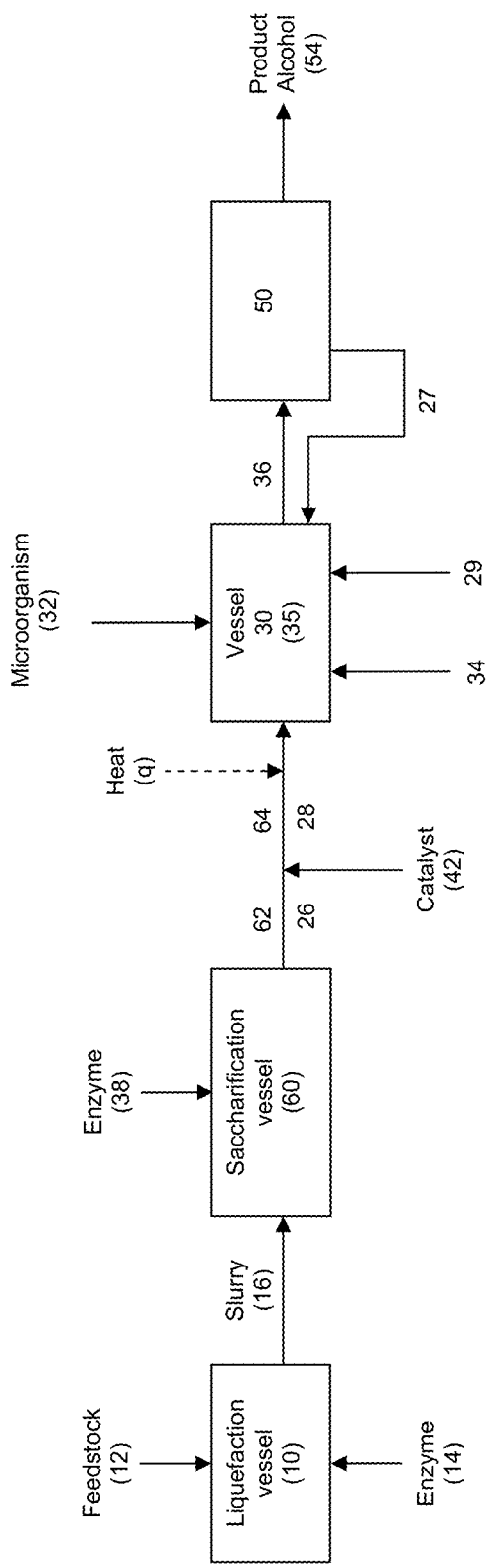

For example, as shown in the embodiment of FIG. 2, the system and processes of FIG. 1 can be modified such that simultaneous saccharification and fermentation (SSF) in fermentation vessel 30 is replaced with a separate saccharification vessel 60 prior to fermentation vessel 30. FIG. 2 is substantially identical to FIG. 1 except for the inclusion of a separate saccharification vessel 60 receiving enzyme 38, with catalyst 42 being introduced to a liquefied, saccharified feedstock stream 62. Feedstock slurry 16 is introduced into saccharification vessel 60 along with enzyme 38 such as glucoamylase, whereby sugars in the form of oligosaccharides in slurry 16 can be broken down into monosaccharides. A liquefied, saccharified feedstock stream 62 exits saccharification vessel 60 to which catalyst 42 is introduced. Feedstock stream 62 includes monosaccharides, oil 26, and undissolved solids derived from the feedstock. Oil 26 is hydrolyzed by the introduction of catalyst 42 resulting in a liquefied, saccharified feedstock slurry 64 having free fatty acids 28 and catalyst 42.

Alternatively, in some embodiments, catalyst 42 can be added with saccharification enzyme 38 to simultaneously produce glucose and hydrolyze oil lipids 26 to free fatty acids 28. The addition of enzyme 38 and catalyst 42 can be stepwise (e.g., catalyst 42, then enzyme 38, or vice versa) or simultaneous. Alternatively, in some embodiments, slurry 62 can be introduced to fermentation vessel with catalyst 42 being added directly to the fermentation vessel 30.

In the embodiment of FIG. 2, heat q is applied to feedstock slurry 64, whereby catalyst 42 becomes inactive, and heat-treated slurry 64 is then introduced to fermentation vessel 30 along with alcohol-producing microorganism 32, which metabolizes the monosaccharides to produce a product alcohol (e.g., butanol). Alternatively, slurry 64 can be fed to fermentation vessel 30 and subjected to heat q while in the fermentation vessel, before inoculation of microorganism 32.

As described above with reference to FIG. 1, free fatty acids 28 can also serve as an ISPR extractant for preferentially partitioning the product alcohol from the aqueous phase. In some embodiments, one or more additional ISPR extractants 29 can also be introduced into fermentation vessel 30. Separation of the biphasic mixture occurs in fermentation vessel 30, whereby alcohol-containing organic phase stream 36 and aqueous phase stream 34 exit directly from fermentation vessel 30. Alternatively, separation of the biphasic mixture can be conducted in a separate vessel 35 as provided in the embodiments of FIG. 1. The remaining process operations of the embodiment of FIG. 2 are identical to FIG. 1 and therefore, will not be described in detail again.

In still other embodiments of the present invention, oil 26 derived from feedstock 12 can be catalytically hydrolyzed into FFA 28 either prior to or during liquefaction. For example, in the embodiment of FIG. 3, feedstock 12 having oil 26 is fed to liquefaction vessel 10, along with catalyst 42 for hydrolysis of at least a portion of the glycerides in oil 26 into FFA 28. Enzyme 14 (e.g., alpha-amylase) for hydrolyzing the starch in feedstock 12 can also be introduced to vessel 10 to produce a liquefied feedstock. The addition of enzyme 14 and catalyst 42 can be stepwise or simultaneous. For example, catalyst 42 can be introduced, and then enzyme 14 can be introduced after at least a portion of oil 26 has been hydrolyzed. Alternatively, enzyme 14 can be introduced, and then catalyst 42 can be introduced. The liquefaction process can involve the application of heat q. In such embodiments, it is preferred that catalyst 42 is introduced prior to or during liquefaction when the process temperature is below that which inactivates catalyst 42, so that oil 26 can be hydrolyzed. Thereafter, application of heat q can provide a two-fold purpose of liquefaction and inactivation of catalyst 42.

In any case, oil 26 in feedstock 12 is converted to FFA 28 in liquefaction vessel 10, such that biphasic feedstock slurry 18 exits liquefaction vessel 10. Biphasic slurry 18 includes both an organic phase of FFA 28 as well as sugar, water, and undissolved solids of an aqueous phase. In some embodiments, the aqueous phase can include glycerol (glycerin) from converting the glycerides in the oil to fatty acids. In some embodiments, such glycerol, if present, can be removed from the stream 18 prior to introduction into fermentation vessel 30.

Figure 3:
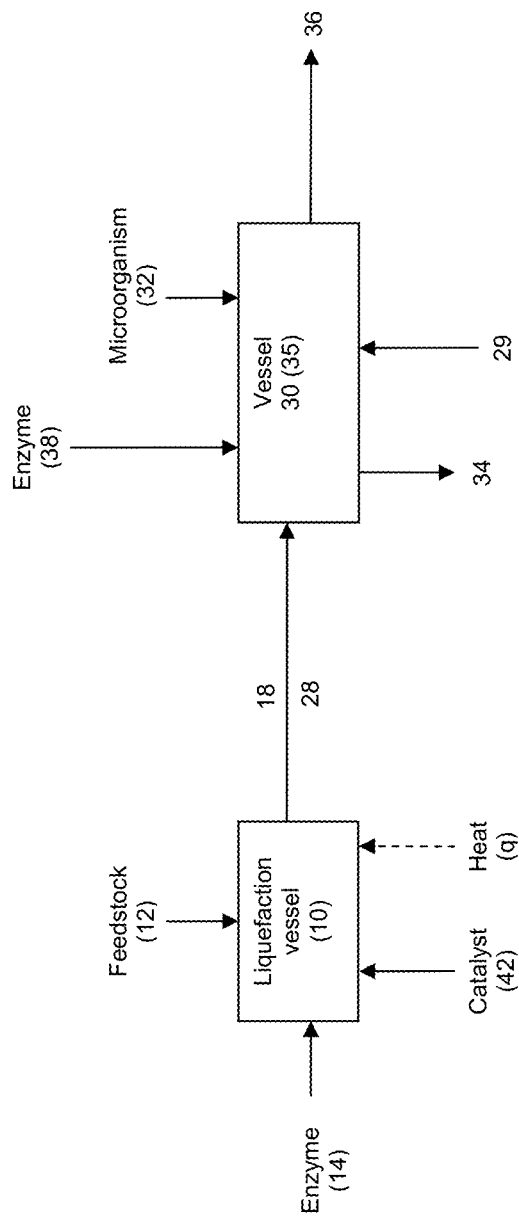

With reference to FIG. 3, biphasic stream 18 is contacted with the fermentation broth in fermentation vessel 30 to form a biphasic mixture. In fermentation vessel 30, product alcohol produced by SSF partitions into the organic phase including FFA 28. Alternatively, in some embodiments, the process can be modified to include a separate saccharification vessel as discussed in connection with FIG. 2. Separation of the biphasic mixture occurs in fermentation vessel 30, whereby alcohol-containing organic phase stream 36 and aqueous phase stream 34 exit directly from fermentation vessel 30. Alternatively, separation of the biphasic mixture can be conducted in a separate vessel 35 as provided in the embodiments of FIG. 1. Optionally, one or more additional extractants 29 can be introduced into fermentation vessel 30 to form an organic phase that preferentially partitions the product alcohol from the aqueous phase. Alcohol-containing organic phase 36 can be introduced to separator 50 for recovery of product alcohol 54 and optional recycle of recovered extractant 27 as shown in FIG. 1. The remaining process operations of the embodiment of FIG. 3 can be identical to the previously described figures and therefore, will not be described in detail again.

Figure 4:
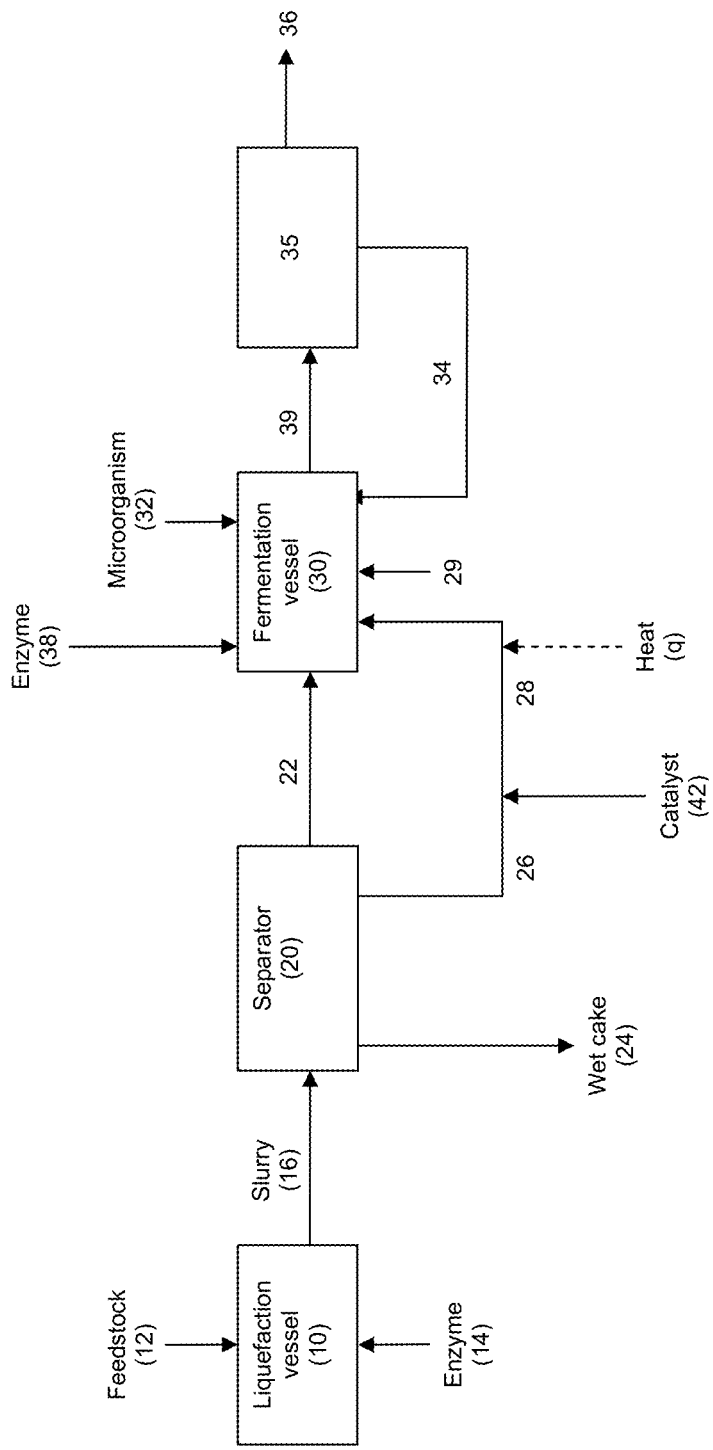

In some embodiments, including any of the earlier described embodiments with respect to FIGS. 1-3, undissolved solids can be removed from the feedstock slurry prior to introduction into fermentation vessel 30. For example, as shown in the embodiment of FIG. 4, feedstock slurry 16 is introduced into an inlet of a separator 20 which is configured to discharge the undissolved solids as a solid phase or wet cake 24. For example, in some embodiments, separator 20 may include a filter press, vacuum filtration, or a centrifuge for separating the undissolved solids from feedstock slurry 16. Optionally, in some embodiments, separator 20 can also be configured to remove some, or substantially all, of oil 26 present in feedstock slurry 16. In such embodiments, separator 20 can be any suitable separator known in the art for removing oil from an aqueous feedstream including, but not limited to, siphoning, decantation, aspiration, centrifugation, using a gravity settler, membrane-assisted phase splitting, and the like. The remaining feedstock including the sugar and water is discharged as an aqueous stream 22 to fermentation vessel 30.

In some embodiments, separator 20 removes oil 26 but not undissolved solids. Thus, aqueous stream 22 fed to fermentation vessel 30 includes undissolved solids. For example, in some embodiments, separator 20 includes a tricanter centrifuge 20 that agitates or spins feedstock slurry 16 to produces a centrifuge product comprising an aqueous layer containing the sugar and water (i.e., stream 22), a solids layer containing the undissolved solids (i.e., wet cake 24), and an oil layer (i.e., oil stream 26). In such a case, catalyst 42 can be contacted with the removed oil 26 to produce a stream of FFA 28 including catalyst 42, as shown in FIG. 4. Heat q can then be applied to the stream of FFA 28, whereby catalyst 42 becomes inactive. The stream of FFA 28 and inactive catalyst 42 can then be introduced into fermentation vessel 30, along with stream 22 and microorganism 32. Alternatively, FFA 28 and active catalyst 42 can be fed to fermentation vessel 30 from vessel 40, and active catalyst 42 can thereafter be subjected to heat q and inactivated while in the fermentation vessel, before inoculation of microorganism 32.

FFA 28 can serve as ISPR extractant 28 and forms a biphasic mixture in fermentation vessel 30. Product alcohol produced by SSF partitions into organic phase 36 constituted by FFA 28. In some embodiments, one or more additional ISPR extractants 29 can also be introduced into fermentation vessel 30. Thus, oil 26 (e.g., from feedstock) can be catalytically hydrolyzed to FFA 28, thereby decreasing the rate of build-up of lipids in an ISPR extractant while also producing an ISPR extractant. The organic phase 36 can be separated from the aqueous phase 34 of the biphasic mixture 39 at vessel 35. In some embodiments, separation of the biphasic mixture 39 can occur in the fermentation vessel, as shown in the embodiments described in FIGS. 2 and 3 in which the alcohol-containing organic phase stream 36 exits directly from fermentation vessel 30. Organic phase 36 can be introduced to separator 50 for recovery of product alcohol 54 and optional recycle of recovered extractant 27 as shown in FIG. 1. The remaining process operations of the embodiment of FIG. 4 are identical to FIG. 1 and therefore, will not be described in detail again.

When wet cake 24 is removed via centrifuge 20, in some embodiments, a portion of the oil from feedstock 12, such as corn oil when the feedstock is corn, remains in wet cake 24. Wet cake 24 can be washed with additional water in the centrifuge once aqueous solution 22 has been discharged from the centrifuge 20. Washing wet cake 24 will recover the sugar (e.g., oligosaccharides) present in the wet cake and the recovered sugar and water can be recycled to the liquefaction vessel 10. After washing, wet cake 20 can be dried to form Dried Distillers' Grains with Solubles (DDGS) through any suitable known process. The formation of the DDGS from wet cake 24 formed in centrifuge 20 has several benefits. Since the undissolved solids do not go to the fermentation vessel, DDGS does not have trapped extractant and/or product alcohol such as butanol, it is not subjected to the conditions of the fermentation vessel, and it does not contact the microorganisms present in the fermentation vessel. All these benefits make it easier to process and sell DDGS, for example, as animal feed. In some embodiments, oil 26 is not discharged separately from wet cake 24, but rather oil 26 is included as part of wet cake 24 and is ultimately present in the DDGS. In such instances, the oil can be separated from the DDGS and converted to an ISPR extractant 29 for subsequent use in the same or different alcohol fermentation process. Methods and systems for removing undissolved solids from feedstock 16 via centrifugation are described in detail in co-pending, commonly owned U.S. Patent Application No. 61/356,290, filed Jun. 18, 2010, which is incorporated herein in its entirety by reference thereto.

In still other embodiments (not shown), saccharification can occur in a separate saccharification vessel 60 (see FIG. 2) which is located between separator 20 and liquefaction vessel 10, as should be apparent to one of skill in the art.

Figure 5:
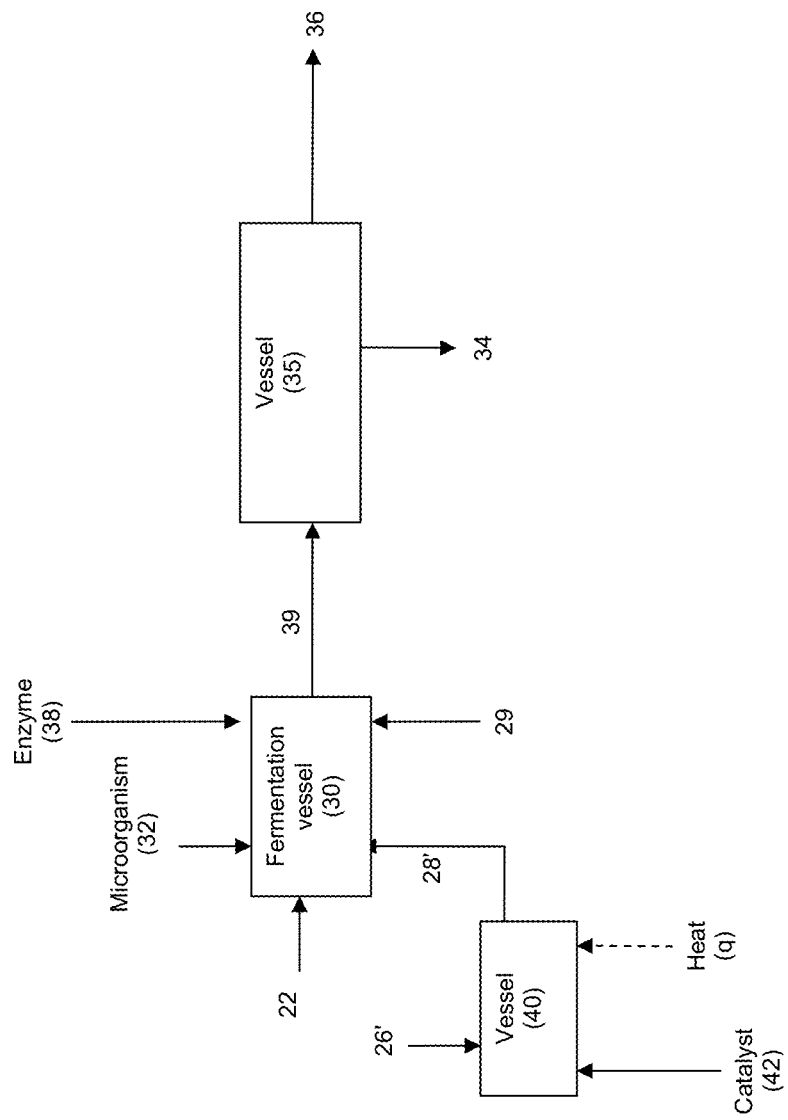

In still other embodiments, as shown, for example, in the embodiment of FIG. 5, a native oil 26' is supplied to a vessel 40 to which catalyst 42 is also supplied, whereby at least a portion of glycerides in oil 26' are hydrolyzed to form FFA 28'. Catalyst 42 can be subsequently inactivated, such as by the application of heat q. A product stream from vessel 40 containing FFA 28' and inactive catalyst 42 are then introduced into fermentation vessel 30, along with aqueous feedstock stream 22 in which feedstock oil 26, and in some embodiments, the undissolved solids have been previously removed by means of separator 20 (see, e.g., the embodiment of FIG. 4). Saccharification enzyme 38 and microorganism 32 are also introduced into fermentation vessel 30, whereby a product alcohol is produced by SSF.

Alternatively, oil 26' and catalyst 42 can be fed directly to fermentation vessel 30 in which oil 26' is hydrolyzed to FFA 28' rather than using vessel 40. Thereafter, active catalyst 42 can be subjected to heat q and inactivated while in the fermentation vessel before inoculation of microorganism 32. Alternatively, FFA 28' and active catalyst 42 can be fed to fermentation vessel 30 from vessel 40, and active catalyst 42 can thereafter be subjected to heat q and inactivated while in the fermentation vessel before inoculation of microorganism 32. In such embodiments, feedstock slurry 16 including oil 26, rather than stream 22 in which oil 26 was removed, can be fed to fermentation vessel 30 and contacted with active catalyst 42. Active catalyst 42 can therefore be used to hydrolyze oil 26 into FFA 28, thereby reducing the loss and/or degradation of the partition coefficient of the extractant over time that is attributable to the presence of the oil in the fermentation vessel.

In some embodiments, the system and processes of FIG. 5 can be modified such that simultaneous saccharification and fermentation in fermentation vessel 30 is replaced with a separate saccharification vessel 60 prior to fermentation vessel 30, as should be apparent to one of skill in the art (see, e.g., the embodiment of FIG. 2).

In some embodiments, native oil 26' can be tallow, corn, canola, capric/caprylic triglycerides, castor, coconut, cottonseed, fish, jojoba, lard, linseed, neetsfoot, oiticica, palm, peanut, rapeseed, rice, safflower, soya, sunflower, tung, jatropha, vegetable oil blends, and mixtures thereof. In some embodiments, native oil 26' is a mixture of two or more native oils, for example, a mixture of palm and soybean oils. In some embodiments, native oil 26' is a plant-derived oil. In some embodiments, the plant-derived oil can be, though not necessarily, derived from biomass that can be used in a fermentation process. The biomass can be the same or different source from which feedstock 12 (shown in FIG. 5 as stream 22) is obtained. Thus, for example, in some embodiments, oil 26' can be derived from corn, whereas feedstock 12 can be cane. For example, in some embodiments, oil 26' can be derived from corn, and the biomass source of feedstock 12 is also corn. Any possible combination of different biomass sources for oil 26' versus feedstock 12 can be used, as should be apparent to one of skill in the art.

FFA 28' can serve as an ISPR extractant 28' to form a two-phase mixture including an aqueous phase and an organic phase, with the product alcohol produced in the fermentation medium preferentially partitioning into the organic phase constituted by ISPR extractant 28'. In some embodiments, one or more additional ISPR extractants 29 can be introduced into fermentation vessel 30 as described above with reference to FIG. 1. The organic phase 36 can be separated from the aqueous phase 34 of the biphasic mixture 39 at vessel 35. In some embodiments, separation of the biphasic mixture 39 can occur in the fermentation vessel, as shown in the embodiments described in FIGS. 2 and 3 in which the alcohol-containing organic phase stream 36 exits directly from fermentation vessel 30. Organic phase 36 can be introduced in separator 50 for recovery of product alcohol 54 and optional recycle of recovered extractant 27 as shown in FIG. 1. The remaining process operations of the embodiment of FIG. 5 are identical to FIG. 1 and therefore, will not be described in detail again.

Figure 6:
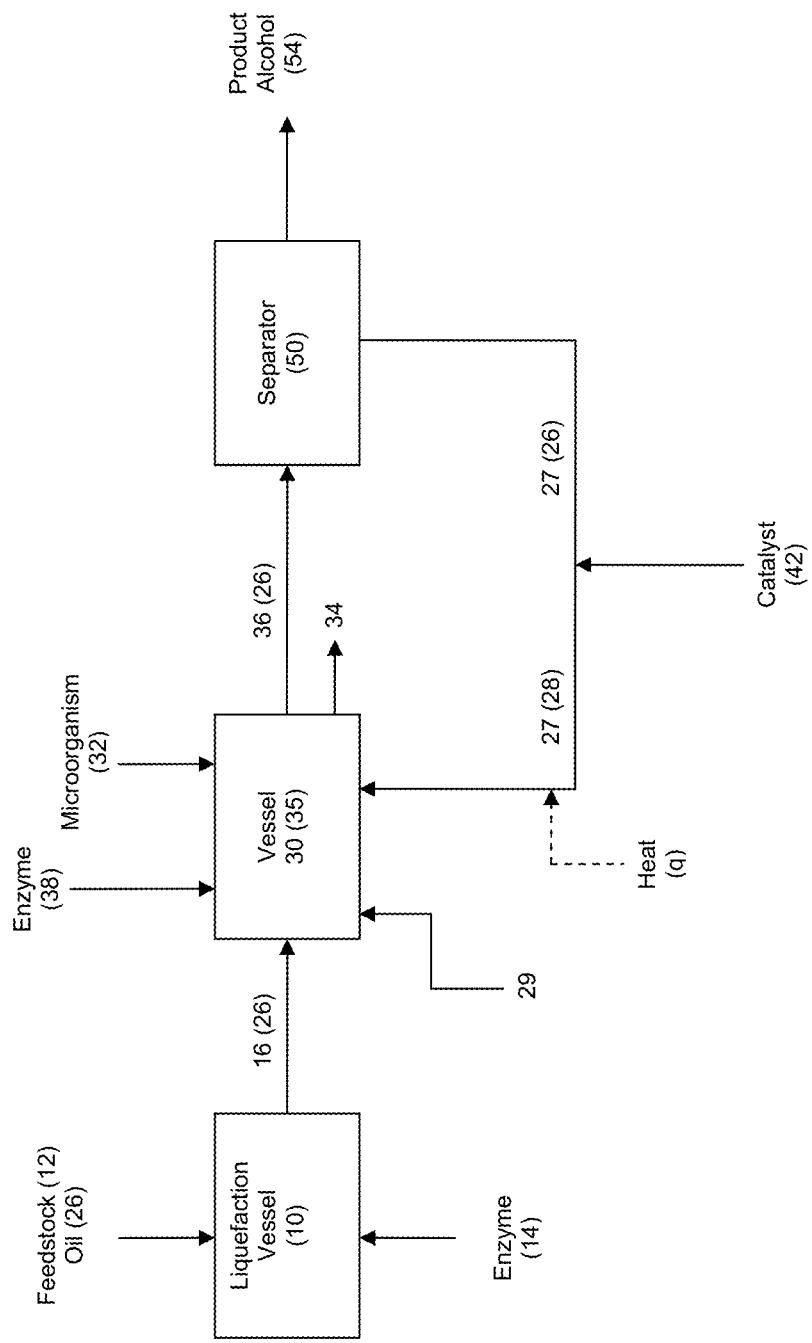

In some embodiments of the present invention, biomass oil present in feedstock 12 can be converted to FFA 28 at a step following alcoholic fermentation. FFA 28 can then be introduced as ISPR extractant 28 in the fermentation vessel. For example, in the embodiment of FIG. 6, feedstock 12 is liquefied to produced feedstock slurry 16 which includes oil 26 derived from the feedstock. Feedstock slurry 16 can also include undissolved solids from the feedstock. Alternatively, the undissolved solids can be separated from slurry 16 via a separator, such as a centrifuge (not shown). Feedstock slurry 16 containing oil 26 is introduced directly to fermentation vessel 30 containing a fermentation broth including saccharification enzyme 38 and microorganism 32. A product alcohol is produced by SSF in fermentation vessel 30. Alternatively, in some embodiments, the process can be modified to include a separate saccharification vessel as discussed in connection with FIG. 2.

ISPR extractant 29 is introduced to fermentation vessel 30 to form a biphasic mixture, and the product alcohol is removed by partitioning into the organic phase of the ISPR extractant 29. Oil 26 also partitions into the organic phase. Separation of the biphasic mixture occurs in fermentation vessel 30, whereby alcohol-containing organic phase stream 36 and aqueous phase stream 34 exit directly from fermentation vessel 30. Alternatively, separation of the biphasic mixture can be conducted in a separate vessel 35 as provided in the embodiments of FIG. 1. Organic phase stream 36 including oil 26 is introduced into separator 50 to recover product alcohol 54 from extractant 29. The resulting alcohol-lean extractant 27 includes recovered extractant 29 and oil 26. Extractant 27 is contacted with catalyst 42, whereby at least a portion of glycerides in oil 26 are hydrolyzed to form FFA 28.

Heat q can then be applied to extractant 27 including FFA 28 so as to inactivate catalyst 42 before being recycled back into fermentation vessel 30. Such recycled extractant stream 27 can be a separate stream or a combined stream with fresh, make-up extractant stream 29. The subsequent withdrawal of alcohol-containing organic phase 36 from fermentation vessel 30 can then include FFA 28 and ISPR extractant 29 (as fresh extractant 29 and recycled extractant 27), in addition to the product alcohol and additional oil 26 from newly introduced feedstock slurry 16. Organic phase 36 can then be treated to recover the product alcohol, and recycled back into fermentation vessel 30 after contacting with catalyst 42 for hydrolysis of additional oil 26, in the same manner as just described. In some embodiments, use of make-up ISPR extractant 29 can be phased out as the fermentation process is operated over time because the process itself can produce FFA 28 as a make-up ISPR extractant for extracting the product alcohol. Thus, the ISPR extractant can be the stream of recycled extractant 27 with FFA 28.

Thus, FIGS. 1-5 provide various non-limiting embodiments of methods and systems involving fermentation processes and FFAs 28 produced from catalytic hydrolysis of biomass derived oil 26, and FFAs 28' produced from catalytic hydrolysis of native oil 26' such as plant-derived oil that can be used as ISPR extractants 28 and 28' to remove product alcohol in extractive fermentation.

In some embodiments, including any of the aforementioned embodiments described with reference to FIGS. 1-6, the fermentation broth in fermentation vessel 30 includes at least one recombinant microorganism 32 which is genetically modified (that is, genetically engineered) to produce butanol via a biosynthetic pathway from at least one fermentable carbon source. In particular, recombinant microorganisms can be grown in a fermentation broth which contains suitable carbon substrates. Additional carbon substrates may include, but are not limited to, monosaccharides such as fructose; oligosaccharides such as lactose, maltose, or sucrose; polysaccharides such as starch or cellulose; or mixtures thereof, and unpurified mixtures from renewable feedstocks such as cheese whey permeate, cornsteep liquor, sugar beet molasses, and barley malt. Other carbon substrates may include ethanol, lactate, succinate, or glycerol.

Additionally the carbon substrate may also be one-carbon substrates such as carbon dioxide or methanol for which metabolic conversion into key biochemical intermediates has been demonstrated. In addition to one and two carbon substrates, methylotrophic organisms are also known to utilize a number of other carbon containing compounds such as methylamine, glucosamine, and a variety of amino acids for metabolic activity. For example, methylotrophic yeasts are known to utilize the carbon from methylamine to form trehalose or glycerol (Bellion, et al., *Microb. Growth C1 Compd., [Int. Symp.]*, 7th (1993), 415-32, Editor(s): Murrell, J. Collin; Kelly, Don P. Publisher: Intercept, Andover, UK). Similarly, various species of *Candida* will metabolize alanine or oleic acid (Sulter, et al., Arch. Microbiol. 153:485-489, 1990). Hence it is contemplated that the source of carbon utilized in the present invention may encompass a wide variety of carbon containing substrates and will only be limited by the choice of organism.

Although it is contemplated that all of the above mentioned carbon substrates and mixtures thereof are suitable, in some embodiments, the carbon substrates are glucose, fructose, and sucrose, or mixtures of these with C5 sugars such as xylose and/or arabinose for yeasts cells modified to use C5 sugars. Sucrose may be derived from renewable sugar sources such as sugar cane, sugar beets, cassava, sweet sorghum, and mixtures thereof. Glucose and dextrose may be derived from renewable grain sources through saccharification of starch based feedstocks including grains such as corn, wheat, rye, barley, oats, and mixtures thereof. In addition, fermentable sugars may be derived from renewable cellulosic or lignocellulosic biomass through processes of pretreatment and saccharification, as described in, for example, in U.S. Patent Application Publication No. 2007/0031918 A1, which is herein incorporated by reference. In addition to an appropriate carbon source (from aqueous stream 22), fermentation broth must contain suitable minerals, salts, cofactors, buffers and other components, known to those skilled in the art, suitable for the growth of the cultures and promotion of an enzymatic pathway comprising a dihydroxyacid dehydratase (DHAD).

Recombinant microorganisms that produce butanol via a biosynthetic pathway can include a member of the genera *Clostridium, Zymomonas, Escherichia, Salmonella, Serratia, Erwinia, Klebsiella, Shigella, Rhodococcus, Pseudomonas, Bacillus, Lactobacillus, Enterococcus, Alcaligenes, Klebsiella, Paenibacillus, Arthrobacter, Corynebacterium, Brevibacterium, Schizosaccharomyces, Kluyveromyces, Yarrowia, Pichia, Candida, Hansenula*, or *Saccharomyces*. In one embodiment, recombinant microorganisms can be selected from the group consisting of *Escherichia coli, Lactobacillus plantarum*, and *Saccharomyces cerevisiae*. In one embodiment, the recombinant microorganism is a crabtree-positive yeast selected from *Saccharomyces, Zygosaccharomyces, Schizosaccharomyces, Dekkera, Torulopsis, Brettanomyces*, and some species of *Candida*. Species of crabtree-positive yeast include, but are not limited to, *Saccharomyces cerevisiae, Saccharomyces kluyveri, Schizosaccharomyces pombe, Saccharomyces bayanus, Saccharomyces mikitae, Saccharomyces paradoxus, Zygosaccharomyces rouxii*, and *Candida glabrata*. For example, the production of butanol utilizing fermentation with a microorganism, as well as which microorganisms produce butanol, is known and is disclosed, for example, in U.S. Patent Application Publication No. 2009/0305370, herein incorporated by reference. In some embodiments, microorganisms comprise a butanol biosynthetic pathway. Suitable isobutanol biosynthetic pathways are known in the art (see, e.g., U.S. Patent Application Publication No. 2007/0092957, herein incorporated by reference). In some embodiments, at least one, at least two, at least three, or at least four polypeptides catalyzing substrate to product conversions of a pathway are encoded by heterologous polynucleotides in the microorganism. In some embodiments, all polypeptides catalyzing substrate to product conversions of a pathway are encoded by heterologous polynucleotides in the microorganism. In some embodiments, the microorganism comprises a reduction or elimination of pyruvate decarboxylase activity. Microorganisms substantially free of pyruvate decarboxylase activity are described in U.S. Patent Application Publication No. 2009/0305363, herein incorporated by reference.

Construction of certain strains, including those used in the Examples, is provided herein.

Construction of *Saccharomyces cerevisiae* Strain BP1083 ("NGCI-070")

The strain BP1064 was derived from CEN.PK 113-7D (CBS 8340; Centraalbureau voor Schimmelcultures (CBS) Fungal Biodiversity Centre, Netherlands) and contains deletions of the following genes: URA3, HIS3, PDC1, PDC5, PDC6, and GPD2. BP1064 was transformed with plasmids pYZ090 (SEQ ID NO: 1, described in U.S. Provisional Application Ser. No. 61/246,844) and pLH468 (SEQ ID NO: 2) to create strain NGCI-070 (BP1083, PNY1504).

Deletions, which completely removed the entire coding sequence, were created by homologous recombination with PCR fragments containing regions of homology upstream and downstream of the target gene and either a G418 resistance marker or URA3 gene for selection of transformants. The G418 resistance marker, flanked by loxP sites, was removed using Cre recombinase. The URA3 gene was removed by homologous recombination to create a scarless deletion or if flanked by loxP sites, was removed using Cre recombinase.

The scarless deletion procedure was adapted from Akada, et al., (Yeast 23:399-405, 2006). In general, the PCR cassette for each scarless deletion was made by combining four fragments, A-B-U-C, by overlapping PCR. The PCR cassette contained a selectable/counter-selectable marker, URA3 (Fragment U), consisting of the native CEN.PK 113-7D URA3 gene, along with the promoter (250 bp upstream of the URA3 gene) and terminator (150 bp downstream of the URA3 gene). Fragments A and C, each 500 bp long, corresponded to the 500 bp immediately upstream of the target gene (Fragment A) and the 3' 500 bp of the target gene (Fragment C). Fragments A and C were used for integration of the cassette into the chromosome by homologous recombination. Fragment B (500 by long) corresponded to the 500 bp immediately downstream of the target gene and was used for excision of the URA3 marker and Fragment C from the chromosome by homologous recombination, as a direct repeat of the sequence corresponding to Fragment B was created upon integration of the cassette into the chromosome. Using the PCR product ABUC cassette, the URA3 marker was first integrated into and then excised from the chromosome by homologous recombination. The initial integration deleted the gene, excluding the 3' 500 bp. Upon excision, the 3' 500 bp region of the gene was also deleted. For integration of genes using this method, the gene to be integrated was included in the PCR cassette between fragments A and B.

URA3 Deletion

To delete the endogenous URA3 coding region, a ura3::loxP-kanMX-loxP cassette was PCR-amplified from pLA54 template DNA (SEQ ID NO: 3). pLA54 contains the *K. lactis* TEF1 promoter and kanMX marker, and is flanked by loxP sites to allow recombination with Cre recombinase and removal of the marker. PCR was done using Phusion® DNA polymerase (New England BioLabs Inc., Ipswich, Mass.) and primers BK505 and BK506 (SEQ ID NOs: 4 and 5). The URA3 portion of each primer was derived from the 5' region upstream of the URA3 promoter and 3' region downstream of the coding region such that integration of the loxP-kanMX-loxP marker resulted in replacement of the URA3 coding region. The PCR product was transformed into CEN.PK 113-7D using standard genetic techniques (Methods in Yeast Genetics, 2005, Cold Spring Harbor Laboratory Press, Cold Spring Harbor, N.Y., pp. 201-202) and transformants were selected on YPD containing G418 (100 µg/mL) at 30° C. Transformants were screened to verify correct integration by PCR using primers LA468 and LA492 (SEQ ID NOs: 6 and 7) and designated CEN.PK 113-7D Δura3::kanMX.

HIS3 Deletion

The four fragments for the PCR cassette for the scarless HIS3 deletion were amplified using Phusion® High Fidelity PCR Master Mix (New England BioLabs Inc., Ipswich, Mass.) and CEN.PK 113-7D genomic DNA as template, prepared with a Gentra® Puregene® Yeast/Bact, kit (Qiagen, Valencia, Calif.). HIS3 Fragment A was amplified with primer oBP452 (SEQ ID NO: 14) and primer oBP453 (SEQ ID NO: 15) containing a 5' tail with homology to the 5' end of HIS3 Fragment B. HIS3 Fragment B was amplified with primer oBP454 (SEQ ID NO: 16) containing a 5' tail with homology to the 3' end of HIS3 Fragment A, and primer oBP455 (SEQ ID NO: 17) containing a 5' tail with homology to the 5' end of HIS3 Fragment U. HIS3 Fragment U was amplified with primer oBP456 (SEQ ID NO: 18) containing a 5' tail with homology to the 3' end of HIS3 Fragment B, and primer oBP457 (SEQ ID NO: 19) containing a 5' tail with homology to the 5' end of HIS3 Fragment C. HIS3 Fragment C was amplified with primer oBP458 (SEQ ID NO: 20) containing a 5' tail with homology to the 3' end of HIS3 Fragment U, and primer oBP459 (SEQ ID NO: 21). PCR products were purified with a PCR Purification kit (Qiagen, Valencia, Calif.). HIS3 Fragment AB was created by overlapping PCR by mixing HIS3 Fragment A and HIS3 Fragment B and amplifying with primers oBP452 (SEQ ID NO: 14) and oBP455 (SEQ ID NO: 17). HIS3 Fragment UC was created by overlapping PCR by mixing HIS3 Fragment U and HIS3 Fragment C and amplifying with primers oBP456 (SEQ ID NO: 18) and oBP459 (SEQ ID NO: 21). The resulting PCR products were purified on an agarose gel followed by a Gel Extraction kit (Qiagen, Valencia, Calif.). The HIS3 ABUC cassette was created by overlapping PCR by mixing HIS3 Fragment AB and HIS3 Fragment UC and amplifying with primers oBP452 (SEQ ID NO: 14) and oBP459 (SEQ ID NO: 21). The PCR product was purified with a PCR Purification kit (Qiagen, Valencia, Calif.).

Competent cells of CEN.PK 113-7D Δura3::kanMX were made and transformed with the HIS3 ABUC PCR cassette using a Frozen-EZ Yeast Transformation II™ kit (Zymo Research Corporation, Irvine, Calif.). Transformation mixtures were plated on synthetic complete media lacking uracil supplemented with 2% glucose at 30° C. Transformants with a his3 knockout were screened for by PCR with primers oBP460 (SEQ ID NO: 22) and oBP461 (SEQ ID NO: 23) using genomic DNA prepared with a Gentra® Puregene® Yeast/Bact. kit (Qiagen, Valencia, Calif.). A correct transformant was selected as strain CEN.PK 113-7D Δura3::kanMX Δhis3::URA3.

KanMX Marker Removal from the Δura3 Site and URA3 Marker Removal from the Δhis3 Site The KanMX marker was removed by transforming CEN.PK 113-7D Δura3::kanMX Δhis3::URA3 with pRS423::PGAL1-cre (SEQ ID NO: 66, described in U.S. Provisional Application No. 61/290,639) using a Frozen-EZ Yeast Transformation II™ kit (Zymo Research Corporation, Irvine, Calif.) and plating on synthetic complete medium lacking histidine and uracil supplemented with 2% glucose at 30° C. Transformants were grown in YP supplemented with 1% galactose at 30° C. for ~6 hours to induce the Cre recombinase and KanMX marker excision and plated onto YPD (2% glucose) plates at 30° C. for recovery. An isolate was grown overnight in YPD and plated on synthetic complete medium containing 5-fluoro-orotic acid (5-FOA, 0.1%) at 30° C. to select for isolates that lost the URA3 marker. 5-FOA resistant isolates were grown in and plated on YPD for removal of the pRS423::PGAL1-cre plasmid. Isolates were checked for loss of the KanMX marker, URA3 marker, and pRS423::PGAL1-cre plasmid by assaying growth on YPD+ G418 plates, synthetic complete medium lacking uracil plates, and synthetic complete medium lacking histidine plates. A correct isolate that was sensitive to G418 and auxotrophic for uracil and histidine was selected as strain CEN.PK 113-7D Δura3::loxP Δhis3 and designated as BP857. The deletions and marker removal were confirmed by PCR and sequencing with primers oBP450 (SEQ ID NO: 24) and oBP451 (SEQ ID NO: 25) for Δura3 and primers oBP460 (SEQ ID NO: 22) and oBP461 (SEQ ID NO: 23) for Δhis3 using genomic DNA prepared with a Gentra® Puregene® Yeast/Bact. kit (Qiagen, Valencia, Calif.).

PDC6 Deletion

The four fragments for the PCR cassette for the scarless PDC6 deletion were amplified using Phusion® High Fidelity PCR Master Mix (New England BioLabs Inc., Ipswich, Mass.) and CEN.PK 113-7D genomic DNA as template, prepared with a Gentra® Puregene® Yeast/Bact. kit (Qiagen, Valencia, Calif.). PDC6 Fragment A was amplified with primer oBP440 (SEQ ID NO: 26) and primer oBP441 (SEQ ID NO: 27) containing a 5' tail with homology to the 5' end of PDC6 Fragment B. PDC6 Fragment B was amplified with primer oBP442 (SEQ ID NO: 28), containing a 5' tail with homology to the 3' end of PDC6 Fragment A, and primer oBP443 (SEQ ID NO: 29) containing a 5' tail with homology to the 5' end of PDC6 Fragment U. PDC6 Fragment U was amplified with primer oBP444 (SEQ ID NO: 30) containing a 5' tail with homology to the 3' end of PDC6 Fragment B, and primer oBP445 (SEQ ID NO: 31) containing a 5' tail with homology to the 5' end of PDC6 Fragment C. PDC6 Fragment C was amplified with primer oBP446 (SEQ ID NO: 32) containing a 5' tail with homology to the 3' end of PDC6 Fragment U, and primer oBP447 (SEQ ID NO: 33). PCR products were purified with a PCR Purification kit (Qiagen, Valencia, Calif.). PDC6 Fragment AB was created by overlapping PCR by mixing PDC6 Fragment A and PDC6 Fragment B and amplifying with primers oBP440 (SEQ ID NO: 26) and oBP443 (SEQ ID NO: 29). PDC6 Fragment UC was created by overlapping PCR by mixing PDC6 Fragment U and PDC6 Fragment C and amplifying with primers oBP444 (SEQ ID NO: 30) and oBP447 (SEQ ID NO: 33). The resulting PCR products were purified on an agarose gel followed by a Gel Extraction kit (Qiagen, Valencia, Calif.). The PDC6 ABUC cassette was created by overlapping PCR by mixing PDC6 Fragment AB and PDC6 Fragment UC and amplifying with primers oBP440 (SEQ ID NO: 26) and oBP447 (SEQ ID NO: 33). The PCR product was purified with a PCR Purification kit (Qiagen, Valencia, Calif.).

Competent cells of CEN.PK 113-7D Δura3::loxP Δhis3 were made and transformed with the PDC6 ABUC PCR cassette using a Frozen-EZ Yeast Transformation II™ kit (Zymo Research Corporation, Irvine, Calif.). Transformation mixtures were plated on synthetic complete media lacking uracil supplemented with 2% glucose at 30° C. Transformants with a pdc6 knockout were screened for by PCR with primers oBP448 (SEQ ID NO: 34) and oBP449 (SEQ ID NO: 35) using genomic DNA prepared with a Gentra® Puregene® Yeast/Bact. kit (Qiagen, Valencia, Calif.). A correct transformant was selected as strain CEN.PK 113-7D Δura3::loxP Δhis3 Δpdc6::URA3.

CEN.PK 113-7D Δura3::loxP Δhis3 Δpdc6::URA3 was grown overnight in YPD and plated on synthetic complete medium containing 5-fluoro-orotic acid (0.1%) at 30° C. to select for isolates that lost the URA3 marker. The deletion and marker removal were confirmed by PCR and sequencing with primers oBP448 (SEQ ID NO: 34) and oBP449 (SEQ ID NO: 35) using genomic DNA prepared with a Gentra® Puregene® Yeast/Bact. kit (Qiagen, Valencia, Calif.). The absence of the PDC6 gene from the isolate was demonstrated by a negative PCR result using primers specific for the coding sequence of PDC6, oBP554 (SEQ ID NO: 36) and oBP555 (SEQ ID NO: 37). The correct isolate was selected as strain CEN.PK 113-7D Δura3::loxP Δhis3 Δpdc6 and designated as BP891.

PDC1 Deletion ilvDSm Integration

The PDC1 gene was deleted and replaced with the ilvD coding region from *Streptococcus mutans* ATCC No. 700610. The A fragment followed by the ilvD coding region from

*Streptococcus mutans* for the PCR cassette for the PDC1 deletion-ilvDSm integration was amplified using Phusion® High Fidelity PCR Master Mix (New England BioLabs Inc., Ipswich, Mass.) and NYLA83 (described herein and in U.S. Provisional Application No. 61/246,709) genomic DNA as template, prepared with a Gentra® Puregene® Yeast/Bact. kit (Qiagen, Valencia, Calif.). PDC1 Fragment A-ilvDSm (SEQ ID NO: 141) was amplified with primer oBP513 (SEQ ID NO: 38) and primer oBP515 (SEQ ID NO: 39) containing a 5' tail with homology to the 5' end of PDC1 Fragment B. The B, U, and C fragments for the PCR cassette for the PDC1 deletion-ilvDSm integration were amplified using Phusion® High Fidelity PCR Master Mix (New England BioLabs Inc., Ipswich, Mass.) and CEN.PK 113-7D genomic DNA as template, prepared with a Gentra® Puregene® Yeast/Bact. kit (Qiagen, Valencia, Calif.). PDC1 Fragment B was amplified with primer oBP516 (SEQ ID NO: 40) containing a 5' tail with homology to the 3' end of PDC1 Fragment A-ilvDSm, and primer oBP517 (SEQ ID NO: 41) containing a 5' tail with homology to the 5' end of PDC1 Fragment U. PDC1 Fragment U was amplified with primer oBP518 (SEQ ID NO: 42) containing a 5' tail with homology to the 3' end of PDC1 Fragment B, and primer oBP519 (SEQ ID NO: 43) containing a 5' tail with homology to the 5' end of PDC1 Fragment C. PDC1 Fragment C was amplified with primer oBP520 (SEQ ID NO: 44), containing a 5' tail with homology to the 3' end of PDC1 Fragment U, and primer oBP521 (SEQ ID NO: 45). PCR products were purified with a PCR Purification kit (Qiagen, Valencia, Calif. PDC1 Fragment A-ilvDSm-B was created by overlapping PCR by mixing PDC1 Fragment A-ilvDSm and PDC1 Fragment B and amplifying with primers oBP513 (SEQ ID NO: 38) and oBP517 (SEQ ID NO: 41). PDC1 Fragment UC was created by overlapping PCR by mixing PDC1 Fragment U and PDC1 Fragment C and amplifying with primers oBP518 (SEQ ID NO: 42) and oBP521 (SEQ ID NO: 45). The resulting PCR products were purified on an agarose gel followed by a Gel Extraction kit (Qiagen, Valencia, Calif.). The PDC1 A-ilvDSm-BUC cassette (SEQ ID NO: 142) was created by overlapping PCR by mixing PDC1 Fragment A-ilvDSm-B and PDC1 Fragment UC and amplifying with primers oBP513 (SEQ ID NO: 38) and oBP521 (SEQ ID NO: 45). The PCR product was purified with a PCR Purification kit (Qiagen, Valencia, Calif.).

Competent cells of CEN.PK 113-7D Δura3::loxP Δhis3 Δpdc6 were made and transformed with the PDC1 A-ilvDSm-BUC PCR cassette using a Frozen-EZ Yeast Transformation II™ kit (Zymo Research Corporation, Irvine, Calif.). Transformation mixtures were plated on synthetic complete media lacking uracil supplemented with 2% glucose at 30° C. Transformants with a pdc1 knockout ilvDSm integration were screened for by PCR with primers oBP511 (SEQ ID NO: 46) and oBP512 (SEQ ID NO: 47) using genomic DNA prepared with a Gentra® Puregene® Yeast/Bact. kit (Qiagen, Valencia, Calif.). The absence of the PDC1 gene from the isolate was demonstrated by a negative PCR result using primers specific for the coding sequence of PDC1, oBP550 (SEQ ID NO: 48) and oBP551 (SEQ ID NO: 49). A correct transformant was selected as strain CEN.PK 113-7D Δura3::loxP Δhis3 Δpdc6 Δpdc1::ilvDSm-URA3.

CEN.PK 113-7D Δura3::loxP Δhis3 Δpdc6 Δpdc1::ilvDSm-URA3 was grown overnight in YPD and plated on synthetic complete medium containing 5-fluoro-orotic acid (0.1%) at 30° C. to select for isolates that lost the URA3 marker. The deletion of PDC1, integration of ilvDSm, and marker removal were confirmed by PCR and sequencing with primers oBP511 (SEQ ID NO: 46) and oBP512 (SEQ ID NO: 47) using genomic DNA prepared with a Gentra® Puregene® Yeast/Bact. kit (Qiagen, Valencia, Calif.). The correct isolate was selected as strain CEN.PK 113-7D Δura3::loxP Δhis3 Δpdc6 Δpdc1::ilvDSm and designated as BP907.

PDC5 Deletion sadB Integration

The PDC5 gene was deleted and replaced with the sadB coding region from *Achromobacter xylosoxidans*. A segment of the PCR cassette for the PDC5 deletion-sadB integration was first cloned into plasmid pUC19-URA3MCS.

pUC19-URA3MCS is pUC19 based and contains the sequence of the URA3 gene from *Saccaromyces cerevisiae* situated within a multiple cloning site (MCS). pUC19 contains the pMB1 replicon and a gene coding for beta-lactamase for replication and selection in *Escherichia coli*. In addition to the coding sequence for URA3, the sequences from upstream and downstream of this gene were included for expression of the URA3 gene in yeast. The vector can be used for cloning purposes and can be used as a yeast integration vector.

The DNA encompassing the URA3 coding region along with 250 bp upstream and 150 bp downstream of the URA3 coding region from *Saccharomyces cerevisiae* CEN.PK 113-7D genomic DNA was amplified with primers oBP438 (SEQ ID NO: 12) containing BamHI, AscI, PmeI, and FseI restriction sites, and oBP439 (SEQ ID NO: 13) containing XbaI, PacI, and NotI restriction sites, using Phusion® High Fidelity PCR Master Mix (New England BioLabs Inc., Ipswich, Mass.). Genomic DNA was prepared using a Gentra® Puregene® Yeast/Bact. kit (Qiagen, Valencia, Calif.). The PCR product and pUC19 (SEQ ID NO: 143) were ligated with T4 DNA ligase after digestion with BamHI and XbaI to create vector pUC19-URA3MCS. The vector was confirmed by PCR and sequencing with primers oBP264 (SEQ ID NO: 10) and oBP265 (SEQ ID NO: 11).

The coding sequence of sadB and PDC5 Fragment B were cloned into pUC19-URA3MCS to create the sadB-BU portion of the PDC5 A-sadB-BUC PCR cassette. The coding sequence of sadB was amplified using pLH468-sadB (SEQ ID NO: 67) as template with primer oBP530 (SEQ ID NO: 50) containing an AscI restriction site, and primer oBP531 (SEQ ID NO: 51) containing a 5' tail with homology to the 5' end of PDC5 Fragment B. PDC5 Fragment B was amplified with primer oBP532 (SEQ ID NO: 52) containing a 5' tail with homology to the 3' end of sadB, and primer oBP533 (SEQ ID NO: 53) containing a PmeI restriction site. PCR products were purified with a PCR Purification kit (Qiagen, Valencia, Calif.). sadB-PDC5 Fragment B was created by overlapping PCR by mixing the sadB and PDC5 Fragment B PCR products and amplifying with primers oBP530 (SEQ ID NO: 50) and oBP533 (SEQ ID NO: 53). The resulting PCR product was digested with AscI and PmeI and ligated with T4 DNA ligase into the corresponding sites of pUC19-URA3MCS after digestion with the appropriate enzymes. The resulting plasmid was used as a template for amplification of sadB-Fragment B-Fragment U using primers oBP536 (SEQ ID NO: 54) and oBP546 (SEQ ID NO: 55) containing a 5' tail with homology to the 5' end of PDC5 Fragment C. PDC5 Fragment C was amplified with primer oBP547 (SEQ ID NO: 56) containing a 5' tail with homology to the 3' end of PDC5 sadB-Fragment B-Fragment U, and primer oBP539 (SEQ ID NO: 57). PCR products were purified with a PCR Purification kit (Qiagen, Valencia, Calif.). PDC5 sadB-Fragment B-Fragment U-Fragment C was created by overlapping PCR by mixing PDC5 sadB-Fragment B-Fragment U and PDC5 Fragment C and amplifying with primers oBP536 (SEQ ID NO: 54) and oBP539 (SEQ ID NO: 57). The resulting PCR product was purified on an agarose gel followed by a Gel Extraction kit (Qiagen, Valencia, Calif.). The PDC5 A-sadB-BUC cassette (SEQ ID NO: 144) was created by amplifying PDC5 sadB-Fragment B-Fragment U-Fragment C with primers oBP542 (SEQ ID NO: 58) containing a 5' tail with homology to the 50 nucleotides immediately upstream of the native PDC5 coding sequence, and oBP539 (SEQ ID NO: 57). The PCR product was purified with a PCR Purification kit (Qiagen, Valencia, Calif.).

Competent cells of CEN.PK 113-7D Δura3::loxP Δhis3 Δpdc6 Δpdc1::ilvDSm were made and transformed with the PDC5 A-sadB-BUC PCR cassette using a Frozen-EZ Yeast Transformation II™ kit (Zymo Research Corporation, Irvine, Calif.). Transformation mixtures were plated on synthetic complete media lacking uracil supplemented with 1% ethanol (no glucose) at 30° C. Transformants with a pdc5 knockout sadB integration were screened for by PCR with primers oBP540 (SEQ ID NO: 59) and oBP541 (SEQ ID NO: 60) using genomic DNA prepared with a Gentra® Puregene® Yeast/Bact. kit (Qiagen, Valencia, Calif.). The absence of the PDC5 gene from the isolate was demonstrated by a negative PCR result using primers specific for the coding sequence of PDC5, oBP552 (SEQ ID NO: 61) and oBP553 (SEQ ID NO: 62). A correct transformant was selected as strain CEN.PK 113-7D Δura3::loxP Δhis3 Δpdc6 Δpdc1::ilvDSm Δpdc5::sadB-URA3.

CEN.PK 113-7D Δura3::loxP Δhis3 Δpdc6 Δpdc1::ilvDSm Δpdc5::sadB-URA3 was grown overnight in YPE (1% ethanol) and plated on synthetic complete medium supplemented with ethanol (no glucose) and containing 5-fluoro-orotic acid (0.1%) at 30° C. to select for isolates that lost the URA3 marker. The deletion of PDC5, integration of sadB, and marker removal were confirmed by PCR with primers oBP540 (SEQ ID NO: 59) and oBP541 (SEQ ID NO: 60) using genomic DNA prepared with a Gentra® Puregene® Yeast/Bact. kit (Qiagen, Valencia, Calif.). The correct isolate was selected as strain CEN.PK 113-7D Δura3::loxP Δhis3 Δpdc6 Δpdc1::ilvDSm Δpdc5::sadB and designated as BP913.

GPD2 Deletion

To delete the endogenous GPD2 coding region, a gpd2::loxP-URA3-loxP cassette (SEQ ID NO: 145) was PCR-amplified using loxP-URA3-loxP (SEQ ID NO: 68) as template DNA. loxP-URA3-loxP contains the URA3 marker from (ATCC No. 77107) flanked by loxP recombinase sites. PCR was done using Phusion® DNA polymerase (New England BioLabs Inc., Ipswich, Mass.) and primers LA512 and LA513 (SEQ ID NOs: 8 and 9). The GPD2 portion of each primer was derived from the 5' region upstream of the GPD2 coding region and 3' region downstream of the coding region such that integration of the loxP-URA3-loxP marker resulted in replacement of the GPD2 coding region. The PCR product was transformed into BP913 and transformants were selected on synthetic complete media lacking uracil supplemented with 1% ethanol (no glucose). Transformants were screened to verify correct integration by PCR using primers oBP582 and AA270 (SEQ ID NOs: 63 and 64).

The URA3 marker was recycled by transformation with pRS423::PGAL1-cre (SEQ ID NO: 66) and plating on synthetic complete media lacking histidine supplemented with 1% ethanol at 30° C. Transformants were streaked on synthetic complete medium supplemented with 1% ethanol and containing 5-fluoro-orotic acid (0.1%) and incubated at 30° C. to select for isolates that lost the URA3 marker. 5-FOA resistant isolates were grown in YPE (1% ethanol) for removal of the pRS423::PGAL1-cre plasmid. The deletion and marker removal were confirmed by PCR with primers oBP582 (SEQ ID NO: 63) and oBP591 (SEQ ID NO: 65). The correct isolate was selected as strain CEN.PK 113-7D Δura3:: loxP Δhis3 Δpdc6 Δpdc1::ilvDSm Δpdc5::sadB Δgpd2::loxP and designated as PNY1503 (BP1064).

BP1064 was transformed with plasmids pYZ090 (SEQ ID NO: 1) and pLH468 (SEQ ID NO: 2) to create strain NGCI-070 (BP1083; PNY1504).

Construction of Strains NYLA74, NYLA83, and NYLA84

Insertion-inactivation of endogenous PDC1 and PDC6 genes of S. cerevisiae. PDC1, PDC5, and PDC6 genes encode the three major isozymes of pyruvate decarboxylase is described as follows:

Construction of pRS425::GPM-sadB

A DNA fragment encoding a butanol dehydrogenase (SEQ ID NO: 70) from Achromobacter xylosoxidans (disclosed in U.S. Patent Application Publication No. 2009/0269823) was cloned. The coding region of this gene called sadB for secondary alcohol dehydrogenase (SEQ ID NO: 69) was amplified using standard conditions from A. xylosoxidans genomic DNA, prepared using a Gentra® Puregene® kit (Qiagen, Valencia, Calif.) following the recommended protocol for gram negative organisms using forward and reverse primers N473 and N469 (SEQ ID NOs: 74 and 75), respectively. The PCR product was TOPO®-Blunt cloned into pCR®4 BLUNT (Invitrogen™, Carlsbad, Calif.) to produce pCR4Blunt::sadB, which was transformed into E. coli Mach-1 cells. Plasmid was subsequently isolated from four clones, and the sequence verified.

The sadB coding region was PCR amplified from pCR4Blunt::sadB. PCR primers contained additional 5' sequences that would overlap with the yeast GPM1 promoter and the ADH1 terminator (N583 and N584, provided as SEQ ID NOs: 76 and 77). The PCR product was then cloned using "gap repair" methodology in Saccharomyces cerevisiae (Ma, et al., Gene 58:201-216, 1987) as follows. The yeast-E. coli shuttle vector pRS425::GPM::kivD::ADH which contains the GPM1 promoter (SEQ ID NO: 72), kivD coding region from Lactococcus lactis (SEQ ID NO: 71), and ADH1 terminator (SEQ ID NO: 73) (described in U.S. Patent Application Publication No. 2007/0092957 A1, Example 17) was digested with BbvCI and PacI restriction enzymes to release the kivD coding region. Approximately 1 μg of the remaining vector fragment was transformed into S. cerevisiae strain BY4741 along with 1 μg of sadB PCR product. Transformants were selected on synthetic complete medium lacking leucine. The proper recombination event, generating pRS425::GPM-sadB, was confirmed by PCR using primers N142 and N459 (SEQ ID NOs: 108 and 109).

Construction of pdc6:: PGPM1-sadB Integration Cassette and PDC6 Deletion:

A pdc6::PGPM1-sadB-ADH1t-URA3r integration cassette was made by joining the GPM-sadB-ADHt segment (SEQ ID NO: 79) from pRS425::GPM-sadB (SEQ ID NO: 78) to the URA3r gene from pUC19-URA3r. pUC19-URA3r (SEQ ID NO:80) contains the URA3 marker from pRS426 (ATCC No. 77107) flanked by 75 bp homologous repeat sequences to allow homologous recombination in vivo and removal of the URA3 marker. The two DNA segments were joined by SOE PCR (as described by Horton, et al., Gene 77:61-68, 1989) using as template pRS425::GPM-sadB and pUC19-URA3r plasmid DNAs, with Phusion® DNA polymerase (New England BioLabs Inc., Ipswich, Mass.) and primers 114117-11A through 114117-11D (SEQ ID NOs: 81, 82, 83, and 84), and 114117-13A and 114117-13B (SEQ ID NOs: 85 and 86).

The outer primers for the SOE PCR (114117-13A and 114117-13B) contained 5' and 3' ~50 bp regions homologous to regions upstream and downstream of the PDC6 promoter and terminator, respectively. The completed cassette PCR fragment was transformed into BY4700 (ATCC No. 200866) and transformants were maintained on synthetic complete media lacking uracil and supplemented with 2% glucose at 30° C. using standard genetic techniques (Methods in Yeast Genetics, 2005, Cold Spring Harbor Laboratory Press, Cold Spring Harbor, N.Y., pp. 201-202). Transformants were screened by PCR using primers 112590-34G and 112590-34H (SEQ ID NOs: 87 and 88), and 112590-34F and 112590-49E (SEQ ID NOs: 89 and 90) to verify integration at the PDC6 locus with deletion of the PDC6 coding region. The URA3r marker was recycled by plating on synthetic complete media supplemented with 2% glucose and 5-FOA at 30° C. following standard protocols. Marker removal was confirmed by patching colonies from the 5-FOA plates onto SD-URA media to verify the absence of growth. The resulting identified strain has the genotype: BY4700 pdc6::PGPM1-sadB-ADH1t.

Construction of pdc1:: PPDC1-ilvD Integration Cassette and PDC1 Deletion:

A pdc1:: PPDC1-ilvD-FBA1t-URA3r integration cassette was made by joining the ilvD-FBA1t segment (SEQ ID NO: 91) from pLH468 (SEQ ID NO: 2) to the URA3r gene from pUC19-URA3r by SOE PCR (as described by Horton, et al., Gene 77:61-68, 1989) using as template pLH468 and pUC19-URA3r plasmid DNAs, with Phusion® DNA polymerase (New England BioLabs Inc., Ipswich, Mass.) and primers 114117-27A through 114117-27D (SEQ ID NOs: 111, 112, 113, and 114).

The outer primers for the SOE PCR (114117-27A and 114117-27D) contained 5' and 3' ~50 bp regions homologous to regions downstream of the PDC1 promoter and downstream of the PDC1 coding sequence. The completed cassette PCR fragment was transformed into BY4700 pdc6::PGPM1-sadB-ADH1t and transformants were maintained on synthetic complete media lacking uracil and supplemented with 2% glucose at 30° C. using standard genetic techniques (Methods in Yeast Genetics, 2005, Cold Spring Harbor Laboratory Press, Cold Spring Harbor, N.Y., pp. 201-202). Transformants were screened by PCR using primers 114117-36D and 135 (SEQ ID NOs: 92 and 93), and primers 112590-49E and 112590-30F (SEQ ID NOs: 90 and 94) to verify integration at the PDC1 locus with deletion of the PDC1 coding sequence. The URA3r marker was recycled by plating on synthetic complete media supplemented with 2% glucose and 5-FOA at 30° C. following standard protocols. Marker removal was confirmed by patching colonies from the 5-FOA plates onto SD-URA media to verify the absence of growth. The resulting identified strain "NYLA67" has the genotype: BY4700 pdc6:: PGPM1-sadB-ADH1t pdc1:: PPDC1-ilvD-FBA1t.

HIS3 Deletion

To delete the endogenous HIS3 coding region, a his3::URA3r2 cassette was PCR-amplified from URA3r2 template DNA (SEQ ID NO: 95). URA3r2 contains the URA3 marker from pRS426 (ATCC No. 77107) flanked by 500 bp homologous repeat sequences to allow homologous recombination in vivo and removal of the URA3 marker. PCR was done using Phusion® DNA polymerase (New England BioLabs Inc., Ipswich, Mass.) and primers 114117-45A and 114117-45B (SEQ ID NOs: 96 and 97) which generated a ~2.3 kb PCR product. The HIS3 portion of each primer was derived from the 5' region upstream of the HIS3 promoter and 3' region downstream of the coding region such that integration of the URA3r2 marker results in replacement of the HIS3 coding region. The PCR product was transformed into NYLA67 using standard genetic techniques (Methods in Yeast Genetics, 2005, Cold Spring Harbor Laboratory Press, Cold Spring Harbor, N.Y., pp. 201-202) and transformants were selected on synthetic complete media lacking uracil and supplemented with 2% glucose at 30° C. Transformants were screened to verify correct integration by replica plating of transformants onto synthetic complete media lacking histidine and supplemented with 2% glucose at 30° C. The URA3r marker was recycled by plating on synthetic complete media supplemented with 2% glucose and 5-FOA at 30° C. following standard protocols. Marker removal was confirmed by patching colonies from the 5-FOA plates onto SD-URA media to verify the absence of growth. The resulting identified strain, called NYLA73, has the genotype: BY4700 pdc6:: PGPM1-sadB-ADH1t pdc1:: PPDC1-ilvD-FBA1t Δhis3.

Construction of pdc5::kanMX Integration Cassette and PDC5 Deletion:

A pdc5::kanMX4 cassette was PCR-amplified from strain YLR134W chromosomal DNA (ATCC No. 4034091) using Phusion® DNA polymerase (New England BioLabs Inc., Ipswich, Mass.) and primers PDC5::KanMXF and PDC5::KanMXR (SEQ ID NOs: 98 and 99) which generated a ~2.2 kb PCR product. The PDC5 portion of each primer was derived from the 5' region upstream of the PDC5 promoter and 3' region downstream of the coding region such that integration of the kanMX4 marker results in replacement of the PDC5 coding region. The PCR product was transformed into NYLA73 using standard genetic techniques (Methods in Yeast Genetics, 2005, Cold Spring Harbor Laboratory Press, Cold Spring Harbor, N.Y., pp. 201-202) and transformants were selected on YP media supplemented with 1% ethanol and geneticin (200 μg/mL) at 30° C. Transformants were screened by PCR to verify correct integration at the PDC locus with replacement of the PDC5 coding region using primers PDC5kofor and N175 (SEQ ID NOs: 100 and 101). The identified correct transformants have the genotype: BY4700 pdc6:: PGPM1-sadB-ADH1t pdc1:: PPDC1-ilvD-FBA1t Δhis3 pdc5::kanMX4. The strain was named NYLA74.

Plasmid vectors pRS423::CUP1-alsS+FBA-budA and pRS426::FBA-budC+GPM-sadB were transformed into NYLA74 to create a butanediol producing strain (NGCI-047).

Plasmid vectors pLH475-Z4B8 (SEQ ID NO: 140) and pLH468 were transformed into NYLA74 to create an isobutanol producing strain (NGCI-049).

Deletion of HXK2 (Hexokinase II):

A hxk2::URA3r cassette was PCR-amplified from URA3r2 template (described above) using Phusion® DNA polymerase (New England BioLabs Inc., Ipswich, Mass.) and primers 384 and 385 (SEQ ID NOs: 102 and 103) which generated a ~2.3 kb PCR product. The HXK2 portion of each primer was derived from the 5' region upstream of the HXK2 promoter and 3' region downstream of the coding region such that integration of the URA3r2 marker results in replacement of the HXK2 coding region. The PCR product was transformed into NYLA73 using standard genetic techniques (Methods in Yeast Genetics, 2005, Cold Spring Harbor Laboratory Press, Cold Spring Harbor, N.Y., pp. 201-202) and transformants were selected on synthetic complete media lacking uracil and supplemented with 2% glucose at 30° C. Transformants were screened by PCR to verify correct integration at the HXK2 locus with replacement of the HXK2 coding region using primers N869 and N871 (SEQ ID NOs: 104 and 105). The URA3r2 marker was recycled by plating on synthetic complete media supplemented with 2% glucose and 5-FOA at 30° C. following standard protocols. Marker removal was confirmed by patching colonies from the 5-FOA plates onto SD-URA media to verify the absence of growth, and by PCR to verify correct marker removal using primers N946 and N947 (SEQ ID NOs: 106 and 107). The resulting identified strain named NYLA83 has the genotype: BY4700 pdc6:: PGPM1-sadB-ADH1t pdc1:: PPDC1-ilvD-FBA1t Δhis3 Δhxk2.

Construction of pdc5::kanMX Integration Cassette and PDC5 Deletion:

A pdc5::kanMX4 cassette was PCR-amplified as described above. The PCR fragment was transformed into NYLA83, and transformants were selected and screened as described above. The identified correct transformants named NYLA84 have the genotype: BY4700 pdc6:: PGPM1-sadB-ADH1t pdc1:: PPDC1-ilvD-FBA1t Δhis3 Δhxk2 pdc5::kanMX4.

Plasmid vectors pLH468 and pLH532 were simultaneously transformed into strain NYLA84 (BY4700 pdc6:: PGPM1-sadB-ADH1t pdc1::PPDC1-ilvD-FBA1t Δhis3 Δhxk2 pdc5::kanMX4) using standard genetic techniques (Methods in Yeast Genetics, 2005, Cold Spring Harbor Laboratory Press, Cold Spring Harbor, N.Y.) and the resulting "butanologen NYLA84" was maintained on synthetic complete media lacking histidine and uracil, and supplemented with 1% ethanol at 30° C.

Expression Vector pLH468

The pLH468 plasmid (SEQ ID NO: 2) was constructed for expression of DHAD, KivD, and HADH in yeast and is described in U.S. Patent Application Publication No. 2009/0305363, herein incorporated by reference. pLH486 was constructed to contain: a chimeric gene having the coding region of the ilvD gene from *Streptococcus mutans* (nt position 3313-4849) expressed from the *S. cerevisiae* FBA1 promoter (nt 2109-3105) followed by the FBA1 terminator (nt 4858-5857) for expression of DHAD; a chimeric gene having the coding region of codon optimized horse liver alcohol dehydrogenase (nt 6286-7413) expressed from the *S. cerevisiae* GPM1 promoter (nt 7425-8181) followed by the ADH1 terminator (nt 5962-6277) for expression of ADH; and a chimeric gene having the coding region of the codon-optimized kivD gene from *Lactococcus lactis* (nt 9249-10895) expressed from the TDH3 promoter (nt 10896-11918) followed by the TDH3 terminator (nt 8237-9235) for expression of KivD.

Coding regions for *Lactococcus* lactis ketoisovalerate decarboxylase (KivD) and horse liver alcohol dehydrogenase (HADH) were synthesized by DNA2.0, Inc. (Menlo Park, Calif.) based on codons that were optimized for expression in *Saccharomyces cerevisiae* (SEQ ID NO: 71 and 118, respectively) and provided in plasmids pKivDy-DNA2.0 and pHadhy-DNA2.0. The encoded proteins are SEQ ID NOs: 117 and 119, respectively. Individual expression vectors for KivD and HADH were constructed. To assemble pLH467 (pRS426::PTDH3-kivDy-TDH3t), vector pNY8 (SEQ ID NO: 121; also named pRS426.GPD-ald-GPDt, described in U.S. Patent Application Publication No. 2008/0182308, Example 17, which is herein incorporated by reference) was digested with AscI and SfiI enzymes, thus excising the GPD promoter and the ald coding region. A TDH3 promoter fragment (SEQ ID NO: 122) from pNY8 was PCR amplified to add an AscI site at the 5' end and an SpeI site at the 3' end, using 5' primer OT1068 and 3' primer OT1067 (SEQ ID NOs: 123 and 124). The AscI/SfiI digested pNY8 vector fragment was ligated with the TDH3 promoter PCR product digested with AscI and SpeI, and the SpeI-SfiI fragment containing the codon optimized kivD coding region isolated from the vector pKivD-DNA2.0. The triple ligation generated vector pLH467 (pRS426::PTDH3-kivDy-TDH3t). pLH467 was verified by restriction mapping and sequencing.

pLH435 (pRS425::PGPM1-Hadhy-ADH1t) was derived from vector pRS425::GPM-sadB (SEQ ID NO: 78) which is described in U.S. Provisional Application Ser. No. 61/058, 970, Example 3, which is herein incorporated by reference. pRS425::GPM-sadB is the pRS425 vector (ATCC No. 77106) with a chimeric gene containing the GPM1 promoter (SEQ ID NO:72), coding region from a butanol dehydrogenase of *Achromobacter xylosoxidans* (sadB; DNA SEQ ID NO: 69; protein SEQ ID NO:70: disclosed in U.S. Patent Application Publication No. 2009/0269823), and ADH1 terminator (SEQ ID NO: 73). pRS425::GPMp-sadB contains BbvI and PacI sites at the 5' and 3' ends of the sadB coding region, respectively. A NheI site was added at the 5' end of the sadB coding region by site-directed mutagenesis using primers OT1074 and OT1075 (SEQ ID NOs: 126 and 127) to generate vector pRS425-GPMp-sadB-NheI, which was verified by sequencing. pRS425::PGPM1-sadB-NheI was digested with NheI and PacI to drop out the sadB coding region, and ligated with the NheI-PacI fragment containing the codon optimized HADH coding region from vector pHadhy-DNA2.0 to create pLH435.

To combine KivD and HADH expression cassettes in a single vector, yeast vector pRS411 (ATCC No. 87474) was digested with SacI and NotI, and ligated with the SacI-SalI fragment from pLH467 that contains the PTDH3-kivDy-TDH3t cassette together with the SalI-NotI fragment from pLH435 that contains the PGPM1-Hadhy-ADH1t cassette in a triple ligation reaction. This yielded the vector pRS411:: PTDH3-kivDy-PGPM1-Hadhy (pLH441) which was verified by restriction mapping.

In order to generate a co-expression vector for all three genes in the lower isobutanol pathway: ilvD, kivDy, and Hadhy, pRS423 FBA ilvD(Strep) (SEQ ID NO: 128) which is described in U.S. Patent Application Publication No. 2010/0081154 as the source of the IlvD gene, was used. This shuttle vector contains an F1 origin of replication (nt 1423 to 1879) for maintenance in *E. coli* and a 2 micron origin (nt 8082 to 9426) for replication in yeast. The vector has an FBA1 promoter (nt 2111 to 3108; SEQ ID NO: 120) and FBA terminator (nt 4861 to 5860; SEQ ID NO: 129). In addition, it carries the His marker (nt 504 to 1163) for selection in yeast and ampicillin resistance marker (nt 7092 to 7949) for selection in *E. coli*. The ilvD coding region (nt 3116 to 4828; SEQ ID NO: 115; protein SEQ ID NO: 116) from *Streptococcus mutans* UA159 (ATCC No. 700610) is between the FBA promoter and FBA terminator forming a chimeric gene for expression. In addition, there is a lumio tag fused to the ilvD coding region (nt 4829-4849).

The first step was to linearize pRS423 FBA ilvD(Strep) (also called pRS423-FBA(SpeI)-IlvD(*Streptococcus mutans*)-Lumio) with SacI and SacII (with SacII site blunt ended using T4 DNA polymerase), to give a vector with total length of 9,482 bp. The second step was to isolate the kivDy-hADHy cassette from pLH441 with SacI and KpnI (with KpnI site blunt ended using T4 DNA polymerase), which gives a 6,063 bp fragment. This fragment was ligated with the 9,482 bp vector fragment from pRS423-FBA(SpeI)-ilvD (*Streptococcus mutans*)-Lumio. This generated vector pLH468 (pRS423::PFBA1-ilvD(Strep) Lumio-FBA1t-PTDH3-kivDy-TDH3t-PGPM1-hadhy-ADH1t) which was confirmed by restriction mapping and sequencing.

pLH532 Construction

The pLH532 plasmid (SEQ ID NO: 130) was constructed for expression of ALS and KARI in yeast. pLH532 is a pHR81 vector (ATCC No. 87541) containing the following chimeric genes: 1) the CUP1 promoter (SEQ ID NO: 139), acetolactate synthase coding region from *Bacillus subtilis*

(AlsS; SEQ ID NO: 137; protein SEQ ID NO: 138) and CYC1 terminator2 (SEQ ID NO: 133); 2) an ILV5 promoter (SEQ ID NO: 134), Pf5.IlvC coding region (SEQ ID NO: 132) and ILV5 terminator (SEQ ID NO: 135); and 3) the FBA1 promoter (SEQ ID NO: 136), *S. cerevisiae* KARI coding region (ILV5; SEQ ID NO: 131); and CYC1 terminator.

The Pf5.IlvC coding region is a sequence encoding KARI derived from *Pseudomonas fluorescens* that was described in U.S. Patent Application Publication No. 2009/0163376, which is herein incorporated by reference.

The Pf5.IlvC coding region was synthesized by DNA2.0, Inc. (Menlo Park, Calif.; SEQ ID NO: 132) based on codons that were optimized for expression in *Saccharomyces cerevisiae*.

pYZ090 Construction pYZ090 (SEQ ID NO: 1) is based on the pHR81 (ATCC No. 87541) backbone and was constructed to contain a chimeric gene having the coding region of the alsS gene from *Bacillus subtilis* (nt position 457-2172) expressed from the yeast CUP1 promoter (nt 2-449) and followed by the CYC1 terminator (nt 2181-2430) for expression of ALS, and a chimeric gene having the coding region of the ilvC gene from *Lactococcus lactis* (nt 3634-4656) expressed from the yeast ILV5 promoter (2433-3626) and followed by the ILV5 terminator (nt 4682-5304) for expression of KARI.

pYZ067 Construction pYZ067 was constructed to contain the following chimeric genes: 1) the coding region of the ilvD gene from *S. mutans* UA159 (nt position 2260-3971) expressed from the yeast FBA1 promoter (nt 1161-2250) followed by the FBA terminator (nt 4005-4317) for expression of dihydroxy acid dehydratase (DHAD), 2) the coding region for horse liver ADH (nt 4680-5807) expressed from the yeast GPM promoter (nt 5819-6575) followed by the ADH1 terminator (nt 4356-4671) for expression of alcohol dehydrogenase, and 3) the coding region of the KivD gene from *Lacrococcus lactis* (nt 7175-8821) expressed from the yeast TDH3 promoter (nt 8830-9493) followed by the TDH3 terminator (nt 5682-7161) for expression of ketoisovalerate decarboxylase.

pRS423::CUP1-alsS+FBA-budA and pRS426::FBA-budC+GPM-sadB and pLH475-Z4B8 Construction Construction of pRS423::CUP1-alsS+FBA-budA and pRS426::FBA-budC+GPM-sadB and pLH475-Z4B8 is described in U.S. Patent Application Publication No. 2009/0305363, incorporated herein by reference.

Further, while various embodiments of the present invention have been described above, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the claims and their equivalents.

All publications, patents, and patent applications mentioned in this specification are indicative of the level of skill of those skilled in the art to which this invention pertains, and are herein incorporated by reference to the same extent as if each individual publication, patent, or patent application was specifically and individually indicated to be incorporated by reference.

EXAMPLES

The following nonlimiting examples will further illustrate the invention. It should be understood that, while the following examples involve corn as feedstock and COFA as carboxylic acid, other biomass sources can be used for feedstock and acids other than COFA can serve as carboxylic acid, without departing from the present invention. Moreover, while the following examples involve butanol and butyl ester production, other alcohols including ethanol, and alcohol esters can be produced without departing from the present invention.

As used herein, the meaning of abbreviations used was as follows: "g" means gram(s), "kg" means kilogram(s), "L" means liter(s), "mL" means milliliter(s), "μL" means microliter(s), "mL/L" means milliliter(s) per liter, "mL/min" means milliliter(s) per min, "DI" means deionized, "uM" means micrometer(s), "nm" means nanometer(s), "w/v" means weight/volume, "OD" means optical density, "$OD_{600}$" means optical density at a wavelength of 600 nM, "dcw" means dry cell weight, "rpm" means revolutions per minute, "° C." means degree(s) Celsius, "° C./min" means degrees Celsius per minute, "slpm" means standard liter(s) per minute, "ppm" means part per million, "pdc" means pyruvate decarboxylase enzyme followed by the enzyme number.

General Methods

Seed Flask Growth

A *Saccharomyces cerevisiae* strain that was engineered to produce isobutanol from a carbohydrate source, with pdc1 deleted, pdc5 deleted, and pdc6 deleted, was grown to 0.55-1.1 g/L dcw ($OD_{600}$ 1.3-2.6—Thermo Helios α Thermo Fisher Scientific Inc., Waltham, Mass.) in seed flasks from a frozen culture. The culture was grown at 26° C. in an incubator rotating at 300 rpm. The frozen culture was previously stored at −80° C. The composition of the first seed flask medium was:
- 3.0 g/L dextrose
- 3.0 g/L ethanol, anhydrous
- 3.7 g/L ForMedium™ Synthetic Complete Amino Acid (Kaiser) Drop-Out: without HIS, without URA (Reference No. DSCK162CK)
- 6.7 g/L Difco Yeast Nitrogen Base without amino acids (No. 291920)

Twelve milliliters from the first seed flask culture was transferred to a 2 L flask and grown at 30° C. in an incubator rotating at 300 rpm. The second seed flask has 220 mL of the following medium:
- 30.0 g/L dextrose
- 5.0 g/L ethanol, anhydrous
- 3.7 g/L ForMedium™ Synthetic Complete Amino Acid (Kaiser) Drop-Out: without HIS, without URA (Reference No. DSCK162CK)
- 6.7 g/L Difco Yeast Nitrogen Base without amino acids (No. 291920)
- 0.2 M MES Buffer titrated to pH 5.5-6.0

The culture was grown to 0.55-1.1 g/L dcw ($OD_{600}$ 1.3-2.6). An addition of 30 mL of a solution containing 200 g/L peptone and 100 g/L yeast extract was added at this cell concentration. Then, an addition of 300 mL of 0.2 uM filter sterilized Cognis, 90-95% oleyl alcohol was added to the flask. The culture continues to grow to >4 g/L dcw ($OD_{600}$>10) before being harvested and added to the fermentation.

Fermentation Preparation

Initial Fermentation Vessel Preparation

A glass jacked, 2 L fermentation vessel (Sartorius AG, Goettingen, Germany) was charged with house water to 66% of the liquefaction weight. A pH probe (Hamilton Easyferm Plus K8, part number: 238627, Hamilton Bonaduz AG, Bonaduz, Switzerland) was calibrated through the Sartorius DCU-3 Control Tower Calibration menu. The zero was calibrated at pH=7. The span was calibrated at pH=4. The probe was then placed into the fermentation vessel through the stainless steel head plate. A dissolved oxygen probe ($pO_2$ probe) was also placed into the fermentation vessel through the head plate. Tubing used for delivering nutrients, seed culture, extracting solvent, and base were attached to the head plate and the ends were foiled. The entire fermentation vessel was placed into a Steris (Steris Corporation, Mentor, Ohio) autoclave and sterilized in a liquid cycle for 30 minutes.

The fermentation vessel was removed from the autoclave and placed on a load cell. The jacket water supply and return line was connected to the house water and clean drain, respectively. The condenser cooling water in and water out lines were connected to a 6-L recirculating temperature bath running at 7° C. The vent line that transfers the gas from the fermentation vessel was connected to a transfer line that was connected to a Thermo mass spectrometer (Prima dB, Thermo Fisher Scientific Inc., Waltham, Mass.). The sparger line was connected to the gas supply line. The tubing for adding nutrients, extract solvent, seed culture, and base was plumbed through pumps or clamped closed.

The fermentation vessel temperature was controlled at 55° C. with a thermocouple and house water circulation loop. Wet corn kernels (#2 yellow dent) were ground using a hammer mill with a 1.0 mm screen, and the resulting ground whole corn kernels were then added to the fermentation vessel at a charge that was 29-30% (dry corn solids weight) of the liquefaction reaction mass.

Lipase Treatment Pre-Liquefaction

A lipase enzyme stock solution was added to the fermentation vessel to a final lipase concentration of 10 ppm. The fermentation vessel was held at 55° C., 300 rpm, and 0.3 slpm $N_2$ overlay for >6 hrs. After the lipase treatment was complete, liquefaction was performed as described below (Liquefaction).

Liquefaction

An alpha-amylase was added to the fermentation vessel per its specification sheet while the fermentation vessel was mixing at 300-1200 rpm, with sterile, house $N_2$ being added at 0.3 slpm through the sparger. The temperature set-point was changed from 55° C. to 85° C. When the temperature was >80° C., the liquefaction cook time was started and the liquefaction cycle was held at >80° C. for 90-120 minutes. The fermentation vessel temperature set-point was set to the fermentation temperature of 30° C. after the liquefaction cycle was complete. $N_2$ was redirected from the sparger to the head space to prevent foaming without the addition of a chemical antifoaming agent.

Lipase Treatment Post-Liquefaction

The fermentation vessel temperature was set to 55° C. instead of 30° C. after the liquefaction cycle was complete (Liquefaction). The pH was manually controlled at pH=5.8 by making bolus additions of acid or base when needed. A lipase enzyme stock solution was added to the fermentation vessel to a final lipase concentration of 10 ppm. The fermentation vessel was held at 55° C., 300 rpm, and 0.3 slpm $N_2$ overlay for >6 hrs. After the Lipase Treatment was complete, the fermentation vessel temperature was set to 30° C.

Lipase Heat Inactivation Treatment (Heat Kill Treatment Method)

The fermentation vessel temperature was held at >80° C. for >15 minutes to inactivate the lipase. After the Heat Inactivation Treatment was complete, the fermentation vessel temperature was set to 30° C.

Nutrient Addition Prior to Inoculation

Ethanol (6.36 mL/L, post-inoculation volume, 200 proof, anhydrous) was added to the fermentation vessel just prior to inoculation. Thiamine was added to a final concentration of 20 mg/L and 100 mg/L nicotinic acid was also added just prior to inoculation.

Oleyl Alcohol or Corn Oil Fatty Acids Addition Prior to Inoculation

Added 1 L/L (post-inoculation volume) of oleyl alcohol or corn oil fatty acids immediately after inoculation.

Fermentation Vessel Inoculation

The fermentation vessels $pO_2$ probe was calibrated to zero while $N_2$ was being added to the fermentation vessel. The fermentation vessels $pO_2$ probe was calibrated to its span with sterile air sparging at 300 rpm. The fermentation vessel was inoculated after the second seed flask with >4 g/L dcw. The shake flask was removed from the incubator/shaker for 5 minutes allowing a phase separation of the oleyl alcohol phase and the aqueous phase. The aqueous phase (110 mL) was transferred to a sterile, inoculation bottle. The inoculum was pumped into the fermentation vessel through a peristaltic pump.

Fermentation Vessel Operating Conditions

The fermentation vessel was operated at 30° C. for the entire growth and production stages. The pH was allowed to drop from a pH between 5.7-5.9 to a control set-point of 5.2 without adding any acid. The pH was controlled for the remainder of the growth and production stage at a pH=5.2 with ammonium hydroxide. Sterile air was added to the fermentation vessel, through the sparger, at 0.3 slpm for the remainder of the growth and production stages. The $pO_2$ was set to be controlled at 3.0% by the Sartorius DCU-3 Control Box PID control loop, using stir control only, with the stirrer minimum being set to 300 rpm and the maximum being set to 2000 rpm. The glucose was supplied through simultaneous saccharification and fermentation of the liquified corn mash by adding a α-amylase (glucoamylase). The glucose was kept excess (1-50 g/L) for as long as starch was available for saccharification.

Analytical

Gas Analysis

Process air was analyzed on a Thermo Prima (Thermo Fisher Scientific Inc., Waltham, Mass.) mass spectrometer. This was the same process air that was sterilized and then added to each fermentation vessel. Each fermentation vessel's off-gas was analyzed on the same mass spectrometer. This Thermo Prima dB has a calibration check run every Monday morning at 6:00 am. The calibration check was scheduled through the Gas Works v1.0 (Thermo Fisher Scientific Inc., Waltham, Mass.) software associated with the mass spectrometer. The gas calibrated for were:

| GAS | Calibration Concentration mole % | Cal Frequency |
| --- | --- | --- |
| Nitrogen | 78% | weekly |
| Oxygen | 21% | weekly |
| Isobutanol | 0.2% | yearly |
| Argon | 1% | weekly |
| Carbon Dioxide | 0.03% | weekly |

Carbon dioxide was checked at 5% and 15% during calibration cycle with other known bottled gases. Oxygen was checked at 15% with other known bottled gases. Based on the analysis of the off-gas of each fermentation vessel, the amount of isobutanol stripped, oxygen consumed, and carbon dioxide respired into the off-gas was measured by using the mass spectrometer's mole fraction analysis and gas flow rates (mass flow controller) into the fermentation vessel. Calculate the gassing rate per hour and then integrating that rate over the course of the fermentation.

Biomass Measurement

A 0.08% Trypan Blue solution was prepared from a 1:5 dilution of 0.4% Trypan Blue in NaCl (VWR BDH8721-0) with 1×PBS. A 1.0 mL sample was pulled from a fermentation vessel and placed in a 1.5 mL Eppendorf centrifuge tube and centrifuged in an Eppendorf, 5415C at 14,000 rpm for 5 minutes. After centrifugation, the top solvent layer was removed with an m200 Variable Channel BioHit pipette with 20-200 µL BioHit pipette tips. Care was made not to remove the layer between the solvent and aqueous layers. Once the solvent layer was removed, the sample was re-suspended using a Vortex-Genie® set at 2700 rpm.

A series of dilutions was required to prepare the ideal concentration for hemacytometer counts. If the OD was 10, a 1:20 dilution would be performed to achieve 0.5 OD which would give the ideal amount of cells to be counted per square, 20-30. In order to reduce inaccuracy in the dilution due to corn solids, multiple dilutions with cut 100-1000 µL BioHit pipette tips were required. Approximately, 1 cm was cut off the tips to increase the opening which prevented the tip from clogging. For a 1:20 final dilution, an initial 1:1 dilution of fermentation sample and 0.9% NaCl solution was prepared. Then, a 1:1 dilution of the previous solution (i.e., the initial 1:1 dilution) and 0.9% NaCl solution (the second dilution) was generated followed by a 1:5 dilution of the second dilution and Trypan Blue Solution. Samples were vortexed between each dilution and cut tips were rinsed into the 0.9% NaCl and Trypan Blue solutions.

The cover slip was carefully placed on top of the hemacytometer (Hausser Scientific Bright-Line 1492). An aliquot (10 µL) was drawn of the final Trypan Blue dilution with an m20 Variable Channel BioHit pipette with 2-20 µL BioHit pipette tips and injected into the hemacytometer. The hemacytometer was placed on the Zeis Axioskop 40 microscope at 40× magnification. The center quadrant was broken into 25 squares and the four corner and center squares in both chambers were then counted and recorded. After both chambers were counted, the average was taken and multiplied by the dilution factor (20), then by 25 for the number for squares in the quadrant in the hemacytometer, and then divided by 0.0001 mL which is the volume of the quadrant that was counted. The sum of this calculation is the number cells per mL.

LC Analysis of Fermentation Products in the Aqueous Phase

Samples were refrigerated until ready for processing. Samples were removed from refrigeration and allowed to reach room temperature (about one hour). Approximately 300 µL of sample was transferred with a m1000 Variable Channel BioHit pipette with 100-1000 µL BioHit pipette tips into a 0.2 um centrifuge filter (Nanosep® MF modified nylon centrifuge filter), then centrifuged using a Eppendorf, 5415C for five minutes at 14,000 rpm. Approximately 200 µL of filtered sample was transferred into a 1.8 auto sampler vial with a 250 µL glass vial insert with polymer feet. A screw cap with PTFE septa was used to cap the vial before vortexing the sample with a Vortex-Genie® set at 2700 rpm.

Sample was then run on Agilent 1200 series LC equipped with binary, isocratic pumps, vacuum degasser, heated column compartment, sampler cooling system, UV DAD detector and RI detector. The column used was an Aminex HPX-87H, 300×7.8 with a Bio-Rad Cation H refill, 30×4.6 guard column. Column temperature was 40° C., with a mobile phase of 0.01 N sulfuric acid, at a flow rate of 0.6 mL/min for 40 minutes. Results are shown in Table 1.

TABLE 1

Retention times of fermentation products in aqueous phase

| HPLC 302/310 Normalized to 10 µL injections | FW | RID Retention Time, min | Range of Standards, g/L | UV Retention Time, min |
|---|---|---|---|---|
| citric acid | 192.12 | 8.025 | 0.3-17 | 7.616 |
| glucose | 180.16 | 8.83 | 0.5-71 | |
| pyruvic acid (Na) | 110.04 | 9.388 | 0.1-5.2 | 8.5 |
| A-Kiv (Na) | 138.1 | 9.91 | 0.07-5.0 | 8.55 |
| 2,3-dihydroxyisovaleric acid (Na) | 156.1 | 10.972 | 0.2-8.8 | 10.529 |
| succinic acid | 118.09 | 11.561 | 0.3-16 | 11.216 |
| lactic acid (Li) | 96.01 | 12.343 | 0.3-17 | 11.948 |
| glycerol | 92.09 | 12.974 | 0.8-39 | |
| formic acid | 46.03 | 13.686 | 0.2-13 | 13.232 |
| acetate (Na) | 82.03 | 14.914 | 0.5-16 | 14.563 |
| meso-butanediol | 90.12 | 17.583 | 0.1-19 | |
| (+/−)-2,3-butanediol | 90.12 | 18.4 | 0.2-19 | |
| isobutyric acid | 88.11 | 19.685 | 0.1-8.0 | 19.277 |
| ethanol | 46.07 | 21.401 | 0.5-34 | |
| isobutyraldehyde | 72.11 | 27.64 | 0.01-0.11 | |
| isobutanol | 74.12 | 32.276 | 0.2-15 | |
| 3-OH-2-butanone (acetoin) | 88.11 | | 0.1-11 | 17.151 |

GC Analysis of Fermentation Products in the Solvent Phase

Samples were refrigerated until ready for processing. Samples were removed from refrigeration and allowed to reach room temperature (about one hour). Approximately 150 µL of sample was transferred using a m1000 Variable Channel BioHit pipette with 100-1000 µL BioHit pipette tips into a 1.8 auto sampler vial with a 250 µL glass vial insert with polymer feet. A screw cap with PTFE septa was used to cap the vial.

Sample was then run on Agilent 7890A GC with a 7683B injector and a G2614A auto sampler. The column was a HP-InnoWax column (30 m×0.32 mm ID, 0.25 µm film). The carrier gas was helium at a flow rate of 1.5 mL/min measured at 45° C. with constant head pressure; injector split was 1:50 at 225° C.; oven temperature was 45° C. for 1.5 minutes, 45° C. to 160° C. at 10° C./min for 0 minutes, then 230° C. at 35° C./min for 14 minutes for a run time of 29 minutes. Flame ionization detection was used at 260° C. with 40 mL/min helium makeup gas. Results are shown in Table 2.

TABLE 2

Retention times of fermentation products in solvent phase.

| GC 302/310 Normalized to 10 µL injections | FW | Solvent Retention Time, min | Range of Standards, g/L |
|---|---|---|---|
| isobutyraldehyde | 72.11 | 2.75 | 0.7-10.4 |
| ethanol | 46.07 | 3.62 | 0.5-34 |
| isobutanol | 74.12 | 5.53 | 0.2-16 |
| 3-OH-2-butanone (acetoin) | 88.11 | 8.29 | 0.1-11 |
| (+/−)-2,3-butanediol | 90.12 | 10.94 | 0.1-19 |
| isobutyric acid | 88.11 | 11.907 | 0.1-7.9 |
| meso-butanediol | 90.12 | 11.26 | 0.1-6.5 |
| glycerol | 92.09 | 16.99 | 0.8-9 |

Samples analyzed for fatty acid butyl esters were run on Agilent 6890 GC with a 7683B injector and a G2614A auto sampler. The column was a HP-DB-FFAP column (15 meters×0.53 mm ID (Megabore), 1-micron film thickness column (30 m×0.32 mm ID, 0.25 µm film). The carrier gas was helium at a flow rate of 3.7 mL/min measured at 45° C. with constant head pressure; injector split was 1:50 at 225° C.; oven temperature was 100° C. for 2.0 minutes, 100° C. to 250° C. at 10° C./min, then 250° C. for 9 minutes for a run time of 26 minutes. Flame ionization detection was used at 300° C. with 40 mL/min helium makeup gas. The following GC standards (Nu-Chek Prep; Elysian, Minn.) were used to confirm the identity of fatty acid isobutyl ester products: iso-butyl palmitate, iso-butyl stearate, iso-butyl oleate, iso-butyl linoleate, iso-butyl linolenate, iso-butyl arachidate.

Examples 1-14 describe various fermentation conditions that may be used for the claimed methods. As an example, some fermentations were subjected to Lipase Treatment pre-liquefaction and others were subjected to Lipase Treatment post-liquefaction. In other examples, the fermentation was subjected to Heat inactivation Treatment. Following fermentation, the effective isobutanol titer (Eff Iso Titer) was measured, that is, the total grams of isobutanol produced per liter aqueous volume. Results are shown in Table 3.

Example 1

Control

Experiment identifier 2010Y014 included: Seed Flask Growth method,

Initial Fermentation Vessel Preparation method, Liquefaction method, Nutrient Addition Prior to Inoculation method, Fermentation Vessel Inoculation method, Fermentation Vessel Operating Conditions method, and all of the Analytical methods. Oleyl alcohol was added in a single batch between 0.1-1.0 hr after inoculation. The butanologen was NGCI-070.

Example 2

Experiment identifier 2010Y015 included: Seed Flask Growth method, Initial Fermentation Vessel Preparation method, Liquefaction method, Lipase Treatment Post-Liquefaction method, Nutrient Addition Prior to Inoculation method, Fermentation Vessel Inoculation method, Fermentation Vessel Operating Conditions method, and all of the Analytical methods. Oleyl alcohol was added in a single batch between 0.1-1.0 hr after inoculation. The butanologen was NGCI-070.

Example 3

Experiment identifier 2010Y016 included: Seed Flask Growth method, Initial Fermentation Vessel Preparation method, Liquefaction method, Lipase Treatment Post-Liquefaction method, Nutrient Addition Prior to Inoculation method with the exception of the exclusion of ethanol, Fermentation Vessel Inoculation method, Fermentation Vessel Operating Conditions method, and all of the Analytical methods. Oleyl alcohol was added in a single batch between 0.1-1.0 hr after inoculation. The butanologen was NGCI-070.

Example 4

Experiment identifier 2010Y017 included: Seed Flask Growth method, Initial Fermentation Vessel Preparation method, Liquefaction method, Heat Kill Treatment method Post-Liquefaction, Nutrient Addition Prior to Inoculation method with the exception of the exclusion of ethanol, Fermentation Vessel Inoculation method, Fermentation Vessel Operating Conditions method, and all of the Analytical methods. Oleyl alcohol was added in a single batch between 0.1-1.0 hr after inoculation. The butanologen was NGCI-070.

Example 5

Experiment identifier 2010Y018 included: Seed Flask Growth method, Initial Fermentation Vessel Preparation method, Liquefaction method, Lipase Treatment Post-Liquefaction method with the exception of only adding 7.2 ppm lipase after liquefaction, Heat Kill Treatment method Post-Liquefaction, Nutrient Addition Prior to Inoculation method, Fermentation Vessel Inoculation method, Fermentation Vessel Operating Conditions method, and all of the Analytical methods. Oleyl alcohol was added in a single batch between 0.1-1.0 hr after inoculation. The butanologen was NGCI-070.

Example 6

Control

Experiment identifier 2010Y019 included: Seed Flask Growth method, Initial Fermentation Vessel Preparation method, Liquefaction method, Heat Kill Treatment method Post-Liquefaction, Nutrient Addition Prior to Inoculation method, Fermentation Vessel Inoculation method, Fermentation Vessel Operating Conditions method, and all of the Analytical methods. Oleyl alcohol was added in a single batch between 0.1-1.0 hr after inoculation. The butanologen was NGCI-070.

Example 7

Control

Experiment identifier 2010Y021 included: Seed Flask Growth method, Initial Fermentation Vessel Preparation method, Lipase Treatment Pre-Liquefaction method, Liquefaction method, Heat Kill Treatment during liquefaction, Nutrient Addition Prior to Inoculation method, Fermentation Vessel Inoculation method, Fermentation Vessel Operating Conditions method, and all of the Analytical methods. Oleyl alcohol was added in a single batch between 0.1-1.0 hr after inoculation. The butanologen was NGCI-070.

Example 8

Experiment identifier 2010Y022 included: Seed Flask Growth method,

Initial Fermentation Vessel Preparation method, Liquefaction method, Nutrient Addition Prior to Inoculation method, Fermentation Vessel Inoculation method, Fermentation Vessel Operating Conditions method, and all of the Analytical methods. Oleyl alcohol was added in a single batch between 0.1-1.0 hr after inoculation. The butanologen was NGCI-070.

Example 9

Experiment identifier 2010Y023 included: Seed Flask Growth method, Initial Fermentation Vessel Preparation method, Liquefaction method, Lipase Treatment Post-Liquefaction method, no Heat Kill Treatment, Nutrient Addition Prior to Inoculation method, Fermentation Vessel Inoculation method, Fermentation Vessel Operating Conditions method, and all of the Analytical methods. Corn oil fatty acids made from crude corn oil was added in a single batch between 0.1-1.0 hr after inoculation. The butanologen was NGCI-070.

Example 10

Experiment identifier 2010Y024 included: Seed Flask Growth method, Initial Fermentation Vessel Preparation method, Lipase Treatment Pre-Liquefaction method, Liquefaction method, Heat Kill Treatment during liquefaction, Nutrient Addition Prior to Inoculation method with the exception of there being no addition of ethanol, Fermentation Vessel Inoculation method, Fermentation Vessel Operating Conditions method, and all of the Analytical methods. Oleyl alcohol was added in a single batch between 0.1-1.0 hr after inoculation. The butanologen was NGCI-070.

Example 11

Experiment identifier 2010Y029 included: Seed Flask Growth method, Initial Fermentation Vessel Preparation method, Lipase Treatment Pre-Liquefaction method, Liquefaction method, Heat Kill Treatment during liquefaction, Nutrient Addition Prior to Inoculation method, Fermentation Vessel Inoculation method, Fermentation Vessel Operating Conditions method, and all of the Analytical methods. Corn oil fatty acids made from crude corn oil was added in a single batch between 0.1-1.0 hr after inoculation. The butanologen was NGCI-070.

Example 12

Experiment identifier 2010Y030 included: Seed Flask Growth method, Initial Fermentation Vessel Preparation method, Lipase Treatment Pre-Liquefaction method, Liquefaction method, Heat Kill Treatment during liquefaction, Nutrient Addition Prior to Inoculation method with the exception of there being no addition of ethanol, Fermentation Vessel Inoculation method, Fermentation Vessel Operating Conditions method, and all of the Analytical methods. Corn oil fatty acids made from crude corn oil was added in a single batch between 0.1-1.0 hr after inoculation. The butanologen was NGCI-070.

Example 13

Control

Experiment identifier 2010Y031 included: Seed Flask Growth method, Initial Fermentation Vessel Preparation method, Liquefaction method, Lipase Treatment Post Liquefaction method, no Heat Kill Treatment, Nutrient Addition Prior to Inoculation method with the exception of there being no addition of ethanol, Fermentation Vessel Inoculation method, Fermentation Vessel Operating Conditions method, and all of the Analytical methods. Corn oil fatty acids made from crude corn oil was added in a single batch between 0.1-1.0 hr after inoculation. The butanologen was NGCI-070.

Example 14

Experiment identifier 2010Y032 included: Seed Flask Growth method, Initial Fermentation Vessel Preparation method, Liquefaction method, Lipase Treatment Post-Liquefaction method, no Heat Kill Treatment, Nutrient Addition Prior to Inoculation method, Fermentation Vessel Inoculation method, Fermentation Vessel Operating Conditions method, and all of the Analytical methods. Corn oil fatty acids made from crude corn oil was added in a single batch between 0.1-1.0 hr after inoculation. The butanologen was NGCI-070.

TABLE 3

Fermentation conditions for Examples 1-14.

| Example # | Experimental Identifier | Lipase | Max cell Count × $10^7$ | Ethanol g/L | Solvent | Heat Kill Lipase | Eff Iso Titer g/L* | max Eff Iso rate g/L/h |
|---|---|---|---|---|---|---|---|---|
| 1 | 2010Y014 | none | 27.2 | 5 | Oleyl alcohol | none | 56.0 | 0.79 |
| 2 | 2010Y015 | 10 ppm | 31.5 | 5 | Oleyl alcohol | none | 52.4 | 0.74 |
| 3 | 2010Y016 | 10 ppm | 6.7 | 0 | Oleyl alcohol | none | 25.9 | 0.36 |
| 4 | 2010Y017 | none | 7.9 | 0 | Oleyl alcohol | post-liquefaction | 17.2 | 0.25 |
| 5 | 2010Y018 | 7.2 ppm | 16.2 | 5 | Oleyl alcohol | post-liquefaction | 45.8 | 0.66 |
| 6 | 2010Y019 | none | 17.5 | 5 | Oleyl alcohol | post-liquefaction | 48.1 | 0.69 |
| 7 | 2010Y021 | 10 ppm | 21.2 | 5 | Oleyl alcohol | during liquefaction | 46.8 | 0.82 |
| 8 | 2010Y022 | none | 9 | 5 | Oleyl alcohol | during liquefaction | 56.2 | 0.87 |
| 9 | 2010Y023 | 10 ppm | 12.8 | 5 | Corn Oil Fatty Acids | none | 60.3 | 1.3 |
| 10 | 2010Y024 | 10 ppm | 25.3 | 0 | Oleyl alcohol | during liquefaction | 19.8 | 0.33 |
| 11 | 2010Y029 | 10 ppm | 21.2 | 5 | Corn Oil Fatty Acids | during liquefaction | 28.36 | 0.52 |
| 12 | 2010Y030 | 10 ppm | 9 | 0 | Corn Oil Fatty Acids | during liquefaction | 12.71 | 0.24 |
| 13 | 2010Y031 | 10 ppm | 12.8 | 0 | Corn Oil Fatty Acids | none | 18.86 | 0.35 |
| 14 | 2010Y032 | 10 ppm | 25.3 | 5 | Corn Oil Fatty Acids | none | 53.36 | 0.92 |

*The "Eff Iso Titer g/L" = total grams of isobutanol produced per liter aqueous volume

Example 15

The experimental identifier was GLNOR432A. NYLA74 (a butanediol producer—NGCI-047) was grown in 25 mL of medium in a 250 mL flask from a frozen vial to ~1OD. The pre-seed culture was transferred to a 2 L flask and grown to 1.7-1.8 OD. The medium for both flasks was:
  3.0 g/L dextrose
  3.0 g/L ethanol, anhydrous
  6.7 g/L Difco Yeast Nitrogen Base without amino acids (No. 291920)
  1.4 g/L Yeast Dropout Mix (Sigma Y2001)
  10 mL/L 1% w/v L-Leucine stock solution
  2 mL/L 1% w/v L-Tryptophan stock solution A 1 L, Applikon fermentation vessel was inoculated with 60 mL of the seed flask. The fermentation vessel contained 700 mL of the following sterile medium:
  20.0 g/L dextrose
  8.0 mL/L ethanol, anhydrous
  6.7 g/L Difco Yeast Nitrogen Base without amino acids (No. 291920)
  2.8 g/L Yeast Dropout Mix (Sigma Y2001)
  20 mL/L 1% w/v L-Leucine stock solution
  4 mL/L 1% w/v L-Tryptophan stock solution
  0.5 mL Sigma 204 Antifoam
  0.8 mL/L 1% w/v Ergesterol solution in 1:1::Tween 80:Ethanol The residual glucose was kept excess with a 50% w/w glucose solution. The dissolved oxygen concentration of the fermentation vessel was controlled at 30% with stir control. The pH was controlled at pH=5.5. The fermentation vessel was sparged with 0.3 slpm of sterile, house air. The temperature was controlled at 30° C.

Example 16

The experimental identifier was GLNOR434A. This example is the same as example 15 with the exception of the addition of 3 g of oleic acid and the addition of 3 g of palmitic acid prior to inoculation. NYLA74 (a butanediol producer—NGCI-047) was the biocatalyst.

Figure 7:
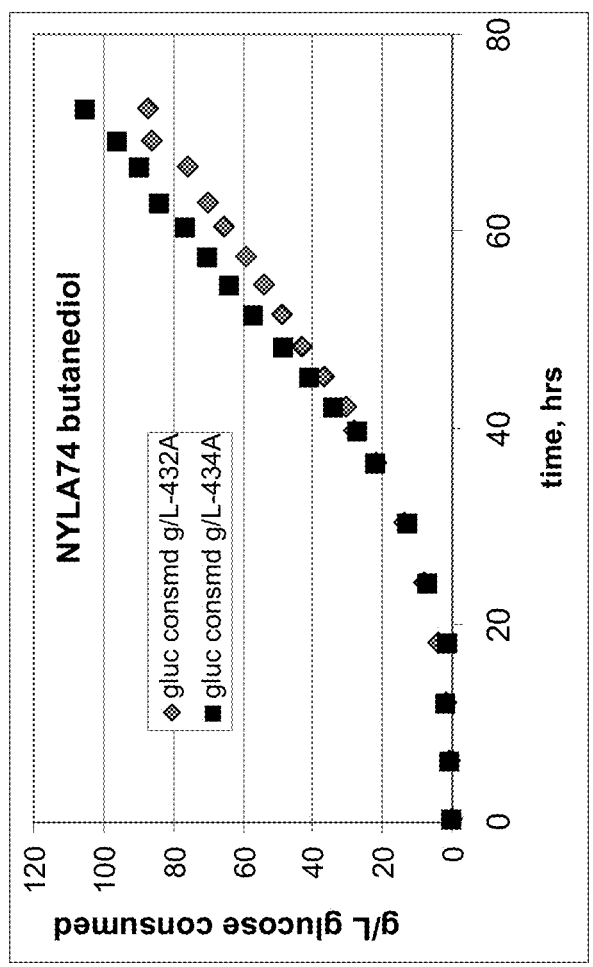
FIG. 7 is a chart illustrating the effect that the presence of fatty acids in a fermentation vessel has on glucose consumption for butanologen strain NGCI-047.

FIG. 7 shows that there were more grams per liter of glucose consumed in the fermentation vessel that received the fatty acids. The squares represent the fermentation vessel that received oleic acid and palmitic acid. The circles represent the fermentation vessel that did not receive any extra fatty acids.

Example 17

The experimental identifier was GLNOR435A. This example was the same as example 15 except it was inoculated with NYLA74 (an isobutanol producer—NGCI-049).

Example 18

The experimental identifier was GLNOR437A. This example was the same as Example 16 except it was inoculated with NYLA74 (an isobutanol producer) (NGCI-049).

Figure 8:
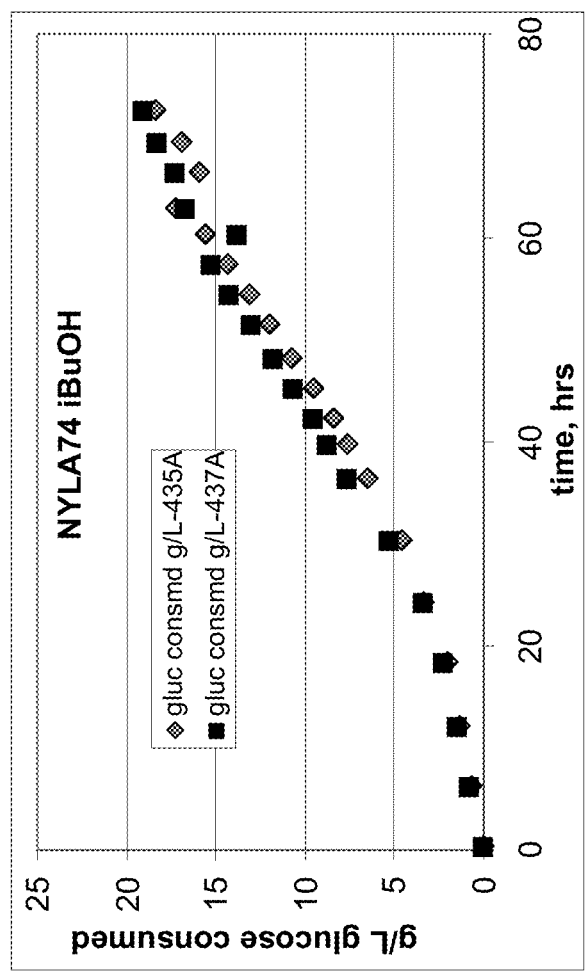
FIG. 8 is a chart illustrating the effect that the presence of fatty acids in a fermentation vessel has on glucose consumption for butanologen strain NGCI-049.

FIG. 8 shows that there were more grams per liter of glucose consumed in the fermentation vessel that received the fatty acids. The squares represent the fermentation vessel that received oleic acid and palmitic acid. The circles represent the fermentation vessel that did not receive any extra fatty acids.

Example 19

The experimental identifier was 090420_3212. This example was run similarly to Example 15 except it was inoculated with butanologen NYLA84 (an isobutanol producer). This fermentation was run in a 1 L Sartorius fermentation vessel.

Example 20

The experimental identifier was 2009Y047. This example was run similarly to Example 16 except it was inoculated with butanologen NYLA84 (an isobutanol producer). This fermentation was run in a 1 L Sartorius fermentation.

Figure 9:
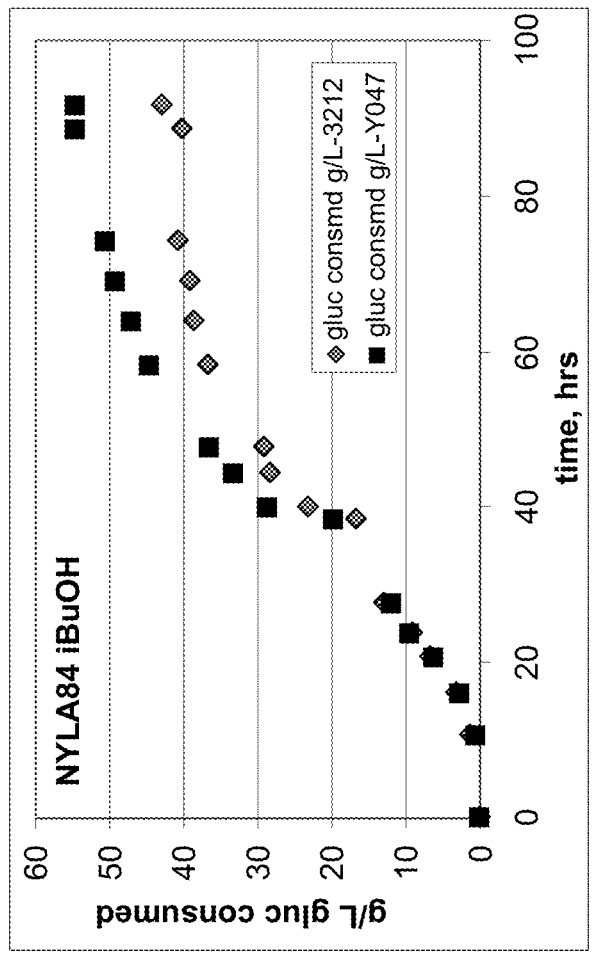
FIG. 9 is a chart illustrating the effect that the presence of fatty acids in a fermentation vessel has on glucose consumption for butanologen strain NYLA84.

FIG. 9 shows that there were more grams per liter of glucose consumed in the fermentation vessel that received the fatty acids. The squares represent the fermentation vessel that received oleic acid and palmitic acid. The circles represent the fermentation vessel that did not receive any extra fatty acids.

Table 4 shows +/−fatty acid addition, maximum optical density, and g/L glucose consumed.

TABLE 4

| Example # | Experimental Identifier | Strain | Fatty Acids Added | Product | 69 hours $OD_{600}$ | 69 hours g/L glucose consumed |
|---|---|---|---|---|---|---|
| 15 | GLNOR432A | NYLA74 | − | butanediol | 12.8 | 86.0 |
| 16 | GLNOR434A | NYLA74 | + | butanediol | 23.1 | 95.9 |
| 17 | GLNOR435A | NYLA74 | − | isobutanol | 2.4 | 16.9 |
| 18 | GLNOR437A | NYLA74 | + | isobutanol | 4.5 | 18.3 |
| 19 | 090420_3212 | NYLA84 | − | isobutanol | 9.6 | 39.3 |
| 20 | 2009Y047 | NYLA84 | + | isobutanol | 20.2 | 49.1 |

Example 21

Lipase Treatment of Liquefied Corn Mash for Simultaneous Saccharification and Fermentation with In-Situ Product Removal Using Oleyl Alcohol Samples of broth and oleyl alcohol taken from fermentations run as described above in Examples 1, 2, and 3 were analyzed for wt % lipid (derivatized as fatty acid methyl esters, FAME) and for wt % free fatty acid (FFA, derivatized as fatty acid methyl esters, FAME) according to the method described by E. G. Bligh and W. J. Dyer (Canadian Journal of Biochemistry and Physiology, 37:911-17, 1959, hereafter Reference 1). The liquefied corn mash that was prepared for each of the three fermentations was also analyzed for wt % lipid and for wt % FFA after treatment with Lipolase® 100 L (Novozymes) (10 ppm of Lipolase® total soluble protein (BCA protein analysis, Sigma Aldrich)) per kg of liquefaction reaction mass containing 30 wt % ground corn kernels). No lipase was added to the liquefied corn mash in Example 1 (control), and the fermentations described in Examples 2 and 3 containing liquefied corn mash treated with lipase (no heat inactivation of lipase) were identical except that no ethanol was added to the fermentation described in Example 3.

The % FFA in lipase-treated liquefied corn mash prepared for fermentations run as described in Examples 2 and 3 was 88% and 89%, respectively, compared to 31% without lipase treatment (Example 1). At 70 h (end of run (EOR)), the concentration of FFA in the OA phase of fermentations run as described in Examples 2 and 3 (containing active lipase) was 14% and 20%, respectively, and the corresponding increase in lipids (measured as corn oil fatty acid methyl ester derivatives) was determined by GC/MS to be due to the lipase-catalyzed esterification of COFA by OA, where COFA was first produced by lipase-catalyzed hydrolysis of corn oil in the liquefied corn mash. Results are shown in Table 5.

increased to 85° C. with stirring at 600 rpm and pH 5.8. After 120 minutes at 85° C., the mixture was cooled to 50° C. and 45.0 mL aliquots of the resulting liquefied corn mash were transferred to 50-mL polypropylene centrifuge tubes and stored frozen at −80° C.

In a first reaction, 50 g of liquefied corn mash prepared as described above was mixed with 10 ppm Lipolase® 100 L (Novozymes) for 6 h at 55° C. and with no inactivation of lipase at 85° C. for 1 h, the mixture was cooled to 30° C. In a second reaction, 50 g of liquefied corn mash was mixed with 10 ppm Lipolase® for 6 h at 55° C., then heated to 85° C. for 1 h (lipase inactivation), then cooled to 30° C. In a third reaction, 50 g of liquefied corn mash without added lipase was mixed for 6 h at 55° C., and with no heating at 85° C. for 1 h, the mixture was cooled to 30° C., 38 g of oleyl alcohol was added, and the resulting mixture stirred for 73 h at 30° C. In a fourth reaction, 50 g of liquefied corn mash without added lipase was mixed for 6 h at 55° C., then heated to 85° C. for 1 h, then cooled to 30° C. Each of the four reaction mixtures was sampled at 6 h, then 38 g of oleyl alcohol added, and the resulting mixtures stirred at 30° C. and sampled at 25 h and 73 h. Samples (both liquefied mash and oleyl alcohol

TABLE 5

Lipid and free fatty acid content of fermentations containing oleyl alcohol as ISPR solvent and active lipase

| fermentation | lipase | time (h), sample | lipids (wt %) | FFA (wt %) | lipids (g) | FFA (g) | lipids + FFA (g) | % FFA |
|---|---|---|---|---|---|---|---|---|
| Example 1 | none | liq. mash | 0.61 | 0.28 | 5.3 | 2.4 | 7.7 | 31 |
| Example 1 | none | 0.8 h, broth | 0.49 | 0.22 | 5.5 | 2.5 | 8.0 | 31 |
| Example 1 | none | 31 h, broth | 0.19 | 0.03 | 2.1 | 0.3 | 2.4 | 13 |
| Example 1 | none | 31 h, OA | 0.36 | 0.21 | 3.4 | 2.0 | 5.3 | 37 |
| Example 1 | none | 70 h, broth | 0.15 | 0.03 | 1.7 | 0.3 | 2.0 | 15 |
| Example 1 | none | 70 h, OA | 0.57 | 0.25 | 5.3 | 2.3 | 7.7 | 31 |
| Example 2 | 10 ppm | liq. mash | 0.13 | 0.97 | 1.1 | 8.5 | 9.6 | 88 |
| Example 2 | 10 ppm | 0.8 h, broth | 0.15 | 0.62 | 1.7 | 7.0 | 8.7 | 81 |
| Example 2 | 10 ppm | 31 h, broth | 0.16 | 0.05 | 1.8 | 0.5 | 2.3 | 23 |
| Example 2 | 10 ppm | 31 h, OA | 0.37 | 0.23 | 3.5 | 2.2 | 5.7 | 38 |
| Example 2 | 10 ppm | 70 h, broth | 0.17 | 0.02 | 1.9 | 0.3 | 2.2 | 13 |
| Example 2 | 10 ppm | 70 h, OA | 0.60 | 0.10 | 5.7 | 1.0 | 6.7 | 14 |
| Example 3 | 10 ppm | liq. mash | 0.12 | 0.97 | 1.0 | 8.5 | 9.5 | 89 |
| Example 3 | 10 ppm | 0.8 h, broth | 0.32 | 0.40 | 3.6 | 4.5 | 8.1 | 56 |
| Example 3 | 10 ppm | 31 h, broth | 0.17 | 0.05 | 1.9 | 0.6 | 2.5 | 24 |
| Example 3 | 10 ppm | 31 h, OA | 0.38 | 0.22 | 3.6 | 2.1 | 5.7 | 37 |
| Example 3 | 10 ppm | 70 h, broth | 0.15 | 0.02 | 1.7 | 0.2 | 1.9 | 13 |
| Example 3 | 10 ppm | 70 h, OA | 0.46 | 0.12 | 4.4 | 1.1 | 5.6 | 20 |

Example 22

Heat Inactivation of Lipase in Lipase-Treated Liquefied Corn Mash to Limit Production of Oleyl Alcohol Esters of Corn Oil Free Fatty Acids Tap water (918.4 g) was added to a jacketed 2-L resin kettle, then 474.6 g wet weight (417.6 g dry weight) of ground whole corn kernels (1.0 mm screen on hammer mill) was added with stirring. The mixture was heated to 55° C. with stirring at 300 rpm, and the pH adjusted to 5.8 with 2 N sulfuric acid. To the mixture was added 14.0 g of an aqueous solution containing 0.672 g of Spezyme®-FRED L (Genencor®, Palo Alto, Calif.), and the temperature of the mixture (OA)) were analyzed for wt % lipid (derivatized as fatty acid methyl esters, FAME) and for wt % free fatty acid (FFA, derivatized as fatty acid methyl esters, FAME) according to the method described by Reference 1.

The % FFA in the OA phase of the second reaction run with heat inactivation of lipase prior to OA addition was 99% at 25 h and 95% at 73 h, compared to only 40% FFA and 21% FFA at 25 h and 73 h, respectively, when the lipase in lipase-treated liquefied corn mash was not heat inactivated (first reaction). No significant change in % FFA was observed in the two control reactions without added lipase. Results are shown in Table 6.

TABLE 6

Lipid and free fatty acid content of a mixture of liquefied corn mash and oleyl alcohol in the presence or absence of active or heat-inactivated lipase

| reaction conditions | time (h), sample | lipids (wt %) | FFA (wt %) | lipids (mg) | FFA (mg) | lipid + FFA (mg) | % FFA |
|---|---|---|---|---|---|---|---|
| 10 ppm active lipase, no 85° C. heat treatment | 6 h, liq. mash | 0.08 | 0.71 | 41 | 345 | 386 | 89 |
|  | 25 h, liq. mash | 0.22 | 0.06 | 105 | 27 | 132 | 20 |
|  | 25 h, OA | 0.58 | 0.39 | 212 | 143 | 355 | 40 |
|  | 73 h, liq. mash | 0.25 | 0.05 | 121 | 22 | 143 | 18 |
|  | 73 h, OA | 0.91 | 0.24 | 333 | 88 | 420 | 21 |
| 10 ppm inactive lipase, 85° C. heat treatment | 6 h, liq. mash | 0.06 | 0.45 | 28 | 224 | 252 | 89 |
|  | 25 h, liq. mash | 0.10 | 0.11 | 49 | 54 | 103 | 53 |
|  | 25 h, OA | 0.02 | 0.96 | 8 | 366 | 374 | 99 |
|  | 73 h, liq. mash | 0.24 | 0.15 | 117 | 72 | 189 | 62 |
|  | 73 h, OA | 0.06 | 1.11 | 23 | 424 | 447 | 95 |
| no lipase, no 85° C. heat treatment | 6 h, liq. mash | 0.80 | 0.40 | 401 | 199 | 599 | 33 |
|  | 25 h, liq. mash | 0.30 | 0.05 | 147 | 25 | 173 | 15 |
|  | 25 h, OA | 0.55 | 0.36 | 212 | 139 | 351 | 40 |
|  | 73 h, liq. mash | 0.23 | 0.05 | 117 | 26 | 143 | 23 |
|  | 73 h, OA | 0.79 | 0.42 | 305 | 162 | 467 | 34 |
| no lipase, 85° C. heat treatment | 6 h, liq. mash | 0.74 | 0.36 | 370 | 183 | 553 | 33 |
|  | 25 h, liq. mash | 0.31 | 0.05 | 156 | 27 | 183 | 15 |
|  | 25 h, OA | 0.60 | 0.35 | 233 | 136 | 369 | 37 |
|  | 73 h, liq. mash | 0.20 | 0.05 | 99 | 23 | 121 | 23 |
|  | 73 h, OA | 0.84 | 0.41 | 326 | 159 | 486 | 33 |

Example 23

Heat Inactivation of Lipase in Lipase-Treated Liquefied Corn Mash for Simultaneous Saccharification and Fermentation with In-Situ Product Removal Using Oleyl Alcohol Three fermentations were run as described above in Examples 4, 5, and 6. No lipase was added to the liquefied corn mash in Examples 4 and 6 prior to fermentation, and the Lipase Treatment of the liquefied corn mash in the fermentation described in Example 5 (using 7.2 ppm of Lipolase® total soluble protein) was followed immediately by Heat Inactivation Treatment (to completely inactivate the lipase), and subsequently followed by Nutrient Addition Prior to Inoculation and fermentation. The % FFA in liquefied corn mash prepared without lipase treatment for fermentations run as described in Examples 4 and 6 was 31% and 34%, respectively, compared to 89% with lipase treatment (Example 5). Over the course of the fermentations listed in Table 10, the concentration of FFA in the OA phase did not decrease in any of the three fermentations, including that containing heat-inactivated lipase. The % FFA in the OA phase of the fermentation run according to Example 5 (with heat inactivation of lipase prior to fermentation) was 95% at 70 h (end of run (EOR)), compared to only 33% FFA for the remaining two fermentations (Examples 4 and 6) where liquefied corn mash was not treated with lipase. Results are shown in Table 7.

TABLE 7

Lipid and free fatty acid content of fermentations containing oleyl alcohol as ISPR solvent and heat-inactivated lipase (after lipase treatment of liquefied mash)

| fermentation | lipase | time (h), sample | lipids (wt %) | FFA (wt %) | lipids (g) | FFA (g) | lipid + FFA (g) | % FFA |
|---|---|---|---|---|---|---|---|---|
| Example 4 | none | liquefied mash | 0.65 | 0.30 | 7.2 | 3.3 | 10.4 | 31 |
| Example 4 | none | 0.2 h, broth | 0.56 | 0.28 | 6.6 | 3.3 | 9.9 | 33 |
| Example 4 | none | 4.3 h, broth | 0.28 | 0.09 | 3.3 | 1.0 | 4.4 | 24 |
| Example 4 | none | 4.3 h, OA | 0.45 | 0.27 | 4.0 | 2.4 | 6.4 | 37 |
| Example 4 | none | 30 h, broth | 0.17 | 0.05 | 2.0 | 0.6 | 2.7 | 24 |
| Example 4 | none | 30 h, OA | 0.63 | 0.29 | 5.7 | 2.6 | 8.3 | 32 |
| Example 4 | none | 53 h, broth | 0.13 | 0.04 | 1.5 | 0.5 | 2.0 | 23 |
| Example 4 | none | 53 h, OA | 0.67 | 0.32 | 6.0 | 2.9 | 8.9 | 32 |
| Example 4 | none | 70 h, broth | 0.13 | 0.04 | 1.5 | 0.4 | 1.9 | 23 |
| Example 4 | none | 70 h, OA | 0.64 | 0.31 | 5.8 | 2.8 | 8.5 | 33 |
| Example 5 | 7.2 ppm | liquefied mash | 0.11 | 0.89 | 1.3 | 9.9 | 11.2 | 89 |
| Example 5 | 7.2 ppm | 0.2 h, broth | 0.25 | 0.83 | 2.9 | 9.8 | 12.8 | 77 |
| Example 5 | 7.2 ppm | 4.3 h, broth | 0.14 | 0.17 | 1.6 | 2.1 | 3.7 | 56 |
| Example 5 | 7.2 ppm | 4.3 h, OA | 0.02 | 0.84 | 0.2 | 7.9 | 8.1 | 97 |
| Example 5 | 7.2 ppm | 30 h, broth | 0.08 | 0.18 | 1.0 | 2.1 | 3.1 | 68 |
| Example 5 | 7.2 ppm | 30 h, OA | 0.04 | 0.92 | 0.3 | 8.6 | 8.9 | 96 |
| Example 5 | 7.2 ppm | 53 h, broth | 0.07 | 0.11 | 0.9 | 1.3 | 2.2 | 61 |
| Example 5 | 7.2 ppm | 53 h, OA | 0.08 | 0.95 | 0.7 | 8.9 | 9.6 | 93 |
| Example 5 | 7.2 ppm | 70 h, broth | 0.08 | 0.10 | 0.9 | 1.2 | 2.1 | 55 |
| Example 5 | 7.2 ppm | 70 h, OA | 0.05 | 0.94 | 0.4 | 8.8 | 9.2 | 95 |
| Example 6 | none | liquefied mash | 0.66 | 0.34 | 7.3 | 3.8 | 11.1 | 34 |
| Example 6 | none | 0.2 h, broth | 0.63 | 0.34 | 7.6 | 4.0 | 11.6 | 34 |
| Example 6 | none | 4.3 h, broth | 0.33 | 0.10 | 3.9 | 1.2 | 5.1 | 23 |
| Example 6 | none | 4.3 h, OA | 0.45 | 0.27 | 4.0 | 2.4 | 6.4 | 38 |

TABLE 7-continued

Lipid and free fatty acid content of fermentations containing oleyl alcohol as ISPR solvent and heat-inactivated lipase (after lipase treatment of liquefied mash)

| fermentation | lipase | time (h), sample | lipids (wt %) | FFA (wt %) | lipids (g) | FFA (g) | lipid + FFA (g) | % FFA |
|---|---|---|---|---|---|---|---|---|
| Example 6 | none | 30 h, broth | 0.17 | 0.06 | 2.1 | 0.8 | 2.8 | 26 |
| Example 6 | none | 30 h, OA | 0.69 | 0.33 | 6.2 | 3.0 | 9.1 | 32 |
| Example 6 | none | 53 h, broth | 0.14 | 0.05 | 1.6 | 0.5 | 2.2 | 25 |
| Example 6 | none | 53 h, OA | 0.72 | 0.35 | 6.4 | 3.1 | 9.5 | 33 |
| Example 6 | none | 70 h, broth | 0.15 | 0.05 | 1.8 | 0.6 | 2.4 | 25 |
| Example 6 | none | 70 h, OA | 0.70 | 0.34 | 6.2 | 3.0 | 9.2 | 33 |

Example 24

Lipase Treatment of Ground Whole Corn Kernels Prior to Liquefaction

Tap water (1377.6 g) was added into each of two jacketed 2-L resin kettles, then 711.9 g wet weight (625.8 g dry weight) of ground whole corn kernels (1.0 mm screen on hammer mill) was added to each kettle with stirring. Each mixture was heated to 55° C. with stirring at 300 rpm, and the pH adjusted to 5.8 with 2 N sulfuric acid. To each mixture was added 21.0 g of an aqueous solution containing 1.008 g of Spezyme®-FRED L (Genencor®, Palo Alto, Calif.). To one mixture was then added 10.5 mL of aqueous solution of Lipolase® 100L Solution (21 mg total soluble protein, 10 ppm lipase final concentration) and to the second mixture was added 1.05 mL of aqueous solution of Lipolase® 100L Solution (2.1 mg total soluble protein, 1.0 ppm lipase final concentration). Samples were withdrawn from each reaction mixture at 1 h, 2 h, 4 h and 6 h at 55° C., then the temperature of the mixture was increased to 85° C. with stirring at 600 rpm and pH 5.8, and a sample was taken when the mixture first reached 85° C. After 120 minutes at 85° C., a sample was taken and the mixtures were cooled to 50° C. and final samples of the resulting liquefied corn mash were transferred to 50-mL polypropylene centrifuge tubes; all samples were stored frozen at −80° C.

In two separate reactions, a 50 g sample of the 10 ppm lipase-treated liquefied corn mash or a 55 g sample of the 1.0 ppm lipase-treated liquefied corn mash prepared as described above was mixed with oleyl alcohol (OA) (38 g) at 30° C. for 20 h, then the liquefied mash and OA in each reaction mixture were separated by centrifugation and each phase analyzed for wt % lipid (derivatized as fatty acid methyl esters, FAME) and for wt % free fatty acid (FFA, derivatized as fatty acid methyl esters, FAME) according to the method described by Reference 1. The % FFA in the OA phase of the liquefied mash/OA mixture prepared using heat inactivation of 10 ppm lipase during liquefaction was 98% at 20 h, compared to only 62% FFA in the OA phase of the liquefied mash/OA mixture prepared using heat inactivation of 1.0 ppm lipase during liquefaction. Results are shown in Table 8.

TABLE 8

Lipid and free fatty acid content of a mixture of liquefied corn mash and oleyl alcohol, using lipase treatment of ground corn suspension prior to liquefaction (heat inactivation of lipase during liquefaction)

| reaction conditions | time (h), sample | lipids (wt %) | FFA (wt %) | lipids (mg) | FFA (mg) | lipid + FFA (mg) | % FFA |
|---|---|---|---|---|---|---|---|
| 10 ppm lipase at 55° C. prior to liquefaction at 85° C., mix with OA for 20 h | 1 h, pre-liquefaction | 0.226 | 0.627 | 112 | 311 | 424 | 74 |
| | 2 h, pre-liquefaction | 0.199 | 0.650 | 99 | 323 | 422 | 77 |
| | 4 h, pre-liquefaction | 0.151 | 0.673 | 75 | 334 | 410 | 82 |
| | 6 h, pre-liquefaction | 0.101 | 0.700 | 50 | 348 | 398 | 87 |
| | 0 h, 85° C., liq. mash | 0.129 | 0.764 | 64 | 380 | 444 | 86 |
| | 2 h, 85° C., liq. mash | 0.129 | 0.751 | 64 | 373 | 437 | 85 |
| | 20 h, 30° C., liq. mash | 0.074 | 0.068 | 37 | 34 | 71 | 48 |
| | 20 h, 30° C., OA | 0.015 | 1.035 | 5.7 | 394 | 400 | 98 |
| 1.0 ppm lipase at 55° C. prior to liquefaction at 85° C., mix with OA for 20 h | 1 h, pre-liquefaction | 0.408 | 0.480 | 226 | 266 | 492 | 54 |
| | 2 h, pre-liquefaction | 0.401 | 0.424 | 222 | 235 | 457 | 51 |
| | 4 h, pre-liquefaction | 0.299 | 0.433 | 165 | 240 | 405 | 58 |
| | 6 h, pre-liquefaction | 0.346 | 0.453 | 192 | 251 | 442 | 57 |
| | 0 h, 85° C., liq. mash | 0.421 | 0.407 | 233 | 225 | 458 | 49 |
| | 2 h, 85° C., liq. mash | 0.424 | 0.429 | 235 | 237 | 472 | 50 |
| | 20 h, 30° C., liq. mash | 0.219 | 0.054 | 121 | 30 | 151 | 20 |
| | 20 h, 30° C., OA | 0.344 | 0.573 | 140 | 233 | 373 | 62 |

Example 25

Lipase Screening for Treatment of Ground Whole Corn Kernels Prior to Liquefaction Seven reaction mixtures containing tap water (67.9 g) and ground whole corn kernels (35.1 g wet wt., ground with 1.0 mm screen using a hammer mill) at pH 5.8 were stirred at 55° C. in stoppered flasks. A 3-mL sample (t=0 h) was removed from each flask and the sample immediately frozen on dry ice, then ca. 0.5 mL of 10 mM sodium phosphate buffer (pH 7.0) containing 1 mg total soluble protein (10 ppm final concentration in reaction mixture) of one of the following lipases (Novozymes) were added to one of each flask: Lipolase® 100 L, Lipex® 100L, Lipoclean® 2000T, Lipozyme® CALB L, Novozyme® CALA L, and Palatase 20000L; no lipase was added to the seventh flask. The resulting mixtures were stirred at 55° C. in stoppered flasks, and 3-mL samples were withdrawn from each reaction mixture at 1 h, 2 h, 4 h and 6 h and immediately frozen in dry ice until analyzed for wt % lipid (derivatized as fatty acid methyl esters, FAME) and for wt % free fatty acid (FFA, derivatized as fatty acid methyl esters, FAME) according to the method described by Reference 1, and the percent free fatty acid content was calculated relative to the total combined concentrations of lipid and free fatty acid was determined for each sample. Results are shown in Table 9.

TABLE 9

Percent free fatty acid content (% FFA) of a mixture of ground whole corn kernels using lipase treatment at 55° C. prior to liquefaction

| | % FFA time | | | | |
|---|---|---|---|---|---|
| | 0 h | 1 h | 2 h | 4 h | 6 h |
| Lipolase ® 100L | 33 | 56 | 74 | 76 | 79 |
| Lipex ® 100L | 34 | 66 | 81 | 83 | 83 |
| Lipoclean ® 2000T | 38 | 55 | 73 | 69 | 65 |
| Lipozyme ® CALB L | 39 | 38 | 37 | 43 | 41 |
| Novozyme ® CALA L | 37 | 40 | 44 | 44 | 45 |
| Palatase ® 20000L | 37 | 49 | 59 | 62 | 66 |
| no enzyme | 38 | 33 | 37 | 41 | 42 |

Example 26

Lipase Treatment of Ground Whole Corn Kernels Prior to Simultaneous Saccharification and Fermentation with In-Situ Product Removal Using Oleyl Alcohol Three fermentations were run as described above in Examples 7, 8, and 10. For fermentations run as described in Examples 7 and 10, lipase (10 ppm of Lipolase® total soluble protein) was added to the suspension of ground corn and heated at 55° C. for 6 h prior to Liquefaction to produce a liquefied corn mash containing heat-inactivated lipase. No lipase was added to the suspension of ground corn used to prepare liquefied corn mash for the fermentation described in Example 8, but the suspension was subjected to the same heating step at 55° C. prior to liquefaction. The % FFA in lipase-treated liquefied corn mash prepared for fermentations run as described in Examples 7 and 10 was 83% and 86%, respectively, compare to 41% without lipase treatment (Example 8). Over the course of the fermentations, the concentration of FFA did not decrease in any of the fermentations, including that containing heat-inactivated lipase. The % FFA in the OA phase of the fermentation run according to Examples 7 and 10 (with heat inactivation of lipase prior to fermentation) was 97% at 70 h (end of run (EOR)), compared to only 49% FFA for the fermentation run according to Example 8 where ground whole corn kernels had not been treated with lipase prior to liquefaction. Results are shown in Table 10.

TABLE 10

Lipid and free fatty acid content of fermentations containing oleyl alcohol as ISPR solvent and heat-inactivated lipase (lipase treatment of ground corn suspension prior to liquefaction)

| fermentation | lipase | time (h), sample | lipids (wt %) | FFA (wt %) | lipids (g) | FFA (g) | lipid + FFA (g) | % FFA |
|---|---|---|---|---|---|---|---|---|
| Example 7 | 10 ppm | pre-lipase/pre-liq. | 0.65 | 0.22 | 7.1 | 2.4 | 9.4 | 25 |
| Example 7 | 10 ppm | post-lipase/pre-liq. | 0.22 | 0.65 | 2.4 | 7.0 | 9.5 | 74 |
| Example 7 | 10 ppm | liquefied mash | 0.17 | 0.79 | 1.8 | 8.5 | 10.3 | 83 |
| Example 7 | 10 ppm | 0.3 h, broth | 0.16 | 0.79 | 1.8 | 8.9 | 10.7 | 83 |
| Example 7 | 10 ppm | 4.8 h, broth | 0.14 | 0.31 | 1.6 | 3.5 | 5.1 | 69 |
| Example 7 | 10 ppm | 4.8 h, OA | 0.04 | 0.68 | 0.3 | 5.4 | 5.6 | 95 |
| Example 7 | 10 ppm | 29 h, broth | 0.10 | 0.12 | 1.2 | 1.3 | 2.5 | 53 |
| Example 7 | 10 ppm | 29 h, OA | 0.03 | 1.05 | 0.2 | 8.2 | 8.4 | 98 |
| Example 7 | 10 ppm | 53 h, broth | | | | | | |
| Example 7 | 10 ppm | 53 h, OA | 0.07 | 1.14 | 0.5 | 9.0 | 9.5 | 95 |
| Example 7 | 10 ppm | 70 h, broth | 0.11 | 0.07 | 1.2 | 0.8 | 2.0 | 39 |
| Example 7 | 10 ppm | 70 h, OA | 0.03 | 1.10 | 0.2 | 8.7 | 8.9 | 97 |
| Example 8 | none | pre-lipase/pre-liq. | 0.62 | 0.23 | 6.7 | 2.5 | 9.2 | 27 |
| Example 8 | none | post-lipase/pre-liq. | 0.57 | 0.26 | 6.2 | 2.8 | 9.0 | 31 |
| Example 8 | none | liquefied mash | 0.52 | 0.36 | 5.6 | 4.0 | 9.6 | 41 |
| Example 8 | none | 0.3 h, broth | 0.50 | 0.33 | 5.7 | 3.8 | 9.4 | 40 |
| Example 8 | none | 4.8 h, broth | 0.47 | 0.14 | 5.3 | 1.6 | 6.9 | 24 |
| Example 8 | none | 4.8 h, OA | 0.12 | 0.32 | 1.0 | 2.9 | 3.9 | 73 |
| Example 8 | none | 29 h, broth | 0.30 | 0.05 | 3.4 | 0.6 | 4.0 | 16 |
| Example 8 | none | 29 h, OA | 0.31 | 0.46 | 2.7 | 4.1 | 6.9 | 60 |
| Example 8 | none | 53 h, broth | | | | | | |
| Example 8 | none | 53 h, OA | 0.47 | 0.50 | 4.2 | 4.4 | 8.6 | 51 |
| Example 8 | none | 70 h, broth | 0.22 | 0.04 | 2.5 | 0.5 | 3.0 | 17 |
| Example 8 | none | 70 h, OA | 0.40 | 0.39 | 3.6 | 3.5 | 7.0 | 49 |
| Example 10 | 10 ppm | pre-lipase/pre-liq. | 0.67 | 0.23 | 7.4 | 2.5 | 9.9 | 25 |
| Example 10 | 10 ppm | post-lipase/pre-liq. | 0.19 | 0.69 | 2.1 | 7.6 | 9.7 | 78 |
| Example 10 | 10 ppm | liquefied mash | 0.14 | 0.85 | 1.6 | 9.4 | 11.0 | 86 |
| Example 10 | 10 ppm | 0.3 h, broth | 0.13 | 0.82 | 1.5 | 9.4 | 10.9 | 86 |
| Example 10 | 10 ppm | 4.8 h, broth | 0.11 | 0.29 | 1.3 | 3.3 | 4.6 | 72 |
| Example 10 | 10 ppm | 4.8 h, OA | 0.04 | 0.60 | 0.3 | 5.2 | 5.6 | 94 |
| Example 10 | 10 ppm | 29 h, broth | 0.09 | 0.14 | 1.0 | 1.6 | 2.6 | 61 |
| Example 10 | 10 ppm | 29 h, OA | 0.01 | 0.96 | 0.1 | 8.4 | 8.5 | 99 |
| Example 10 | 10 ppm | 53 h, broth | | | | | | |
| Example 10 | 10 ppm | 53 h, OA | 0.02 | 0.95 | 0.2 | 8.3 | 8.4 | 98 |
| Example 10 | 10 ppm | 70 h, broth | 0.09 | 0.08 | 1.1 | 0.9 | 1.9 | 45 |
| Example 10 | 10 ppm | 70 h, OA | 0.03 | 0.99 | 0.3 | 8.7 | 9.0 | 97 |

Example 27

Lipase Treatment of Ground Whole Corn Kernels or Liquefied Corn Mash for Simultaneous Saccharification and Fermentation with In-Situ Product Removal Using Corn Oil Fatty Acids (COFA)

Five fermentations were run as described above in Examples 9, 11, 12, 13, and 14. For the fermentations run as described in Examples 9, 13, and 14, lipase (10 ppm of Lipolase® total soluble protein) was added after Liquefaction and there was no heat-inactivation of lipase. Fermentations run as described in Examples 9 and 14 had 5 g/L of ethanol added prior to inoculation, whereas the fermentation run as described in Example 13 had no added ethanol. The fermentations run as described in Examples 11 and 12 employed the addition of 10 ppm Lipolase® total soluble protein to the suspension of ground corn prior to liquefaction, resulting in heat inactivation of lipase during liquefaction. The fermentation run as described in Example 11 had 5 g/L of ethanol added prior to inoculation, whereas the fermentation run as described in Example 12 had no added ethanol. The final total grams of isobutanol (i-BuOH) present in the COFA phase of the fermentations containing active lipase was significantly greater than the final total grams of i-BuOH present in the COFA phase of the fermentations containing inactive lipase. The final total grams of isobutanol (i-BuOH) present in the fermentation broths containing active lipase were only slightly less than the final total grams of i-BuOH present in the fermentation broths containing inactive lipase, such that the overall production of i-BuOH (as a combination of free i-BuOH and isobutyl esters of COFA (FABE)) was significantly greater in the presence of active lipase when compared to that obtained in the presence of heat-inactivated lipase. Results are shown in Tables 11 and 12.

TABLE 11

Dependence of the production of free isobutanol (i-BuOH) and isobutyl esters of COFA (FABE) in fermentations containing corn oil fatty acids (COFA) as ISPR solvent on presence (Examples 9, 13, and 14) or absence (Examples 11 and 12) of active lipase (COFA phase analysis)

| fermentation | fermentation time (h) | g i-BuOH/ kg COFA | g FABE/ kg COFA | g i-BuOH from FABE/ kg COFA | total g i-BuOH/ kg COFA |
|---|---|---|---|---|---|
| Example 9  | 4.5  | 2.4  | 0.0   | 0    | 2.4  |
| Example 9  | 28.8 | 5.4  | 70.9  | 16.5 | 22.0 |
| Example 9  | 52.4 | 8.9  | 199.0 | 46.4 | 55.3 |
| Example 9  | 69.3 | 4.9  | 230.9 | 53.9 | 69.3 |
| Example 11 | 6.6  | 2.3  | 0.0   | 0.0  | 2.3  |
| Example 11 | 53.5 | 25.1 | 2.9   | 0.6  | 25.7 |
| Example 11 | 71.1 | 24.4 | 6.3   | 1.4  | 25.8 |
| Example 12 | 6.6  | 2.3  | 0.0   | 0.0  | 2.3  |
| Example 12 | 53.5 | 12.8 | 1.6   | 0.4  | 13.2 |
| Example 12 | 71.1 | 12.8 | 3.0   | 0.7  | 13.5 |
| Example 13 | 6.6  | 2.3  | 0.0   | 0.0  | 2.3  |
| Example 13 | 53.5 | 4.9  | 72.1  | 16.0 | 20.9 |
| Example 13 | 71.1 | 4.6  | 91.4  | 20.3 | 24.9 |
| Example 14 | 6.6  | 2.1  | 0.0   | 0.0  | 2.1  |
| Example 14 | 53.5 | 9.8  | 197.2 | 43.8 | 53.6 |
| Example 14 | 71.1 | 4.9  | 244.5 | 54.3 | 59.2 |

TABLE 12

Dependence of the production of free isobutanol (i-BuOH) and isobutyl esters of COFA (FABE) in fermentations containing corn oil fatty acids (COFA) as ISPR solvent on presence (Examples 9, 13, and 14) or absence (Examples 11 and 12) of active lipase (fermentation broth analysis)

| sample | fermentation time (h) | g i-BuOH/ kg broth | g FABE/ kg broth | g i-BuOH from FABE/ kg broth | total g i-BuOH/ kg broth |
|---|---|---|---|---|---|
| Example 9  | 4.5  | 0.0 | 0.0  | 0   | 0   |
| Example 9  | 28.8 | 0.0 | 12.6 | 2.9 | 2.9 |
| Example 9  | 52.4 | 0.0 | 30.3 | 7.1 | 7.1 |
| Example 9  | 69.3 | 0.0 | 24.7 | 5.8 | 5.8 |
| Example 11 | 6.6  | 0.0 | 0.0  | 0   | 0.0 |
| Example 11 | 53.5 | 9.8 | 0.0  | 0   | 9.8 |
| Example 11 | 71.1 | 9.5 | 0.0  | 0   | 9.5 |
| Example 12 | 6.6  | 0.0 | 0.0  | 0   | 0   |
| Example 12 | 53.5 | 3.8 | 0.0  | 0.0 | 3.8 |
| Example 12 | 71.1 | 5.1 | 0.0  | 0.0 | 5.1 |
| Example 13 | 6.6  | 0.0 | 0.0  | 0   | 0   |
| Example 13 | 53.5 | 2.1 | 3.0  | 0.7 | 2.8 |
| Example 13 | 71.1 | 2.1 | 7.4  | 1.6 | 3.7 |
| Example 14 | 6.6  | 0.0 | 0.0  | 0   | 0.0 |
| Example 14 | 53.5 | 2.9 | 22.4 | 5.0 | 7.9 |
| Example 14 | 71.1 | 3.3 | 19.3 | 4.3 | 7.6 |

Example 28

Dependence of Isobutyl-COFA Ester Concentration on Aqueous/COFA Ratio in Lipase-Catalyzed Reactions Reaction mixtures containing aqueous 2-(N-morpholino) ethanesulfonic acid buffer (0.20 M, pH 5.2), isobutanol (2-methyl-1-propanol), lipase (Lipolase® 100 L; Novozymes) and corn oil fatty acids prepared from corn oil (Table 13) were stirred at 30° C., and samples were withdrawn from each reaction mixture at predetermined times, immediately centrifuged, and the aqueous and organic layers separated and analyzed for isobutanol (i-BuOH) and isobutyl esters of corn oil fatty acids (i-BuO-COFA) (Table 14).

TABLE 13

Reaction conditions for conversion of isobutanol (i-BuOH) to isobutyl esters of corn oil fatty acids (i-BuO-COFA)

| reaction | MES (0.2M) (g) | i-BuOH (g) | COFA (g) | lipase (ppm) |
|---|---|---|---|---|
| 1 | 45.96 | 3.6 | 43.4  | 10 |
| 2 | 45.96 | 3.6 | 21.7  | 10 |
| 3 | 45.96 | 3.6 | 10.85 | 10 |
| 4 | 45.96 | 3.6 | 43.4  | 4  |
| 5 | 45.96 | 3.6 | 43.4  | 0  |

TABLE 14

Weights of isobutanol (i-BuOH) and isobutyl esters of corn oil fatty acids (i-BuO-COFA) present in the aqueous fraction (AQ) and organic fraction (ORG) for reactions described in Table 13

| reaction | time (h) | total i-BuOH (g) (AQ) | total i-BuOH (g) (ORG) | free i-BuOH (g) (ORG) | i-BuOH from i-BuO-COFA (g) (ORG) | i-BuO-COFA (g) (ORG) |
|---|---|---|---|---|---|---|
| 1 | 0.1 | 0.77 | 2.83 | 2.77 | 0.05 | 0.24 |
| 1 | 1   | 0.76 | 2.84 | 2.58 | 0.25 | 1.13 |
| 1 | 2   | 0.74 | 2.86 | 2.41 | 0.44 | 2.00 |

TABLE 14-continued

Weights of isobutanol (i-BuOH) and isobutyl esters of corn oil fatty acids (i-BuO-COFA) present in the aqueous fraction (AQ) and organic fraction (ORG) for reactions described in Table 13

| reaction | time (h) | total i-BuOH (g) (AQ) | total i-BuOH (g) (ORG) | free i-BuOH (g) (ORG) | i-BuOH from i-BuO-COFA (g) (ORG) | i-BuO-COFA (g) (ORG) |
|---|---|---|---|---|---|---|
| 1 | 4 | 0.66 | 2.94 | 2.05 | 0.89 | 4.03 |
| 1 | 6 | 0.63 | 2.97 | 1.43 | 1.54 | 6.93 |
| 1 | 21.5 | 0.28 | 3.32 | 0.34 | 2.98 | 13.4 |
| 1 | 25.5 | 0.23 | 3.37 | 0.29 | 3.08 | 13.8 |
| 2 | 0.1 | 1.17 | 2.43 | 2.36 | 0.07 | 0.30 |
| 2 | 1 | 1.09 | 2.51 | 2.26 | 0.24 | 1.10 |
| 2 | 2 | 1.07 | 2.53 | 2.19 | 0.34 | 1.52 |
| 2 | 4 | 1.03 | 2.57 | 1.99 | 0.59 | 2.64 |
| 2 | 6 | 1.00 | 2.60 | 1.70 | 0.90 | 4.04 |
| 2 | 21.5 | 0.75 | 2.85 | 0.58 | 2.27 | 10.2 |
| 2 | 25.5 | 0.59 | 3.01 | 0.49 | 2.52 | 11.4 |
| 3 | 0.1 | 1.56 | 2.04 | 1.98 | 0.06 | 0.27 |
| 3 | 1 | 1.55 | 2.05 | 1.77 | 0.28 | 1.24 |
| 3 | 2 | 1.49 | 2.11 | 1.65 | 0.46 | 2.08 |
| 3 | 4 | 1.45 | 2.15 | 1.28 | 0.87 | 3.92 |
| 3 | 6 | 1.33 | 2.27 | 0.96 | 1.31 | 5.92 |
| 3 | 21.5 | 1.12 | 2.48 | 0.26 | 2.22 | 10.0 |
| 3 | 25.5 | 0.88 | 2.72 | 0.26 | 2.46 | 11.1 |
| 4 | 0.1 | 0.84 | 2.76 | 2.75 | 0.02 | 0.07 |
| 4 | 1 | 0.78 | 2.82 | 2.73 | 0.09 | 0.40 |
| 4 | 2 | 0.83 | 2.77 | 2.59 | 0.17 | 0.79 |
| 4 | 4 | 0.78 | 2.82 | 2.44 | 0.38 | 1.71 |
| 4 | 6 | 0.78 | 2.82 | 2.10 | 0.72 | 3.25 |
| 4 | 21.5 | 0.58 | 3.02 | 1.12 | 1.90 | 8.57 |
| 4 | 25.5 | 0.51 | 3.09 | 0.97 | 2.11 | 9.51 |
| 5 | 0.1 | 0.90 | 2.70 | 2.70 | 0.00 | 0.00 |
| 5 | 1 | 0.90 | 2.70 | 2.70 | 0.00 | 0.00 |
| 5 | 2 | 0.92 | 2.68 | 2.68 | 0.00 | 0.00 |
| 5 | 4 | 0.89 | 2.71 | 2.70 | 0.00 | 0.02 |
| 5 | 6 | 0.92 | 2.68 | 2.62 | 0.06 | 0.29 |
| 5 | 21.5 | 0.90 | 2.70 | 2.62 | 0.08 | 0.37 |
| 5 | 25.5 | 0.89 | 2.71 | 2.62 | 0.09 | 0.41 |

Example 29

Dependence of Isobutyl-COFA Ester Concentration on Aqueous/COFA Ratio in Lipase-Catalyzed Reactions Reaction mixtures containing aqueous 2-(N-morpholino) ethanesulfonic acid buffer (0.20 M, pH 5.2), isobutanol (2-methyl-1-propanol) or n-butanol, lipase (Lipolase® 100 L; Novozymes) and corn oil fatty acids prepared from corn oil (Table 15) were stirred at 30° C., and samples were withdrawn from each reaction mixture at predetermined times, immediately centrifuged, and the aqueous and organic layers separated and analyzed for isobutanol (i-BuOH) or n-butanol (n-BuOH) and isobutyl- or butyl esters of corn oil fatty acids (BuO-COFA) (Table 16).

TABLE 15

Reaction conditions for conversion of isobutanol (i-BuOH) or n-butanol (n-BuOH) to butyl esters of corn oil fatty acids (BuO-COFA)

| reaction | butanol | MES (0.2M) (g) | butanol (g) | COFA (g) | lipase (ppm) |
|---|---|---|---|---|---|
| 6 | iso-butanol | 45.96 | 3.6 | 13.5 | 10 |
| 7 | n-butanol | 45.96 | 3.6 | 13.5 | 10 |
| 8 | iso-butanol | 45.96 | 3.6 | 13.5 | 0 |
| 9 | isobutanol | 45.96 | 3.6 | 13.5 | 4 |

TABLE 16

Weights of isobutanol (i-BuOH) or n-butanol (n-BuOH) and butyl esters of corn oil fatty acids (BuO-COFA) present in the aqueous fraction (AQ) and organic fraction (ORG) for reactions described in Table 15

| reaction | time (h) | total i-BuOH (g) (AQ) | total i-BuOH (g) (ORG) | total i-BuOH (g) (ORG) | i-BuOH (g) (ORG) | i-BuO-from i-BuO-COFA (g) (ORG) |
|---|---|---|---|---|---|---|
| 6 | 0 | 1.46 | 2.14 | 2.11 | 0.04 | 0.16 |
| 6 | 2 | 1.41 | 2.19 | 1.63 | 0.56 | 2.51 |
| 6 | 4 | 1.27 | 2.33 | 1.31 | 1.02 | 4.58 |
| 6 | 21 | 0.66 | 2.94 | 0.29 | 2.65 | 12.0 |
| 6 | 25 | 0.60 | 3.00 | 0.26 | 2.73 | 12.3 |
| 6 | 46 | 0.54 | 3.06 | 0.22 | 2.83 | 12.8 |

| reaction | time (h) | total n-BuOH (g) (AQ) | total n-BuOH (g) (ORG) | n-BuOH (g) (ORG) | n-BuOH from n-BuO-COFA (g) (ORG) | n-BuO-COFA (g) (ORG) |
|---|---|---|---|---|---|---|
| 7 | 0 | 1.31 | 2.29 | 2.26 | 0.03 | 0.11 |
| 7 | 2 | 1.26 | 2.34 | 1.89 | 0.45 | 2.03 |
| 7 | 4 | 1.20 | 2.40 | 1.66 | 0.74 | 3.35 |
| 7 | 21 | 0.81 | 2.79 | 0.50 | 2.29 | 10.3 |
| 7 | 25 | 0.77 | 2.83 | 0.40 | 2.43 | 11.0 |
| 7 | 46 | 0.50 | 3.10 | 0.23 | 2.87 | 12.9 |

| | | total i- | total i- | i-BuOH | i-BuOH from i- | i-BuO-COFA |

TABLE 16-continued

Weights of isobutanol (i-BuOH) or n-butanol (n-BuOH) and butyl esters of corn oil fatty acids (BuO-COFA) present in the aqueous fraction (AQ) and organic fraction (ORG) for reactions described in Table 15

| reaction | time (h) | BuOH (g) (AQ) | BuOH (g) (ORG) | (g) (ORG) | BuO-COFA (g) (ORG) | (g) (ORG) |
|---|---|---|---|---|---|---|
| 8 | 0 | 1.62 | 1.98 | 1.98 | 0.00 | 0.01 |
| 8 | 2 | 1.56 | 2.04 | 2.04 | 0.00 | 0.00 |
| 8 | 4 | 1.59 | 2.01 | 2.01 | 0.00 | 0.00 |
| 8 | 21 | 1.59 | 2.01 | 2.00 | 0.01 | 0.04 |
| 8 | 25 | 1.55 | 2.05 | 2.04 | 0.01 | 0.04 |
| 8 | 46 | 1.45 | 2.15 | 2.12 | 0.02 | 0.11 |

| reaction | time (h) | total i-BuOH (g) (AQ) | total i-BuOH (g) (ORG) | i-BuOH (g) (ORG) | i-BuOH from i-BuO-COFA (g) (ORG) | i-BuO-COFA (g) (ORG) |
|---|---|---|---|---|---|---|
| 9 | 0 | 1.57 | 2.03 | 2.02 | 0.01 | 0.04 |
| 9 | 2 | 1.54 | 2.06 | 1.86 | 0.19 | 0.86 |
| 9 | 4 | 1.44 | 2.16 | 1.79 | 0.36 | 1.64 |
| 9 | 21 | 1.14 | 2.46 | 0.95 | 1.51 | 6.82 |
| 9 | 25 | 1.10 | 2.50 | 0.83 | 1.67 | 7.50 |
| 9 | 46 | 0.78 | 2.82 | 0.44 | 2.37 | 10.7 |

Example 30

Production of Iso-Butyl Oleate by Lipase-Catalyzed Reaction of Iso-Butanol and Oleic Acid Reaction mixtures containing aqueous 2-(N-morpholino) ethanesulfonic acid buffer (0.20 M, pH 5.2), isobutanol (2-methyl-1-propanol), lipase (0 ppm or 10 ppm Lipolase® 100 L; Novozymes) and oleic acid (Alfa Aesar) (Table 17) were stirred at 30° C., and samples were withdrawn from each reaction mixture at predetermined times, immediately centrifuged, and the aqueous and organic layers separated and analyzed for isobutanol (i-BuOH) and iso-butyl oleate (i-BuO-oleate) (Table 18).

TABLE 17

Reaction conditions for conversion of isobutanol (i-BuOH) to iso-butyl oleate (i-BuO-oleate)

| reaction | MES (0.2M) (g) | i-BuOH (g) | oleic acid (g) | lipase (ppm) |
|---|---|---|---|---|
| 10 | 46.11 | 3.64 | 14.62 | 10 |
| 11 | 46.10 | 3.59 | 14.40 | 0 |

TABLE 18

Weights of isobutanol (i-BuOH) and iso-butyl oleate (i-BuO-COFA) present in the aqueous fraction (AQ) and organic fraction (ORG) for reactions described in Table 17

| reaction | time (h) | total i-BuOH (g) (AQ) | total i-BuOH (g) (ORG) | i-BuOH (g) (ORG) | i-BuOH from i-BuO-oleate (g) (ORG) | i-BuO-oleate (g) (ORG) |
|---|---|---|---|---|---|---|
| 10 | 0 | 1.37 | 2.28 | 2.24 | 0.04 | 0.18 |
| 10 | 2 | 1.30 | 2.34 | 1.95 | 0.40 | 1.81 |
| 10 | 4 | 1.28 | 2.37 | 1.82 | 0.55 | 2.53 |
| 10 | 6 | 1.22 | 2.42 | 1.71 | 0.72 | 3.27 |
| 10 | 23 | 0.92 | 2.72 | 0.71 | 2.01 | 9.20 |
| 10 | 27 | 0.89 | 2.75 | 0.65 | 2.11 | 9.62 |
| 10 | 47 | 0.81 | 2.84 | 0.55 | 2.29 | 10.5 |
| 10 | 51 | 0.82 | 2.83 | 0.54 | 2.29 | 10.5 |
| 11 | 0 | 1.44 | 2.16 | 2.16 | 0.00 | 0.00 |
| 11 | 2 | 1.45 | 2.15 | 2.15 | 0.00 | 0.00 |
| 11 | 4 | 1.44 | 2.16 | 2.16 | 0.00 | 0.00 |
| 11 | 6 | 1.43 | 2.16 | 2.16 | 0.00 | 0.00 |
| 11 | 23 | 1.49 | 2.10 | 2.10 | 0.01 | 0.02 |
| 11 | 27 | 1.46 | 2.14 | 2.13 | 0.01 | 0.04 |
| 11 | 47 | 1.48 | 2.12 | 2.09 | 0.02 | 0.10 |
| 11 | 51 | 1.52 | 2.07 | 2.05 | 0.02 | 0.11 |

Example 31

Production of Iso-Butyl Oleate by Lipase-Catalyzed Reaction of Iso-Butanol and Oleic Acid Reaction mixtures containing aqueous 2-(N-morpholino) ethanesulfonic acid buffer (MES, 0.20 M, pH 5.2), isobutanol (2-methyl-1-propanol), oleic acid (Alfa Aesar), and lipase (10 ppm) from Lipolase® 100L, Lipex® 100L, Lipozyme® CALB L, Novozyme® CALA L, Palatase® from Novozymes, or lipase (10 ppm) from *Pseudomonas fluorescens, Pseudomonas cepacia, Mucor miehei*, hog pancreas, *Candida cylindracea, Rhizopus niveus, Candida antarctica, Rhizopus arrhizus* or *Aspergillus* from SigmaAldrich (Table 19), were stirred at 30° C., and samples were withdrawn from each reaction mixture at predetermined times, immediately centrifuged, and the aqueous and organic layers separated and analyzed for isobutanol (i-BuOH) and iso-butyl oleate (1-BuO-oleate) (Table 20).

TABLE 19

Reaction conditions for conversion of isobutanol (i-BuOH) to iso-butyl oleate (i-BuO-oleate)

| MES (0.2M) (g) | i-BuOH (g) | oleic acid (g) | lipase (ppm) |
|---|---|---|---|
| 46.105 | 3.601 | 13.72 | 10 |

TABLE 20

Weights of isobutanol (i-BuOH) and iso-butyl oleate (i-BuO-oleate) present in the aqueous fraction (AQ) and organic fraction (ORG) for reactions described in Table 19

| lipase | time (h) | total i-BuOH (g) (AQ) | total i-BuOH (g) (ORG) | i-BuOH (g) (ORG) | i-BuOH from i-BuO-oleate (g) (ORG) | i-BuO-oleate (g) (ORG) |
|---|---|---|---|---|---|---|
| Lipolase ® 100L | 23 | 1.55 | 2.05 | 1.47 | 0.59 | 2.68 |
| Lipex ® 100L | 23 | 0.65 | 2.95 | 0.30 | 2.65 | 12.09 |
| Lipozyme ® CALB L | 23 | 1.01 | 2.59 | 0.82 | 1.77 | 8.08 |
| Novozyme ® CALA L | 23 | 1.39 | 2.22 | 2.16 | 0.06 | 0.27 |
| Palatase ® | 23 | 1.27 | 2.33 | 1.43 | 0.91 | 4.14 |
| *Pseudomonas fluorescens* | 23 | 1.38 | 2.22 | 1.97 | 0.25 | 1.14 |
| *Pseudomonas cepacia* | 23 | 1.39 | 2.21 | 1.95 | 0.26 | 1.20 |
| *Mucor miehei* | 23 | 1.29 | 2.31 | 1.57 | 0.75 | 3.42 |
| hog pancreas | 23 | 1.40 | 2.20 | 2.19 | 0.01 | 0.04 |
| *Candida cylindracea* | 23 | 1.15 | 2.45 | 1.08 | 1.37 | 6.25 |
| *Rhizopus niveus* | 23 | 1.39 | 2.21 | 2.19 | 0.02 | 0.11 |
| *Candida antarctica* | 23 | 1.37 | 2.24 | 2.08 | 0.15 | 0.69 |
| *Rhizopus arrhizus* | 23 | 1.01 | 2.59 | 0.81 | 1.78 | 8.12 |
| *Aspergillus* | 23 | 1.36 | 2.24 | 2.06 | 0.18 | 0.82 |

Example 32

Production of Iso-Butyl COFA Esters by Phospholipase-Catalyzed Reaction of Iso-Butanol and Corn Oil Fatty Acids (COFA)

Reaction mixtures containing aqueous 2-(N-morpholino) ethanesulfonic acid buffer (0.20 M, pH 5.3), isobutanol (2-methyl-1-propanol), phospholipase (Phospholipase A; SigmaAldrich, L3295-250) and corn oil fatty acids prepared from corn oil were stirred at 30° C. (Table 21), and samples were withdrawn from each reaction mixture at predetermined times, immediately centrifuged, and the aqueous and organic layers separated and analyzed for isobutanol (i-BuOH) and isobutyl esters of corn oil fatty acids (1-BuO-COFA) (Table 22).

TABLE 21

Reaction conditions for conversion of isobutanol (i-BuOH) to isobutyl esters of corn oil fatty acids (i-BuO-COFA)

| reaction # | MES buffer (0.2M) (g) | i-BuOH (g) | COFA (g) | lipase (ppm) |
|---|---|---|---|---|
| 1 | 46.1 | 3.6 | 14.7 | 10 |
| 2 | 46.1 | 3.6 | 14.7 | 3 |
| 3 | 46.1 | 3.6 | 14.7 | 0 |

TABLE 22

Weights of isobutanol (i-BuOH) and isobutyl esters of corn oil fatty acids (i-BuO-COFA) present in the aqueous fraction (AQ) and organic fraction (ORG) for reactions described in Table 21

| reaction | time (h) | total i-BuOH (g) (AQ) | total i-BuOH (g) (ORG) | free i-BuOH (g) (ORG) | i-BuOH - from i-BuO-COFA (g) (ORG) | i-BuO-COFA (g) (ORG) |
|---|---|---|---|---|---|---|
| 1 | 0.1 | 1.29 | 2.39 | 2.39 | 0.00 | 0.00 |
| 1 | 2 | 1.24 | 2.44 | 2.38 | 0.06 | 0.26 |
| 1 | 20 | 1.25 | 2.43 | 2.22 | 0.21 | 0.96 |
| 1 | 24 | 1.26 | 2.42 | 2.19 | 0.23 | 1.03 |
| 1 | 44 | 1.27 | 2.41 | 2.13 | 0.28 | 1.28 |
| 1 | 48 | 1.22 | 2.46 | 2.15 | 0.31 | 1.41 |
| 2 | 0.1 | 1.27 | 2.34 | 2.34 | 0.00 | 0.00 |
| 2 | 2 | 1.25 | 2.35 | 2.33 | 0.02 | 0.08 |
| 2 | 20 | 1.24 | 2.37 | 2.30 | 0.07 | 0.30 |
| 2 | 24 | 1.22 | 2.38 | 2.31 | 0.07 | 0.32 |
| 2 | 44 | 1.33 | 2.28 | 2.18 | 0.10 | 0.44 |
| 2 | 48 | 1.23 | 2.38 | 2.27 | 0.11 | 0.48 |
| 3 | 0.1 | 1.27 | 2.33 | 2.33 | 0.00 | 0.00 |
| 3 | 2 | 1.26 | 2.34 | 2.34 | 0.00 | 0.00 |
| 3 | 20 | 1.22 | 2.38 | 2.37 | 0.01 | 0.07 |
| 3 | 24 | 1.25 | 2.35 | 2.33 | 0.02 | 0.08 |
| 3 | 44 | 1.24 | 2.36 | 2.32 | 0.04 | 0.18 |
| 3 | 48 | 1.24 | 2.36 | 2.32 | 0.04 | 0.18 |

Example 33

Comparison of Partition Coefficients for Isobutanol Between Water and Extractant Aqueous solutions of isobutanol (30 g/L) were mixed with corn oil fatty acids (COFA), oleic acid, or corn oil triglycerides, and their measured partition coefficients reported in the table relative to the measured partition coefficient for oleyl alcohol. Results are shown in Table 23.

TABLE 23

Relative partition coefficients for isobutanol (30 g/L) between water and extractant

| extractant | isobutanol partition coefficient, relative to oleyl alcohol |
|---|---|
| oleyl alcohol | 100% |
| corn oil fatty acids | 91% |
| corn oil fatty acid isobutyl esters | 43% |
| corn oil triglycerides | 10% |

Example 34

Hydroxylated Triglycerides from Corn Oil

To a three-neck 500 mL flask equipped with a mechanical stirrer and addition funnel was added corn oil (50.0 g), toluene (25.0 mL), Amberlyte IR-120 resin (12.5 g), and glacial acetic acid (7.5 g). The resulting mixture was heated to 60° C., and then hydrogen peroxide (41.8 g of 30% $H_2O_2$ in water) was added dropwise over one hour. The mixture was stirred at 60° C. for two hours, upon which time the reaction mixture was worked up: resin was removed by filtration, and the filtrate partitioned between ethyl acetate (75 mL) and water (50 mL). After the layers were separated, the organic layer was washed with sat. aq. $NaHCO_3$ solution (50 mL), and brine (50 mL). The organic layer was dried over anh. $Na_2SO_4$ and concentrated in vacuo to obtain 48.9 g of yellow oil. The $^1H$ NMR analysis of the crude reaction product showed that 63% of double bonds were epoxidized.

A. Corn Oil Hydroxylation (63% Hydroxylation)

To a three-neck 500 mL flask equipped with a mechanical stirrer and addition funnel was added corn oil (50.0 g), toluene (25.0 mL), Amberlyte IR-120 resin (12.5 g), and glacial acetic acid (7.5 g). The resulting mixture was heated to 60° C., and then hydrogen peroxide (41.8 g of 30% $H_2O_2$ in water) was added dropwise over one hour. The mixture was stirred at 60° C. for two hours, upon which time the reaction mixture was worked up: resin was removed by filtration, and the filtrate partitioned between ethyl acetate (75 mL) and water (50 mL). After the layers were separated, the organic layer was washed with sat. aq. $NaHCO_3$ solution (50 mL), and brine (50 mL). The organic layer was dried over anh. $Na_2SO_4$ and concentrated in vacuo to obtain 48.9 g of yellow oil. The $^1H$ NMR analysis of the crude reaction product showed that 63% of double bonds were epoxidized.

To a 500 mL round bottom flask was added epoxidized corn oil (20.0 g), tetrahydrofuran (THF) (100.0 mL), and sulfuric acid (50 mL of 1.7 M aqueous solution). The cloudy mixture was stirred for two hours at 50° C., and then worked up by partitioning between water (100 mL) and ethyl acetate (200 mL). The organic layer was washed with water (3×50 mL) and then brine (50 mL). The organic layer was dried over anh. $Na_2SO_4$ and concentrated in vacuo to obtain 19.9 g of dark yellow oil (63% hydroxylation corn oil).

B. Corn Oil Hydroxylation (47% Hydroxylation)

To a three-neck 500 mL flask, equipped with a mechanical stirrer and addition funnel was added corn oil (50.0 g), toluene (25.0 mL), Amberlyte IR-120 resin (12.5 g), and glacial acetic acid (7.5 g). The resulting mixture was heated to 60° C., and then hydrogen peroxide (41.8 g of 30% $H_2O_2$ in water) was added dropwise over one hour. The mixture was stirred at 60° C. for one hour, upon which time the reaction mixture was worked up: the resin was removed by filtration, and the filtrate partitioned between ethyl acetate (75 mL) and water (50 mL). After the layers were separated, the organic layer was washed with sat. aq. $NaHCO_3$ solution (50 mL), and brine (50 mL). The organic layer was dried over anh. $Na_2SO_4$ and concentrated in vacuo to obtain 49.8 g of yellow oil. The $^1H$ NMR analysis of the crude reaction product showed that 47% of double bonds were epoxidized.

To a 500 mL round bottom flask was added epoxidized corn oil (20.0 g), THF (100.0 mL), and sulfuric acid (50 mL of 1.7M aqueous solution). The cloudy mixture was stirred for two hours at 50° C., and then worked up by partitioning between water (100 mL) and ethyl acetate (200 mL). The organic layer was washed with water (3×50 mL) and then brine (50 mL). The organic layer was dried over anh. $Na_2SO_4$ and concentrated in vacuo to obtain 19.2 g of dark yellow oil (47% hydroxylation corn oil).

C. Corn Oil Hydroxylation (28% Hydroxylation)

To a three-neck 500 mL flask, equipped with a mechanical stirrer and addition funnel was added corn oil (50.0 g), toluene (25.0 mL), Amberlyte IR-120 resin (12.5 g), and glacial acetic acid (7.5 g). The resulting mixture was heated to 60° C., and then hydrogen peroxide (41.8 g of 30% $H_2O_2$ in water) was added dropwise over one hour. The mixture was stirred at 60° C. for two hours, upon which time the reaction mixture was worked up: the resin was removed by filtration, and the filtrate partitioned between ethyl acetate (75 mL) and water (50 mL). After the layers were separated, the organic layer was washed with sat. aq. $NaHCO_3$ solution (50 mL), and brine (50 mL). The organic layer was dried over anh. $Na_2SO_4$ and concentrated in vacuo to obtain 47.2 g of yellow oil. The $^1H$ NMR analysis of the crude reaction product showed that 28% of double bonds were epoxidized.

To a 500 mL round bottom flask was added epoxidized corn oil (20.0 g), THF (100.0 mL), and sulfuric acid (50 mL of 1.7M aqueous solution). The cloudy mixture was stirred for two hours at 50° C., and then worked up by partitioning between water (100 mL) and ethyl acetate (200 mL). The organic layer was washed with water (3×50 mL) and then brine (50 mL). The organic layer was dried over anh. $Na_2SO_4$ and concentrated in vacuo to obtain 20.3 g of dark yellow oil (28% hydroxylation corn oil).

Partition Coefficient Measurement

To a 5 mL vial was added 0.910 g of the 67% hydroxylated corn oil, and 0.910 mL of 3 wt % i-BuOH water solution. The biphasic mixture was vigorously stirred using Vortex Genie® for 10 minutes. Upon mixing, the separation of layers was aided by centrifuging the mixture using Fisher Scientific Centrific 228 centrifuge (3300 rpm) for 10 minutes. 0.100 g of both layers were taken. The organic, upper layer was diluted to 1.00 mL with toluene solution of ethylene glycol diethylether (10.1 mg/mL), and the water layer was diluted to 1.00 mL with methanol solution of ethylene glycol diethylether (10.2 mg/mL). The concentrations of i-BuOH in both phases were measured using a calibrated gas chromatograph (GC). The same procedure was repeated for 47% and 28% hydroxylated corn oil. The partition coefficient thus measured was 3.2 for the 67% hydroxylated corn oil, 2.3 for the 47% hydroxylated corn oil, and 2.1 for the 28% hydroxylated corn oil.

The above outlined procedure was repeated with 6% i-BuOH water solution. The partition coefficients for 67%-, 47%-, and 28%-hydroxylated corn oils were 2.9, 2.9, and 2.0, respectively.

Example 34

Fatty Amides Plus Fatty Acids, and Pure Fatty Amides from Corn Oil

Corn oil was reacted with aqueous ammonium hydroxide in a manner similar to that described by Roe, et al., J. Am. Oil Chem. Soc. 29:18-22, 1952. Mazola® corn oil (0.818 L, 755 g) was placed in a 1 gallon stainless steel reactor to which was added 1.71 L (1540 g) of aqueous ammonium hydroxide (28% as $NH_3$). The reactor was heated with stirring to 160° C. and was maintained at that temperature with stirring for 7 h during which time the pressure reached 400 psi. The reactor was cooled and the product, a creamy white solid, was removed and the reactor rinsed with ethyl acetate. The product was dissolved in 5 L ethyl acetate and washed 5 times with 500 mL each of water which was neutralized with $H_2SO_4$. The ethyl acetate was then dried over anhydrous $Na_2SO_4$ and the solvent removed on a rotary evaporator leaving a light brown soft solid.

$^{13}C$ NMR in $CDCl_3$ indicated that the product contained an approximate 2:1 ratio of fatty amide to fatty acid and that the conversion of the corn oil to product was quantitative. The product had a melting point of 57-58° C., but dropped about 11° C. when saturated with water.

Pure corn oil fatty amide was synthesized from corn oil according to Kohlhase, et al., J. Am. Oil Chem. Soc. 48:265-270, 1971 using anhydrous ammonia with ammonium acetate as a catalyst.

Three grams of ammonium acetate were placed in a 400 mL stainless steel shaker tube to which was added 51.8 g of corn oil. Anhydrous ammonia (89.7 g) was then added and the reactor sealed and heated for 7 h at 125° C. during which time the pressure reached 1300 psi. The reactor was cooled, the light colored solid removed and the reactor rinsed with ethyl acetate. The product dissolved in ethyl acetate was then worked up as in the case of the fatty amide/fatty acid mixture above.

Fatty acids were synthesized from corn oil by base hydrolysis using NaOH. Round bottom flask (5 L) was equipped with a mechanical stirrer, thermocouple, heating mantle, condenser, and nitrogen tee. Charged with 500 g of food grade corn oil, 1 L of water and 75 g of sodium hydroxide. Mixture was heated to 90° C. and held for three hours, during which time it became a single thick, emulsion-like single phase. At the end of this time, TLC shows no remaining corn oil in the mixture. The mixture was then cooled to 72° C. and 500 mL of 25% sulfuric acid was added to acidify the mixture. It was then cooled to room temperature and 2 L of diethyl ether was added. The ether layer was washed 3×1 L with 1% sulfuric acid, 1×1 L with saturated brine, dried over $MgSO_4$, and filtered. The ether was removed by rotovap and then the oil was purged with nitrogen overnight, obtaining 470 g of a yellow oil that partially crystallized overnight. Titration for free fatty acids via AOCS method Ca 5a-40 shows a fatty acid content of 95% expressed as oleic acid. A sample was silanized by reacting 104 mg with 100 uL of N-methyl-N-(trimethylsilyl)trifluoroacetamide in 1 mL of dry pyridine. Gas chromatography-mass spectrometry (GCMS) analysis of the silanized product shows the presence of the TMS derivatives of the 16:0, 18:2, 18:1, 18:0, and 20:0 acids Three preparations: (1) the 2:1 mixture of corn oil fatty amide and corn oil fatty acid from aqueous ammonia, (2) a 2:1 mixture of pure corn oil fatty amide:pure corn oil fatty acid, and (3) a 1:2 mixture of pure corn oil fatty amide:corn oil fatty acid, were all tested for their ability to extract isobutanol from a 3% solution in water. Seven hundred milligrams of each was added to 2.1 mL of water containing 3% isobutanol in a 20 mL scintillation vial and placed on a rotary shaker overnight at 30° C. In all three cases, the organic phase became liquid at this temperature, indicating a further lowering of the melting point with the uptake of isobutanol. Fifty microliters of the upper phase were diluted with either 200 μL of toluene containing ethylene glycol diethylether (10.068 mg/mL) as a GC standard or 200 μL of isopropanol containing the same concentration of ethylene glycol diethylether. Fifty microliters of the lower phase was diluted with 150 μL of methanol and 50 μL of isopropanol containing the same concentration of ethylene glycol diethylether. The concentrations of isobutanol in both phases were determined using a calibrated GC. The partition coefficients measured were as follows: 3.81 for (1), 4.31 for (2), and 3.58 for (3).

Fatty amide/fatty acid aqueous ammonia preparation (1), and a preparation (1a) constituted by preparation (1) mixed 1:1 with pure corn oil fatty acid (equivalent to 1:2 fatty amide:fatty acid) were incubated in shake flasks with fermentation broth containing the *Saccharomyces* butanologen NGCI-070 at a ratio of 3 parts broth to 1 part amide/acid mixture. Preparation (1) was a soft solid, while preparation (1a) was a liquid at 30° C. Starting at a glucose concentration of 8.35 g/L, the shake flasks were then incubated for 25 h on an incubator shaker and the consumption of glucose followed as a function of time. Table 24 indicates that the fatty amide/fatty acid mixtures at both ratios were not toxic to the butanologen and even showed higher rates of glucose uptake than with oleyl alcohol.

TABLE 24

| | Glucose conc. (g/L) | | |
| --- | --- | --- | --- |
| Flask | Time = 0 | 18 hrs | 25 hrs |
| Oleyl Alcohol | 8.35 | 4.26 | 0 |
| Oleyl Alcohol | 8.35 | 4.46 | 0 |
| 2:1 Synthesized Fatty Amide:Fatty Acid Mix (Preparation (1)) | 8.35 | 3.06 | 0 |
| 2:1 Synthesized Fatty Amide:Fatty Acid Mix (Preparation (1)) | 8.35 | 3.22 | 0 |
| 1:1 Synthesized Fatty Amide Fatty Acid Mix:Pure Fatty Acids (Preparation (1a)) | 8.35 | 2.73 | 0 |
| 1:1 Synthesized Fatty Amide Fatty Acid Mix:Pure Fatty Acids (Preparation (1a)) | 8.35 | 2.73 | 0 |

Example 35

Fatty Alcohols from Corn Oil

With reference to the reaction of Equation IV above for producing fatty alcohols from corn oil, a 22 L, round-bottom flask equipped with a mechanical stirrer, reflux condenser with $N_2$ source, addition funnel, internal thermocouple, and rubber septum was flame-dried under nitrogen. The flask was charged with 132 g (3.30 moles) of 95% lithium aluminum hydride powder that is weighed out in a dry box and loaded into a solids addition funnel. The 22 L flask was cooled with an ice bath, and 9.0 liters of anhydrous THF were added into the reactor via a cannula. The resulting slurry was cooled to 0-5° C. and a solution of 956 g (1.10 moles) of Wesson® corn oil in 1.00 liter of anhydrous THF was added dropwise over 2-3 hours while holding the reaction temperature at 5-20° C. After adding the corn oil, the slurry was stirred overnight at ambient temperature. When the reaction was done, as verified by TLC chromatography, it was quenched by the dropwise addition of a solution of 130 g of water dissolved in 370 mL of THF. Then 130 g of 15% aqueous NaOH solution was added followed by the addition of 400 g of water. The mixture was vigorously stirred while warming to room temperature and produced a white granular solid. The solids were filtered off using a fritted-glass filter funnel and washed with additional THF. The THF was removed on a rotary evaporator and the residue was taken up in 3.00 liters of ethyl acetate. The product solution was washed with 2×1.00 L of water, 1×1.00 L of brine, dried over $Na_2SO_4$, filtered, and concentrated in vacuo to give 836 g (97%) of fatty alcohols as yellow oil. The crude fatty alcohol mixture was then distilled (140° C./1 mmHg), and used in the following partition coefficients experiments.

Partition Coefficient Experiments

To each of the five 5-mL vials were added 1 mL of fatty alcohol mixture, and 1 mL of 3 wt % i-BuOH water solution. The biphasic mixture was vigorously stirred using Vortex Genie® for 10, 20, 30, 40, and 60 minutes, respectively. Upon mixing, the separation of layers was aided by centrifuging the mixture using Fisher Scientific Centrific 228 centrifuge (3300 rpm) for 10 minutes. 0.100 mL of both layers were taken. The organic, upper layer was diluted to 1.00 mL with toluene solution of ethylene glycol diethylether, and the water layer was diluted to 1.00 mL with methanol solution of ethylene glycol diethylether. The concentrations of i-BuOH in both phases were measured using a calibrated GC. The partition coefficient thus measured was 2.70.

The same partition coefficient measurement, as described above was run for 6 wt % i-BuOH concentration. The partition coefficient thus measured was 3.06.

While various embodiments of the present invention have been described above, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the following claims and their equivalents.

All publications, patents and patent applications mentioned in this specification are indicative of the level of skill of those skilled in the art to which this invention pertains, and are herein incorporated by reference to the same extent as if each individual publication, patent or patent application was specifically and individually indicated to be incorporated by reference.

---

What is claimed is:

1. A composition comprising:
   (a) a recombinant microorganism capable of producing butanol;
   (b) fermentable carbon source selected from monosaccharides, disaccharides, oligosaccharides, polysaccharides, C5 sugars, and mixtures thereof;
   (c) at least one enzyme capable of hydrolyzing glycerides into fatty acids;
   (d) oil comprising glycerides; and
   (e) fatty acids.

2. The composition of claim 1, wherein the at least one enzyme is esterase.

3. The composition of claim 1, wherein the oil is corn, tallow, canola, capric/caprylic triglycerides, castor, coconut, cottonseed, fish, jojoba, lard, linseed, neetsfoot, oiticica, palm, peanut, rapeseed, rice, safflower, soya, sunflower, tung, jatropha and vegetable oil blends.

4. The composition of claim 1, wherein the fermentable carbon source and the oil are derived from biomass.

5. The composition of claim 4, wherein the biomass comprises corn grain, corn cobs, corn husks, corn stover, wheat, rye, wheat straw, barley, barley straw, hay, rice straw, switchgrass, sugar cane bagasse, sorghum, sugar cane, soy, and mixtures thereof.

6. The composition of claim 1, further comprising a saccharification enzyme.

7. The composition of claim 1, further comprising undissolved solids.

8. The composition of claim 1, further comprising glycerol and/or butanol.

9. The composition of claim 8, wherein the butanol is 1-butanol, 2-butanol, isobutanol, or mixtures thereof.

10. The composition of claim 2, wherein the esterase is selected from lipase, phospholipase, and lysophospholipase.

11. The composition of claim 1, wherein the recombinant microorganism comprises a butanol biosynthetic pathway.

12. The composition of claim 11, wherein the recombinant microorganism comprises an isobutanol biosynthetic pathway.

13. The composition of claim 12, wherein the recombinant microorganism comprises a reduction or elimination of pyruvate decarboxylase activity.

14. The composition of claim 1, wherein the recombinant microorganism is yeast.

15. The composition of claim 14, wherein the yeast is *Saccharomyces cerevisiae*.

* * * * *

SEQUENCE LISTING

<160> NUMBER OF SEQ ID NOS: 145

<210> SEQ ID NO 1
<211> LENGTH: 11844
<212> TYPE: DNA
<213> ORGANISM: Artificial Sequence
<220> FEATURE:
<223> OTHER INFORMATION: Plasmid

<400> SEQUENCE: 1

```
tcccattacc gacatttggg cgctatacgt gcatatgttc atgtatgtat ctgtatttaa      60
aacacttttg tattattttt cctcatatat gtgtataggt ttatacggat gatttaatta     120
ttacttcacc acccttatt tcaggctgat atcttagcct tgttactagt tagaaaaaga     180 cattttgct gtcagtcact gtcaagagat tcttttgctg gcatttcttc tagaagcaaa     240
aagagcgatg cgtctttcc gctgaaccgt tccagcaaaa aagactacca acgcaatatg     300
gattgtcaga atcatataaa agagaagcaa ataactcctt gtcttgtatc aattgcatta     360
taatatcttc ttgttagtgc aatatcatat agaagtcatc gaaatagata ttaagaaaaa     420
caaactgtac aatcaatcaa tcaatcatcg ctgaggatgt tgacaaaagc aacaaaagaa     480
caaaaatccc ttgtgaaaaa cagaggggcg gagcttgttg ttgattgctt agtggagcaa     540
ggtgtcacac atgtatttgg cattccaggt gcaaaaattg atgcggtatt tgacgcttta     600
caagataaag gacctgaaat tatcgttgcc cggcacgaac aaaacgcagc attcatggcc     660
caagcagtcg gccgtttaac tggaaaaccg ggagtcgtgt tagtcacatc aggaccgggt     720
gcctctaact tggcaacagg cctgctgaca gcgaacactg aaggagaccc tgtcgttgcg     780
cttgctggaa acgtgatccg tgcagatcgt ttaaaacgga cacatcaatc tttggataat     840
gcggcgctat tccagccgat tacaaaatac agtgtagaag ttcaagatgt aaaaaatata     900
ccggaagctg ttacaaatgc atttaggata gcgtcagcag ggcaggctgg ggccgctttt     960
gtgagctttc gcaagatgt tgtgaatgaa gtcacaaata cgaaaaacgt gcgtgctgtt    1020
gcagcgccaa aactcggtcc tgcagcagat gatgcaatca gtgcggccat agcaaaaatc    1080
caaacagcaa aacttcctgt cgttttggtc ggcatgaaag gcggaagacc ggaagcaatt    1140
aaagcggttc gcaagctttt gaaaaaggtt cagcttccat ttgttgaaac atatcaagct    1200
```

```
gccggtaccc tttctagaga tttagaggat caatattttg gccgtatcgg tttgttccgc   1260
aaccagcctg gcgatttact gctagagcag gcagatgttg ttctgacgat cggctatgac   1320
ccgattgaat atgatccgaa attctggaat atcaatggag accggacaat tatccattta   1380
gacgagatta tcgctgacat tgatcatgct taccagcctg atcttgaatt gatcggtgac   1440
attccgtcca cgatcaatca tatcgaacac gatgctgtga agtggaatt tgcagagcgt    1500 gagcagaaaa tccttctga tttaaaacaa tatatgcatg aaggtgagca ggtgcctgca    1560
gattggaaat cagacagagc gcaccctctt gaaatcgtta aagagttgcg taatgcagtc   1620
gatgatcatg ttacagtaac ttgcgatatc ggttcgcacg ccatttggat gtcacgttat   1680
ttccgcagct acgagccgtt aacattaatg atcagtaacg gtatgcaaac actcggcgtt   1740
gcgcttcctt gggcaatcgg cgcttcattg gtgaaaccgg gagaaaaagt ggtttctgtc   1800
tctggtgacg gcggtttctt attctcagca atggaattag agacagcagt tcgactaaaa   1860
gcaccaattg tacacattgt atggaacgac agcacatatg acatggttgc attccagcaa   1920
ttgaaaaaat ataaccgtac atctgcggtc gatttcggaa atatcgatat cgtgaaatat   1980
gcggaaagct tcggagcaac tggcttgcgc gtagaatcac cagaccagct ggcagatgtt   2040
ctgcgtcaag gcatgaacgc tgaaggtcct gtcatcatcg atgtcccggt tgactacagt   2100
gataacatta atttagcaag tgacaagctt ccgaaagaat tcggggaact catgaaaacg   2160
aaagctctct agttaattaa tcatgtaatt agttatgtca cgcttacatt cacgccctcc   2220
ccccacatcc gctctaaccg aaaaggaagg agttagacaa cctgaagtct aggtccctat   2280
ttattttttt atagttatgt tagtattaag aacgttattt atatttcaaa tttttctttt   2340
ttttctgtac agacgcgtgt acgcatgtaa cattatactg aaaaccttgc ttgagaaggt   2400
tttgggacgc tcgaaggctt taatttgcgg gcggccgcac ctggtaaaac ctctagtgga   2460
gtagtagatg taatcaatga agcggaagcc aaaagaccag agtagaggcc tatagaagaa   2520
actgcgatac cttttgtgat ggctaaacaa acagacatct ttttatatgt ttttacttct   2580
gtatatcgtg aagtagtaag tgataagcga atttggctaa gaacgttgta agtgaacaag   2640
ggacctcttt tgccttcaa aaaggatta aatggagtta atcattgaga tttagttttc     2700
gttagattct gtatccctaa ataactccct tacccgacgg gaaggcacaa aagacttgaa   2760
taatagcaaa cggccagtag ccaagaccaa ataatactag agttaactga tggtcttaaa   2820
caggcattac gtggtgaact ccaagaccaa tatacaaaat atcgataagt tattcttgcc   2880
caccaattta aggagcctac atcaggacag tagtaccatt cctcagagaa gaggtataca   2940
taacaagaaa atcgcgtgaa caccttatat aacttagccc gttattgagc taaaaaacct   3000
tgcaaaattt cctatgaata agaatacttc agacgtgata aaaatttact ttctaactct   3060
tctcacgctg ccctatctg ttcttccgct ctaccgtgag aaataaagca tcgagtacgg   3120
cagttcgctg tcactgaact aaaacaataa ggctagttcg aatgatgaac ttgcttgctg   3180
tcaaacttct gagttgccgc tgatgtgaca ctgtgacaat aaattcaaac cggttatagc   3240
ggtctcctcc ggtaccggtt ctgccacctc aatagagct cagtaggagt cagaacctct   3300
gcggtggctg tcagtgactc atccgcgttt cgtaagttgt gcgcgtgcac atttcgcccg   3360
ttcccgctca tcttgcagca ggcggaaatt ttcatcacgc tgtaggacgc aaaaaaaaaa   3420
taattaatcg tacaagaatc ttggaaaaaa aattgaaaaa ttttgtataa aagggatgac   3480
ctaacttgac tcaatggctt ttacacccag tattttccct ttccttgttt gttacaatta   3540
tagaagcaag acaaaaacat atagacaacc tattcctagg agttatattt ttttacccta   3600
```

```
ccagcaatat aagtaaaaaa ctgtttaaac agtatggcag ttacaatgta ttatgaagat    3660
gatgtagaag tatcagcact tgctggaaag caaattgcag taatcggtta tggttcacaa    3720
ggacatgctc acgcacagaa tttgcgtgat tctggtcaca acgttatcat tggtgtgcgc    3780
cacgaaaat cttttgataa agcaaaagaa gatggctttg aaacatttga agtaggagaa    3840
gcagtagcta aagctgatgt tattatggtt ttggcaccag atgaacttca acaatccatt    3900
tatgaagagg acatcaaacc aaacttgaaa gcaggttcag cacttggttt tgctcacgga    3960
tttaatatcc attttggcta tattaaagta ccagaagacg ttgacgtctt tatggttgcg    4020
cctaaggctc caggtcacct tgtccgtcgg acttatactg aaggttttgg tacaccagct    4080
ttgtttgttt cacaccaaaa tgcaagtggt catgcgcgtg aaatcgcaat ggattgggcc    4140
aaaggaattg gttgtgctcg agtgggaatt attgaaacaa cttttaaaga agaaacagaa    4200
gaagatttgt ttggagaaca agctgttcta tgtggaggtt tgacagcact tgttgaagcc    4260
ggttttgaaa cactgacaga agctggatac gctggcgaat tggcttactt tgaagttttg    4320
cacgaaatga aattgattgt tgacctcatg tatgaaggtg gttttactaa aatgcgtcaa    4380
tccatctcaa atactgctga gtttggcgat tatgtgactg gtccacggat tattactgac    4440
gaagttaaaa agaatatgaa gcttgttttg gctgatattc aatctggaaa atttgctcaa    4500
gatttcgttg atgacttcaa agcggggcgt ccaaaattaa tagcctatcg cgaagctgca    4560
aaaaatcttg aaattgaaaa aattggggca gagctacgtc aagcaatgcc attcacacaa    4620
tctggtgatg acgatgcctt taaaatctat cagtaaggcc ctgcaggcct atcaagtgct    4680
ggaaactttt tctcttggaa tttttgcaac atcaagtcat agtcaattga attgacccaa    4740
tttcacattt aagattttt tttttcatc cgacatacat ctgtacacta ggaagccctg    4800
tttttctgaa gcagcttcaa atatatatat tttttacata tttattatga ttcaatgaac    4860
aatctaatta aatcgaaaac aagaaccgaa acgcgaataa ataatttatt tagatggtga    4920
caagtgtata agtcctcatc gggacagcta cgatttctct ttcggttttg gctgagctac    4980
tggttgctgt gacgcagcgg cattagcgcg gcgttatgag ctaccctcgt ggcctgaaag    5040
atggcgggaa taaagcggaa ctaaaaatta ctgactgagc catattgagg tcaatttgtc    5100
aactcgtcaa gtcacgtttg gtggacggcc ccttttccaac gaatcgtata tactaacatg    5160
cgcgcgcttc ctatatacac atatacatat atatatatat atatatgtgt gcgtgtatgt    5220
gtacacctgt atttaatttc cttactcgcg ggttttttctt ttttctcaat tcttggcttc    5280
ctctttctcg agcggaccgg atcctccgcg gtgccggcag atctatttaa atggcgcgcc    5340
gacgtcaggt ggcactttc ggggaaatgt gcgcggaacc cctatttgtt tatttttcta    5400
aatacattca aatatgtatc cgctcatgag acaataaccc tgataaatgc ttcaataata    5460
ttgaaaaagg aagagtatga gtattcaaca tttccgtgtc gcccttattc ccttttttgc    5520
ggcattttgc cttcctgttt ttgctcaccc agaaacgctg tgaaagtaa aagatgctga    5580
agatcagttg ggtgcacgag tgggttacat cgaactggat ctcaacagcg gtaagatcct    5640
tgagagtttt cgccccgaag aacgttttcc aatgatgagc acttttaaag ttctgctatg    5700
tggcgcggta ttatcccgta ttgacgccgg gcaagagcaa ctcggtcgcc gcatacacta    5760
ttctcagaat gacttggttg agtactcacc agtcacagaa aagcatctta cggatggcat    5820
gacagtaaga gaattatgca gtgctgccat aaccatgagt gataacactg cggccaactt    5880
acttctgaca acgatcggag gaccgaagga gctaaccgct ttttttgcaca acatggggga    5940
```

```
tcatgtaact cgccttgatc gttgggaacc ggagctgaat gaagccatac caaacgacga   6000
gcgtgacacc acgatgcctg tagcaatggc aacaacgttg cgcaaactat taactggcga   6060
actacttact ctagcttccc ggcaacaatt aatagactgg atggaggcgg ataaagttgc   6120
aggaccactt ctgcgctcgg cccttccggc tggctggttt attgctgata atctggagc    6180
cggtgagcgt gggtctcgcg gtatcattgc agcactgggg ccagatggta agccctcccg   6240
tatcgtagtt atctcacacga cggggagtca ggcaactatg gatgaacgaa atagacagat  6300
cgctgagata ggtgcctcac tgattaagca ttggtaactg tcagaccaag tttactcata   6360
tatactttag attgatttaa aacttcattt ttaatttaaa aggatctagg tgaagatcct   6420
ttttgataat ctcatgacca aaatccctta acgtgagttt cgttccact gagcgtcaga    6480
ccccgtagaa aagatcaaag gatcttcttg agatcctttt tttctgcgcg taatctgctg   6540
cttgcaaaca aaaaaaccac cgctaccagc ggtggtttgt ttgccggatc aagagctacc   6600
aactcttttt ccgaaggtaa ctggcttcag cagagcgcag ataccaaata ctgttcttct   6660
agtgtagccg tagttaggcc accacttcaa gaactctgta gcaccgccta catacctcgc   6720
tctgctaatc ctgttaccag tggctgctgc cagtggcgat aagtcgtgtc ttaccgggtt   6780
ggactcaaga cgatagttac cggataaggc gcagcggtcg ggctgaacgg ggggttcgtg   6840
cacacagccc agcttggagc gaacgaccta caccgaactg agataccttac agcgtgagct  6900
atgagaaagc gccacgcttc ccgaagggag aaaggcggac aggtatccgg taagcggcag   6960
ggtcggaaca ggagagcgca cgagggagct tccaggggga aacgcctggt atctttatag   7020
tcctgtcggg tttcgccacc tctgacttga gcgtcgattt ttgtgatgct cgtcaggggg   7080
gcggagccta tggaaaaacg ccagcaacgc ggccttttta cggttcctgg ccttttgctg   7140
gccttttgct cacatgttct ttcctgcgtt atcccctgat tctgtggata accgtattac   7200
cgcctttgag tgagctgata ccgctcgccg cagccgaacg accgagcgca gcgagtcagt   7260
gagcgaggaa gcggaagagc gcccaatacg caaaccgcct ctccccgcgc gttggccgat   7320
tcattaatgc agctggcacg acaggtttcc cgactggaaa gcgggcagtg agcgcaacgc   7380
aattaatgtg agttagctca ctcattaggc accccaggct ttacacttta tgcttccggc   7440
tcgtatgttg tgtggaattg tgagcggata acaatttcac acaggaaaca gctatgacca   7500
tgattacgcc aagcttttc tttccaattt ttttttttc gtcattataa aaatcattac     7560
gaccgagatt cccgggtaat aactgatata attaaattga agctctaatt tgtgagttta   7620
gtatacatgc atttacttat aatacagttt tttagttttg ctggccgcat cttctcaaat   7680
atgcttccca gcctgctttt ctgtaacgtt caccctctac cttagcatcc cttccctttg   7740
caaatagtcc tcttccaaca ataataatgt cagatcctgt agagaccaca tcatccacgg   7800
ttctatactg ttgacccaat gcgtctccct tgtcatctaa acccacaccg ggtgtcataa   7860
tcaaccaatc gtaaccttca tctcttccac ccatgtctct tgagcaata aagccgataa    7920
caaaatcttt gtcgctcttc gcaatgtcaa cagtacccct agtatattct ccagtagata   7980
gggagcccct tgcatgacaat tctgctaaca tcaaaaggcc tctaggttcc tttgttactt   8040
cttctgccgc ctgcttcaaa ccgctaacaa tacctgggcc caccacccg tgtgcattcg    8100
taatgtctgc ccattctgct attctgtata caccccgcaga gtactgcaat ttgactgtat  8160
taccaatgtc agcaaatttt ctgtcttcga agagtaaaaa attgtacttg gcggataatg   8220
cctttagcgg cttaactgtg ccctccatgg aaaaatcagt caagatatcc acatgtgttt   8280
ttagtaaaca aattttggga cctaatgctt caactaactc cagtaattcc ttggtggtac   8340
```

```
gaacatccaa tgaagcacac aagtttgttt gcttttcgtg catgatatta aatagcttgg   8400
cagcaacagg actaggatga gtagcagcac gttccttata tgtagctttc gacatgattt   8460
atcttcgttt cctgcaggtt tttgttctgt gcagttgggt taagaatact gggcaatttc   8520
atgtttcttc aacactacat atgcgtatat ataccaatct aagtctgtgc tccttccttc   8580
gttcttcctt ctgttcggag attaccgaat caaaaaaatt tcaaggaaac cgaaatcaaa   8640
aaaaagaata aaaaaaaaat gatgaattga aaagcttgca tgcctgcagg tcgactctag   8700
tatactccgt ctactgtacg atacacttcc gctcaggtcc ttgtccttta acgaggcctt   8760
accactcttt tgttactcta ttgatccagc tcagcaaagg cagtgtgatc taagattcta   8820
tcttcgcgat gtagtaaaac tagctagacc gagaaagaga ctagaaatgc aaaaggcact   8880
tctacaatgg ctgccatcat tattatccga tgtgacgctg catttttttt ttttttttt   8940 ttttttttt tttttttttt tttttttttt ttttgtacaa atatcataaa aaagagaat    9000 cttttaagc aaggattttc ttaacttctt cggcgacagc atcaccgact tcggtggtac   9060
tgttggaacc acctaaatca ccagttctga tacctgcatc caaaaccttt ttaactgcat   9120
cttcaatggc tttaccttct tcaggcaagt tcaatgacaa tttcaacatc attgcagcag   9180
acaagatagt ggcgataggg ttgaccttat tctttggcaa atctggagcg gaaccatggc   9240
atggttcgta caaaccaaat gcggtgttct tgtctggcaa agaggccaag gacgcagatg   9300
gcaacaaacc caaggagcct gggataacgg aggcttcatc ggagatgata tcaccaaaca   9360
tgttgctggt gattataata ccatttaggt gggttgggtt cttaactagg atcatggcgg   9420
cagaatcaat caattgatgt tgaactttca atgtagggaa ttcgttcttg atggtttcct   9480
ccacagtttt tctccataat cttgaagagg ccaaaacatt agcttatcc aaggaccaaa    9540 taggcaatgg tggctcatgt tgtagggcca tgaaagcggc cattcttgtg attctttgca   9600
cttctggaac ggtgtattgt tcactatccc aagcgacacc atcaccatcg tcttcctttc   9660
tcttaccaaa gtaaatacct cccactaatt ctctaacaac aacgaagtca gtacctttag   9720
caaattgtgg cttgattgga gataagtcta aaagagagtc ggatgcaaag ttacatggtc   9780
ttaagttggc gtacaattga agttctttac ggattttag taaaccttgt tcaggtctaa    9840
cactaccggt accccattta ggaccaccca cagcacctaa caaaacggca tcagccttct   9900
tggaggcttc cagcgcctca tctggaagtg gaacacctgt agcatcgata gcagcaccac   9960
caattaaatg attttcgaaa tcgaacttga cattggaacg aacatcagaa atagctttaa  10020
gaaccttaat ggcttcggct gtgatttctt gaccaacgtg gtcacctggc aaaacgacga  10080
tcttcttagg ggcagacatt acaatggtat atccttgaaa tatatataaa aaaaaaaaa   10140 aaaaaaaaaa aaaaaaatgc agcttctcaa tgatattcga atacgctttg aggagataca  10200
gcctaatatc cgacaaactg ttttacagat ttacgatcgt acttgttacc catcattgaa  10260
ttttgaacat ccgaacctgg gagttttccc tgaaacagat agtatatttg aacctgtata  10320
ataatatata gtctagcgct ttacggaaga caatgtatgt atttcggttc ctggagaaac  10380
tattgcatct attgcatagg taatcttgca cgtcgcatcc ccggttcatt ttctgcgttt  10440
ccatcttgca cttcaatagc atatctttgt taacgaagca tctgtgcttc attttgtaga  10500
acaaaaatgc aacgcgagag cgctaatttt tcaaacaaag aatctgagct gcattttac   10560 agaacagaaa tgcaacgcga aagcgctatt ttaccaacga agaatctgtg cttcattttt  10620
gtaaaacaaa aatgcaacgc gagagcgcta attttttcaaa caaagaatct gagctgcatt 10680
```

```
tttacagaac agaaatgcaa cgcgagagcg ctattttacc aacaaagaat ctatacttct   10740 ttttttgttct acaaaaatgc atcccgagag cgctattttt ctaacaaagc atcttagatt   10800 acttttttc tcctttgtgc gctctataat gcagtctctt gataactttt tgcactgtag   10860
gtccgttaag gttagaagaa ggctactttg gtgtctattt tctcttccat aaaaaaagcc   10920
tgactccact tcccgcgttt actgattact agcgaagctg cgggtgcatt ttttcaagat   10980
aaaggcatcc ccgattatat tctataccga tgtggattgc gcatactttg tgaacagaaa   11040
gtgatagcgt tgatgattct tcattggtca gaaaattatg aacggtttct tctattttgt   11100
ctctatatac tacgtatagg aaatgtttac attttcgtat tgttttcgat tcactctatg   11160
aatagttctt actacaattt ttttgtctaa agagtaatac tagagataaa cataaaaaat   11220
gtagaggtcg agtttagatg caagttcaag gagcgaaagg tggatgggta ggttatatag   11280
ggatatagca cagagatata tagcaaagag atactttga gcaatgtttg tggaagcggt   11340
attcgcaata ttttagtagc tcgttacagt ccggtgcgtt tttggttttt tgaaagtgcg   11400
tcttcagagc gcttttggtt ttcaaaagcg ctctgaagtt cctatacttt ctagagaata   11460
ggaacttcgg aataggaact tcaaagcgtt tccgaaaacg agcgcttccg aaaatgcaac   11520
gcgagctgcg cacatacagc tcactgttca cgtcgcacct atatctgcgt gttgcctgta   11580
tatatatata catgagaaga acggcatagt gcgtgtttat gcttaaatgc gtacttatat   11640
gcgtctattt atgtaggatg aaaggtagtc tagtacctcc tgtgatatta tcccattcca   11700
tgcggggtat cgtatgcttc cttcagcact acccttttagc tgttctatat gctgccactc   11760
ctcaattgga ttagtctcat ccttcaatgc tatcatttcc tttgatattg gatcatatgc   11820
atagtaccga gaaactagag gatc   11844
```

<210> SEQ ID NO 2
<211> LENGTH: 15539
<212> TYPE: DNA
<213> ORGANISM: Artificial Sequence
<220> FEATURE:
<223> OTHER INFORMATION: Plasmid

<400> SEQUENCE: 2

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcgggctgg cttaactatg cggcatcaga gcagattgta ctgagagtgc    180
accataaatt cccgttttaa gagcttggtg agcgctagga gtcactgcca ggtatcgttt    240
gaacacggca ttagtcaggg aagtcataac acagtccttt cccgcaattt tcttttttcta    300 ttactcttgg cctcctctag tacactctat attttttttat gcctcggtaa tgattttcat    360 ttttttttt ccacctagcg gatgactctt ttttttttctt agcgattggc attatcacat    420
aatgaattat acattatata agtaatgtg atttcttcga agaatatact aaaaaatgag    480
caggcaagat aaacgaaggc aaagatgaca gagcagaaag ccctagtaaa gcgtattaca    540
aatgaaacca agattcagat tgcgatctct ttaaagggtg gtcccctagc gatagagcac    600
tcgatcttcc cagaaaaaga ggcagaagca gtagcagaac aggccacaca atcgcaagtg    660
attaacgtcc acacaggtat agggtttctg gaccatatga tacatgctct ggccaagcat    720
tccggctggt cgctaatcgt tgagtgcatt ggtgacttac acatagacga ccatcacacc    780
actgaagact gcgggattgc tctcggtcaa gcttttaaag aggccctagg ggccgtgcgt    840
ggagtaaaaa ggtttggatc aggatttgcg ccttttggatg aggcactttc cagagcggtg    900
```

-continued

```
gtagatctttt cgaacaggcc gtacgcagtt gtcgaacttg gtttgcaaag ggagaaagta      960
ggagatctct cttgcgagat gatcccgcat tttcttgaaa gctttgcaga ggctagcaga     1020
attaccctcc acgttgattg tctgcgaggc aagaatgatc atcaccgtag tgagagtgcg     1080
ttcaaggctc ttgcggttgc cataagagaa gccacctcgc ccaatggtac caacgatgtt     1140
ccctccacca aaggtgttct tatgtagtga caccgattat ttaaagctgc agcatacgat     1200
atatatacat gtgtatatat gtatacctat gaatgtcagt aagtatgtat acgaacagta     1260
tgatactgaa gatgacaagg taatgcatca ttctatacgt gtcattctga acgaggcgcg     1320
cttttccttt ttcttttttgc ttttttcttt ttttctctt gaactcgacg gatctatgcg     1380
gtgtgaaata ccgcacagat gcgtaaggag aaaataccgc atcaggaaat tgtaagcgtt     1440
aatattttgt taaaattcgc gttaaatttt tgttaaatca gctcattttt taaccaatag     1500
gccgaaatcg gcaaaatccc ttataaatca aagaataga ccgagatagg gttgagtgtt     1560
gttccagttt ggaacaagag tccactatta agaacgtgg actccaacgt caaagggcga     1620 aaaccgtct atcagggcga tggcccacta cgtgaaccat caccctaatc aagttttttg     1680
gggtcgaggt gccgtaaagc actaaatcgg aaccctaaag ggagccccg atttagagct     1740 tgacggggaa agccggcgaa cgtggcgaga aggaaggga agaaagcgaa aggagcgggc     1800
gctagggcgc tggcaagtgt agcggtcacg ctgcgcgtaa ccaccacacc cgccgcgctt     1860
aatgcgccgc tacagggcgc gtccattcgc cattcaggct gcgcaactgt tgggaagggc     1920
gcggtgcggg cctcttcgct attacgccag ctggcgaaag gggatgtgc tgcaaggcga     1980 ttaagttggg taacgccagg gttttcccag tcacgacgtt gtaaaacgac ggccagtgag     2040
cgcgcgtaat acgactcact atagggcgaa ttgggtaccg gccccccct cgaggtcgac     2100 ggcgcgccac tggtagagag cgactttgta tgccccaatt gcgaaacccg cgatatcctt     2160
ctcgattctt tagtacccga ccaggacaag gaaaaggagg tcgaaacgtt tttgaagaaa     2220
caagaggaac tacacggaag ctctaaagat ggcaaccagc cagaaactaa gaaaatgaag     2280
ttgatggatc caactggcac cgctggcttg aacaacaata ccagccttcc aacttctgta     2340
aataacggcg gtacgccagt gccaccagta ccgttacctt tcggtatacc tccttttcccc     2400 atgtttccaa tgcccttcat gcctccaacg gctactatca caaatcctca tcaagctgac     2460
gcaagcccta agaaatgaat aacaatactg acagtactaa ataattgcct acttggcttc     2520
acatacgttg catacgtcga tatagataat aatgataatg acagcaggat tatcgtaata     2580
cgtaatagct gaaaatctca aaaatgtgtg ggtcattacg taaataatga taggaatggg     2640
attcttctat ttttcctttt tccattctag cagccgtcgg gaaaacgtgg catcctctct     2700
ttcgggctca attggagtca cgctgccgtg agcatcctct ctttccatat ctaacaactg     2760
agcacgtaac caatggaaaa gcatgagctt agcgttgctc caaaaaagta ttggatggtt     2820
aataccattt gtctgttctc ttctgacttt gactcctcaa aaaaaaaaat ctacaatcaa     2880
cagatcgctt caattacgcc ctcacaaaaa cttttttcct tcttcttcgc ccacgttaaa     2940
ttttatccct catgttgtct aacggatttc tgcacttgat ttattataaa aagacaaaga     3000
cataatactt ctctatcaat ttcagttatt gttcttcctt gcgttattct tctgttcttc     3060
ttttttcttt gtcatatata accataacca agtaatacat attcaaacta gtatgactga     3120
caaaaaaact cttaaagact taagaaatcg tagttctgtt tacgattcaa tggttaaatc     3180
acctaatcgt gctatgttgc gtgcaactgg tatgcaagat gaagactttg aaaaacctat     3240
```

```
cgtcggtgtc atttcaactt gggctgaaaa cacaccttgt aatatccact tacatgactt    3300
tggtaaacta gccaaagtcg gtgttaagga agctggtgct tggccagttc agttcggaac    3360
aatcacggtt tctgatggaa tcgccatggg aacccaagga atgcgtttct ccttgacatc    3420
tcgtgatatt attgcagatt ctattgaagc agccatggga ggtcataatg cggatgcttt    3480
tgtagccatt ggcggttgtg ataaaaacat gcccggttct gttatcgcta tggctaacat    3540
ggatatccca gccattttg cttacggcgg aacaattgca cctggtaatt tagacggcaa    3600
agatatcgat ttagtctctg tctttgaagg tgtcggccat tggaaccacg gcgatatgac    3660
caaagaagaa gttaaagctt tggaatgtaa tgcttgtccc ggtcctggag ctgcggtgg    3720 tatgtatact gctaacacaa tggcgacagc tattgaagtt ttgggactta gccttccggg    3780
ttcatcttct cacccggctg aatccgcaga aagaaagca gatattgaag aagctggtcg    3840
cgctgttgtc aaaatgctcg aaatgggctt aaaaccttct gacattttaa cgcgtgaagc    3900
ttttgaagat gctattactg taactatggc tctgggaggt tcaaccaact caaccccttca    3960 cctcttagct attgcccatg ctgctaatgt ggaattgaca cttgatgatt tcaatacttt    4020
ccaagaaaaa gttcctcatt tggctgattt gaaaccttct ggtcaatatg tattccaaga    4080
cctttacaag gtcggagggg taccagcagt tatgaaatat ctccttaaaa atggcttcct    4140
tcatggtgac cgtatcactt gtactggcaa acagtcgct gaaaatttga aggcttttga    4200
tgatttaaca cctggtcaaa aggttattat gccgcttgaa atcctaaac gtgaagatgg    4260 tccgctcatt attctccatg gtaacttggc tccagacggt gccgttgcca agtttctgg    4320 tgtaaaagtg cgtcgtcatg tcggtcctgc taaggtcttt aattctgaag aagaagccat    4380
tgaagctgtc ttgaatgatg atattgttga tggtgatgtt gttgtcgtac gttttgtagg    4440
accaaagggc ggtcctggta tgcctgaaat gctttcctt tcatcaatga ttgttggtaa    4500
agggcaaggt gaaaaagttg ccttctgac agatggccgc ttctcaggtg gtacttatgg    4560
tcttgtcgtg ggtcatatcg ctcctgaagc acaagatggc ggtccaatcg cctacctgca    4620
aacaggagac atagtcacta ttgaccaaga cactaaggaa ttacactttg atatctccga    4680
tgaagagtta aaacatcgtc aagagaccat tgaattgcca ccgctctatt cacgcggtat    4740
ccttggtaaa tatgctcaca tcgtttcgtc tgcttctagg ggagccgtaa cagactttg    4800 gaagcctgaa gaaactggca aaaaatgttg tcctggttgc tgtggttaag cggccgcgtt    4860
aattcaaatt aattgatata gttttttaat gagtattgaa tctgtttaga aataatggaa    4920
tattattttt atttatttat ttatattatt ggtcggctct tttcttctga aggtcaatga    4980
caaaatgata tgaaggaaat aatgatttct aaaattttac aacgtaagat attttacaa    5040 aagcctagct catcttttgt catgcactat tttactcacg cttgaaatta acggccagtc    5100
cactgcggag tcatttcaaa gtcatcctaa tcgatctatc gttttgata gctcattttg    5160 gagttcgcga ttgtcttctg ttattcacaa ctgttttaat tttattttca ttctggaact    5220
cttcgagttc tttgtaaagt ctttcatagt agcttacttt atcctccaac atatttaact    5280
tcatgtcaat ttcggctctt aaattttcca catcatcaag ttcaacatca tcttttaact    5340
tgaatttatt ctctagctct tccaaccaag cctcattgct ccttgattta ctggtgaaaa    5400
gtgatacact ttgcgcgcaa tccaggtcaa aactttcctg caaagaattc accaatttct    5460
cgacatcata gtacaatttg ttttgttctc ccatcacaat ttaatatacc tgatggattc    5520
ttatgaagcg ctgggtaatg gacgtgtcac tctacttcgc cttttteeet actcctttta    5580 gtacggaaga caatgctaat aaataagagg gtaataataa tattattaat cggcaaaaaa    5640
```

```
gattaaacgc caagcgttta attatcagaa agcaaacgtc gtaccaatcc ttgaatgctt    5700
cccaattgta tattaagagt catcacagca acatattctt gttattaaat taattattat    5760 tgattttga tattgtataa aaaaaccaaa tatgtataaa aaagtgaat aaaaaatacc       5820 aagtatggag aaatatatta gaagtctata cgttaaacca cccgggcccc cctcgaggt     5880 cgacggtatc gataagcttg atatcgaatt cctgcagccc gggggatcca ctagttctag    5940
agcggccgct ctagaactag taccacaggt gttgtcctct gaggacataa aatacacacc    6000
gagattcatc aactcattgc tggagttagc atatctacaa ttgggtgaaa tggggagcga    6060
tttgcaggca tttgctcggc atgccggtag aggtgtggtc aataagagcg acctcatgct    6120
atacctgaga aagcaacctg acctacagga aagagttact caagaataag aattttcgtt    6180
ttaaaaccta agagtcactt taaaatttgt atacacttat ttttttata acttatttaa      6240 taataaaat cataaatcat aagaaattcg cttactctta attaatcaaa aagttaaaat     6300
tgtacgaata gattcaccac ttcttaacaa atcaaaccct tcattgattt tctcgaatgg    6360
caatacatgt gtaattaaag gatcaagagc aaacttcttc gccataaagt cggcaacaag    6420
ttttggaaca ctatccttgc tcttaaaacc gccaaatata gctcccttcc atgtacgacc    6480
gcttagcaac agcataggat tcatcgacaa attttgtgaa tcaggaggaa cacctacgat    6540
cacactgact ccatatgcct cttgacagca ggacaacgca gttaccatag tatcaagacg    6600
gcctataact tcaaaagaga aatcaactcc accgtttgac atttcagtaa ggacttcttg    6660
tattggtttc ttataatctt gagggttaac acattcagta gccccgacct ccttagcttt    6720
tgcaaatttg tccttattga tgtctacacc tataatcctc gctgcgcctg cagctttaca    6780
ccccataata acgcttagtc ctactcctcc taaaccgaat actgcacaag tcgaaccctg    6840
tgtaaccttt gcaactttaa ctgcggaacc gtaaccggtg gaaaatccgc accctatcaa    6900
gcaaactttt tccagtggtg aagctgcatc gattttagcg acagatatct cgtccaccac    6960
tgtgtattgg gaaaatgtag aagtaccaag gaaatggtgt ataggtttcc ctctgcatgt    7020
aaatctgctt gtaccatcct gcatagtacc tctaggcata gacaaatcat ttttaaggca    7080
gaaattaccc tcaggatgtt tgcagactct acacttacca cattgaggag tgaacagtgg    7140
gatcacttta tcaccaggac gaacagtggt aacaccttca cctatggatt caacgattcc    7200
ggcagcctcg tgtcccgcga ttactggcaa aggagtaact agagtgccac tcaccacatg    7260
gtcgtcggat ctacagattc cggtggcaac catcttgatt ctaacctcgt gtgcttttgg    7320
tggcgctact tctacttctt ctatgctaaa cggcttttc tcttcccaca aaactgccgc     7380
tttacactta ataactttac cggctgttga catcctcagc tagctattgt aatatgtgtg    7440 tttgttgga ttattaagaa gaataattac aaaaaaaatt acaaaggaag gtaattacaa     7500
cagaattaag aaaggacaag aaggaggaag agaatcagtt cattatttct tctttgttat    7560
ataacaaacc caagtagcga tttggccata cattaaaagt tgagaaccac cctccctggc    7620
aacagccaca actcgttacc attgttcatc acgatcatga aactcgctgt cagctgaaat    7680
ttcacctcag tggatctctc ttttattct tcatcgttcc actaacctt ttccatcagc       7740 tggcagggaa cggaaagtgg aatcccattt agcgagcttc tcttttctt caagaaaaga     7800 cgaagcttgt gtgtgggtgc gcgcgctagt atctttccac attaagaaat ataccataaa    7860
ggttacttag acatcactat ggctatatat atatatatat atatatgtaa cttagcacca    7920
tcgcgcgtgc atcactgcat gtgttaaccg aaaagtttgg cgaacacttc accgacacgg    7980
```

```
tcatttagat ctgtcgtctg cattgcacgt cccttagcct taaatcctag gcgggagcat    8040
tctcgtgtaa ttgtgcagcc tgcgtagcaa ctcaacatag cgtagtctac ccagttttc     8100 aagggtttat cgttagaaga ttctccctt tcttcctgct cacaaatctt aaagtcatac     8160
attgcacgac taaatgcaag catgcggatc ccccgggctg caggaattcg atatcaagct    8220
tatcgatacc gtcgactggc cattaatctt tcccatatta gatttcgcca agccatgaaa    8280
gttcaagaaa ggtctttaga cgaattaccc ttcattctc aaactggcgt caagggatcc     8340
tggtatggtt ttatcgtttt atttctggtt cttatagcat cgttttggac ttctctgttc    8400
ccattaggcg gttcaggagc cagcgcagaa tcattctttg aaggatactt atccttcca     8460 attttgattg tctgttacgt tggacataaa ctgtatacta gaaattggac tttgatggtg    8520
aaactagaag atatggatct tgataccggc agaaaacaag tagatttgac tcttcgtagg    8580
gaagaaatga ggattgagcg agaaacatta gcaaaaagat ccttcgtaac aagatttta    8640 catttctggt gttgaaggga agatatgag ctatacagcg gaatttccat atcactcaga     8700
ttttgttatc taattttttc cttcccacgt ccgcgggaat ctgtgtatat tactgcatct    8760
agatatatgt tatcttatct tggcgcgtac atttaatttt caacgtattc tataagaaat    8820
tgcgggagtt tttttcatgt agatgatact gactgcacgc aaatataggc atgatttata    8880
ggcatgattt gatggctgta ccgataggaa cgctaagagt aacttcagaa tcgttatcct    8940
ggcggaaaaa attcatttgt aaactttaaa aaaaaagcc aatatcccca aaattattaa     9000
gagcgcctcc attattaact aaaatttcac tcagcatcca caatgtatca ggtatctact    9060
acagatatta catgtggcga aaaagacaag aacaatgcaa tagcgcatca agaaaaaaca    9120
caaagctttc aatcaatgaa tcgaaaatgt cattaaaata gtatataaat tgaaactaag    9180
tcataaagct ataaaagaa aatttattta atgcaagat ttaaagtaaa ttcacggccc       9240
tgcaggcctc agctcttgtt ttgttctgca ataacttac ccatctttt caaaacttta      9300 ggtgcaccct ccttgctag aataagttct atccaataca tcctatttgg atctgcttga     9360
gcttctttca tcacggatac gaattcattt tctgttctca caattttgga cacaactctg    9420
tcttccgttg ccccgaaact ttctggcagt tttgagtaat tccacatagg aatgtcatta    9480
taactctggt tcggaccatg aatttccctc tcaaccgtgt aaccatcgtt attaatgata    9540
aagcagattg ggtttatctt ctctctaatg gctagtccta attcttggac agtcagttgc    9600
aatgatccat ctccgataaa caataaatgt ctagattctt tatctgcaat ttggctgcct    9660
agagctgcgg ggaaagtgta tcctatagat ccccacaagg gttgaccaat aaaatgtgat    9720
ttcgatttca gaaatataga tgaggcaccg aagaagaag tgccttgttc agccacgatc     9780
gtctcattac tttgggtcaa attttcgaca gcttgccaca gtctatcttg tgacaacagc    9840
gcgttagaag gtacaaaatc ttcttgcttt ttatctatgt acttgccttt atattcaatt    9900
tcggacaagt caagaagaga tgatatcagg gattcgaagt cgaaattttg gattctttcg    9960
ttgaaaattt taccttcatc gatattcaag gaaatcattt tattttcatt aagatggtga   10020
gtaaatgcac ccgtactaga atcggtaagc tttacaccca acataagaat aaaatcagca   10080
gattccacaa attccttcaa gtttggctct gacagagtac cgttgtaaat ccccaaaaat   10140
gagggcaatg cttcatcaac agatgattta ccaaagttca agtagtaat aggtaactta    10200 gtctttgaaa taaactgagt aacagtcttc tctaggccga acgatataat ttcatggcct   10260
gtgattacaa ttggttcctt ggcattcttc agacttcct gtatttgtt cagaatctct     10320 tgatcagatg tattcgacgt ggaattttcc ttcttaagag gcaaggatgg ttttcagcc    10380
```

```
ttagcggcag ctacatctac aggtaaattg atgtaaaccg gctttctttc ctttagtaag   10440
gcagacaaca ctctatcaat ttcaacagtt gcattctcgg ctgtcaataa agtcctggca   10500
gcagtaaccg gttcgtgcat cttcataaag tgcttgaaat caccatcagc caacgtatgg   10560
tgaacaaact taccttcgtt ctgcactttc gaggtaggag atcccacgat ctcaacaaca   10620
ggcaggttct cagcatagga gcccgctaag ccattaactg cggataattc gccaacacca   10680
aatgtagtca agaatgccgc agccttttc gttcttgcgt acccgtcggc catataggag    10740
gcatttaact cattagcatt tcccacccat tcatatctt tgtgtgaaat aatttgatct    10800
agaaattgca aattgtagtc acctggtact ccgaatattt cttctatacc taattcgtgt   10860
aatctgtcca acagatagtc acctactgta tacattttgt ttactagttt atgtgtgttt   10920
attcgaaact aagttcttgg tgttttaaaa ctaaaaaaaa gactaactat aaagtagaa    10980 tttaagaagt ttaagaaata gatttacaga attacaatca atacctaccg tctttatata   11040
cttattagtc aagtagggga ataatttcag ggaactggtt tcaaccttt ttttcagctt    11100 tttccaaatc agagagagca gaaggtaata gaaggtgtaa gaaaatgaga tagatacatg   11160
cgtgggtcaa ttgccttgtg tcatcattta ctccaggcag gttgcatcac tccattgagg   11220
ttgtgcccgt ttttgcctg tttgtgcccc tgttctctgt agttgcgcta agagaatgga    11280
cctatgaact gatggttggt gaagaaaaca atattttggt gctgggattc tttttttttc   11340
tggatgccag cttaaaaagc gggctccatt atatttagtg gatgccagga ataaactgtt   11400
cacccagaca cctacgatgt tatatattct gtgtaacccg cccctatt tgggcatgta     11460 cgggttacag cagaattaaa aggctaattt tttgactaaa taaagttagg aaaatcacta   11520
ctattaatta tttacgtatt ctttgaaatg gcagtattga taatgataaa ctcgaactga   11580
aaaagcgtgt ttttattca aaatgattct aactccctta cgtaatcaag gaatctttt     11640 gccttggcct ccgcgtcatt aaacttcttg ttgttgacgc taacattcaa cgctagtata   11700
tattcgtttt tttcaggtaa gttcttttca acgggtctta ctgatgaggc agtcgcgtct   11760
gaacctgtta agaggtcaaa tatgtcttct tgaccgtacg tgtcttgcat gttattagct   11820
ttgggaattt gcatcaagtc ataggaaaat ttaaatcttg gctctcttgg gctcaaggtg   11880
acaaggtcct cgaaaatagg gcgcgcccca ccgcggtgga gctccagctt tgttcccctt   11940
tagtgagggt taattgcgcg cttggcgtaa tcatggtcat agctgtttcc tgtgtgaaat   12000
tgttatccgc tcacaattcc acacaacata cgagccggaa gcataaagtg taaagcctgg   12060
ggtgcctaat gagtgagcta actcacatta attgcgttgc gctcactgcc cgctttccag   12120
tcgggaaacc tgtcgtgcca gctgcattaa tgaatcggcc aacgcgcggg gagaggcggt   12180
ttgcgtattg ggcgctcttc cgcttcctcg ctcactgact cgctgcgctc ggtcgttcgg   12240
ctgcggcgag cggtatcagc tcactcaaag gcggtaatac ggttatccac agaatcaggg   12300
gataacgcag gaaagaacat gtgagcaaaa ggccagcaaa aggccaggaa ccgtaaaaag   12360
gccgcgttgc tggcgttttt ccataggctc cgcccccctg acgagcatca caaaaatcga   12420
cgctcaagtc agaggtggcg aaacccgaca ggactataaa gataccaggc gtttccccct   12480
ggaagctccc tcgtgcgctc tcctgttccg accctgccgc ttaccggata cctgtccgcc   12540
tttctccctt cgggaagcgt ggcgctttct catagctcac gctgtaggta tctcagttcg   12600
gtgtaggtcg ttcgctccaa gctgggctgt gtgcacgaac ccccgttca gcccgaccgc    12660 tgcgccttat ccggtaacta tcgtcttgag tccaacccgg taagacacga cttatcgcca   12720
```

```
ctggcagcag ccactggtaa caggattagc agagcgaggt atgtaggcgg tgctacagag    12780
ttcttgaagt ggtggcctaa ctacggctac actagaagaa cagtatttgg tatctgcgct    12840
ctgctgaagc cagttacctt cggaaaaaga gttggtagct cttgatccgg caaacaaacc    12900
accgctggta gcggtggttt ttttgtttgc aagcagcaga ttacgcgcag aaaaaaagga    12960
tctcaagaag atcctttgat cttttctacg gggtctgacg ctcagtggaa cgaaaactca    13020
cgttaaggga ttttggtcat gagattatca aaaaggatct tcacctagat ccttttaaat    13080
taaaaatgaa gttttaaatc aatctaaagt atatatgagt aaacttggtc tgacagttac    13140
caatgcttaa tcagtgaggc acctatctca gcgatctgtc tatttcgttc atccatagtt    13200
gcctgactcc ccgtcgtgta gataactacg atacgggagg cttaccatc tggccccagt    13260 gctgcaatga taccgcgaga cccacgctca ccggctccag atttatcagc aataaaccag    13320
ccagccggaa gggccgagcg cagaagtggt cctgcaactt tatccgcctc catccagtct    13380
attaattgtt gccgggaagc tagagtaagt agttcgccag ttaatagttt gcgcaacgtt    13440
gttgccattg ctacaggcat cgtggtgtca cgctcgtcgt ttggtatggc ttcattcagc    13500
tccggttccc aacgatcaag gcgagttaca tgatccccca tgttgtgcaa aaaagcggtt    13560
agctccttcg gtcctccgat cgttgtcaga agtaagttgg ccgcagtgtt atcactcatg    13620
gttatggcag cactgcataa ttctcttact gtcatgccat ccgtaagatg cttttctgtg    13680
actggtgagt actcaaccaa gtcattctga aatagtgta tgcggcgacc gagttgctct    13740
tgcccggcgt caatacggga taataccgcg ccacatagca gaactttaaa agtgctcatc    13800
attggaaaac gttcttcggg gcgaaaactc tcaaggatct taccgctgtt gagatccagt    13860
tcgatgtaac ccactcgtgc acccaactga tcttcagcat cttttacttt caccagcgtt    13920
tctgggtgag caaaaacagg aaggcaaaat gccgcaaaaa agggaataag ggcgacacgg    13980
aaatgttgaa tactcatact cttccttttt caatattatt gaagcattta tcagggttat    14040
tgtctcatga gcggatacat atttgaatgt atttagaaaa ataaacaaat aggggttccg    14100
cgcacatttc cccgaaaagt gccacctgaa cgaagcatct gtgcttcatt ttgtagaaca    14160
aaaatgcaac gcgagagcgc taattttca aacaaagaat ctgagctgca ttttacaga    14220 acagaaatgc aacgcgaaag cgctatttta ccaacgaaga atctgtgctt cattttgta    14280 aaacaaaaat gcaacgcgag agcgctaatt tttcaaacaa agaatctgag ctgcatttt    14340 acagaacaga aatgcaacgc gagagcgcta ttttaccaac aaagaatcta tacttctttt    14400
ttgttctaca aaaatgcatc ccgagagcgc tatttttcta caaagcatc ttagattact    14460 tttttctcc tttgtgcgct ctataatgca gtctcttgat aacttttgc actgtaggtc    14520 cgttaaggtt agaagaaggc tactttggtg tctattttct cttccataaa aaagcctga    14580 ctccacttcc cgcgtttact gattactagc gaagctgcgg gtgcatttt tcaagataaa    14640 ggcatccccg attatattct ataccgatgt ggattgcgca tactttgtga acagaaagtg    14700
atagcgttga tgattcttca ttggtcagaa aattatgaac ggtttcttct attttgtctc    14760
tatatactac gtataggaaa tgtttacatt ttcgtattgt tttcgattca ctctatgaat    14820
agttcttact acaatttttt tgtctaaaga gtaatactag agataaacat aaaaaatgta    14880
gaggtcgagt ttagatgcaa gttcaaggag cgaaaggtgg atgggtaggt tatataggga    14940
tatagcacag agatatatag caaagagata cttttgagca atgtttgtgg aagcggtatt    15000
cgcaatattt tagtagctcg ttacagtccg gtgcgttttt ggttttttga agtgcgtct    15060 tcagagcgct tttggttttc aaaagcgctc tgaagttcct atactttcta gagaatagga    15120
```

```
acttcggaat aggaacttca aagcgttttcc gaaaacgagc gcttccgaaa atgcaacgcg    15180
agctgcgcac atacagctca ctgttcacgt cgcacctata tctgcgtgtt gcctgtatat    15240
atatatacat gagaagaacg gcatagtgcg tgtttatgct taaatgcgta cttatatgcg    15300
tctatttatg taggatgaaa ggtagtctag tacctcctgt gatattatcc cattccatgc    15360
ggggtatcgt atgcttcctt cagcactacc ctttagctgt tctatatgct gccactcctc    15420
aattggatta gtctcatcct tcaatgctat catttccttt gatattggat catactaaga    15480
aaccattatt atcatgacat taacctataa aaataggcgt atcacgaggc cctttcgtc    15539

<210> SEQ ID NO 3
<211> LENGTH: 4586
<212> TYPE: DNA
<213> ORGANISM: Artificial Sequence
<220> FEATURE:
<223> OTHER INFORMATION: pLA54 plasmid

<400> SEQUENCE: 3
gggtaccgag ctcgaattca ctggccgtcg ttttacaacg tcgtgactgg gaaaaccctg      60
gcgttaccca acttaatcgc cttgcagcac atccccettt cgccagctgg cgtaatagcg     120
aagaggcccg caccgatcgc ccttcccaac agttgcgcag cctgaatggc gaatggcgcc     180
tgatgcggta ttttctcctt acgcatctgt gcggtatttc acaccgcata tggtgcactc     240
tcagtacaat ctgctctgat gccgcatagt taagccagcc ccgacacccg ccaacacccg     300
ctgacgcgcc ctgacgggct tgtctgctcc cggcatccgc ttacagacaa gctgtgaccg     360
tctccgggag ctgcatgtgt cagaggtttt caccgtcatc accgaaacgc gcgagacgaa     420
agggcctcgt gatacgccta ttttataggt taatgtcat gataataatg gtttcttaga     480
cgtcaggtgg cacttttcgg ggaaatgtgc gcggaacccc tatttgttta ttttttctaaa    540 tacattcaaa tatgtatccg ctcatgagac aataaccctg ataaatgctt caataatatt    600
gaaaaaggaa gagtatgagt attcaacatt tccgtgtcgc ccttattccc ttttttgcgg    660
cattttgcct tcctgttttt gctcacccag aaacgctggt gaaagtaaaa gatgctgaag    720
atcagttggg tgcacgagtg ggttacatcg aactggatct caacagcggt aagatccttg    780
agagttttcg ccccgaagaa cgttttccaa tgatgagcac ttttaaagtt ctgctatgtg    840
gcgcggtatt atcccgtatt gacgccgggc aagagcaact cggtcgccgc atacactatt    900
ctcagaatga cttggttgag tactcaccag tcacagaaaa gcatcttacg gatggcatga    960
cagtaagaga attatgcagt gctgccataa ccatgagtga taacactgcg gccaacttac   1020
ttctgacaac gatcggagga ccgaaggagc taaccgcttt tttgcacaac atgggggatc   1080
atgtaactcg ccttgatcgt tgggaaccgg agctgaatga agccatacca aacgacgagc   1140
gtgacaccac gatgcctgta gcaatggcaa caacgttgcg caaactatta actggcgaac   1200
tacttactct agcttcccgg caacaattaa tagactggat ggaggcggat aaagttgcag   1260
gaccacttct gcgctcggcc cttccggctg gctggtttat tgctgataaa tctggagccg   1320
gtgagcgtgg gtctcgcggt atcattgcag cactggggcc agatggtaag ccctcccgta   1380
tcgtagttat ctacacgacg gggagtcagg caactatgga tgaacgaaat agacagatcg   1440
ctgagatagg tgcctcactg attaagcatt ggtaactgtc agaccaagtt tactcatata   1500
tactttagat tgatttaaaa cttcattttt aatttaaaag gatctaggtg aagatccttt   1560
ttgataatct catgaccaaa atcccttaac gtgagttttc gttccactga gcgtcagacc   1620
```

```
ccgtagaaaa gatcaaagga tcttcttgag atccttttt tctgcgcgta atctgctgct    1680
tgcaaacaaa aaaaccaccg ctaccagcgg tggtttgttt gccggatcaa gagctaccaa    1740 ctcttttttcc gaaggtaact ggcttcagca gagcgcagat accaaatact gtccttctag   1800
tgtagccgta gttaggccac cacttcaaga actctgtagc accgcctaca tacctcgctc    1860
tgctaatcct gttaccagtg gctgctgcca gtggcgataa gtcgtgtctt accgggttgg    1920
actcaagacg atagttaccg gataaggcgc agcggtcggg ctgaacgggg ggttcgtgca    1980
cacagcccag cttggagcga acgacctaca ccgaactgag atacctacag cgtgagctat    2040
gagaaagcgc cacgcttccc gaagggagaa aggcggacag gtatccggta agcggcaggg    2100
tcggaacagg agagcgcacg agggagcttc caggggaaa cgcctggtat ctttatagtc     2160
ctgtcgggtt tcgccacctc tgacttgagc gtcgatttt gtgatgctcg tcagggggc      2220 ggagcctatg gaaaaacgcc agcaacgcgg ccttttacg gttcctggcc ttttgctggc     2280
cttttgctca catgttcttt cctgcgttat cccctgattc tgtggataac cgtattaccg    2340
cctttgagtg agctgatacc gctcgccgca gccgaacgac cgagcgcagc gagtcagtga    2400
gcgaggaagc ggaagagcgc ccaatacgca aaccgcctct ccccgcgcgt tggccgattc    2460
attaatgcag ctggcacgac aggtttcccg actggaaagc gggcagtgag cgcaacgcaa    2520
ttaatgtgag ttagctcact cattaggcac cccaggcttt acactttatg cttccggctc    2580
gtatgttgtg tggaattgtg agcggataac aatttcacac aggaaacagc tatgaccatg    2640
attacgccaa gcttgcatgc ctgcaggtcg actctagagg atccccgcat tgcggattac    2700
gtattctaat gttcagataa cttcgtatag catacattat acgaagttat ctagggattc    2760
ataaccattt tctcaatcga attacacaga acacaccgta caaacctctc tatcataact    2820
acttaatagt cacacacgta ctcgtctaaa tacacatcat cgtcctacaa gttcatcaaa    2880
gtgttggaca gacaactata ccagcatgga tctcttgtat cggttctttt ctcccgctct    2940
ctcgcaataa caatgaacac tgggtcaatc atagcctaca caggtgaaca gagtagcgtt    3000
tatacagggt ttatacggtg attcctacgg caaaaatttt tcatttctaa aaaaaaaag     3060 aaaaattttt ctttccaacg ctagaaggaa aagaaaaatc taattaaatt gatttggtga    3120
ttttctgaga gttcccttttt tcatatatcg aattttgaat ataaaaggag atcgaaaaaa   3180
tttttctatt caatctgttt tctggtttta tttgatagtt ttttttgtgta ttattattat   3240 ggattagtac tggtttatat gggttttttct gtataacttc tttttatttt agtttgttta   3300
atcttatttt gagttacatt atagttccct aactgcaaga gaagtaacat taaaactcga    3360
gatgggtaag gaaaagactc acgtttcgag gccgcgatta aattccaaca tggatgctga    3420
tttatatggg tataaatggg ctcgcgataa tgtcgggcaa tcaggtgcga caatctatcg    3480
attgtatggg aagcccgatg cgccagagtt gtttctgaaa catggcaaag gtagcgttgc    3540
caatgatgtt acagatgaga tggtcagact aaactggctg acggaattta tgcctcttcc    3600
gaccatcaag cattttatcc gtactcctga tgatgcatgg ttactcacca ctgcgatccc    3660
cggcaaaaca gcattccagg tattagaaga atatcctgat tcaggtgaaa atattgttga    3720
tgcgctggca gtgttcctgc gccggttgca ttcgattcct gtttgtaatt gtcctttaa     3780 cagcgatcgc gtatttcgtc tcgctcaggc gcaatcacga atgaataacg gtttggttga    3840
tgcgagtgat tttgatgacg agcgtaatgg ctggcctgtt gaacaagtct ggaaagaaat    3900
gcataagctt ttgccattct caccggattc agtcgtcact catggtgatt tctcacttga    3960
taaccttatt tttgacgagg ggaaattaat aggttgtatt gatgttggac gagtcggaat    4020
```

```
cgcagaccga taccaggatc ttgccatcct atggaactgc ctcggtgagt tttctccttc    4080
attacagaaa cggcttttc aaaaatatgg tattgataat cctgatatga ataaattgca    4140
gtttcatttg atgctcgatg agtttttcta agtttaactt gatactacta gatttttct    4200 cttcattat aaaattttg gttataattg aagcttaga agtatgaaaa atccttttt      4260 tttcattctt tgcaaccaaa ataagaagct tctttattc attgaaatga tgaatataaa    4320
cctaacaaaa gaaaaagact cgaatatcaa acattaaaaa aaaataaaag aggttatctg    4380
ttttcccatt tagttggagt ttgcatttc taatagatag aactctcaat taatgtggat    4440
ttagtttctc tgttcgtttt tttttgtttt gttctcactg tatttacatt tctatttagt    4500
atttagttat tcatataatc tataacttcg tatagcatac attatacgaa gttatccagt    4560
gatgatacaa cgagttagcc aaggtg                                        4586

<210> SEQ ID NO 4
<211> LENGTH: 80
<212> TYPE: DNA
<213> ORGANISM: Artificial Sequence
<220> FEATURE:
<223> OTHER INFORMATION: Primer

<400> SEQUENCE: 4
ttccggtttc tttgaaattt ttttgattcg gtaatctccg agcagaagga gcattgcgga    60
ttacgtattc taatgttcag                                                80

<210> SEQ ID NO 5
<211> LENGTH: 81
<212> TYPE: DNA
<213> ORGANISM: Artificial Sequence
<220> FEATURE:
<223> OTHER INFORMATION: Primer

<400> SEQUENCE: 5
gggtaataac tgatataatt aaattgaagc tctaatttgt gagtttagta caccttggct    60
aactcgttgt atcatcactg g                                              81

<210> SEQ ID NO 6
<211> LENGTH: 38
<212> TYPE: DNA
<213> ORGANISM: Artificial Sequence
<220> FEATURE:
<223> OTHER INFORMATION: Primer

<400> SEQUENCE: 6
gcctcgagtt ttaatgttac ttctcttgca gttaggga                            38

<210> SEQ ID NO 7
<211> LENGTH: 31
<212> TYPE: DNA
<213> ORGANISM: Artificial Sequence
<220> FEATURE:
<223> OTHER INFORMATION: Primer

<400> SEQUENCE: 7
gctaaattcg agtgaaacac aggaagacca g                                   31

<210> SEQ ID NO 8
<211> LENGTH: 90
<212> TYPE: DNA
<213> ORGANISM: Artificial Sequence
<220> FEATURE:
```

<223> OTHER INFORMATION: Primer

<400> SEQUENCE: 8
gtattttggt agattcaatt ctctttccct ttccttttcc ttcgctcccc ttccttatca    60
gcattgcgga ttacgtattc taatgttcag    90

<210> SEQ ID NO 9
<211> LENGTH: 90
<212> TYPE: DNA
<213> ORGANISM: Artificial Sequence
<220> FEATURE:
<223> OTHER INFORMATION: Primer

<400> SEQUENCE: 9
ttggttgggg gaaaaagagg caacaggaaa gatcagaggg ggaggggggg ggagagtgtc    60
accttggcta actcgttgta tcatcactgg    90

<210> SEQ ID NO 10
<211> LENGTH: 21
<212> TYPE: DNA
<213> ORGANISM: Artificial Sequence
<220> FEATURE:
<223> OTHER INFORMATION: Primer

<400> SEQUENCE: 10
tcggtgcggg cctcttcgct a    21

<210> SEQ ID NO 11
<211> LENGTH: 21
<212> TYPE: DNA
<213> ORGANISM: Artificial Sequence
<220> FEATURE:
<223> OTHER INFORMATION: Primer

<400> SEQUENCE: 11
aatgtgagtt agctcactca t    21

<210> SEQ ID NO 12
<211> LENGTH: 57
<212> TYPE: DNA
<213> ORGANISM: Artificial Sequence
<220> FEATURE:
<223> OTHER INFORMATION: Primer

<400> SEQUENCE: 12
aattggatcc ggcgcgccgt ttaaacggcc ggccaatgtg gctgtggttt cagggtc    57

<210> SEQ ID NO 13
<211> LENGTH: 49
<212> TYPE: DNA
<213> ORGANISM: Artificial Sequence
<220> FEATURE:
<223> OTHER INFORMATION: Primer

<400> SEQUENCE: 13
aatttctaga ttaattaagc ggccgcaagg ccatgaagct ttttctttc    49

<210> SEQ ID NO 14
<211> LENGTH: 24
<212> TYPE: DNA
<213> ORGANISM: Artificial Sequence
<220> FEATURE:
<223> OTHER INFORMATION: Primer

<400> SEQUENCE: 14

```
ttctcgacgt gggccttttt cttg                                              24

<210> SEQ ID NO 15
<211> LENGTH: 49
<212> TYPE: DNA
<213> ORGANISM: Artificial Sequence
<220> FEATURE:
<223> OTHER INFORMATION: Primer

<400> SEQUENCE: 15
tgcagcttta aataatcggt gtcactactt tgccttcgtt tatcttgcc                   49

<210> SEQ ID NO 16
<211> LENGTH: 49
<212> TYPE: DNA
<213> ORGANISM: Artificial Sequence
<220> FEATURE:
<223> OTHER INFORMATION: Primer

<400> SEQUENCE: 16
gagcaggcaa gataaacgaa ggcaaagtag tgacaccgat tatttaaag                   49

<210> SEQ ID NO 17
<211> LENGTH: 49
<212> TYPE: DNA
<213> ORGANISM: Artificial Sequence
<220> FEATURE:
<223> OTHER INFORMATION: Primer

<400> SEQUENCE: 17
tatggaccct gaaaccacag ccacattgta accaccacga cggttgttg                   49

<210> SEQ ID NO 18
<211> LENGTH: 49
<212> TYPE: DNA
<213> ORGANISM: Artificial Sequence
<220> FEATURE:
<223> OTHER INFORMATION: Primer

<400> SEQUENCE: 18
tttagcaaca accgtcgtgg tggttacaat gtggctgtgg tttcagggt                   49

<210> SEQ ID NO 19
<211> LENGTH: 49
<212> TYPE: DNA
<213> ORGANISM: Artificial Sequence
<220> FEATURE:
<223> OTHER INFORMATION: Primer

<400> SEQUENCE: 19
ccagaaaccc tatacctgtg tggacgtaag gccatgaagc ttttctttt                  49

<210> SEQ ID NO 20
<211> LENGTH: 49
<212> TYPE: DNA
<213> ORGANISM: Artificial Sequence
<220> FEATURE:
<223> OTHER INFORMATION: Primer

<400> SEQUENCE: 20
attggaaaga aaaagcttca tggccttacg tccacacagg tatagggtt                   49

<210> SEQ ID NO 21
<211> LENGTH: 22
<212> TYPE: DNA
```

```
<213> ORGANISM: Artificial Sequence
<220> FEATURE:
<223> OTHER INFORMATION: Primer

<400> SEQUENCE: 21
cataagaaca cctttggtgg ag                                              22

<210> SEQ ID NO 22
<211> LENGTH: 22
<212> TYPE: DNA
<213> ORGANISM: Artificial Sequence
<220> FEATURE:
<223> OTHER INFORMATION: Primer

<400> SEQUENCE: 22
aggattatca ttcataagtt tc                                              22

<210> SEQ ID NO 23
<211> LENGTH: 23
<212> TYPE: DNA
<213> ORGANISM: Artificial Sequence
<220> FEATURE:
<223> OTHER INFORMATION: Primer

<400> SEQUENCE: 23
ttcttggagc tgggacatgt ttg                                             23

<210> SEQ ID NO 24
<211> LENGTH: 22
<212> TYPE: DNA
<213> ORGANISM: Artificial Sequence
<220> FEATURE:
<223> OTHER INFORMATION: Primer

<400> SEQUENCE: 24
tgatgatatt tcataaataa tg                                              22

<210> SEQ ID NO 25
<211> LENGTH: 23
<212> TYPE: DNA
<213> ORGANISM: Artificial Sequence
<220> FEATURE:
<223> OTHER INFORMATION: Primer

<400> SEQUENCE: 25
atgcgtccat ctttacagtc ctg                                             23

<210> SEQ ID NO 26
<211> LENGTH: 22
<212> TYPE: DNA
<213> ORGANISM: Artificial Sequence
<220> FEATURE:
<223> OTHER INFORMATION: Primer

<400> SEQUENCE: 26
tacgtacgga ccaatcgaag tg                                              22

<210> SEQ ID NO 27
<211> LENGTH: 49
<212> TYPE: DNA
<213> ORGANISM: Artificial Sequence
<220> FEATURE:
<223> OTHER INFORMATION: Primer

<400> SEQUENCE: 27
aattcgtttg agtacactac taatggcttt gttggcaata tgttttgc                  49
```

<210> SEQ ID NO 28
<211> LENGTH: 49
<212> TYPE: DNA
<213> ORGANISM: Artificial Sequence
<220> FEATURE:
<223> OTHER INFORMATION: Primer

<400> SEQUENCE: 28
atatagcaaa aacatattgc caacaaagcc attagtagtg tactcaaac                49

<210> SEQ ID NO 29
<211> LENGTH: 49
<212> TYPE: DNA
<213> ORGANISM: Artificial Sequence
<220> FEATURE:
<223> OTHER INFORMATION: Primer

<400> SEQUENCE: 29
tatggaccct gaaaccacag ccacattctt gttatttata aaaagacac                49

<210> SEQ ID NO 30
<211> LENGTH: 49
<212> TYPE: DNA
<213> ORGANISM: Artificial Sequence
<220> FEATURE:
<223> OTHER INFORMATION: Primer

<400> SEQUENCE: 30
ctcccgtgtc tttttataaa taacaagaat gtggctgtgg tttcagggt                49

<210> SEQ ID NO 31
<211> LENGTH: 49
<212> TYPE: DNA
<213> ORGANISM: Artificial Sequence
<220> FEATURE:
<223> OTHER INFORMATION: Primer

<400> SEQUENCE: 31
taccgtaggc gtccttagga aagatagaag gccatgaagc ttttctttt                49

<210> SEQ ID NO 32
<211> LENGTH: 49
<212> TYPE: DNA
<213> ORGANISM: Artificial Sequence
<220> FEATURE:
<223> OTHER INFORMATION: Primer

<400> SEQUENCE: 32
attggaaaga aaaagcttca tggccttcta tctttcctaa ggacgccta                49

<210> SEQ ID NO 33
<211> LENGTH: 21
<212> TYPE: DNA
<213> ORGANISM: Artificial Sequence
<220> FEATURE:
<223> OTHER INFORMATION: Primer

<400> SEQUENCE: 33
ttattgtttg gcatttgtag c                                              21

<210> SEQ ID NO 34
<211> LENGTH: 22
<212> TYPE: DNA
<213> ORGANISM: Artificial Sequence
<220> FEATURE:

<223> OTHER INFORMATION: Primer

<400> SEQUENCE: 34
ccaagcatct cataaaccta tg                                           22

<210> SEQ ID NO 35
<211> LENGTH: 22
<212> TYPE: DNA
<213> ORGANISM: Artificial Sequence
<220> FEATURE:
<223> OTHER INFORMATION: Primer

<400> SEQUENCE: 35
tgtgcagatg cagatgtgag ac                                           22

<210> SEQ ID NO 36
<211> LENGTH: 17
<212> TYPE: DNA
<213> ORGANISM: Artificial Sequence
<220> FEATURE:
<223> OTHER INFORMATION: Primer

<400> SEQUENCE: 36
agttattgat accgtac                                                 17

<210> SEQ ID NO 37
<211> LENGTH: 19
<212> TYPE: DNA
<213> ORGANISM: Artificial Sequence
<220> FEATURE:
<223> OTHER INFORMATION: Primer

<400> SEQUENCE: 37
cgagataccg taggcgtcc                                               19

<210> SEQ ID NO 38
<211> LENGTH: 24
<212> TYPE: DNA
<213> ORGANISM: Artificial Sequence
<220> FEATURE:
<223> OTHER INFORMATION: Primer

<400> SEQUENCE: 38
ttatgtatgc tcttctgact tttc                                         24

<210> SEQ ID NO 39
<211> LENGTH: 49
<212> TYPE: DNA
<213> ORGANISM: Artificial Sequence
<220> FEATURE:
<223> OTHER INFORMATION: Primer

<400> SEQUENCE: 39
aataattaga gattaaatcg ctcatttttt gccagtttct tcaggcttc              49

<210> SEQ ID NO 40
<211> LENGTH: 49
<212> TYPE: DNA
<213> ORGANISM: Artificial Sequence
<220> FEATURE:
<223> OTHER INFORMATION: Primer

<400> SEQUENCE: 40
agcctgaaga aactggcaaa aaatgagcga tttaatctct aattattag              49

```
<210> SEQ ID NO 41
<211> LENGTH: 49
<212> TYPE: DNA
<213> ORGANISM: Artificial Sequence
<220> FEATURE:
<223> OTHER INFORMATION: Primer

<400> SEQUENCE: 41
tatggaccct gaaaccacag ccacattttt caatcattgg agcaatcat          49

<210> SEQ ID NO 42
<211> LENGTH: 49
<212> TYPE: DNA
<213> ORGANISM: Artificial Sequence
<220> FEATURE:
<223> OTHER INFORMATION: Primer

<400> SEQUENCE: 42
taaaatgatt gctccaatga ttgaaaaatg tggctgtggt ttcagggtc          49

<210> SEQ ID NO 43
<211> LENGTH: 49
<212> TYPE: DNA
<213> ORGANISM: Artificial Sequence
<220> FEATURE:
<223> OTHER INFORMATION: Primer

<400> SEQUENCE: 43
accgtaggtg ttgtttggga aagtggaagg ccatgaagct ttttctttc          49

<210> SEQ ID NO 44
<211> LENGTH: 49
<212> TYPE: DNA
<213> ORGANISM: Artificial Sequence
<220> FEATURE:
<223> OTHER INFORMATION: Primer

<400> SEQUENCE: 44
ttggaaagaa aaagcttcat ggccttccac tttcccaaac aacacctac          49

<210> SEQ ID NO 45
<211> LENGTH: 23
<212> TYPE: DNA
<213> ORGANISM: Artificial Sequence
<220> FEATURE:
<223> OTHER INFORMATION: Primer

<400> SEQUENCE: 45
ttattgctta gcgttggtag cag          23

<210> SEQ ID NO 46
<211> LENGTH: 21
<212> TYPE: DNA
<213> ORGANISM: Artificial Sequence
<220> FEATURE:
<223> OTHER INFORMATION: Primer

<400> SEQUENCE: 46
tttttggtgg ttccggcttc c          21

<210> SEQ ID NO 47
<211> LENGTH: 22
<212> TYPE: DNA
<213> ORGANISM: Artificial Sequence
<220> FEATURE:
<223> OTHER INFORMATION: Primer
```

<400> SEQUENCE: 47
aaagttggca tagcggaaac tt                                          22

<210> SEQ ID NO 48
<211> LENGTH: 16
<212> TYPE: DNA
<213> ORGANISM: Artificial Sequence
<220> FEATURE:
<223> OTHER INFORMATION: Primer

<400> SEQUENCE: 48
gtcattgaca ccatct                                                 16

<210> SEQ ID NO 49
<211> LENGTH: 19
<212> TYPE: DNA
<213> ORGANISM: Artificial Sequence
<220> FEATURE:
<223> OTHER INFORMATION: Primer

<400> SEQUENCE: 49
agagataccg taggtgttg                                              19

<210> SEQ ID NO 50
<211> LENGTH: 33
<212> TYPE: DNA
<213> ORGANISM: Artificial Sequence
<220> FEATURE:
<223> OTHER INFORMATION: Primer

<400> SEQUENCE: 50
aattggcgcg ccatgaaagc tctggtttat cac                              33

<210> SEQ ID NO 51
<211> LENGTH: 49
<212> TYPE: DNA
<213> ORGANISM: Artificial Sequence
<220> FEATURE:
<223> OTHER INFORMATION: Primer

<400> SEQUENCE: 51
tgaatcatga gtttatgtt aattagctca ggcagcgcct gcgttcgag              49

<210> SEQ ID NO 52
<211> LENGTH: 49
<212> TYPE: DNA
<213> ORGANISM: Artificial Sequence
<220> FEATURE:
<223> OTHER INFORMATION: Primer

<400> SEQUENCE: 52
atcctctcga acgcaggcgc tgcctgagct aattaacata aaactcatg             49

<210> SEQ ID NO 53
<211> LENGTH: 34
<212> TYPE: DNA
<213> ORGANISM: Artificial Sequence
<220> FEATURE:
<223> OTHER INFORMATION: Primer

<400> SEQUENCE: 53
aattgtttaa acaagtaaat aaattaatca gcat                             34

<210> SEQ ID NO 54
<211> LENGTH: 49

```
<212> TYPE: DNA
<213> ORGANISM: Artificial Sequence
<220> FEATURE:
<223> OTHER INFORMATION: Primer

<400> SEQUENCE: 54
acacaataca ataacaagaa gaacaaaatg aaagctctgg tttatcacg          49

<210> SEQ ID NO 55
<211> LENGTH: 49
<212> TYPE: DNA
<213> ORGANISM: Artificial Sequence
<220> FEATURE:
<223> OTHER INFORMATION: Primer

<400> SEQUENCE: 55
agcgtataca tctgttggga aagtagaagg ccatgaagct ttttctttc          49

<210> SEQ ID NO 56
<211> LENGTH: 49
<212> TYPE: DNA
<213> ORGANISM: Artificial Sequence
<220> FEATURE:
<223> OTHER INFORMATION: Primer

<400> SEQUENCE: 56
ttggaaagaa aaagcttcat ggccttctac tttcccaaca gatgtatac          49

<210> SEQ ID NO 57
<211> LENGTH: 22
<212> TYPE: DNA
<213> ORGANISM: Artificial Sequence
<220> FEATURE:
<223> OTHER INFORMATION: Primer

<400> SEQUENCE: 57
ttattgttta gcgttagtag cg                                       22

<210> SEQ ID NO 58
<211> LENGTH: 72
<212> TYPE: DNA
<213> ORGANISM: Artificial Sequence
<220> FEATURE:
<223> OTHER INFORMATION: Primer

<400> SEQUENCE: 58
cataatcaat ctcaaagaga acaacacaat acaataacaa gaagaacaaa atgaaagctc   60
tggtttatca cg                                                 72

<210> SEQ ID NO 59
<211> LENGTH: 21
<212> TYPE: DNA
<213> ORGANISM: Artificial Sequence
<220> FEATURE:
<223> OTHER INFORMATION: Primer

<400> SEQUENCE: 59
taggcataat caccgaagaa g                                       21

<210> SEQ ID NO 60
<211> LENGTH: 21
<212> TYPE: DNA
<213> ORGANISM: Artificial Sequence
<220> FEATURE:
<223> OTHER INFORMATION: Primer
```

<400> SEQUENCE: 60
aaaatggtaa gcagctgaaa g                                              21

<210> SEQ ID NO 61
<211> LENGTH: 17
<212> TYPE: DNA
<213> ORGANISM: Artificial Sequence
<220> FEATURE:
<223> OTHER INFORMATION: Primer

<400> SEQUENCE: 61
agttgttaga actgttg                                                   17

<210> SEQ ID NO 62
<211> LENGTH: 19
<212> TYPE: DNA
<213> ORGANISM: Artificial Sequence
<220> FEATURE:
<223> OTHER INFORMATION: Primer

<400> SEQUENCE: 62
gacgatagcg tatacatct                                                 19

<210> SEQ ID NO 63
<211> LENGTH: 22
<212> TYPE: DNA
<213> ORGANISM: Artificial Sequence
<220> FEATURE:
<223> OTHER INFORMATION: Primer

<400> SEQUENCE: 63
cttagcctct agccatagcc at                                             22

<210> SEQ ID NO 64
<211> LENGTH: 23
<212> TYPE: DNA
<213> ORGANISM: Artificial Sequence
<220> FEATURE:
<223> OTHER INFORMATION: Primer

<400> SEQUENCE: 64
ttagttttgc tggccgcatc ttc                                            23

<210> SEQ ID NO 65
<211> LENGTH: 21
<212> TYPE: DNA
<213> ORGANISM: Artificial Sequence
<220> FEATURE:
<223> OTHER INFORMATION: Primer

<400> SEQUENCE: 65
cccattaata tactattgag a                                              21

<210> SEQ ID NO 66
<211> LENGTH: 7523
<212> TYPE: DNA
<213> ORGANISM: Artificial Sequence
<220> FEATURE:
<223> OTHER INFORMATION: Plasmid

<400> SEQUENCE: 66
ccagcttttg ttcccttag tgagggttaa ttgcgcgctt ggcgtaatca tggtcatagc      60
tgtttcctgt gtgaaattgt tatccgctca caattccaca caacatagga gccggaagca    120
taaagtgtaa agcctggggt gcctaatgag tgaggtaact cacattaatt gcgttgcgct    180

```
cactgcccgc tttccagtcg ggaaacctgt cgtgccagct gcattaatga atcggccaac    240
gcgcggggag aggcggtttg cgtattgggc gctcttccgc ttcctcgctc actgactcgc    300
tgcgctcggt cgttcggctg cggcgagcgg tatcagctca ctcaaaggcg gtaatacggt    360
tatccacaga atcaggggat aacgcaggaa agaacatgtg agcaaaaggc cagcaaaagg    420
ccaggaaccg taaaaaggcc gcgttgctgg cgtttttcca taggctccgc cccctgacg    480 agcatcacaa aaatcgacgc tcaagtcaga ggtggcgaaa cccgacagga ctataaagat    540
accaggcgtt ccccctgga agctccctcg tgcgctctcc tgttccgacc ctgccgctta    600
ccggatacct gtccgccttt ctcccttcgg gaagcgtggc gctttctcat agctcacgct    660
gtaggtatct cagttcggtg taggtcgttc gctccaagct gggctgtgtg cacgaaccc    720 ccgttcagcc cgaccgctgc gccttatccg gtaactatcg tcttgagtcc aacccggtaa    780
gacacgactt atcgccactg gcagcagcca ctggtaacag gattagcaga gcgaggtatg    840
taggcggtgc tacagagttc ttgaagtggt ggcctaacta cggctacact agaaggacag    900
tatttggtat ctgcgctctg ctgaagccag ttaccttcgg aaaagagtt ggtagctctt    960 gatccggcaa acaaaccacc gctggtagcg gtggtttttt tgtttgcaag cagcagatta   1020
cgcgcagaaa aaaggatct caagaagatc ctttgatctt ttctacgggg tctgacgctc   1080
agtggaacga aaactcacgt taagggattt tggtcatgag attatcaaaa aggatcttca   1140
cctagatcct tttaaattaa aaatgaagtt ttaaatcaat ctaaagtata tatgagtaaa   1200
cttggtctga cagttaccaa tgcttaatca gtgaggcacc tatctcagcg atctgtctat   1260
ttcgttcatc catagttgcc tgactccccg tcgtgtagat aactacgata cgggagggct   1320
taccatctgg ccccagtgct gcaatgatac cgcgagaccc acgctcaccg gctccagatt   1380
tatcagcaat aaaccagcca gccggaaggg ccgagcgcag aagtggtcct gcaactttat   1440
ccgcctccat ccagtctatt aattgttgcc gggaagctag agtaagtagt tcgccagtta   1500
atagtttgcg caacgttgtt gccattgcta caggcatcgt ggtgtcacgc tcgtcgtttg   1560
gtatggcttc attcagctcc ggttcccaac gatcaaggcg agttacatga tcccccatgt   1620
tgtgcaaaaa agcggttagc tccttcggtc ctccgatcgt tgtcagaagt aagttggccg   1680
cagtgttatc actcatggtt atggcagcac tgcataattc tcttactgtc atgccatccg   1740
taagatgctt ttctgtgact ggtgagtact caaccaagtc attctgagaa tagtgtatgc   1800
ggcgaccgag ttgctcttgc ccggcgtcaa tacgggataa taccgcgcca catagcagaa   1860
ctttaaaagt gctcatcatt ggaaaacgtt cttcggggcg aaaactctca aggatcttac   1920
cgctgttgag atccagttcg atgtaaccca ctcgtgcacc caactgatct tcagcatctt   1980
ttactttcac cagcgtttct gggtgagcaa aaacaggaag gcaaaatgcc gcaaaaaagg   2040
gaataagggc gacacggaaa tgttgaatac tcatactctt ccttttttcaa tattattgaa   2100 gcatttatca gggttattgt ctcatgagcg gatacatatt tgaatgtatt tagaaaaata   2160
aacaaatagg ggttccgcgc acatttcccc gaaaagtgcc acctgaacga agcatctgtg   2220
cttcattttg tagaacaaaa atgcaacgcg agagcgctaa ttttcaaac aaagaatctg   2280 agctgcattt ttacagaaca gaaatgcaac gcgaaagcgc tattttacca acgaagaatc   2340
tgtgcttcat ttttgtaaaa caaaaatgca acgcgagagc gctaattttt caaacaaaga   2400
atctgagctg cattttacaa gaacagaaat gcaacgcgag agcgctattt taccaacaaa   2460
gaatctatac ttcttttttg ttctacaaaa atgcatcccg agagcgctat ttttctaaca   2520
```

```
aagcatctta gattactttt tttctccttt gtgcgctcta taatgcagtc tcttgataac   2580 ttttttgcact gtaggtccgt taaggttaga agaaggctac tttggtgtct attttctctt   2640
ccataaaaaa agcctgactc cacttcccgc gtttactgat tactagcgaa gctgcgggtg   2700
cattttttca agataaaggc atccccgatt atattctata ccgatgtgga ttgcgcatac   2760
tttgtgaaca gaaagtgata gcgttgatga ttcttcattg gtcagaaaat tatgaacggt   2820
ttcttctatt ttgtctctat atactacgta taggaaatgt ttacattttc gtattgtttt   2880
cgattcactc tatgaatagt tcttactaca attttttttgt ctaaagagta atactagaga   2940
taaacataaa aaatgtagag gtcgagttta gatgcaagtt caaggagcga aaggtggatg   3000
ggtaggttat atagggatat agcacagaga tatatagcaa agagatactt ttgagcaatg   3060 tttgtgaag cggtattcgc aatattttag tagctcgtta cagtccggtg cgttttttggt    3120 tttttgaaag tgcgtcttca gagcgctttt ggttttcaaa agcgctctga agttcctata   3180
ctttctagag aataggaact tcggaatagg aacttcaaag cgtttccgaa aacgagcgct   3240
tccgaaaatg caacgcgagc tgcgcacata cagctcactg ttcacgtcgc acctatatct   3300
gcgtgttgcc tgtatatata tatacatgag aagaacggca tagtgcgtgt ttatgcttaa   3360
atgcgtactt tatatgcgtct attatatgtag gatgaaaggt agtctagtac ctcctgtgat   3420
attatcccat tccatgcggg gtatcgtatg cttccttcag cactacccctt tagctgttct   3480 atatgctgcc actcctcaat tggattagtc tcatccttca atgctatcat ttcctttgat   3540
attggatcat ctaagaaacc attattatca tgacattaac ctataaaaat aggcgtatca   3600 cgaggcccctt tcgtctcgcg cgtttcggtg atgacggtga aaacctctga cacatgcagc   3660
tcccggagac ggtcacagct tgtctgtaag cggatgccgg gagcagacaa gcccgtcagg   3720
gcgcgtcagc gggtgttggc gggtgtcggg gctggcttaa ctatgcggca tcagagcaga   3780
ttgtactgag agtgcaccat aaattcccgt tttaagagct tggtgagcgc taggagtcac   3840
tgccaggtat cgtttgaaca cggcattagt cagggaagtc ataacacagt ccttttccgc   3900 aattttctttt ttctattact cttggcctcc tctagtacac tctatatttt tttatgcctc   3960
ggtaatgatt ttcattttttt tttttcccct agcggatgac tctttttttt tcttagcgat   4020
tggcattatc acataatgaa ttatacatta tataagtaa tgtgatttct tcgaagaata    4080 tactaaaaaaa tgagcaggca agataaacga aggcaaagat gacagagcag aaagccctag   4140
taaagcgtat tacaaatgaa accaagattc agattgcgat ctctttaaag ggtggtcccc   4200
tagcgataga gcactcgatc ttcccagaaa aagaggcaga agcagtagca gaacaggcca   4260
cacaatcgca agtgattaac gtccacacag gtatagggtt tctggaccat atgatacatg   4320
ctctggccaa gcattccggc tggtcgctaa tcgttgagtg cattggtgac ttacacatag   4380
acgaccatca caccactgaa gactgcggga ttgctctcgg tcaagctttt aaagaggccc   4440
tactggcgcg tggagtaaaa aggtttggat caggatttgc gcctttggat gaggcacttt   4500
ccagagcggt ggtagatctt tcgaacaggc cgtacgcagt tgtcgaactt ggtttgcaaa   4560
gggagaaagt aggagatctc tcttgcgaga tgatcccgca ttttcttgaa agctttgcag   4620
aggctagcag aattaccctc cacgttgatt gtctgcgagg caagaatgat catcaccgta   4680
gtgagagtgc gttcaaggct cttgcggttg ccataagaga agccacctcg cccaatggta   4740
ccaacgatgt tccctccacc aaaggtgttc ttatgtagtg acaccgatta tttaaagctg   4800
cagcatacga tatatataca tgtgtatata tgtataccta tgaatgtcag taagtatgta   4860
tacgaacagt atgatactga agatgacaag gtaatgcatc attctatacg tgtcattctg   4920
```

```
aacgaggcgc gctttccttt tttcttttg cttttcttt tttttctct tgaactcgac    4980
ggatctatgc ggtgtgaaat accgcacaga tgcgtaagga gaaataccg catcaggaaa  5040
ttgtaaacgt taatattttg ttaaaattcg cgttaaattt tgttaaatc agctcatttt  5100
ttaaccaata ggccgaaatc ggcaaaatcc cttataaatc aaaagaatag accgagatag 5160
ggttgagtgt tgttccagtt tggaacaaga gtccactatt aaagaacgtg gactccaacg 5220
tcaaagggcg aaaaaccgtc tatcagggcg atggcccact acgtgaacca tcaccctaat 5280
caagtttttt ggggtcgagg tgccgtaaag cactaaatcg aaccctaaa gggagccccc  5340
gatttagagc ttgacgggga agccggcga acgtggcgag aaaggaaggg aagaaagcga  5400
aaggagcggg cgctagggcg ctggcaagtg tagcggtcac gctgcgcgta accaccacac 5460
ccgccgcgct taatgcgccg ctacaggcg cgtcgcgcca ttcgccattc aggctgcgca  5520
actgttggga agggcgatcg gtgcgggcct cttcgctatt acgccagctg gcgaaagggg 5580
gatgtgctgc aaggcgatta agttgggtaa cgccagggtt ttcccagtca cgacgttgta  5640
aaacgacggc cagtgagcgc gcgtaatacg actcactata gggcgaattg ggtaccgggc  5700
cccccctcga ggtattagaa gccgccgagc gggcgacagc cctccgacgg aagactctcc  5760
tccgtgcgtc ctcgtcttca ccggtcgcgt tcctgaaacg cagatgtgcc tcgcgccgca 5820
ctgctccgaa caataaagat tctacaatac tagcttttat ggttatgaag aggaaaaatt 5880
ggcagtaacc tggccccaca aaccttcaaa ttaacgaatc aaattaacaa ccataggatg 5940
ataatgcgat tagttttta gccttatttc tggggtaatt aatcagcgaa gcgatgattt  6000
ttgatctatt aacagatata taaatggaaa agctgcataa ccactttaac taatactttc  6060
aacattttca gtttgtatta cttcttattc aaatgtcata aaagtatcaa caaaaaattg 6120
ttaatatacc tctatacttt aacgtcaagg agaaaaatgt ccaatttact gcccgtacac 6180
caaaatttgc ctgcattacc ggtcgatgca acgagtgatg aggttcgcaa gaacctgatg 6240
gacatgttca gggatcgcca ggcgttttct gagcatacct ggaaaatgct tctgtccgtt  6300
tgccggtcgt gggcggcatg gtgcaagttg aataaccgga atggtttcc cgcagaacct  6360
gaagatgttc gcgattatct tctatatctt caggcgcgcg gtctggcagt aaaaactatc 6420
cagcaacatt tgggccagct aaacatgctt catcgtcggt ccgggctgcc acgaccaagt 6480
gacagcaatg ctgtttcact ggttatgcgg cggatccgaa agaaaacgt tgatgccggt  6540
gaacgtgcaa acaggctct agcgttcgaa cgcactgatt tcgaccaggt tcgttcactc  6600
atggaaaata gcgatcgctg ccaggatata cgtaatctgg catttctggg gattgcttat  6660
aacaccctgt tacgtatagc cgaaattgcc aggatcaggg ttaaagatat ctcacgtact 6720
gacggtggga gaatgttaat ccatattggc agaacgaaaa cgctggttag caccgcaggt 6780
gtagagaagg cacttagcct gggggtaact aaactggtcg agcgatggat tccgtctct  6840
ggtgtagctg atgatccgaa taactacctg ttttgccggg tcagaaaaaa tggtgttgcc 6900
gcgccatctg ccaccagcca gctatcaact cgcgccctgg aagggatttt tgaagcaact 6960
catcgattga tttacggcgc taaggatgac tctggtcaga gatacctggc ctggtctgga 7020
cacagtgccc gtgtcggagc cgcgcgagat atggcccgcg ctggagtttc aataccggag 7080
atcatgcaag ctggtggctg gaccaatgta atatttgtca tgaactatat ccgtaacctg 7140
gatagtgaaa caggggcaat ggtgcgcctg ctggaagatg gcgattagga gtaagcgaat 7200
ttcttatgat ttatgatttt tattattaaa taagttataa aaaaaataag tgtatacaaa 7260
```

```
ttttaaagtg actcttaggt tttaaaacga aaattcttat tcttgagtaa ctcttttcctg    7320 taggtcaggt tgctttctca ggtatagcat gaggtcgctc ttattgacca cacctctacc    7380
ggcatgccga gcaaatgcct gcaaatcgct ccccatttca cccaattgta gatatgctaa    7440
ctccagcaat gagttgatga atctcggtgt gtattttatg tcctcagagg acaacacctg    7500
tggtccgcca ccgcggtgga gct                                            7523

<210> SEQ ID NO 67
<211> LENGTH: 15456
<212> TYPE: DNA
<213> ORGANISM: Artificial Sequence
<220> FEATURE:
<223> OTHER INFORMATION: Template

<400> SEQUENCE: 67
aaagagtaat actagagata acataaaaa atgtagaggt cgagtttaga tgcaagttca       60
aggagcgaaa ggtggatggg taggttatat agggatatag cacagagata tatagcaaag    120
agatactttt gagcaatgtt tgtggaagcg gtattcgcaa tattttagta gctcgttaca    180
gtccggtgcg ttttggtttt tttgaaagtg cgtcttcaga gcgcttttgg ttttcaaaag    240
cgctctgaag ttcctatact ttctagagaa taggaacttc ggaataggaa cttcaaagcg    300
tttccgaaaa cgagcgcttc cgaaaatgca acgcgagctg cgcacataca gctcactgtt    360
cacgtcgcac ctatatctgc gtgttgcctg tatatatata tacatgagaa gaacggcata    420
gtgcgtgttt atgcttaaat gcgtacttat atgcgtctat ttatgtagga tgaaaggtag    480
tctagtacct cctgtgatat tatcccattc catgcgggt atcgtatgct tccttcagca     540
ctacccttta gctgttctat atgctgccac tcctcaattg gattagtctc atccttcaat    600
gctatcattt cctttgatat tggatcatac taagaaacca ttattatcat gacattaacc    660
tataaaaata ggcgtatcac gaggcccttt cgtctcgcgc gtttcggtga tgacggtgaa    720
aacctctgac acatgcagct cccggagacg gtcacagctt gtctgtaagc ggatgccggg    780
agcagacaag cccgtcaggg cgcgtcagcg ggtgttggcg ggtgtcgggg ctggcttaac    840
tatgcggcat cagagcagat tgtactgaga gtgcaccata aattcccgtt ttaagagctt    900
ggtgagcgct aggagtcact gccaggtatc gtttgaacac ggcattagtc agggaagtca    960
taacacagtc ctttcccgca atttttcttt tctattactc ttggcctcct ctagtacact   1020
ctatattttt ttatgcctcg gtaatgattt tcattttttt ttttccacct agcggatgac   1080
tctttttttt tcttagcgat tggcattatc acataatgaa ttatacatta tataaagtaa   1140
tgtgatttct tcgaagaata tactaaaaaa tgagcaggca agataaacga aggcaaagat   1200
gacagagcag aaagccctag taaagcgtat tacaaatgaa accaagattc agattgcgat   1260 ctcttaaag ggtggtcccc tagcgataga gcactcgatc ttcccagaaa aagaggcaga    1320
agcagtagca gaacaggcca cacaatcgca agtgattaac gtccacacag gtatagggtt   1380
tctggaccat atgatacatg ctctggccaa gcattccggc tggtcgctaa tcgttgagtg   1440
cattggtgac ttacacatag acgaccatca caccactgaa gactgcggga ttgctctcgg   1500
tcaagctttt aaagaggccc tagggccgt gcgtggagta aaaaggtttg gatcaggatt     1560
tgcgcctttg gatgaggcac tttccagagc ggtggtagat ctttcgaaca ggccgtacgc   1620
agttgtcgaa cttggtttgc aaagggagaa agtaggagat ctctcttgcg agatgatccc   1680
gcattttctt gaaagctttg cagaggctag cagaattacc ctccacgttg attgtctgcg   1740
aggcaagaat gatcatcacc gtagtgagag tgcgttcaag gctcttgcgg ttgccataag   1800
```

```
agaagccacc tcgcccaatg gtaccaacga tgttccctcc accaaaggtg ttcttatgta   1860
gtgacaccga ttatttaaag ctgcagcata cgatatatat acatgtgtat atatgtatac   1920
ctatgaatgt cagtaagtat gtatacgaac agtatgatac tgaagatgac aaggtaatgc   1980
atcattctat acgtgtcatt ctgaacgagg cgcgctttcc ttttttcttt ttgcttttc    2040
ttttttttc tcttgaactc gacggatcta tgcggtgtga ataccgcac agatgcgtaa     2100
ggagaaaata ccgcatcagg aaattgtaag cgttaatatt ttgttaaaat cgcgttaaa    2160
tttttgttaa atcagctcat tttttaacca ataggccgaa atcggcaaaa tcccttataa   2220
atcaaaagaa tagaccgaga tagggttgag tgttgttcca gtttggaaca agagtccact   2280
attaaagaac gtggactcca acgtcaaagg gcgaaaaacc gtctatcagg gcgatggccc   2340
actacgtgaa ccatcaccct aatcaagttt ttggggtcg aggtgccgta aagcactaaa    2400
tcggaaccct aaagggagcc cccgatttag agcttgacgg ggaaagccgg cgaacgtggc   2460
gagaaaggaa gggaagaaag cgaaaggagc gggcgctagg gcgctggcaa gtgtagcggt   2520
cacgctgcgc gtaaccacca cacccgccgc gcttaatgcg ccgctacagg gcgcgtccat   2580
tcgccattca ggctgcgcaa ctgttgggaa gggcgcggtg cgggcctctt cgctattacg   2640
ccagctggcg aaaggggat gtgctgcaag gcgattaagt tgggtaacgc cagggttttc    2700
ccagtcacga cgttgtaaaa cgacggccag tgagcgcgcg taatacgact cactataggg   2760
cgaattgggt accgggcccc cctcgaggt cgacggcgcg ccactggtag agagcgactt    2820
tgtatgcccc aattgcgaaa cccgcgatat ccttctcgat tctttagtac ccgaccagga   2880
caaggaaaag gaggtcgaaa cgttttgaa gaaacaagag gaactacacg gaagctctaa    2940
agatggcaac cagccagaaa ctaagaaat gaagttgatg gatccaactg gcaccgctgg    3000
cttgaacaac aataccagcc ttccaacttc tgtaaataac ggcggtacgc cagtgccacc   3060
agtaccgtta cctttcggta tacctccttt ccccatgttt ccaatgccct tcatgcctcc   3120
aacggctact atcacaaatc ctcatcaagc tgacgcaagc cctaagaaat gaataacaat   3180
actgacagta ctaaataatt gcctacttgg cttcacatac gttgcatacg tcgatataga   3240
taataatgat aatgacagca ggattatcgt aatacgtaat agctgaaaat ctcaaaaatg   3300
tgtgggtcat tacgtaaata atgataggaa tgggattctt ctattttcc ttttccatt     3360
ctagcagccg tcgggaaaac gtggcatcct ctctttcggg ctcaattgga gtcacgctgc   3420
cgtgagcatc ctctctttcc atatctaaca actgagcacg taaccaatgg aaaagcatga   3480
gcttagcgtt gctccaaaaa agtattggat ggttaatacc atttgtctgt tctcttctga   3540
ctttgactcc tcaaaaaaaa aaatctacaa tcaacagatc gcttcaatta cgccctcaca   3600
aaaactttt tccttcttct tcgcccacgt taaatttat ccctcatgtt gtctaacgga    3660
tttctgcact tgatttatta taaaagaca aagacataat acttctctat caatttcagt    3720
tattgttctt ccttgcgtta ttcttctgtt cttcttttc ttttgtcata tataaccata   3780
accaagtaat acatattcaa actagtatga ctgacaaaaa aactcttaaa gacttaagaa   3840
atcgtagttc tgtttacgat tcaatggtta aatcacctaa tcgtgctatg ttgcgtgcaa   3900
ctggtatgca agatgaagac tttgaaaaac ctatcgtcgg tgtcatttca acttgggctg   3960
aaaacacacc ttgtaatatc cacttacatg actttggtaa actagccaaa gtcggtgtta   4020
aggaagctgg tgcttggcca gttcagttcg gaacaatcac ggtttctgat ggaatcgcca   4080
tgggaaccca aggaatgcgt ttctccttga catctcgtga tattattgca gattctattg   4140
```

```
aagcagccat gggaggtcat aatgcggatg cttttgtagc cattggcggt tgtgataaaa    4200
acatgcccgg ttctgttatc gctatggcta acatggatat cccagccatt tttgcttacg    4260
gcggaacaat tgcacctggt aatttagacg gcaaagatat cgatttagtc tctgtctttg    4320
aaggtgtcgg ccattggaac cacggcgata tgaccaaaga agaagttaaa gctttggaat    4380
gtaatgcttg tcccggtcct ggaggctgcg gtggtatgta tactgctaac acaatggcga    4440
cagctattga agtttttggga cttagccttc cgggttcatc ttctcacccg gctgaatccg    4500
cagaaaagaa agcagatatt gaagaagctg gtcgcgctgt tgtcaaaatg ctcgaaatgg    4560
gcttaaaacc ttctgacatt ttaacgcgtg aagcttttga agatgctatt actgtaacta    4620
tggctctggg aggttcaacc aactcaaccc ttcacctctt agctattgcc catgctgcta    4680
atgtggaatt gacacttgat gatttcaata ctttccaaga aaaagttcct catttggctg    4740
atttgaaacc ttctggtcaa tatgtattcc aagacctttta caaggtcgga ggggtaccag    4800
cagttatgaa atatctcctt aaaaatggct tccttcatgg tgaccgtatc acttgtactg    4860
gcaaaacagt cgctgaaaat ttgaaggctt ttgatgattt aacacctggt caaaaggtta    4920
ttatgccgct tgaaaatcct aaacgtgaag atggtccgct cattattctc catggtaact    4980
tggctccaga cggtgccgtt gccaaagttt ctggtgtaaa agtgcgtcgt catgtcggtc    5040
ctgctaaggt cttttaattct gaagaagaag ccattgaagc tgtcttgaat gatgatattg    5100
ttgatggtga tgttgttgtc gtacgttttg taggaccaaa gggcggtcct ggtatgcctg    5160
aaatgctttc cctttcatca atgattgttg gtaaagggca aggtgaaaaa gttgcccttc    5220
tgacagatgg ccgcttctca ggtggtactt atggtcttgt cgtgggtcat atcgctcctg    5280
aagcacaaga tggcggtcca atcgcctacc tgcaaacagg agacatagtc actattgacc    5340
aagacactaa ggaattacac tttgatatct ccgatgaaga gttaaaacat cgtcaagaga    5400
ccattgaatt gccaccgctc tattcacgcg gtatccttgg taaatatgct cacatcgttt    5460
cgtctgcttc tagggggagcc gtaacagact tttggaagcc tgaagaaact ggcaaaaaat    5520
gttgtcctgg ttgctgtggt taagcggccg cgttaattca aattaattga tatagttttt    5580
taatgagtat tgaatctgtt tagaaataat ggaatattat ttttatttat ttatttatat    5640
tattggtcgg ctcttttctt ctgaaggtca atgacaaaat gatatgaagg aaataatgat    5700
ttctaaaatt ttacaacgta agatattttt acaaaagcct agctcatctt ttgtcatgca    5760 ctatttact cacgcttgaa attaacggcc agtccactgc ggagtcattt caaagtcatc    5820
ctaatcgatc tatcgttttt gatagctcat tttggagttc gcgattgtct tctgttattc    5880
acaactgttt taatttttat ttcattctgg aactcttcga gttctttgta aagtctttca    5940
tagtagctta ctttatcctc caacatattt aacttcatgt caatttcggc tcttaaattt    6000
tccacatcat caagttcaac atcatctttt aacttgaatt tattctctag ctcttccaac    6060
caagcctcat tgctccttga tttactggtg aaaagtgata cactttgcgc gcaatccagg    6120
tcaaaacttt cctgcaaaga attcaccaat ttctcgacat catagtacaa tttgttttgt    6180
tctcccatca caatttaata tacctgatgg attcttatga agcgctgggt aatggacgtg    6240
tcactctact tcgcctttttt ccctactcct tttagtacgg aagacaatgc taataaataa    6300
gagggtaata ataatattat taatcggcaa aaaagattaa acgccaagcg tttaattatc    6360
agaaagcaaa cgtcgtacca atccttgaat gcttcccaat tgtatattaa gagtcatcac    6420
agcaacatat tcttgttatt aaattaatta ttattgattt ttgatattgt ataaaaaaac    6480
caaatatgta taaaaaaagt gaataaaaaa taccaagtat ggagaaatat attagaagtc    6540
```

```
tatacgttaa accacccggg ccccccctcg aggtcgacgg tatcgataag cttgatatcg   6600
aattcctgca gcccggggga tccactagtt ctagagcggc cgctctagaa ctagtaccac   6660
aggtgttgtc ctctgaggac ataaaataca caccgagatt catcaactca ttgctggagt   6720
tagcatatct acaattgggt gaaatgggga gcgatttgca ggcatttgct cggcatgccg   6780
gtagaggtgt ggtcaataag agcgacctca tgctatacct gagaaagcaa cctgacctac   6840
aggaaagagt tactcaagaa taagaatttt cgttttaaaa cctaagagtc actttaaaat   6900
ttgtatacac ttatttttt tataacttat ttaataataa aaatcataaa tcataagaaa   6960
ttcgcttact cttaattaat caggcagcgc ctgcgttcga gaggatgatc ttcatcgcct   7020
tctccttggc gccattgagg aatacctgat aggcgtgctc gatctcggcc agctcgaagc   7080
gatgggtaat catcttcttc aacggaagct tgtcggtcga ggcgaccttc atcagcatgg   7140
gcgtcgtgtt cgtgttcacc agtcccgtgg tgatcgtcag gttcttgatc cagagcttct   7200
gaatctcgaa gtcaaccttg acgccatgca cgccgacgtt ggcgatgtgc gcgccgggct   7260
tgacgatctc ctggcagatg tcccaagtcg ccggtatgcc caccgcctcg atcgcaacat   7320
cgactccctc tgccgcaatc ctatgcacgg cttcgacaac gttctccgtg ccggagttga   7380
tggtgtgcgt tgccccgagc tccttggcga gctggaggcg attctcgtcc atgtcgatca   7440
cgatgatggt cgaggggag tagaactggg cggtcaacag tacggacatg ccgacggggc   7500
ccgcgccgac aatagccacc gcatcgcccg gctggacatt cccatactgg acgccgattt   7560
cgtggccggt gggcaggatg tcgctcagca ggacggcgat ttcgtcgtca attgtctggg   7620
ggatcttgta gaggctgttg tcggcatgcg ggatgcggac gtattcggcc tgcacgccat   7680
cgatcatgta acccaggatc cacccgccgt cgcggcaatg ggagtaaagc tgcttcttgc   7740
agtagtcgca cgagccgcaa gaagtgacgc aggaaatcag gaccttgtcg cctttcttga   7800
actgcgtgac actctcgccc acttcctcga tgacgcctac cccttcatgg cccaggatgc   7860
gcccgtcggc gacctctgga ttcttgcctt tgtagatgcc gagatccgtg ccgcagatcg   7920
tggtcttcaa aacccgtact actacatccg tgggcttttg aagggtgggc ttggcttgt    7980
cttcaagcga gatcttgtgg tcaccgtgat aaaccagagc tttcatcctc agctattgta   8040
atatgtgtgt ttgttggat tattaagaag aataattaca aaaaaaatta caaaggaagg    8100
taattacaac agaattaaga aaggacaaga aggaggaaga gaatcagttc attatttctt   8160
ctttgttata taacaaaccc aagtagcgat ttggccatac attaaaagtt gagaaccacc   8220
ctccctggca acagccacaa ctcgttacca ttgttcatca cgatcatgaa actcgctgtc   8280
agctgaaatt tcacctcagt ggatctctct ttttattctt catcgttcca ctaacctttt   8340
tccatcagct ggcagggaac ggaaagtgga atcccattta gcgagcttcc tctttcttc    8400
aagaaaagac gaagcttgtg tgtgggtgcg cgcgctagta tctttccaca ttaagaaata   8460
taccataaag gttacttaga catcactatg gctatatata tatatatata tatatatgta   8520
acttagcacc atcgcgcgtg catcactgca tgtgttaacc gaaaagtttg gcgaacactt   8580
caccgacacg gtcatttaga tctgtcgtct gcattgcacg tcccttagcc ttaaatccta   8640
ggcgggagca ttctcgtgta attgtgcagc ctgcgtagca actcaacata gcgtagtcta   8700
cccagttttt caagggttta tcgttagaag attctccctt ttcttcctgc tcacaaatct   8760
taaagtcata cattgcacga ctaaatgcaa gcatgcggat cccccgggct gcaggaattc   8820
gatatcaagc ttatcgatac cgtcgactgg ccattaatct ttcccatatt agatttcgcc   8880
```

```
aagccatgaa agttcaagaa aggtctttag acgaattacc cttcatttct caaactggcg    8940
tcaagggatc ctggtatggt tttatcgttt tatttctggt tcttatagca tcgttttgga    9000
cttctctgtt cccattaggc ggttcaggag ccagcgcaga atcattcttt gaaggatact    9060
tatcctttcc aattttgatt gtctgttacg ttggacataa actgtatact agaaattgga    9120
ctttgatggt gaaactagaa gatatggatc ttgataccgg cagaaaacaa gtagatttga    9180
ctcttcgtag ggaagaaatg aggattgagc gagaaacatt agcaaaaaga tccttcgtaa    9240
caagattttt acatttctgg tgttgaaggg aaagatatga gctatacagc ggaatttcca    9300
tatcactcag attttgttat ctaatttttt ccttcccacg tccgcgggaa tctgtgtata    9360
ttactgcatc tagatatatg ttatcttatc ttggcgcgta catttaattt tcaacgtatt    9420
ctataagaaa ttgcgggagt tttttcatg tagatgatac tgactgcacg caaatatagg    9480
catgatttat aggcatgatt tgatggctgt accgatagga acgctaagag taacttcaga    9540
atcgttatcc tggcggaaaa aattcatttg taaactttaa aaaaaaaagc caatatcccc    9600
aaaattatta agagcgcctc cattattaac taaaatttca ctcagcatcc acaatgtatc    9660
aggtatctac tacagatatt acatgtggcg aaaaagacaa gaacaatgca atagcgcatc    9720
aagaaaaaac acaaagcttt caatcaatga atcgaaaatg tcattaaaat agtatataaa    9780
ttgaaactaa gtcataaagc tataaaaaga aaatttattt aaatgcaaga tttaaagtaa    9840
attcacggcc ctgcaggcct cagctcttgt tttgttctgc aaataactta cccatctttt    9900
tcaaaacttt aggtgcaccc tcctttgcta gaataagttc tatccaatac atcctatttg    9960
gatctgcttg agcttctttc atcacggata cgaattcatt ttctgttctc acaatttggg   10020
acacaactct gtcttccgtt gccccgaaac tttctggcag ttttgagtaa ttccacatag   10080
gaatgtcatt ataactctgg ttcggaccat gaatttccct ctcaaccgtg taaccatcgt   10140
tattaatgat aaagcagatt gggtttatct tctctctaat ggctagtcct aattcttgga   10200
cagtcagttg caatgatcca tctccgataa acaataaatg tctagattct ttatctgcaa   10260
tttggctgcc tagagctgcg gggaaagtgt atcctataga tccccacaag ggttgaccaa   10320
taaaatgtga tttcgatttc agaaatatag atgaggcacc gaagaaagaa gtgccttgtt   10380
cagccacgat cgtctcatta ctttgggtca aattttcgac agcttgccac agtctatctt   10440
gtgacaacag cgcgttagaa ggtacaaaat cttcttgctt tttatctatg tacttgcctt   10500
tatattcaat ttcggacaag tcaagaagag atgatatcag ggattcgaag tcgaaatttt   10560
ggattctttc gttgaaaatt ttaccttcat cgatattcaa ggaaatcatt ttattttcat   10620
taagatggtg agtaaatgca cccgtactag aatcggtaag ctttacaccc aacataagaa   10680
taaaatcagc agattccaca aattccttca gtttggctc tgacagagta ccgttgtaaa   10740
tccccaaaaa tgagggcaat gcttcatcaa cagatgattt accaaagttc aaagtagtaa   10800
taggtaactt agtctttgaa ataaactgag taacagtctt ctctaggccg aacgatataa   10860
tttcatggcc tgtgattaca attggtttct tggcattctt cagactttcc tgtattttgt   10920
tcagaatctc ttgatcagat gtattcgacg tggaattttc cttcttaaga ggcaaggatg   10980 gttttcagc cttagcggca gctacatcta caggtaaatt gatgtaaacc ggctttcttt   11040
cctttagtaa ggcagacaac actctatcaa tttcaacagt tgcattctcg gctgtcaata   11100
aagtcctggc agcagtaacc ggttcgtgca tcttcataaa gtgcttgaaa tcaccatcag   11160
ccaacgtatg tgaacaaac ttaccttcgt tctgcacttt cgaggtagga gatcccacga   11220
tctcaacaac aggcaggttc tcagcatagg agcccgctaa gccattaact gcggataatt   11280
```

```
cgccaacacc aaatgtagtc aagaatgccg cagccttttt cgttcttgcg tacccgtcgg   11340
ccatatagga ggcatttaac tcattagcat ttcccaccca tttcatatct ttgtgtgaaa   11400
taatttgatc tagaaattgc aaattgtagt cacctggtac tccgaatatt tcttctatac   11460
ctaattcgtg taatctgtcc aacagatagt cacctactgt atacattttg tttactagtt   11520
tatgtgtgtt tattcgaaac taagttcttg gtgttttaaa actaaaaaaa agactaacta   11580
taaaagtaga atttaagaag tttaagaaat agatttacag aattacaatc aatacctacc   11640
gtctttatat acttattagt caagtagggg aataatttca gggaactggt ttcaaccttt   11700
tttttcagct ttttccaaat cagagagagc agaaggtaat agaaggtgta agaaaatgag   11760
atagatacat gcgtgggtca attgccttgt gtcatcattt actccaggca ggttgcatca   11820
ctccattgag gttgtgcccg ttttttgcct gtttgtgccc ctgttctctg tagttgcgct   11880
aagagaatgg acctatgaac tgatggttgg tgaagaaaac aatattttgg tgctgggatt   11940 ctttttttt ctggatgcca gcttaaaaag cgggctccat tatatttagt ggatgccagg   12000
aataaactgt tcacccagac acctacgatg ttatatattc tgtgtaaccc gcccectatt   12060 ttgggcatgt acgggttaca gcagaattaa aaggctaatt ttttgactaa ataaagttag   12120
gaaaatcact actattaatt atttacgtat tctttgaaat ggcagtattg ataatgataa   12180
actcgaactg aaaaagcgtg ttttttattc aaaatgattc taactcccett acgtaatcaa   12240 ggaatctttt tgccttggcc tccgcgtcat taaacttctt gttgttgacg ctaacattca   12300
acgctagtat atattcgttt ttttcaggta agttcttttc aacgggtctt actgatgagg   12360
cagtcgcgtc tgaacctgtt aagaggtcaa atatgtcttc ttgaccgtac gtgtcttgca   12420
tgttattagc tttgggaatt tgcatcaagt cataggaaaa tttaaatctt ggctctcttg   12480
ggctcaaggt gacaaggtcc tcgaaaatag ggcgcgcccc accgcggtgg agctccagct   12540
tttgttccct ttagtgaggg ttaattgcgc gcttggcgta atcatggtca tagctgtttc   12600
ctgtgtgaaa ttgttatccg ctcacaattc cacacaacat acgagccgga agcataaagt   12660
gtaaagcctg gggtgcctaa tgagtgagct aactcacatt aattgcgttg cgctcactgc   12720
ccgctttcca gtcgggaaac ctgtcgtgcc agctgcatta atgaatcggc caacgcgcgg   12780
ggagaggcgg tttgcgtatt gggcgctctt ccgcttcctc gctcactgac tcgctgcgct   12840
cggtcgttcg gctgcggcga gcggtatcag ctcactcaaa ggcggtaata cggttatcca   12900
cagaatcagg ggataacgca ggaaagaaca tgtgagcaaa aggccagcaa aaggccagga   12960
accgtaaaaa ggccgcgttg ctggcgtttt tccataggct ccgcccccct gacgagcatc   13020
acaaaaatcg acgctcaagt cagaggtggc gaaacccgac aggactataa agataccagg   13080
cgtttccccc tggaagctcc ctcgtgcgct ctcctgttcc gaccctgccg cttaccggat   13140
acctgtccgc ctttctccct tcgggaagcg tggcgctttc tcatagctca cgctgtaggt   13200
atctcagttc ggtgtaggtc gttcgctcca agctgggctg tgtgcacgaa ccccccgttc   13260
agcccgaccg ctgcgcctta tccggtaact atcgtcttga gtccaacccg gtaagacacg   13320
acttatcgcc actggcagca gccactggta acaggattag cagagcgagg tatgtaggcg   13380
gtgctacaga gttcttgaag tggtggccta actacggcta cactagaaga acagtatttg   13440
gtatctgcgc tctgctgaag ccagttacct tcggaaaaag agttggtagc tcttgatccg   13500
gcaaacaaac caccgctggt agcggtggtt tttttgtttg caagcagcag attacgcgca   13560
gaaaaaaagg atctcaagaa gatcctttga tcttttctac ggggtctgac gctcagtgga   13620
```

```
acgaaaactc acgttaaggg attttggtca tgagattatc aaaaaggatc ttcacctaga    13680 tcctttaaa ttaaaaatga agttttaaat caatctaaag tatatatgag taaacttggt    13740
ctgacagtta ccaatgctta atcagtgagg cacctatctc agcgatctgt ctatttcgtt    13800
catccatagt tgcctgactc cccgtcgtgt agataactac gatacgggag ggcttaccat    13860
ctggccccag tgctgcaatg ataccgcgag acccacgctc accggctcca gatttatcag    13920
caataaacca gccagccgga agggccgagc gcagaagtgg tcctgcaact ttatccgcct    13980
ccatccagtc tattaattgt tgccgggaag ctagagtaag tagttcgcca gttaatagtt    14040
tgcgcaacgt tgttgccatt gctacaggca tcgtggtgtc acgctcgtcg tttggtatgg    14100
cttcattcag ctccggttcc caacgatcaa ggcgagttac atgatccccc atgttgtgca    14160
aaaaagcggt tagctccttc ggtcctccga tcgttgtcag aagtaagttg gccgcagtgt    14220
tatcactcat ggttatggca gcactgcata attctcttac tgtcatgcca tccgtaagat    14280
gcttttctgt gactggtgag tactcaacca agtcattctg agaatagtgt atgcggcgac    14340
cgagttgctc ttgcccggcg tcaatacggg ataataccgc gccacatagc agaactttaa    14400
aagtgctcat cattggaaaa cgttcttcgg ggcgaaaact ctcaaggatc ttaccgctgt    14460
tgagatccag ttcgatgtaa cccactcgtg cacccaactg atcttcagca tcttttactt    14520
tcaccagcgt ttctgggtga gcaaaaacag gaaggcaaaa tgccgcaaaa aagggaataa    14580
gggcgacacg gaaatgttga atactcatac tcttcctttt tcaatattat tgaagcattt    14640
atcagggtta ttgtctcatg agcggataca tatttgaatg tatttagaaa aataaacaaa    14700
taggggttcc gcgcacattt ccccgaaaag tgccacctga acgaagcatc tgtgcttcat    14760
tttgtagaac aaaaatgcaa cgcgagagcg ctaattttc aaacaaagaa tctgagctgc    14820
atttttacag aacagaaatg caacgcgaaa gcgctatttt accaacgaag aatctgtgct    14880 tcattttgt aaaacaaaaa tgcaacgcga gagcgctaat ttttcaaaca aagaatctga    14940
gctgcatttt tacagaacag aaatgcaacg cgagagcgct attttaccaa caaagaatct    15000
atacttcttt tttgttctac aaaaatgcat cccgagagcg ctattttct aacaaagcat    15060 cttagattac tttttttctc ctttgtgcgc tctataatgc agtctcttga taactttttg    15120
cactgtaggt ccgttaaggt tagaagaagg ctactttggt gtctattttc tcttccataa    15180
aaaaagcctg actccacttc ccgcgtttac tgattactag cgaagctgcg ggtgcatttt    15240
ttcaagataa aggcatcccc gattatattc tataccgatg tggattgcgc atactttgtg    15300
aacagaaagt gatagcgttg atgattcttc attggtcaga aaattatgaa cggtttcttc    15360 tatttgtct ctatatacta cgtataggaa atgtttacat tttcgtattg ttttcgattc    15420
actctatgaa tagttcttac tacaattttt ttgtct                             15456
```

<210> SEQ ID NO 68  
<211> LENGTH: 1559  
<212> TYPE: DNA  
<213> ORGANISM: Artificial Sequence  
<220> FEATURE:  
<223> OTHER INFORMATION: Template

<400> SEQUENCE: 68

```
gcattgcgga ttacgtattc taatgttcag taccgttcgt ataatgtatg ctatacgaag     60
ttatgcagat tgtactgaga gtgcaccata ccacctttc aattcatcat ttttttttta    120 ttctttttt tgatttcggt ttccttgaaa ttttttgat tcggtaatct ccgaacagaa    180
ggaagaacga aggaaggagc acagacttag attggtatat atacgcatat gtagtgttga    240
```

```
agaaacatga aattgcccag tattcttaac ccaactgcac agaacaaaaa cctgcaggaa    300
acgaagataa atcatgtcga aagctacata taaggaacgt gctgctactc atcctagtcc    360
tgttgctgcc aagctattta atatcatgca cgaaaagcaa acaaacttgt gtgcttcatt    420
ggatgttcgt accaccaagg aattactgga gttagttgaa gcattaggtc ccaaaatttg    480
tttactaaaa acacatgtgg atatcttgac tgattttttcc atggagggca cagttaagcc    540
gctaaaggca ttatccgcca agtacaattt tttactcttc gaagacagaa aatttgctga    600
cattggtaat acagtcaaat tgcagtactc tgcgggtgta tacagaatag cagaatgggc    660
agacattacg aatgcacacg tgtggtgggc cccaggtatt gttagcggtt tgaagcaggc    720
ggcagaagaa gtaacaaagg aacctagagg ccttttgatg ttagcagaat tgtcatgcaa    780
gggctcccta tctactggag aatatactaa gggtactgtt gacattgcga agagcgacaa    840
agattttgtt atcggcttta ttgctcaaag agacatgggt ggaagagatg aaggttacga    900
ttggttgatt atgacacccg tgtgggtttt agatgacaag ggagacgcat gggtcaaca     960 gtatagaacc gtggatgatg tggtctctac aggatctgac attattattg ttggaagagg   1020
actatttgca aagggaaggg atgctaaggt agagggtgaa cgttacagaa aagcaggctg   1080
ggaagcatat ttgagaagat gcggccagca aaactaaaaa actgtattat aagtaaatgc   1140
atgtatacta aactcacaaa ttagagcttc aatttaatta tatcagttat taccctatgc   1200
ggtgtgaaat accgcacaga tgcgtaagga gaaaataccg catcaggaaa ttgtaaacgt   1260
taatattttg ttaaaattcg cgttaaattt ttgttaaatc agctcatttt ttaaccaata   1320
ggccgaaatc ggcaaaatcc cttataaatc aaaagaatag accgagatag ggttgagtgt   1380
tgttccagtt tggaacaaga gtccactatt aaagaacgtg gactccaacg tcaaagggcg   1440
aaaaaccgtc tatcagggcg atggcccact acgtgaacca tcaccctaat caagataact   1500
tcgtataatg tatgctatac gaacggtacc agtgatgata caacgagtta gccaaggtg    1559
```

<210> SEQ ID NO 69
<211> LENGTH: 1047
<212> TYPE: DNA
<213> ORGANISM: Alcaligenes xylosoxydans

<400> SEQUENCE: 69

```
atgaaagctc tggtttatca cggtgaccac aagatctcgc ttgaagacaa gcccaagccc     60
acccttcaaa agcccacgga tgtagtagta cgggttttga agaccacgat ctgcggcacg    120
gatctcggca tctacaaagg caagaatcca gaggtcgccg acgggcgcat cctgggccat    180
gaaggggtag gcgtcatcga ggaagtgggc gagagtgtca cgcagttcaa gaaaggcgac    240
aaggtcctga tttcctgcgt cacttcttgc ggctcgtgcg actactgcaa gaagcagctt    300
tactcccatt gccgcgacgg cgggtggatc ctgggttaca tgatcgatgg cgtgcaggcc    360
gaatacgtcc gcatcccgca tgccgacaac agcctctaca agatccccca gacaattgac    420
gacgaaatcg ccgtcctgct gagcgacatc ctgcccaccg ccacgaaat cggcgtccag    480 tatgggaatg tccagccggg cgatgcggtg ctattgtcg gcgcgggccc cgtcggcatg    540
tccgtactgt tgaccgccca gttctactcc ccctcgacca tcatcgtgat cgacatggac    600
gagaatcgcc tccagctcgc caaggagctc ggggcaacgc acaccatcaa ctccggcacg    660
gagaacgttg tcgaagccgt gcataggatt cggcagagg gagtcgatgt tgcgatcgag    720
gcggtgggca taccggcgac ttgggacatc tgccaggaga tcgtcaagcc cggcgcgcac    780
```

```
atcgccaacg tcggcgtgca tggcgtcaag gttgacttcg agattcagaa gctctggatc    840
aagaacctga cgatcaccac gggactggtg aacacgaaca cgacgcccat gctgatgaag    900
gtcgcctcga ccgacaagct tccgttgaag aagatgatta cccatcgctt cgagctggcc    960
gagatcgagc acgcctatca ggtattcctc aatggcgcca aggagaaggc gatgaagatc   1020
atcctctcga acgcaggcgc tgcctga                                       1047
```

<210> SEQ ID NO 70
<211> LENGTH: 348
<212> TYPE: PRT
<213> ORGANISM: Alcaligenes xylosoxydans

<400> SEQUENCE: 70

```
Met Lys Ala Leu Val Tyr His Gly Asp His Lys Ile Ser Leu Glu Asp
1               5                   10                  15

Lys Pro Lys Pro Thr Leu Gln Lys Pro Thr Asp Val Val Arg Val
            20                  25                  30

Leu Lys Thr Thr Ile Cys Gly Thr Asp Leu Gly Ile Tyr Lys Gly Lys
        35                  40                  45

Asn Pro Glu Val Ala Asp Gly Arg Ile Leu Gly His Glu Gly Val Gly
50                  55                  60

Val Ile Glu Glu Val Gly Glu Ser Val Thr Gln Phe Lys Lys Gly Asp
65                  70                  75                  80

Lys Val Leu Ile Ser Cys Val Thr Ser Cys Gly Ser Cys Asp Tyr Cys
                85                  90                  95

Lys Lys Gln Leu Tyr Ser His Cys Arg Asp Gly Gly Trp Ile Leu Gly
            100                 105                 110

Tyr Met Ile Asp Gly Val Gln Ala Glu Tyr Val Arg Ile Pro His Ala
        115                 120                 125

Asp Asn Ser Leu Tyr Lys Ile Pro Gln Thr Ile Asp Asp Glu Ile Ala
    130                 135                 140

Val Leu Leu Ser Asp Ile Leu Pro Thr Gly His Glu Ile Gly Val Gln
145                 150                 155                 160

Tyr Gly Asn Val Gln Pro Gly Asp Ala Val Ala Ile Val Gly Ala Gly
                165                 170                 175

Pro Val Gly Met Ser Val Leu Leu Thr Ala Gln Phe Tyr Ser Pro Ser
            180                 185                 190

Thr Ile Ile Val Ile Asp Met Asp Glu Asn Arg Leu Gln Leu Ala Lys
        195                 200                 205

Glu Leu Gly Ala Thr His Thr Ile Asn Ser Gly Thr Glu Asn Val Val
    210                 215                 220

Glu Ala Val His Arg Ile Ala Ala Glu Gly Val Asp Val Ala Ile Glu
225                 230                 235                 240

Ala Val Gly Ile Pro Ala Thr Trp Asp Ile Cys Gln Glu Ile Val Lys
                245                 250                 255

Pro Gly Ala His Ile Ala Asn Val Gly Val His Gly Val Lys Val Asp
            260                 265                 270

Phe Glu Ile Gln Lys Leu Trp Ile Lys Asn Leu Thr Ile Thr Thr Gly
        275                 280                 285

Leu Val Asn Thr Asn Thr Thr Pro Met Leu Met Lys Val Ala Ser Thr
    290                 295                 300

Asp Lys Leu Pro Leu Lys Lys Met Ile Thr His Arg Phe Glu Leu Ala
305                 310                 315                 320

Glu Ile Glu His Ala Tyr Gln Val Phe Leu Asn Gly Ala Lys Glu Lys
```

```
            325                 330                 335
Ala Met Lys Ile Ile Leu Ser Asn Ala Gly Ala Ala
        340                 345
```

<210> SEQ ID NO 71
<211> LENGTH: 1644
<212> TYPE: DNA
<213> ORGANISM: Artificial Sequence
<220> FEATURE:
<223> OTHER INFORMATION: codon optimized L. lactis kivD coding region
      for S. cerevisiae expression

<400> SEQUENCE: 71

| | | | | | |
|---|---|---|---|---|---|
| atgtatacag | taggtgacta | tctgttggac | agattacacg | aattaggtat | agaagaaata | 60 |
| ttcggagtac | caggtgacta | caatttgcaa | tttctagatc | aaattatttc | acacaaagat | 120 |
| atgaaatggg | tgggaaatgc | taatgagtta | aatgcctcct | atatggccga | cgggtacgca | 180 |
| agaacgaaaa | aggctgcggc | attcttgact | catttggtg | ttggcgaatt | atccgcagtt | 240 |
| aatggcttag | cgggctccta | tgctgagaac | ctgcctgttg | ttgagatcgt | gggatctcct | 300 |
| acctcgaaag | tgcagaacga | aggtaagttt | gttcaccata | cgttggctga | tggtgatttc | 360 |
| aagcacttta | tgaagatgca | cgaaccggtt | actgctgcca | ggactttatt | gacagccgag | 420 |
| aatgcaactg | ttgaaattga | tagagtgttg | tctgccttac | taaggaaag | aaagccggtt | 480 |
| tacatcaatt | tacctgtaga | tgtagctgcc | gctaaggctg | aaaaaccatc | cttgcctctt | 540 |
| aagaaggaaa | attccacgtc | gaatacatct | gatcaagaga | ttctgaacaa | aatacaggaa | 600 |
| agtctgaaga | atgccaagaa | accaattgta | atcacaggcc | atgaaattat | atcgttcggc | 660 |
| ctagagaaga | ctgttactca | gtttatttca | aagactaagt | tacctattac | tactttgaac | 720 |
| tttggtaaat | catctgttga | tgaagcattg | ccctcatttt | tggggattta | caacggtact | 780 |
| ctgtcagagc | caaacttgaa | ggaatttgtg | gaatctgctg | attttattct | tatgttgggt | 840 |
| gtaaagctta | ccgattctag | tacgggtgca | tttactcacc | atcttaatga | aaataaaatg | 900 |
| atttccttga | atatcgatga | aggtaaaatt | ttcaacgaaa | gaatccaaaa | tttcgacttc | 960 |
| gaatccctga | tatcatctct | tcttgacttg | tccgaaattg | aatataaagg | caagtacata | 1020 |
| gataaaaagc | aagaagattt | tgtaccttct | aacgcgctgt | tgtcacaaga | tagactgtgg | 1080 |
| caagctgtcg | aaaatttgac | ccaaagtaat | gagacgatcg | tggctgaaca | aggcacttct | 1140 |
| ttcttcggtg | cctcatctat | atttctgaaa | tcgaaatcac | attttattgg | tcaaccttg | 1200 |
| tggggatcta | taggatacac | tttccccgca | gctctaggca | gccaaattgc | agataaagaa | 1260 |
| tctagacatt | tattgtttat | cggagatgga | tcattgcaac | tgactgtcca | agaattagga | 1320 |
| ctagccatta | gagagaagat | aaacccaatc | tgctttatca | ttaataacga | tggttacacg | 1380 |
| gttgagaggg | aaattcatgg | tccgaaccag | agttataatg | acattcctat | gtggaattac | 1440 |
| tcaaaactgc | cagaaagttt | cggggcaacg | gaagacagag | ttgtgtccaa | aattgtgaga | 1500 |
| acagaaaatg | aattcgtatc | cgtgatgaaa | gaagctcaag | cagatccaaa | taggatgtat | 1560 |
| tggatagaac | ttattctagc | aaaggagggt | gcacctaaag | ttttgaaaaa | gatgggtaag | 1620 |
| ttatttgcag | aacaaaacaa | gagc | | | | 1644 |

<210> SEQ ID NO 72
<211> LENGTH: 753
<212> TYPE: DNA
<213> ORGANISM: Saccharomyces cerevisiae

<400> SEQUENCE: 72

```
gcatgcttgc atttagtcgt gcaatgtatg actttaagat ttgtgagcag gaagaaaagg      60
gagaatcttc taacgataaa cccttgaaaa actgggtaga ctacgctatg ttgagttgct     120
acgcaggctg cacaattaca cgagaatgct cccgcctagg atttaaggct aagggacgtg     180
caatgcagac gacagatcta aatgaccgtg tcggtgaagt gttcgccaaa cttttcggtt     240
aacacatgca gtgatgcacg cgcgatggtg ctaagttaca tatatatata tatagccata     300
gtgatgtcta agtaaccttt atggtatatt tcttaatgtg gaaagatact agcgcgcgca     360
cccacacaca agcttcgtct tttcttgaag aaaagaggaa gctcgctaaa tgggattcca     420
ctttccgttc cctgccagct gatggaaaaa ggttagtgga acgatgaaga ataaaaagag     480
agatccactg aggtgaaatt tcagctgaca gcgagtttca tgatcgtgat gaacaatggt     540
aacgagttgt ggctgttgcc agggagggtg gttctcaact tttaatgtat ggccaaatcg     600
ctacttgggt ttgttatata acaaagaaga aataatgaac tgattctctt cctccttctt     660
gtcctttctt aattctgttg taattacctt cctttgtaat ttttttttgta attattcttc     720 ttaataatcc aaacaaacac acatattaca ata                                  753
```

<210> SEQ ID NO 73
<211> LENGTH: 316
<212> TYPE: DNA
<213> ORGANISM: Saccharomyces cerevisiae

<400> SEQUENCE: 73

```
gagtaagcga atttcttatg atttatgatt tttattatta aataagttat aaaaaaaata      60
agtgtataca aattttaaag tgactcttag gttttaaaac gaaaattctt attcttgagt     120
aactctttcc tgtaggtcag gttgctttct caggtatagc atgaggtcgc tcttattgac     180
cacacctcta ccggcatgcc gagcaaatgc ctgcaaatcg ctccccattt cacccaattg     240
tagatatgct aactccagca atgagttgat gaatctcggt gtgtattta tgtcctcaga     300 ggacaacacc tgtggt                                                     316
```

<210> SEQ ID NO 74
<211> LENGTH: 30
<212> TYPE: DNA
<213> ORGANISM: Artificial Sequence
<220> FEATURE:
<223> OTHER INFORMATION: primer

<400> SEQUENCE: 74

```
ggaattcaca catgaaagct ctggtttatc                                       30
```

<210> SEQ ID NO 75
<211> LENGTH: 28
<212> TYPE: DNA
<213> ORGANISM: Artificial Sequence
<220> FEATURE:
<223> OTHER INFORMATION: Primer

<400> SEQUENCE: 75

```
gcgtccaggg cgtcaaagat caggcagc                                         28
```

<210> SEQ ID NO 76
<211> LENGTH: 55
<212> TYPE: DNA
<213> ORGANISM: Artificial Sequence
<220> FEATURE:
<223> OTHER INFORMATION: Primer

<400> SEQUENCE: 76
aaacaaacac acatattaca atagctgagg atgaaagctc tggtttatca cggtg            55

<210> SEQ ID NO 77
<211> LENGTH: 55
<212> TYPE: DNA
<213> ORGANISM: Artificial Sequence
<220> FEATURE:
<223> OTHER INFORMATION: primer

<400> SEQUENCE: 77
atcataagaa attcgcttac tcttaattaa tcaggcagcg cctgcgttcg agagg            55

<210> SEQ ID NO 78
<211> LENGTH: 8994
<212> TYPE: DNA
<213> ORGANISM: Artificial Sequence
<220> FEATURE:
<223> OTHER INFORMATION: constructed plasmid

<400> SEQUENCE: 78
ctagttctag agcggccgcc accgcggtgg agctccagct tttgttccct ttagtgaggg     60
ttaattgcgc gcttggcgta atcatggtca tagctgtttc ctgtgtgaaa ttgttatccg    120
ctcacaattc cacacaacat aggagccgga agcataaagt gtaaagcctg gggtgcctaa    180
tgagtgaggt aactcacatt aattgcgttg cgctcactgc ccgctttcca gtcgggaaac    240
ctgtcgtgcc agctgcatta atgaatcggc caacgcgcgg ggagaggcgg tttgcgtatt    300
gggcgctctt ccgcttcctc gctcactgac tcgctgcgct cggtcgttcg gctgcggcga    360
gcggtatcag ctcactcaaa ggcggtaata cggttatcca cagaatcagg ggataacgca    420
ggaaagaaca tgtgagcaaa aggccagcaa aaggccagga accgtaaaaa ggccgcgttg    480
ctggcgtttt tccataggct ccgcccccct gacgagcatc acaaaaatcg acgctcaagt    540
cagaggtggc gaaacccgac aggactataa agataccagg cgtttccccc tggaagctcc    600
ctcgtgcgct ctcctgttcc gaccctgccg cttaccggat acctgtccgc ctttctccct    660
tcgggaagcg tggcgctttc tcatagctca cgctgtaggt atctcagttc ggtgtaggtc    720
gttcgctcca agctgggctg tgtgcacgaa ccccccgttc agcccgaccg ctgcgcctta    780
tccggtaact atcgtcttga gtccaacccg gtaagacacg acttatcgcc actggcagca    840
gccactggta acaggattag cagagcgagg tatgtaggcg gtgctacaga gttcttgaag    900
tggtggccta actacggcta cactagaagg acagtatttg gtatctgcgc tctgctgaag    960
ccagttacct tcggaaaaag agttggtagc tcttgatccg gcaaacaaac caccgctggt   1020
agcggtggtt tttttgtttg caagcagcag attacgcgca gaaaaaaagg atctcaagaa   1080
gatcctttga tcttttctac ggggtctgac gctcagtgga acgaaaactc acgttaaggg   1140
attttggtca tgagattatc aaaaaggatc ttcacctaga tccttttaaa ttaaaaatga   1200
agttttaaat caatctaaag tatatatgag taaacttggt ctgacagtta ccaatgctta   1260
atcagtgagg cacctatctc agcgatctgt ctatttcgtt catccatagt tgcctgactc   1320
cccgtcgtgt agataactac gatacgggag ggcttaccat ctggccccag tgctgcaatg   1380
ataccgcgag acccacgctc accggctcca gatttatcag caataaacca gccagccgga   1440
agggccgagc gcagaagtgg tcctgcaact ttatccgcct ccatccagtc tattaattgt   1500
tgccgggaag ctagagtaag tagttcgcca gttaatagtt tgcgcaacgt tgttgccatt   1560
gctacaggca tcgtggtgtc acgctcgtcg tttggtatgg cttcattcag ctccggttcc   1620

```
caacgatcaa ggcgagttac atgatccccc atgttgtgca aaaaagcggt tagctccttc   1680
ggtcctccga tcgttgtcag aagtaagttg gccgcagtgt tatcactcat ggttatggca   1740
gcactgcata attctcttac tgtcatgcca tccgtaagat gcttttctgt gactggtgag   1800
tactcaacca agtcattctg agaatagtgt atgcggcgac cgagttgctc ttgcccggcg   1860
tcaatacggg ataataccgc gccacatagc agaactttaa aagtgctcat cattggaaaa   1920
cgttcttcgg ggcgaaaact ctcaaggatc ttaccgctgt tgagatccag ttcgatgtaa   1980
cccactcgtg cacccaactg atcttcagca tcttttactt tcaccagcgt ttctgggtga   2040
gcaaaaacag gaaggcaaaa tgccgcaaaa aagggaataa gggcgacacg gaaatgttga   2100
atactcatac tcttcctttt tcaatattat tgaagcattt atcagggtta ttgtctcatg   2160
agcggataca tatttgaatg tatttagaaa aataaacaaa taggggttcc gcgcacattt   2220
ccccgaaaag tgccacctga acgaagcatc tgtgcttcat tttgtagaac aaaaatgcaa   2280
cgcgagagcg ctaattttc aaacaaagaa tctgagctgc attttacag aacagaaatg   2340
caacgcgaaa gcgctatttt accaacgaag aatctgtgct tcattttgt aaaacaaaaa   2400
tgcaacgcga gagcgctaat ttttcaaaca aagaatctga ctgcatttt tacagaacag   2460
aaatgcaacg cgagagcgct attttaccaa caaagaatct atacttcttt tttgttctac   2520
aaaaatgcat cccgagagcg ctattttct aacaaagcat cttagattac ttttttctc   2580
ctttgtgcgc tctataatgc agtctcttga taactttttg cactgtaggt ccgttaaggt   2640
tagaagaagg ctactttggt gtctattttc tcttccataa aaaagcctg actccacttc   2700
ccgcgtttac tgattactag cgaagctgcg ggtgcatttt ttcaagataa aggcatcccc   2760
gattatattc tataccgatg tggattgcgc atactttgtg aacagaaagt gatagcgttg   2820
atgattcttc attggtcaga aaattatgaa cggtttcttc tattttgtct ctatatacta   2880
cgtataggaa atgtttacat tttcgtattg ttttcgattc actctatgaa tagttcttac   2940
tacaattttt ttgtctaaag agtaaactaa gagataaaca taaaaaatgt agaggtcgag   3000
tttagatgca agttcaagga gcgaaaggtg gatgggtagg ttatataggg atatagcaca   3060
gagatatata gcaaagagat acttttgagc aatgtttgtg gaagcggtat tcgcaatatt   3120
ttagtagctc gttacagtcc ggtgcgtttt tggttttttg aaagtgcgtc ttcagagcgc   3180
ttttggtttt caaaagcgct ctgaagttcc tatactttct agagaatagg aacttcggaa   3240
taggaacttc aaagcgtttc cgaaaacgag cgcttccgaa aatgcaacgc gagctgcgca   3300
catacagctc actgttcacg tcgcacctat atctgcgtgt tgcctgtata tatatataca   3360
tgagaagaac ggcatagtgc gtgtttatgc ttaaatgcgt acttatatgc gtctatttat   3420
gtaggatgaa aggtagtcta gtacctcctg tgatattatc ccattccatg cggggtatcg   3480
tatgcttcct tcagcactac cctttagctg ttctatatgc tgccactcct caattggatt   3540
agtctcatcc ttcaatgcta tcatttcctt tgatattgga tcatactaag aaaccattat   3600
tatcatgaca ttaacctata aaaataggcg tatcacgagg ccctttcgtc tcgcgcgttt   3660
cggtgatgac ggtgaaaacc tctgacacat gcagctcccg gagacggtca cagcttgtct   3720
gtaagcggat gccgggagca gacaagcccg tcagggcgcg tcagcgggtg ttggcgggtg   3780
tcggggctgg cttaactatg cggcatcaga gcagattgta ctgagagtgc accatatcga   3840
ctacgtcgta aggccgtttc tgacagagta aaattcttga gggaactttc accattatgg   3900
gaaatgcttc aagaaggtat tgacttaaac tccatcaaat ggtcaggtca ttgagtgttt   3960
```

```
tttatttgtt gtattttttt tttttagag aaaatcctcc aatatcaaat taggaatcgt    4020
agtttcatga ttttctgtta cacctaactt tttgtgtggt gccctcctcc ttgtcaatat    4080
taatgttaaa gtgcaattct ttttccttat cacgttgagc cattagtatc aatttgctta    4140
cctgtattcc tttactatcc tccttttctt ccttcttgat aaatgtatgt agattgcgta    4200
tatagtttcg tctaccctat gaacatattc cattttgtaa tttcgtgtcg tttctattat    4260
gaatttcatt tataaagttt atgtacaaat atcataaaaa aagagaatct ttttaagcaa    4320
ggattttctt aacttcttcg gcgacagcat caccgacttc ggtggtactg ttggaaccac    4380
ctaaatcacc agttctgata cctgcatcca aaacctttt aactgcatct tcaatggcct    4440
taccttcttc aggcaagttc aatgacaatt tcaacatcat tgcagcagac aagatagtgg    4500
cgatagggtc aaccttattc tttggcaaat ctggagcaga accgtggcat ggttcgtaca    4560
aaccaaatgc ggtgttcttg tctggcaaag aggccaagga cgcagatggc aacaaaccca    4620
aggaacctgg gataacggag gcttcatcgg agatgatatc accaaacatg ttgctggtga    4680
ttataatacc atttaggtgg gttgggttct taactaggat catggcggca gaatcaatca    4740
attgatgttg aaccttcaat gtagggaatt cgttcttgat ggtttcctcc acagtttttc    4800
tccataatct tgaagaggcc aaaagattag ctttatccaa ggaccaaata ggcaatggtg    4860
gctcatgttg tagggccatg aaagcggcca ttcttgtgat tctttgcact tctggaacgg    4920
tgtattgttc actatcccaa gcgacaccat caccatcgtc ttccttctc ttaccaaagt    4980
aaatacctcc cactaattct ctgacaacaa cgaagtcagt acctttagca aattgtggct    5040
tgattggaga taagtctaaa agagagtcgg atgcaaagtt acatggtctt aagttggcgt    5100
acaattgaag ttctttacgg attttttagta aaccttgttc aggtctaaca ctaccggtac    5160
cccatttagg accagccaca gcacctaaca aaacggcatc aaccttcttg gaggcttcca    5220
gcgcctcatc tggaagtggg acacctgtag catcgatagc agcaccacca attaaatgat    5280
tttcgaaatc gaacttgaca ttggaacgaa catcagaaat agctttaaga accttaatgg    5340
cttcggctgt gatttcttga ccaacgtggt cacctggcaa aacgacgatc ttcttagggg    5400
cagacatagg ggcagacatt agaatggtat atccttgaaa tatatatata tattgctgaa    5460
atgtaaaagg taagaaaagt tagaaagtaa gacgattgct aaccacctat tggaaaaaac    5520
aataggtcct taaataatat tgtcaacttc aagtattgtg atgcaagcat ttagtcatga    5580
acgcttctct attctatatg aaaagccggt tccggcctct cacctttcct ttttctccca    5640
atttttcagt tgaaaaaggt atatgcgtca ggcgacctct gaaattaaca aaaaatttcc    5700
agtcatcgaa tttgattctg tgcgatagcg cccctgtgtg ttctcgttat gttgaggaaa    5760
aaaataatgg ttgctaagag attcgaactc ttgcatctta cgatacctga gtattcccac    5820
agttaactgc ggtcaagata tttcttgaat caggcgcctt agaccgctcg gccaaacaac    5880
caattacttg ttgagaaata gagtataatt atcctataaa tataacgttt ttgaacacac    5940
atgaacaagg aagtacagga caattgattt tgaagagaat gtggattttg atgtaattgt    6000
tgggattcca tttttaataa ggcaataata ttaggtatgt ggatatacta gaagttctcc    6060
tcgaccgtcg atatgcggtg tgaaataccg cacagatgcg taaggagaaa ataccgcatc    6120
aggaaattgt aaacgttaat attttgttaa aattcgcgtt aaattttgt taaatcagct    6180
catttttta ccaataggcc gaaatcggca aaatccctta taaatcaaaa gaatagaccg    6240
agatagggtt gagtgttgtt ccagtttgga acaagagtcc actattaaag aacgtggact    6300
ccaacgtcaa agggcgaaaa accgtctatc agggcgatgg cccactacgt gaaccatcac    6360
```

```
cctaatcaag ttttttgggg tcgaggtgcc gtaaagcact aaatcggaac cctaaaggga    6420
gcccccgatt tagagcttga cggggaaagc cggcgaacgt ggcgagaaag gaagggaaga    6480
aagcgaaagg agcgggcgct agggcgctgg caagtgtagc ggtcacgctg cgcgtaacca    6540
ccacacccgc cgcgcttaat gcgccgctac agggcgcgtc gcgccattcg ccattcaggc    6600
tgcgcaactg ttgggaaggg cgatcggtgc gggcctcttc gctattacgc cagctggcga    6660
aagggggatg tgctgcaagg cgattaagtt gggtaacgcc agggttttcc cagtcacgac    6720
gttgtaaaac gacggccagt gagcgcgcgt aatacgactc actatagggc gaattgggta    6780
ccgggccccc cctcgaggtc gacggtatcg ataagcttga tatcgaattc ctgcagcccg    6840
ggggatccgc atgcttgcat ttagtcgtgc aatgtatgac tttaagattt gtgagcagga    6900
agaaaaggga gaatcttcta acgataaacc cttgaaaaac tgggtagact acgctatgtt    6960
gagttgctac gcaggctgca caattacacg agaatgctcc cgcctaggat ttaaggctaa    7020
gggacgtgca atgcagacga cagatctaaa tgaccgtgtc ggtgaagtgt tcgccaaact    7080
tttcggttaa cacatgcagt gatgcacgcg cgatggtgct aagttacata tatatatata    7140
tatatatata tagccatagt gatgtctaag taacctttat ggtatatttc ttaatgtgga    7200
aagatactag cgcgcgcacc cacacacaag cttcgtcttt tcttgaagaa aagaggaagc    7260
tcgctaaatg ggattccact ttccgttccc tgccagctga tggaaaaagg ttagtggaac    7320
gatgaagaat aaaagagag atccactgag gtgaaatttc agctgacagc gagtttcatg    7380
atcgtgatga acaatggtaa cgagttgtgg ctgttgccag ggagggtggt tctcaacttt    7440
taatgtatgg ccaaatcgct acttgggttt gttatataac aaagaagaaa taatgaactg    7500
attctcttcc tccttcttgt cctttcttaa ttctgttgta attaccttcc tttgtaattt    7560
tttttgtaat tattcttctt aataatccaa acaaacacac atattacaat agctagctga    7620
ggatgaaggc attagtttat catggggatc acaaaatttc gttagaagac aaaccaaaac    7680
ccactctgca gaaaccaaca gacgttgtgg ttagggtgtt gaaaacaaca atttgcggta    7740
ctgacttggg aatatacaaa ggtaagaatc ctgaagtggc agatggcaga atcctgggtc    7800
atgagggcgt tggcgtcatt gaagaagtgg gcgaatccgt gacacaattc aaaaaggggg    7860
ataaagtttt aatctcctgc gttactagct gtggatcgtg tgattattgc aagaagcaac    7920
tgtattcaca ctgtagagac ggtggctgga ttttaggtta catgatcgac ggtgtccaag    7980
ccgaatacgt cagaatacca catgctgaca attcattgta taagatcccg caaactatcg    8040
atgatgaaat tgcagtacta ctgtccgata ttttacctac tggacatgaa attggtgttc    8100
aatatggtaa cgttcaacca ggcgatgctg tagcaattgt aggagcaggt cctgttggaa    8160
tgtcagtttt gttaactgct caattttact cgcctagtac cattattgtt atcgacatgg    8220
acgaaaaccg tttacaatta gcgaaggagc ttggggccac acacactatt aactccggta    8280
ctgaaaatgt tgtcgaagct gtgcatcgta tagcagccga aggagtggat gtagcaatag    8340
aagctgttgg tataccgca acctgggaca tctgtcagga aattgtaaaa cccggcgctc    8400
atattgccaa cgtgggagtt catggtgtta aggtggactt tgaaattcaa aagttgtgga    8460
ttaagaatct aaccatcacc actggtttgg ttaacactaa tactacccca atgttgatga    8520
aggtagcctc tactgataaa ttgcctttaa agaaaatgat tactcacagg tttgagttag    8580
ctgaaatcga acacgcatat caggttttct tgaatgcgc taaagaaaaa gctatgaaga    8640
ttattctatc taatgcaggt gccgcctaat taattaagag taagcgaatt tcttatgatt    8700
```

```
tatgattttt attattaaat aagttataaa aaaaataagt gtatacaaat tttaaagtga      8760
ctcttaggtt ttaaaacgaa aattcttatt cttgagtaac tctttcctgt aggtcaggtt      8820
gctttctcag gtatagcatg aggtcgctct tattgaccac acctctaccg gcatgccgag      8880
caaatgcctg caaatcgctc cccatttcac ccaattgtag atatgctaac tccagcaatg      8940
agttgatgaa tctcggtgtg tattttatgt cctcagagga caacacctgt ggta            8994

<210> SEQ ID NO 79
<211> LENGTH: 2145
<212> TYPE: DNA
<213> ORGANISM: Artificial Sequence
<220> FEATURE:
<223> OTHER INFORMATION: constructed chimeric gene

<400> SEQUENCE: 79
gcatgcttgc atttagtcgt gcaatgtatg actttaagat tgtgagcag  gaagaaaagg        60 gagaatcttc taacgataaa cccttgaaaa actgggtaga ctacgctatg ttgagttgct      120
acgcaggctg cacaattaca cgagaatgct cccgcctagg atttaaggct aagggacgtg      180
caatgcagac gacagatcta aatgaccgtg tcggtgaagt gttcgccaaa cttttcggtt      240
aacacatgca gtgatgcacg cgcgatggtg ctaagttaca tatatatata tatatatata      300
tatagccata gtgatgtcta agtaacctTt atggtatatt tcttaatgtg aaagatact      360 agcgcgcgca cccacacaca agcttcgtct tttcttgaag aaaagaggaa gctcgctaaa      420
tgggattcca ctttccgttc cctgccagct gatggaaaaa ggttagtgga acgatgaaga      480
ataaaaagag agatccactg aggtgaaatt tcagctgaca gcgagtttca tgatcgtgat      540
gaacaatggt aacgagttgt ggctgttgcc agggagggtg gttctcaact tttaatgtat      600
ggccaaatcg ctactgggt tgttatata acaaagaaga aataatgaac tgattctctt       660
cctccttctt gtcctttctt aattctgttg taattacctt cctttgtaat ttttttttgta     720 attattcttc ttaataatcc aaacaaacac acatattaca atagctagct gaggatgaag      780
gcattagttt atcatgggga tcacaaaatt tcgttagaag acaaaccaaa acccactctg      840
cagaaaccaa cagacgttgt ggttagggtg ttgaaaacaa caatttgcgg tactgacttg      900
ggaatataca aaggtaagaa tcctgaagtg gcagatggca gaatcctggg tcatgagggc      960
gttggcgtca ttgaagaagt gggcgaatcc gtgacacaat tcaaaaaggg ggataaagtt     1020
ttaatctcct gcgttactag ctgtggatcg tgtgattatt gcaagaagca actgtattca     1080
cactgtagag acgtggctg gattttaggt tacatgatcg acggtgtcca agccgaatac     1140
gtcagaatac cacatgctga caattcattg tataagatcc cgcaaactat cgatgatgaa     1200
attgcagtac tactgtccga tattttacct actggacatg aaattggtgt tcaatatggt     1260
aacgttcaac caggcgatgc tgtagcaatt gtaggagcag gtcctgttgg aatgtcagtt     1320
ttgttaactg ctcaatttta ctcgcctagt accattattg ttatcgacat ggacgaaaac     1380
cgtttacaat tagcgaagga gcttggggcc acacacacta ttaactccgg tactgaaaat     1440
gttgtcgaag ctgtgcatcg tatagcagcc gaaggagtgg atgtagcaat agaagctgtt     1500
ggtatacccg caacctggga catctgtcag gaaattgtaa aacccggcgc tcatattgcc     1560
aacgtgggag ttcatggtgt taaggtggac tttgaaattc aaaagttgtg gattaagaat     1620
ctaaccatca ccactggttt ggttaacact aatactaccc caatgttgat gaaggtagcc     1680
tctactgata aattgccttt aaagaaaatg attactcaca ggtttgagtt agctgaaatc     1740
gaacacgcat atcaggtttt cttgaatggc gctaaagaaa aagctatgaa gattattcta     1800
```

```
tctaatgcag gtgccgccta attaattaag agtaagcgaa tttcttatga tttatgattt     1860
ttattattaa ataagttata aaaaaaataa gtgtatacaa atttttaaagt gactcttagg     1920 ttttaaaacg aaaattctta ttcttgagta actctttcct gtaggtcagg ttgctttctc     1980
aggtatagca tgaggtcgct cttattgacc acacctctac cggcatgccg agcaaatgcc     2040
tgcaaatcgc tccccatttc acccaattgt agatatgcta actccagcaa tgagttgatg     2100
aatctcggtg tgtattttat gtcctcagag gacaacacct gtggt                     2145
```

<210> SEQ ID NO 80
<211> LENGTH: 4280
<212> TYPE: DNA
<213> ORGANISM: Artificial Sequence
<220> FEATURE:
<223> OTHER INFORMATION: vector

<400> SEQUENCE: 80

```
ggggatcctc tagagtcgac ctgcaggcat gcaagcttgg cgtaatcatg gtcatagctg       60
tttcctgtgt gaaattgtta tccgctcaca attccacaca acatacgagc cggaagcata      120
aagtgtaaag cctggggtgc ctaatgagtg agctaactca cattaattgc gttgcgctca      180
ctgcccgctt tccagtcggg aaacctgtcg tgccagctgc attaatgaat cggccaacgc      240
gcggggagag gcggtttgcg tattgggcgc tcttccgctt cctcgctcac tgactcgctg      300
cgctcggtcg ttcggctgcg gcgagcggta tcagctcact caaaggcggt aatacggtta      360
tccacagaat caggggataa cgcaggaaag aacatgtgag caaaaggcca gcaaaaggcc      420
aggaaccgta aaaaggccgc gttgctggcg ttttccata ggctccgccc ccctgacgag       480
catcacaaaa atcgacgctc aagtcagagg tggcgaaacc cgacaggact ataaagatac      540
caggcgtttc ccctggaag ctccctcgtg cgctctcctg ttccgaccct gccgcttacc       600
ggatacctgt ccgcctttct cccttcggga agcgtggcgc tttctcatag ctcacgctgt      660
aggtatctca gttcggtgta ggtcgttcgc tccaagctgg gctgtgtgca cgaacccccc      720
gttcagcccg accgctgcgc cttatccggt aactatcgtc ttgagtccaa cccggtaaga      780
cacgacttat cgccactggc agcagccact ggtaacagga ttagcagagc gaggtatgta      840
ggcggtgcta cagagttctt gaagtggtgg cctaactacg gctacactag aaggacagta      900
tttggtatct gcgctctgct gaagccagtt accttcggaa aaagagttgg tagctcttga      960
tccggcaaac aaaccaccgc tggtagcggt ggtttttttg tttgcaagca gcagattacg     1020
cgcagaaaaa aaggatctca agaagatcct ttgatctttt ctacggggtc tgacgctcag     1080
tggaacgaaa actcacgtta agggattttg gtcatgagat tatcaaaaag gatcttcacc     1140
tagatccttt taaattaaaa atgaagtttt aaatcaatct aaagtatata tgagtaaact     1200
tggtctgaca gttaccaatg cttaatcagt gaggcaccta tctcagcgat ctgtctattt     1260
cgttcatcca tagttgcctg actccccgtc gtgtagataa ctacgatacg ggagggctta     1320
ccatctggcc ccagtgctgc aatgataccg cgagacccac gctcaccggc tccagattta     1380
tcagcaataa accagccagc cggaagggcc gagcgcagaa gtggtcctgc aactttatcc     1440
gcctccatcc agtctattaa ttgttgccgg gaagctagag taagtagttc gccagttaat     1500
agtttgcgca acgttgttgc cattgctaca ggcatcgtgg tgtcacgctc gtcgtttggt     1560
atggcttcat tcagctccgg ttcccaacga tcaaggcgag ttacatgatc ccccatgttg     1620
tgcaaaaaag cggttagctc cttcggtcct ccgatcgttg tcagaagtaa gttggccgca     1680
```

-continued

| | |
|---|---|
| gtgttatcac tcatggttat ggcagcactg cataattctc ttactgtcat gccatccgta | 1740 |
| agatgctttt ctgtgactgg tgagtactca accaagtcat tctgagaata gtgtatgcgg | 1800 |
| cgaccgagtt gctcttgccc ggcgtcaata cgggataata ccgcgccaca tagcagaact | 1860 |
| ttaaaagtgc tcatcattgg aaaacgttct tcggggcgaa aactctcaag gatcttaccg | 1920 |
| ctgttgagat ccagttcgat gtaacccact cgtgcaccca actgatcttc agcatctttt | 1980 |
| actttcacca gcgtttctgg gtgagcaaaa acaggaaggc aaaatgccgc aaaaaaggga | 2040 |
| ataagggcga cacggaaatg ttgaatactc atactcttcc ttttcaata ttattgaagc | 2100 |
| atttatcagg gttattgtct catgagcgga tacatatttg aatgtattta gaaaaataaa | 2160 |
| caaatagggg ttccgcgcac atttccccga aaagtgccac ctgacgtcta agaaaccatt | 2220 |
| attatcatga cattaaccta taaaaatagg cgtatcacga ggcccttcg tctcgcgcgt | 2280 |
| ttcggtgatg acggtgaaaa cctctgacac atgcagctcc cggagacggt cacagcttgt | 2340 |
| ctgtaagcgg atgccgggag cagacaagcc cgtcagggcg cgtcagcggg tgttggcggg | 2400 |
| tgtcggggct ggcttaacta tgcggcatca gagcagattg tactgagagt gcaccatatg | 2460 |
| cggtgtgaaa taccgcacag atgcgtaagg agaaaatacc gcatcaggcg ccattcgcca | 2520 |
| ttcaggctgc gcaactgttg ggaagggcga tcggtgcggg cctcttcgct attacgccag | 2580 |
| ctggcgaaag gggatgtgc tgcaaggcga ttaagttggg taacgccagg gttttcccag | 2640 |
| tcacgacgtt gtaaaacgac ggccagtgaa ttcgagctcg gtaccccgg ctctgagaca | 2700 |
| gtagtaggtt agtcatcgct ctaccgacgc gcaggaaaag aaagaagcat tgcggattac | 2760 |
| gtattctaat gttcagcccg cggaacgcca gcaaatcacc acccatgcgc atgatactga | 2820 |
| gtcttgtaca cgctgggctt ccagtgtact gagagtgcac cataccacag cttttcaatt | 2880 |
| caattcatca ttttttttt attcttttt ttgatttcgg tttctttgaa attttttga | 2940 |
| ttcggtaatc tccgaacaga aggaagaacg aaggaaggag cacagactta gattggtata | 3000 |
| tatacgcata tgtagtgttg aagaaacatg aaattgccca gtattcttaa cccaactgca | 3060 |
| cagaacaaaa acctgcagga aacgaagata atcatgtcg aaagctacat ataaggaacg | 3120 |
| tgctgctact catccagtc ctgttgctgc caagctattt aatatcatgc acgaaaagca | 3180 |
| aacaaacttg tgtgcttcat ggatgttcg taccaccaag gaattactgg agttagttga | 3240 |
| agcattaggt cccaaaattt gtttactaaa aacacatgtg gatatcttga ctgatttttc | 3300 |
| catggagggc acagttaagc cgctaaaggc attatccgcc aagtacaatt ttttactctt | 3360 |
| cgaagacaga aaatttgctg acattggtaa tacagtcaaa ttgcagtact ctgcgggtgt | 3420 |
| atacagaata gcagaatggg cagacattac gaatgcacac ggtgtggtgg gcccaggtat | 3480 |
| tgttagcggt ttgaagcagg cggcagaaga agtaacaaag gaacctagag gccttttgat | 3540 |
| gttagcagaa ttgtcatgca agggctccct atctactgga gaatatacta agggtactgt | 3600 |
| tgacattgcg aagagcgaca agatttttgt tatcggcttt attgctcaaa gagacatggg | 3660 |
| tggaagagat gaaggttacg attggttgat tatgacaccc ggtgtgggtt tagatgacaa | 3720 |
| gggagacgca ttgggtcaac agtatagaac cgtggatgat gtggtctcta caggatctga | 3780 |
| cattattatt gttggaagag gactattgc aaagggaagg gatgctaagg tagagggtga | 3840 |
| acgttacaga aaagcaggct gggaagcata tttgagaaga tgcggccagc aaaactaaaa | 3900 |
| aactgtatta taagtaaatg catgtatact aaactcacaa attagagctt caatttaatt | 3960 |
| atatcagtta tttacctatg cggtgtgaaa taccgcacag atgcgtaagg agaaaatacc | 4020 |
| gcatcaggaa attgtaaacg ttaatatttt gttaaaattc gcgttaaatt tttgttaaat | 4080 |

```
cagctcattt tttaaccaat aggccgaaat cggcaaaatc ttcagcccgc ggaacgccag    4140
caaatcacca cccatgcgca tgatactgag tcttgtacac gctgggcttc cagtgatgat    4200
acaacgagtt agccaaggtg agcacggatg tctaaattag aattacgttt taatatcttt    4260
ttttccatat ctagggctag                                                4280

<210> SEQ ID NO 81
<211> LENGTH: 30
<212> TYPE: DNA
<213> ORGANISM: Artificial Sequence
<220> FEATURE:
<223> OTHER INFORMATION: primer

<400> SEQUENCE: 81
gcatgcttgc atttagtcgt gcaatgtatg                                       30

<210> SEQ ID NO 82
<211> LENGTH: 54
<212> TYPE: DNA
<213> ORGANISM: Artificial Sequence
<220> FEATURE:
<223> OTHER INFORMATION: primer

<400> SEQUENCE: 82
gaacattaga atacgtaatc cgcaatgcac tagtaccaca ggtgttgtcc tctg             54

<210> SEQ ID NO 83
<211> LENGTH: 54
<212> TYPE: DNA
<213> ORGANISM: Artificial Sequence
<220> FEATURE:
<223> OTHER INFORMATION: primer

<400> SEQUENCE: 83
cagaggacaa cacctgtggt actagtgcat tgcggattac gtattctaat gttc             54

<210> SEQ ID NO 84
<211> LENGTH: 28
<212> TYPE: DNA
<213> ORGANISM: Artificial Sequence
<220> FEATURE:
<223> OTHER INFORMATION: primer

<400> SEQUENCE: 84
caccttggct aactcgttgt atcatcac                                         28

<210> SEQ ID NO 85
<211> LENGTH: 100
<212> TYPE: DNA
<213> ORGANISM: Artificial Sequence
<220> FEATURE:
<223> OTHER INFORMATION: primer

<400> SEQUENCE: 85
ttttaagccg aatgagtgac agaaaaagcc cacaacttat caagtgatat tgaacaaagg    60
gcgaaacttc gcatgcttgc atttagtcgt gcaatgtatg                           100

<210> SEQ ID NO 86
<211> LENGTH: 98
<212> TYPE: DNA
<213> ORGANISM: Artificial Sequence
<220> FEATURE:
<223> OTHER INFORMATION: primer
```

```
<400> SEQUENCE: 86
cccaattggt aaatattcaa caagagacgc gcagtacgta acatgcgaat tgcgtaattc      60
acggcgataa caccttggct aactcgttgt atcatcac                              98

<210> SEQ ID NO 87
<211> LENGTH: 29
<212> TYPE: DNA
<213> ORGANISM: Artificial Sequence
<220> FEATURE:
<223> OTHER INFORMATION: primer

<400> SEQUENCE: 87
caaaagccca tgtcccacac caaaggatg                                        29

<210> SEQ ID NO 88
<211> LENGTH: 26
<212> TYPE: DNA
<213> ORGANISM: Artificial Sequence
<220> FEATURE:
<223> OTHER INFORMATION: primer

<400> SEQUENCE: 88
caccatcgcg cgtgcatcac tgcatg                                           26

<210> SEQ ID NO 89
<211> LENGTH: 28
<212> TYPE: DNA
<213> ORGANISM: Artificial Sequence
<220> FEATURE:
<223> OTHER INFORMATION: primer

<400> SEQUENCE: 89
tcggtttttg caatatgacc tgtgggcc                                         28

<210> SEQ ID NO 90
<211> LENGTH: 22
<212> TYPE: DNA
<213> ORGANISM: Artificial Sequence
<220> FEATURE:
<223> OTHER INFORMATION: primer

<400> SEQUENCE: 90
gagaagatgc ggccagcaaa ac                                               22

<210> SEQ ID NO 91
<211> LENGTH: 2745
<212> TYPE: DNA
<213> ORGANISM: Artificial Sequence
<220> FEATURE:
<223> OTHER INFORMATION: constructed coding region-terminator segment

<400> SEQUENCE: 91
atgactgaca aaaaaactct taaagactta agaaatcgta gttctgttta cgattcaatg      60
gttaaatcac ctaatcgtgc tatgttgcgt gcaactggta tgcaagatga agactttgaa     120
aaacctatcg tcggtgtcat ttcaacttgg gctgaaaaca caccttgtaa tatccactta     180
catgactttg gtaaactagc caaagtcggt gttaaggaag ctggtgcttg gccagttcag     240
ttcggaacaa tcacggtttc tgatggaatc gccatgggaa cccaaggaat gcgtttctcc     300
ttgacatctc gtgatattat tgcagattct attgaagcag ccatgggagg tcataatgcg     360
gatgcttttg tagccattgg cggttgtgat aaaaacatgc ccggttctgt tatcgctatg     420
gctaacatgg atatcccagc cattttttgct tacggcggaa caattgcacc tggtaattta     480
```

```
gacggcaaag atatcgattt agtctctgtc tttgaaggtg tcggccattg gaaccacggc    540
gatatgacca agaagaagt taaagctttg aatgtaatg cttgtcccgg tcctggaggc    600
tgcggtggta tgtatactgc taacacaatg gcgacagcta ttgaagtttt gggacttagc    660
cttccgggtt catcttctca cccggctgaa tccgcagaaa agaaagcaga tattgaagaa    720
gctggtcgcg ctgttgtcaa aatgctcgaa atgggcttaa aaccttctga cattttaacg    780
cgtgaagctt ttgaagatgc tattactgta actatggctc tgggaggttc aaccaactca    840
accettcacc tcttagctat tgcccatgct gctaatgtgg aattgacact tgatgatttc    900
aatactttcc aagaaaaagt tcctcatttg gctgatttga accttctgg tcaatatgta    960
ttccaagacc tttacaaggt cggaggggta ccagcagtta tgaaatatct ccttaaaaat   1020
ggcttccttc atggtgaccg tatcacttgt actggcaaaa cagtcgctga aaatttgaag   1080
gcttttgatg atttaacacc tggtcaaaag gttattatgc cgcttgaaaa tcctaaacgt   1140
gaagatggtc cgctcattat tctccatggt aacttggctc cagacggtgc cgttgccaaa   1200
gtttctggtg taaaagtgcg tcgtcatgtc ggtcctgcta aggtctttaa ttctgaagaa   1260
gaagccattg aagctgtctt gaatgatgat attgttgatg gtgatgttgt tgtcgtacgt   1320
tttgtaggac caaagggcgg tcctggtatg cctgaaatgc tttccctttc atcaatgatt   1380
gttggtaaag ggcaaggtga aaaagttgcc cttctgacag atggccgctt ctcaggtggt   1440
acttatggtc ttgtcgtggg tcatatcgct cctgaagcac aagatggcgg tccaatcgcc   1500
tacctgcaaa caggagacat agtcactatt gaccaagaca ctaaggaatt acactttgat   1560
atctccgatg aagagttaaa acatcgtcaa gagaccattg aattgccacc gctctattca   1620
cgcggtatcc ttggtaaata tgctcacatc gtttcgtctg cttctagggg agccgtaaca   1680
gacttttgga agcctgaaga aactggcaaa aaatgttgtc ctggttgctg tggttaagcg   1740
gccgcgttaa ttcaaattaa ttgatatagt tttttaatga gtattgaatc tgtttagaaa   1800
taatggaata ttattttat ttatttattt atattattgg tcggctcttt tcttctgaag   1860
gtcaatgaca aaatgatatg aaggaaataa tgatttctaa aattttacaa cgtaagatat   1920
ttttacaaaa gcctagctca tcttttgtca tgcactattt tactcacgct tgaaattaac   1980
ggccagtcca ctgcggagtc atttcaaagt catcctaatc gatctatcgt ttttgatagc   2040
tcattttgga gttcgcgatt gtcttctgtt attcacaact gtttttaattt ttatttcatt   2100
ctggaactct tcgagttctt tgtaaagtct ttcatagtag cttactttat cctccaacat   2160
atttaacttc atgtcaattt cggctcttaa attttccaca tcatcaagtt caacatcatc   2220
ttttaacttg aatttattct ctagctcttc caaccaagcc tcattgctcc ttgatttact   2280
ggtgaaaagt gatacacttt gcgcgcaatc caggtcaaaa ctttcctgca agaattcac    2340
caatttctcg acatcatagt acaatttgtt ttgttctccc atcacaattt aatatacctg   2400
atggattctt atgaagcgct gggtaatgga cgtgtcactc tacttcgcct tttcccctac   2460
tcctttagt acggaagaca atgctaataa ataagagggt aataataata ttattaatcg   2520
gcaaaaaaga ttaaacgcca agcgtttaat tatcagaaag caaacgtcgt accaatcctt   2580
gaatgcttcc caattgtata ttaagagtca tcacagcaac atattcttgt tattaaatta   2640
attattattg attttgata ttgtataaaa aaaccaaata tgtataaaaa aagtgaataa   2700
aaaataccaa gtatggagaa atatattaga agtctatacg ttaaa                  2745
```

<210> SEQ ID NO 92

```
<211> LENGTH: 27
<212> TYPE: DNA
<213> ORGANISM: Artificial Sequence
<220> FEATURE:
<223> OTHER INFORMATION: primer

<400> SEQUENCE: 92
gacttttgga agcctgaaga aactggc                                          27

<210> SEQ ID NO 93
<211> LENGTH: 20
<212> TYPE: DNA
<213> ORGANISM: Artificial Sequence
<220> FEATURE:
<223> OTHER INFORMATION: primer

<400> SEQUENCE: 93
cttggcagca acaggactag                                                  20

<210> SEQ ID NO 94
<211> LENGTH: 26
<212> TYPE: DNA
<213> ORGANISM: Artificial Sequence
<220> FEATURE:
<223> OTHER INFORMATION: primer

<400> SEQUENCE: 94
ccaggccaat tcaacagact gtcggc                                           26

<210> SEQ ID NO 95
<211> LENGTH: 2347
<212> TYPE: DNA
<213> ORGANISM: Artificial Sequence
<220> FEATURE:
<223> OTHER INFORMATION: constructed URA3 marker with flanking
      homologous repeat sequences for HIS gene replacement and marker
      excision

<400> SEQUENCE: 95
gcattgcgga ttacgtattc taatgttcag gtgctggaag aagagctgct taaccgccgc       60
gcccagggtg aagatccacg ctactttacc ctgcgtcgtc tggatttcgg cggctgtcgt      120
ctttcgctgg caacgccggt tgatgaagcc tgggacggtc cgctctcctt aaacggtaaa      180
cgtatcgcca cctcttatcc tcacctgctc aagcgttatc tcgaccagaa aggcatctct      240
tttaaatcct gcttactgaa cggttctgtt gaagtcgccc cgcgtgccgg actggcggat      300
gcgatttgcg atctggtttc caccggtgcc acgctggaag ctaacggcct gcgcgaagtc      360
gaagttatct atcgctcgaa agcctgcctg attcaacgcg atggcgaaat ggaagaatcc      420
aaacagcaac tgatcgacaa actgctgacc cgtattcagg gtgtgatcca ggcgcgcgaa      480
tcaaaataca tcatgatgca cgcaccgacc gaacgtctgg atgaagtcat ggtacctact      540
gagagtgcac cataccacag cttttcaatt caattcatca tttttttttt attcttttt      600 ttgatttcgg tttctttgaa attttttttga ttcggtaatc tccgaacaga aggaagaacg      660
aaggaaggag cacagactta gattggtata tatacgcata tgtagtgttg aagaaacatg      720
aaattgccca gtattcttaa cccaactgca cagaacaaaa acctgcagga acgaagata       780 aatcatgtcg aaagctacat ataaggaacg tgctgctact catcctagtc ctgttgctgc      840
caagctattt aatatcatgc acgaaaagca aacaaacttg tgtgcttcat tggatgttcg      900
taccaccaag gaattactgg agttagttga agcattaggt cccaaaattt gtttactaaa      960
aacacatgtg gatatcttga ctgatttttc catggagggc acagttaagc gctaaaggc     1020
```

```
attatccgcc aagtacaatt ttttactctt cgaagacaga aaatttgctg acattggtaa    1080
tacagtcaaa ttgcagtact ctgcgggtgt atacagaata gcagaatggg cagacattac    1140
gaatgcacac ggtgtggtgg gcccaggtat tgttagcggt ttgaagcagg cggcagaaga    1200
agtaacaaag gaacctagag gccttttgat gttagcagaa ttgtcatgca agggctccct    1260
atctactgga gaatatacta agggtactgt tgacattgcg aagagcgaca aagattttgt    1320
tatcggcttt attgctcaaa gagacatggg tggaagagat gaaggttacg attggttgat    1380
tatgacaccc ggtgtgggtt tagatgacaa gggagacgca ttgggtcaac agtatagaac    1440
cgtggatgat gtggtctcta caggatctga cattattatt gttggaagag gactatttgc    1500
aaagggaagg gatgctaagg tagagggtga acgttacaga aaagcaggct gggaagcata    1560
tttgagaaga tgcggccagc aaaactaaaa aactgtatta taagtaaatg catgtatact    1620
aaactcacaa attagagctt caatttaatt atatcagtta ttaccctatg cggtgtgaaa    1680
taccgcacag atgcgtaagg agaaaatacc gcatcaggaa attgtaaacg ttaatatttt    1740
gttaaaattc gcgttaaatt tttgttaaat cagctcattt tttaaccaat aggccgaaat    1800
cggcaaaatc tctagagtgc tggaagaaga gctgcttaac cgccgcgccc agggtgaaga    1860
tccacgctac tttaccctgc gtcgtctgga tttcggcggc tgtcgtcttt cgctggcaac    1920
gccggttgat gaagcctggg acggtccgct ctccttaaac ggtaaacgta tcgccacctc    1980
ttatcctcac ctgctcaagc gttatctcga ccagaaaggc atctctttta aatcctgctt    2040
actgaacggt tctgttgaag tcgccccgcg tgccggactg gcggatgcga tttgcgatct    2100
ggtttccacc ggtgccacgc tggaagctaa cggcctgcgc gaagtcgaag ttatctatcg    2160
ctcgaaagcc tgcctgattc aacgcgatgg cgaaatggaa gaatccaaac agcaactgat    2220
cgacaaactg ctgacccgta ttcagggtgt gatccaggcg cgcgaatcaa aatacatcat    2280
gatgcacgca ccgaccgaac gtctggatga agtcatccag tgatgataca acgagttagc    2340
caaggtg                                                              2347

<210> SEQ ID NO 96
<211> LENGTH: 80
<212> TYPE: DNA
<213> ORGANISM: Artificial Sequence
<220> FEATURE:
<223> OTHER INFORMATION: primer

<400> SEQUENCE: 96
cttcgaagaa tatactaaaa aatgagcagg caagataaac gaaggcaaag gcattgcgga    60
ttacgtattc taatgttcag                                                80

<210> SEQ ID NO 97
<211> LENGTH: 81
<212> TYPE: DNA
<213> ORGANISM: Artificial Sequence
<220> FEATURE:
<223> OTHER INFORMATION: primer

<400> SEQUENCE: 97
tatacacatg tatatatatc gtatgctgca gctttaaata atcggtgtca caccttggct    60
aactcgttgt atcatcactg g                                              81

<210> SEQ ID NO 98
<211> LENGTH: 26
<212> TYPE: DNA
```

<213> ORGANISM: Artificial Sequence
<220> FEATURE:
<223> OTHER INFORMATION: primer

<400> SEQUENCE: 98
gacttgaata atgcagcggc gcttgc                                          26

<210> SEQ ID NO 99
<211> LENGTH: 30
<212> TYPE: DNA
<213> ORGANISM: Artificial Sequence
<220> FEATURE:
<223> OTHER INFORMATION: primer

<400> SEQUENCE: 99
ccaccctctt caattagcta agatcatagc                                      30

<210> SEQ ID NO 100
<211> LENGTH: 25
<212> TYPE: DNA
<213> ORGANISM: Artificial Sequence
<220> FEATURE:
<223> OTHER INFORMATION: primer

<400> SEQUENCE: 100
aaaaattgat tctcatcgta aatgc                                           25

<210> SEQ ID NO 101
<211> LENGTH: 20
<212> TYPE: DNA
<213> ORGANISM: Artificial Sequence
<220> FEATURE:
<223> OTHER INFORMATION: primer

<400> SEQUENCE: 101
ctgcagcgag gagccgtaat                                                 20

<210> SEQ ID NO 102
<211> LENGTH: 90
<212> TYPE: DNA
<213> ORGANISM: Artificial Sequence
<220> FEATURE:
<223> OTHER INFORMATION: primer

<400> SEQUENCE: 102
atggttcatt taggtccaaa aaaaccacaa gccagaaagg gttccatggc cgatgtgcca     60
gcattgcgga ttacgtattc taatgttcag                                      90

<210> SEQ ID NO 103
<211> LENGTH: 91
<212> TYPE: DNA
<213> ORGANISM: Artificial Sequence
<220> FEATURE:
<223> OTHER INFORMATION: primer

<400> SEQUENCE: 103
ttaagcaccg atgataccaa cggacttacc ttcagcaatt ctttttttggg ccaaagcagc    60 caccttggct aactcgttgt atcatcactg g                                    91

<210> SEQ ID NO 104
<211> LENGTH: 24
<212> TYPE: DNA
<213> ORGANISM: Artificial Sequence
<220> FEATURE:
<223> OTHER INFORMATION: primer

```
<400> SEQUENCE: 104
ctaggatgag tagcagcacg ttcc                                              24

<210> SEQ ID NO 105
<211> LENGTH: 26
<212> TYPE: DNA
<213> ORGANISM: Artificial Sequence
<220> FEATURE:
<223> OTHER INFORMATION: primer

<400> SEQUENCE: 105
ccaattccgt gatgtctctt tgttgc                                            26

<210> SEQ ID NO 106
<211> LENGTH: 20
<212> TYPE: DNA
<213> ORGANISM: Artificial Sequence
<220> FEATURE:
<223> OTHER INFORMATION: primer

<400> SEQUENCE: 106
gtgaacgagt tcacaaccgc                                                   20

<210> SEQ ID NO 107
<211> LENGTH: 22
<212> TYPE: DNA
<213> ORGANISM: Artificial Sequence
<220> FEATURE:
<223> OTHER INFORMATION: primer

<400> SEQUENCE: 107
gttcgttcca gaattatcac gc                                                22

<210> SEQ ID NO 108
<211> LENGTH: 28
<212> TYPE: DNA
<213> ORGANISM: Artificial Sequence
<220> FEATURE:
<223> OTHER INFORMATION: primer

<400> SEQUENCE: 108
ggatccgcat gcttgcattt agtcgtgc                                          28

<210> SEQ ID NO 109
<211> LENGTH: 20
<212> TYPE: DNA
<213> ORGANISM: Artificial Sequence
<220> FEATURE:
<223> OTHER INFORMATION: primer

<400> SEQUENCE: 109
gggatgcgga cgtattcggc                                                   20

<210> SEQ ID NO 110
<211> LENGTH: 4506
<212> TYPE: DNA
<213> ORGANISM: Saccharomyces cerevisiae

<400> SEQUENCE: 110
atgtcgaata ccccttataa ttcatctgtg ccttccattg catccatgac ccagtcttcg       60
gtctcaagaa gtcctaacat gcatacagca actacgcccg gtgccaacac cagctctaac      120
tctccaccct tgcacatgtc ttcagattcg tccaagatca gaggaagcg taacagaatt      180
```

```
ccgctcagtt gcaccatttg tcggaaaagg aaagtcaaat gtgacaaact cagaccacac    240
tgccagcagt gcactaaaac tggggtagcc catctctgcc actacatgga acagacctgg    300
gcagaagagg cagagaaaga attgctgaag acaacgaat  taaagaagct tagggagcgc    360
gtaaaatctt tagaaaagac tcttctaag  gtgcactctt ctccttcgtc taactccttg    420
aaaagttaca cactcccga  gagcagcaac ctgtttatgg gtagcgatga acacaccacc    480
cttgttaatg caaatacagg ctctgcttcc tctgcctcgc atatgcatca gcaacaacag    540
caacagcagc aacaggaaca acaacaagac ttttccagaa gtgcgaacgc caacgcgaat    600
tcctcgtccc tttctatctc aaataaatat gacaacgatg agctggactt aactaaggac    660
tttgatcttt tgcatatcaa aagtaacgga accatccact taggtgccac ccactggttg    720
tctatcatga aggtgaccc  gtacctaaaa cttttgtggg gtcatatctt cgctatgagg    780
gaaaagttaa atgaatggta ctaccaaaaa aattcgtact ctaagctgaa gtcaagcaaa    840
tgtcccatca atcacgcgca agcgccgcct tctgccgctg ccgccgctac cagaaaatgt    900
cctgttgatc actccgcgtt ttcgtctggc atggtggccc caaggaggga gactcctctt    960
cctaggaaat gtccagttga ccacaccatg ttctcttcgg gaatgattcc tcccagagag   1020
gacacttcgt cccagaagag gtgtcccgtt gaccacacca tgtattccgc aggaatgatg   1080
ccgcccaagg acgagacacc ttccccattt tccactaaag ctatgataga ccataacaag   1140
catacaatga atccgcctca gtcaaaatgt cctgtggacc atagaaacta tatgaaggat   1200
tatccctctg acatggcaaa ttcttcttcg aacccggcaa gtcgttgccc cattgaccat   1260
tcaagcatga aaaatacagc ggccttacca gcttcaacgc acaataccat cccacaccac   1320
caaccacagt ccggatctca tgctcgttcg catcccgcac aaagcaggaa acatgattcc   1380 tacatgcacag aatctgaagt cctcgcaaca cttttgtgaga tgttgccacc aaagcgcgtc   1440
atcgcattat tcatcgagaa attcttcaaa catttatacc ctgccattcc aatcttagat   1500
gaacagaatt tcaaaaatca cgtgaatcaa atgctttcgt tgtcttcgat gaatcccaca   1560
gttaacaact ttggtatgag catgccatct tcatctacac tagagaacca acccataaca   1620
caaatcaatc ttccaaaact ttccgattct tgtaacttag gtattctgat aataatcttg   1680
agattgacat ggctatccat accttctaat tcctgcgaag tcgacctggg agaagaaagt   1740
ggctcatttt tagtgcccaa cgaatctagc aatatgtctg catctgcatt gacctcgatg   1800
gctaaagaag aatcacttct gctaaagcat gagacaccgg tcgaggcact ggagctatgt   1860
caaaaatact tgattaaatt cgatgaactt tctagtattt ccaataacaa cgttaattta   1920
accacggtgc agtttgccat ttttttacaac ttctatatga aaagtgcctc taatgatttg   1980
actaccttga caaataccaa caacactggc atggccaatc ctggtcacga ttccgagtct   2040
caccagatcc tattgtccaa tattactcaa atggccttta gttgtgggtt acacagagac   2100
cctgataatt ttcctcaatt aaacgctacc attccagcaa ccagccagga cgtgtctaac   2160
aacgggagca aaaaggcaaa ccctagcacc aatccaactt tgaataacaa catgtctgct   2220
gccactacca acagcagtag cagatctggc agtgctgatt caagaagtgg ttctaaccct   2280
gtgaacaaga aggaaaatca ggttagtatc gaaagattta acacacttg  gaggaaaatt   2340 tggtattaca ttgttagcat ggatgttaac caatctcttt ccctggggag ccctcgacta   2400
ctaagaaatc tgagggattt cagcgataca aagctaccaa gtgcgtcaag gattgattat   2460
gttcgcgata tcaaagagtt aatcattgtg aagaatttta ctcttttttt ccaaattgat   2520
ttgtgtatta ttgctgtatt aaatcacatt ttgaatgttt ctttagcaag aagcgtgaga   2580
```

```
aaatttgaac tggattcatt gattaattta ttgaaaaatc tgacctatgg tactgagaat    2640
gtcaatgatg tagtgagctc cttgatcaac aaagggttat taccaacttc ggaaggtggt    2700
tctgtagatt caaataatga tgaaatttac ggtctaccga aactacccga tattctaaac    2760
catggtcaac ataaccaaaa cttgtatgct gatggaagaa atacttctag tagtgatata    2820
gataagaaat tggaccttcc tcacgaatct acaacgagag ctctattctt ttccaagcat    2880
atgacaatta gaatgttgct gtacttattg aactacattt tgtttactca ttatgaacca    2940
atgggcagtg aagatcctgg tactaatatc ctagctaagg agtacgctca agaggcatta    3000
aattttgcca tggatggcta cagaaactgc atgattttct tcaacaatat cagaaacacc    3060
aattcactat tcgattacat gaatgttatc ttgtcttacc cttgtttgga cattggacat    3120
cgttctttac aatttatcgt ttgtttgatc ctgagagcta aatgtggccc attgactggt    3180
atgcgtgaat catcgatcat tactaatggt acatcaagtg gatttaatag ttcggtagaa    3240
gatgaggacg tcaaagttaa acaagaatct tctgatgaat tgaaaaaaga cgatttcatg    3300
aaagatgtaa atttggattc aggcgattca ttagcagaga ttctaatgtc aagaatgctg    3360
ctatttcaaa aactaacaaa acaactatca aagaagtaca actacgctat tcgtatgaac    3420
aaatccactg gattctttgt ctctttacta gatacacctt caaagaaatc agactcgaaa    3480
tcgggtggta gttcattcat gttgggtaat tggaaacatc caaggtttc aaacatgagc    3540 ggatttcttg ctggtgacaa agaccaatta cagaaatgcc ccgtgtacca agatgcgctg    3600
gggtttgtta gtccaaccgg tgctaatgaa ggttctgctc cgatgcaagg catgtcctta    3660
cagggctcta ctgctaggat gggagggacc cagttgccac caattagatc atacaaacct    3720
atcacgtaca caagtagtaa tctacgtcgt atgaatgaaa cgggtgaggc agaagctaag    3780
agaagaagat ttaatgatgg ctatattgat aataatagta caacgatat acctagagga    3840 atcagcccaa aaccttcaaa tgggctatca tcggtgcagc cactattatc gtcattttcc    3900
atgaaccagc taaacggggg taccattcca acggttccat cgttaaccaa cattacttca    3960
caaatgggag ctttaccatc tttagatagg atcaccacta atcaaataaa tttgccagac    4020
ccatctagag atgaagcatt tgacaactcc atcaagcaaa tgacgccat gacaagtgca    4080 ttcatgaatg ctaatactac aattccaagt tcaactttaa acgggaatat gaacatgaat    4140
ggagctggaa ctgcgaatac agatacaagt gccaacggca gtgctttatc gacactgaca    4200
agcccacaag gctcagactt agcatccaat tctgctacac agtataaacc tgacttagaa    4260 gacttttga tgcaaaattc taactttaat gggctaatga taaatccttc cagtctggta    4320
gaagttgttg gtggatacaa cgatcctaat aaccttggaa gaaatgacgc ggttgatttt    4380
ctacccgttg ataatgttga aattgatggt gttggaataa aaatcaacta tcatctacta    4440
actagtattt acgttactag tatattatca tatacggtgt tagaagatga cgcaaatgat    4500
gagaaa                                                               4506
```

<210> SEQ ID NO 111
<211> LENGTH: 99
<212> TYPE: DNA
<213> ORGANISM: Artificial Sequence
<220> FEATURE:
<223> OTHER INFORMATION: primer

<400> SEQUENCE: 111

```
tcctttctca attattattt tctactcata acctcacgca aaataacaca gtcaaatcaa     60
```
tcaaagtatg actgacaaaa aaactcttaa agacttaag    99

<210> SEQ ID NO 112
<211> LENGTH: 77
<212> TYPE: DNA
<213> ORGANISM: Artificial Sequence
<220> FEATURE:
<223> OTHER INFORMATION: primer

<400> SEQUENCE: 112
gaacattaga atacgtaatc cgcaatgctt ctttctttc cgtttaacgt atagacttct    60
aatatatttc tccatac    77

<210> SEQ ID NO 113
<211> LENGTH: 45
<212> TYPE: DNA
<213> ORGANISM: Artificial Sequence
<220> FEATURE:
<223> OTHER INFORMATION: primer

<400> SEQUENCE: 113
aaacggaaaa gaaagaagca ttgcggatta cgtattctaa tgttc    45

<210> SEQ ID NO 114
<211> LENGTH: 88
<212> TYPE: DNA
<213> ORGANISM: Artificial Sequence
<220> FEATURE:
<223> OTHER INFORMATION: primer

<400> SEQUENCE: 114
tatttttcgt tacataaaaa tgcttataaa actttaacta ataattagag attaaatcgc    60
caccttggct aactcgttgt atcatcac    88

<210> SEQ ID NO 115
<211> LENGTH: 1713
<212> TYPE: DNA
<213> ORGANISM: Streptococcus mutans

<400> SEQUENCE: 115
atgactgaca aaaaaactct taaagactta agaaatcgta gttctgttta cgattcaatg    60
gttaaatcac ctaatcgtgc tatgttgcgt gcaactggta tgcaagatga agactttgaa    120
aaacctatcg tcggtgtcat ttcaacttgg gctgaaaaca caccttgtaa tatccactta    180
catgactttg gtaaactagc caaagtcggt gttaaggaag ctggtgcttg gccagttcag    240
ttcggaacaa tcacggtttc tgatggaatc gccatgggaa cccaaggaat gcgtttctcc    300 ttgcatctc gtgatattat tgcagattct attgaagcag ccatgggagg tcataatgcg    360
gatgcttttg tagccattgg cggttgtgat aaaaacatgc ccggttctgt tatcgctatg    420
gctaacatgg atatcccagc cattttttgct tacggcggaa caattgcacc tggtaattta    480
gacggcaaag atatcgattt agtctctgtc tttgaaggtg tcggccattg gaaccacggc    540
gatatgacca agaagaagt taaagctttg gaatgtaatg cttgtcccgg tcctggaggc    600
tgcggtggta tgtatactgc taacacaatg gcgacagctc ttgaagtttt gggacttagc    660
cttccgggtt catcttctca cccggctgaa tccgcagaaa agaaagcaga tattgaagaa    720
gctggtcgcg ctgttgtcaa aatgctcgaa atgggcttaa aaccttctga cattttaacg    780
cgtgaagctt ttgaagatgc tattactgta actatggctc tgggaggttc aaccaactca    840
acccttcacc tcttagctat tgcccatgct gctaatgtgg aattgacact tgatgatttc    900

```
aatactttcc aagaaaaagt tcctcatttg gctgatttga aaccttctgg tcaatatgta      960
ttccaagacc tttacaaggt cggaggggta ccagcagtta tgaaatatct ccttaaaaat     1020
ggcttccttc atggtgaccg tatcacttgt actggcaaaa cagtcgctga aaatttgaag     1080
gcttttgatg atttaacacc tggtcaaaag gttattatgc cgcttgaaaa tcctaaacgt     1140
gaagatggtc cgctcattat tctccatggt aacttggctc agacggtgc cgttgccaaa      1200
gtttctggtg taaaagtgcg tcgtcatgtc ggtcctgcta aggtctttaa ttctgaagaa     1260
gaagccattg aagctgtctt gaatgatgat attgttgatg gtgatgttgt tgtcgtacgt     1320
tttgtaggac caaggggcgg tcctggtatg cctgaaatgc tttcccttc atcaatgatt      1380
gttggtaaag ggcaaggtga aaagttgcc cttctgacag atggccgctt ctcaggtggt      1440
acttatggtc ttgtcgtggg tcatatcgct cctgaagcac aagatggcgg tccaatcgcc     1500
tacctgcaaa caggagacat agtcactatt gaccaagaca ctaaggaatt acactttgat     1560
atctccgatg aagagttaaa acatcgtcaa gagaccattg aattgccacc gctctattca     1620
cgcggtatcc ttggtaaata tgctcacatc gtttcgtctg cttctagggg agccgtaaca     1680
gacttttgga agcctgaaga aactggcaaa aaa                                  1713

<210> SEQ ID NO 116
<211> LENGTH: 571
<212> TYPE: PRT
<213> ORGANISM: Streptococcus mutans

<400> SEQUENCE: 116

Met Thr Asp Lys Lys Thr Leu Lys Asp Leu Arg Asn Arg Ser Ser Val
1               5                   10                  15

Tyr Asp Ser Met Val Lys Ser Pro Asn Arg Ala Met Leu Arg Ala Thr
            20                  25                  30

Gly Met Gln Asp Glu Asp Phe Glu Lys Pro Ile Val Gly Val Ile Ser
        35                  40                  45

Thr Trp Ala Glu Asn Thr Pro Cys Asn Ile His Leu His Asp Phe Gly
    50                  55                  60

Lys Leu Ala Lys Val Gly Val Lys Glu Ala Gly Ala Trp Pro Val Gln
65                  70                  75                  80

Phe Gly Thr Ile Thr Val Ser Asp Gly Ile Ala Met Gly Thr Gln Gly
                85                  90                  95

Met Arg Phe Ser Leu Thr Ser Arg Asp Ile Ile Ala Asp Ser Ile Glu
            100                 105                 110

Ala Ala Met Gly Gly His Asn Ala Asp Ala Phe Val Ala Ile Gly Gly
        115                 120                 125

Cys Asp Lys Asn Met Pro Gly Ser Val Ile Ala Met Ala Asn Met Asp
    130                 135                 140

Ile Pro Ala Ile Phe Ala Tyr Gly Gly Thr Ile Ala Pro Gly Asn Leu
145                 150                 155                 160

Asp Gly Lys Asp Ile Asp Leu Val Ser Val Phe Glu Gly Val Gly His
                165                 170                 175

Trp Asn His Gly Asp Met Thr Lys Glu Glu Val Lys Ala Leu Glu Cys
            180                 185                 190

Asn Ala Cys Pro Gly Pro Gly Gly Cys Gly Gly Met Tyr Thr Ala Asn
        195                 200                 205

Thr Met Ala Thr Ala Ile Glu Val Leu Gly Leu Ser Leu Pro Gly Ser
    210                 215                 220
```

```
Ser Ser His Pro Ala Glu Ser Ala Glu Lys Lys Ala Asp Ile Glu Glu
225                 230                 235                 240

Ala Gly Arg Ala Val Val Lys Met Leu Glu Met Gly Leu Lys Pro Ser
                245                 250                 255

Asp Ile Leu Thr Arg Glu Ala Phe Glu Asp Ala Ile Thr Val Thr Met
                260                 265                 270

Ala Leu Gly Gly Ser Thr Asn Ser Thr Leu His Leu Leu Ala Ile Ala
            275                 280                 285

His Ala Ala Asn Val Glu Leu Thr Leu Asp Asp Phe Asn Thr Phe Gln
        290                 295                 300

Glu Lys Val Pro His Leu Ala Asp Leu Lys Pro Ser Gly Gln Tyr Val
305                 310                 315                 320

Phe Gln Asp Leu Tyr Lys Val Gly Val Pro Ala Val Met Lys Tyr
                325                 330                 335

Leu Leu Lys Asn Gly Phe Leu His Gly Asp Arg Ile Thr Cys Thr Gly
                340                 345                 350

Lys Thr Val Ala Glu Asn Leu Lys Ala Phe Asp Asp Leu Thr Pro Gly
            355                 360                 365

Gln Lys Val Ile Met Pro Leu Glu Asn Pro Lys Arg Glu Asp Gly Pro
        370                 375                 380

Leu Ile Ile Leu His Gly Asn Leu Ala Pro Asp Gly Ala Val Ala Lys
385                 390                 395                 400

Val Ser Gly Val Lys Val Arg Arg His Val Gly Pro Ala Lys Val Phe
                405                 410                 415

Asn Ser Glu Glu Glu Ala Ile Glu Ala Val Leu Asn Asp Asp Ile Val
                420                 425                 430

Asp Gly Asp Val Val Val Arg Phe Val Gly Pro Lys Gly Gly Pro
            435                 440                 445

Gly Met Pro Glu Met Leu Ser Leu Ser Ser Met Ile Val Gly Lys Gly
            450                 455                 460

Gln Gly Glu Lys Val Ala Leu Leu Thr Asp Gly Arg Phe Ser Gly Gly
465                 470                 475                 480

Thr Tyr Gly Leu Val Val Gly His Ile Ala Pro Glu Ala Gln Asp Gly
                485                 490                 495

Gly Pro Ile Ala Tyr Leu Gln Thr Gly Asp Ile Val Thr Ile Asp Gln
            500                 505                 510

Asp Thr Lys Glu Leu His Phe Asp Ile Ser Asp Glu Glu Leu Lys His
        515                 520                 525

Arg Gln Glu Thr Ile Glu Leu Pro Pro Leu Tyr Ser Arg Gly Ile Leu
530                 535                 540

Gly Lys Tyr Ala His Ile Val Ser Ser Ala Ser Arg Gly Ala Val Thr
545                 550                 555                 560

Asp Phe Trp Lys Pro Glu Glu Thr Gly Lys Lys
                565                 570
```

<210> SEQ ID NO 117
<211> LENGTH: 548
<212> TYPE: PRT
<213> ORGANISM: Lactococcus lactis

<400> SEQUENCE: 117

```
Met Tyr Thr Val Gly Asp Tyr Leu Leu Asp Arg Leu His Glu Leu Gly
1               5                   10                  15

Ile Glu Glu Ile Phe Gly Val Pro Gly Asp Tyr Asn Leu Gln Phe Leu
                20                  25                  30
```

```
Asp Gln Ile Ile Ser His Lys Asp Met Lys Trp Val Gly Asn Ala Asn
             35                  40                  45

Glu Leu Asn Ala Ser Tyr Met Ala Asp Gly Tyr Ala Arg Thr Lys Lys
 50                  55                  60

Ala Ala Ala Phe Leu Thr Thr Phe Gly Val Gly Glu Leu Ser Ala Val
 65                  70                  75                  80

Asn Gly Leu Ala Gly Ser Tyr Ala Glu Asn Leu Pro Val Val Glu Ile
                 85                  90                  95

Val Gly Ser Pro Thr Ser Lys Val Gln Asn Glu Gly Lys Phe Val His
                100                 105                 110

His Thr Leu Ala Asp Gly Asp Phe Lys His Phe Met Lys Met His Glu
                115                 120                 125

Pro Val Thr Ala Ala Arg Thr Leu Leu Thr Ala Glu Asn Ala Thr Val
130                 135                 140

Glu Ile Asp Arg Val Leu Ser Ala Leu Leu Lys Glu Arg Lys Pro Val
145                 150                 155                 160

Tyr Ile Asn Leu Pro Val Asp Val Ala Ala Ala Lys Ala Glu Lys Pro
                165                 170                 175

Ser Leu Pro Leu Lys Lys Glu Asn Ser Thr Ser Asn Thr Ser Asp Gln
                180                 185                 190

Glu Ile Leu Asn Lys Ile Gln Glu Ser Leu Lys Asn Ala Lys Lys Pro
                195                 200                 205

Ile Val Ile Thr Gly His Glu Ile Ile Ser Phe Gly Leu Glu Lys Thr
                210                 215                 220

Val Thr Gln Phe Ile Ser Lys Thr Lys Leu Pro Ile Thr Thr Leu Asn
225                 230                 235                 240

Phe Gly Lys Ser Ser Val Asp Glu Ala Leu Pro Ser Phe Leu Gly Ile
                245                 250                 255

Tyr Asn Gly Thr Leu Ser Glu Pro Asn Leu Lys Glu Phe Val Glu Ser
                260                 265                 270

Ala Asp Phe Ile Leu Met Leu Gly Val Lys Leu Thr Asp Ser Ser Thr
                275                 280                 285

Gly Ala Phe Thr His His Leu Asn Glu Asn Lys Met Ile Ser Leu Asn
                290                 295                 300

Ile Asp Glu Gly Lys Ile Phe Asn Glu Arg Ile Gln Asn Phe Asp Phe
305                 310                 315                 320

Glu Ser Leu Ile Ser Ser Leu Asp Leu Ser Glu Ile Glu Tyr Lys
                325                 330                 335

Gly Lys Tyr Ile Asp Lys Lys Gln Glu Asp Phe Val Pro Ser Asn Ala
                340                 345                 350

Leu Leu Ser Gln Asp Arg Leu Trp Gln Ala Val Glu Asn Leu Thr Gln
                355                 360                 365

Ser Asn Glu Thr Ile Val Ala Glu Gln Gly Thr Ser Phe Phe Gly Ala
370                 375                 380

Ser Ser Ile Phe Leu Lys Ser Lys Ser His Phe Ile Gly Gln Pro Leu
385                 390                 395                 400

Trp Gly Ser Ile Gly Tyr Thr Phe Pro Ala Ala Leu Gly Ser Gln Ile
                405                 410                 415

Ala Asp Lys Glu Ser Arg His Leu Leu Phe Ile Gly Asp Gly Ser Leu
                420                 425                 430

Gln Leu Thr Val Gln Glu Leu Gly Leu Ala Ile Arg Glu Lys Ile Asn
                435                 440                 445
```

| | | | | | | | | | | | | |
|---|---|---|---|---|---|---|---|---|---|---|---|---|
|Pro|Ile|Cys|Phe|Ile|Ile|Asn|Asn|Asp|Gly|Tyr|Thr|Val|Glu|Arg|Glu|
| |450| | | | |455| | | | |460| | | | |

| | | | | | | | | | | | | |
|---|---|---|---|---|---|---|---|---|---|---|---|---|
|Ile|His|Gly|Pro|Asn|Gln|Ser|Tyr|Asn|Asp|Ile|Pro|Met|Trp|Asn|Tyr|
|465| | | | |470| | | | |475| | | | |480|

| | | | | | | | | | | | | |
|---|---|---|---|---|---|---|---|---|---|---|---|---|
|Ser|Lys|Leu|Pro|Glu|Ser|Phe|Gly|Ala|Thr|Glu|Asp|Arg|Val|Val|Ser|
| | | | |485| | | | |490| | | | |495| |

| | | | | | | | | | | | | |
|---|---|---|---|---|---|---|---|---|---|---|---|---|
|Lys|Ile|Val|Arg|Thr|Glu|Asn|Glu|Phe|Val|Ser|Val|Met|Lys|Glu|Ala|
| | | |500| | | | |505| | | | |510| | |

| | | | | | | | | | | | | |
|---|---|---|---|---|---|---|---|---|---|---|---|---|
|Gln|Ala|Asp|Pro|Asn|Arg|Met|Tyr|Trp|Ile|Glu|Leu|Ile|Leu|Ala|Lys|
| | |515| | | | |520| | | | |525| | | |

| | | | | | | | | | | | | |
|---|---|---|---|---|---|---|---|---|---|---|---|---|
|Glu|Gly|Ala|Pro|Lys|Val|Leu|Lys|Lys|Met|Gly|Lys|Leu|Phe|Ala|Glu|
| |530| | | | |535| | | | |540| | | | |

Gln Asn Lys Ser
545

<210> SEQ ID NO 118
<211> LENGTH: 1125
<212> TYPE: DNA
<213> ORGANISM: Artificial Sequence
<220> FEATURE:
<223> OTHER INFORMATION: horse ADH coding region codon optimized for S.
       cerevisiae expression

<400> SEQUENCE: 118

```
atgtcaacag ccggtaaagt tattaagtgt aaagcggcag ttttgtggga agagaaaaag      60
ccgtttagca tagaagaagt agaagtagcg ccaccaaaag cacacgaggt tagaatcaag     120
atggttgcca ccggaatctg tagatccgac gaccatgtgg tgagtggcac tctagttact     180
cctttgccag taatcgcggg acacgaggct gccggaatcg ttgaatccat aggtgaaggt     240
gttaccactg ttcgtcctgg tgataaagtg atcccactgt tcactcctca atgtggtaag     300
tgtagagtct gcaaacatcc tgagggtaat ttctgcctta aaaatgattt gtctatgcct     360
agaggtacta tgcaggatgg tacaagcaga tttacatgca gagggaaacc tatacaccat     420
ttccttggta cttctacatt tcccaatac acagtggtgg acgagatatc tgtcgctaaa      480
atcgatgcag cttcaccact ggaaaaagtt tgcttgatag ggtgcggatt ttccaccggt     540
tacggttccg cagttaaagt tgcaaaggtt acacagggtt cgacttgtgc agtattcggt     600
ttaggaggag taggactaag cgttattatg gggtgtaaag ctgcaggcgc agcgaggatt     660
ataggtgtag acatcaataa ggacaaattt gcaaaagcta aggaggtcgg ggctactgaa     720
tgtgttaacc ctcaagatta taagaaacca atacaagaag tccttactga aatgtcaaac     780
ggtggagttg atttctcttt tgaagttata ggccgtcttg atactatggt aactgcgttg     840
tcctgctgtc aagaggcata tggagtcagt gtgatcgtag tgttcctcc tgattcacaa      900
aatttgtcga tgaatcctat gctgttgcta agcggtcgta catggaaggg agctatattt     960
ggcggtttta agagcaagga tagtgttcca aaacttgttg ccgactttat ggcgaagaag    1020
tttgctcttg atcctttaat tacacatgta ttgccattcg agaaaatcaa tgaagggttt    1080
gatttgttaa gaagtggtga atctattcgt acaattttaa ctttt                    1125
```

<210> SEQ ID NO 119
<211> LENGTH: 375
<212> TYPE: PRT
<213> ORGANISM: Equus caballus

<400> SEQUENCE: 119

Met Ser Thr Ala Gly Lys Val Ile Lys Cys Lys Ala Ala Val Leu Trp

```
             1               5                  10                 15
         Glu Glu Lys Lys Pro Phe Ser Ile Glu Glu Val Glu Val Ala Pro Pro
                         20                 25                 30

Lys Ala His Glu Val Arg Ile Lys Met Val Ala Thr Gly Ile Cys Arg
                         35                 40                 45

Ser Asp Asp His Val Val Ser Gly Thr Leu Val Thr Pro Leu Pro Val
                         50                 55                 60

Ile Ala Gly His Glu Ala Ala Gly Ile Val Glu Ser Ile Gly Glu Gly
         65                  70                 75                 80

Val Thr Thr Val Arg Pro Gly Asp Lys Val Ile Pro Leu Phe Thr Pro
                         85                 90                 95

Gln Cys Gly Lys Cys Arg Val Cys Lys His Pro Glu Gly Asn Phe Cys
                         100                105                110

Leu Lys Asn Asp Leu Ser Met Pro Arg Gly Thr Met Gln Asp Gly Thr
                         115                120                125

Ser Arg Phe Thr Cys Arg Gly Lys Pro Ile His His Phe Leu Gly Thr
                         130                135                140

Ser Thr Phe Ser Gln Tyr Thr Val Val Asp Glu Ile Ser Val Ala Lys
         145                 150                155                160

Ile Asp Ala Ala Ser Pro Leu Glu Lys Val Cys Leu Ile Gly Cys Gly
                         165                170                175

Phe Ser Thr Gly Tyr Gly Ser Ala Val Lys Val Ala Lys Val Thr Gln
                         180                185                190

Gly Ser Thr Cys Ala Val Phe Gly Leu Gly Gly Val Gly Leu Ser Val
                         195                200                205

Ile Met Gly Cys Lys Ala Ala Gly Ala Ala Arg Ile Ile Gly Val Asp
                         210                215                220

Ile Asn Lys Asp Lys Phe Ala Lys Ala Lys Glu Val Gly Ala Thr Glu
         225                 230                235                240

Cys Val Asn Pro Gln Asp Tyr Lys Lys Pro Ile Gln Glu Val Leu Thr
                         245                250                255

Glu Met Ser Asn Gly Gly Val Asp Phe Ser Phe Glu Val Ile Gly Arg
                         260                265                270

Leu Asp Thr Met Val Thr Ala Leu Ser Cys Cys Gln Glu Ala Tyr Gly
                         275                280                285

Val Ser Val Ile Val Gly Val Pro Pro Asp Ser Gln Asn Leu Ser Met
                         290                295                300

Asn Pro Met Leu Leu Leu Ser Gly Arg Thr Trp Lys Gly Ala Ile Phe
         305                 310                315                320

Gly Gly Phe Lys Ser Lys Asp Ser Val Pro Lys Leu Val Ala Asp Phe
                         325                330                335

Met Ala Lys Lys Phe Ala Leu Asp Pro Leu Ile Thr His Val Leu Pro
                         340                345                350

Phe Glu Lys Ile Asn Glu Gly Phe Asp Leu Leu Arg Ser Gly Glu Ser
                         355                360                365

Ile Arg Thr Ile Leu Thr Phe
         370                 375

<210> SEQ ID NO 120
<211> LENGTH: 643
<212> TYPE: DNA
<213> ORGANISM: Saccharomyces cerevisiae

<400> SEQUENCE: 120
```

```
gaaatgaata acaatactga cagtactaaa taattgccta cttggcttca catacgttgc      60
atacgtcgat atagataata atgataatga cagcaggatt atcgtaatac gtaatagttg     120
aaaatctcaa aaatgtgtgg gtcattacgt aaataatgat aggaatggga ttcttctatt     180
tttccttttt ccattctagc agccgtcggg aaaacgtggc atcctctctt tcgggctcaa     240
ttggagtcac gctgccgtga gcatcctctc tttccatatc taacaactga gcacgtaacc     300
aatgaaaaag catgagctta gcgttgctcc aaaaaagtat tggatggtta ataccatttg     360
tctgttctct tctgactttg actcctcaaa aaaaaaaat  ctacaatcaa cagatcgctt     420
caattacgcc ctcacaaaaa cttttttcct tcttcttcgc ccacgttaaa ttttatccct     480
catgttgtct aacggatttc tgcacttgat ttattataaa aagacaaaga cataatactt     540
ctctatcaat ttcagttatt gttcttcctt gcgttattct tctgttcttc ttttttctttt    600 gtcatatata accataacca agtaatacat attcaaatct aga                      643
```

<210> SEQ ID NO 121
<211> LENGTH: 9089
<212> TYPE: DNA
<213> ORGANISM: Artificial Sequence
<220> FEATURE:
<223> OTHER INFORMATION: constructed plasmid

<400> SEQUENCE: 121

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcgggctgg  cttaactatg cggcatcaga gcagattgta ctgagagtgc     180
accataccac agcttttcaa ttcaattcat catttttttt ttattctttt ttttgatttc     240
ggtttctttg aaatttttt  gattcggtaa tctccgaaca gaaggaagaa cgaaggaagg     300
agcacagact tagattggta tatatacgca tatgtagtgt tgaagaaaca tgaaattgcc     360
cagtattctt aacccaactg cacagaacaa aaacctgcag gaaacgaaga taatcatgt     420 cgaaagctac atataaggaa cgtgctgcta ctcatcctag tcctgttgct gccaagctat     480
ttaatatcat gcacgaaaag caaacaaact tgtgtgcttc attggatgtt cgtaccacca     540
aggaattact ggagttagtt gaagcattag gtcccaaaat ttgtttacta aaaacacatg     600
tggatatctt gactgatttt tccatggagg gcacagttaa gccgctaaag gcattatccg     660
ccaagtacaa tttttactc  ttcgaagaca gaaaatttgc tgacattggt aatacagtca     720
aattgcagta ctctgcgggt gtatacgaaa tagcagaatg gcagacatt  acgaatgcac     780 acggtgtggt gggcccaggt attgttagcg gtttgaagca ggcggcagaa gaagtaacaa     840
aggaacctag aggccttttg atgttagcag aattgtcatg caagggctcc ctatctactg     900
gagaatatac taagggtact gttgacattg cgaagagcga caaagatttt gttatcggct     960
ttattgctca agagacatg  ggtggaagag atgaaggtta cgattggttg attatgacac    1020
ccggtgtggg tttagatgac aagggagacg cattgggtca acagtataga accgtggatg    1080
atgtggtctc tacaggatct gacattatta ttgttggaag aggactattt gcaaagggaa    1140
gggatgctaa ggtagagggt gaacgttaca gaaaagcagg ctgggaagca tatttgagaa    1200
gatgcggcca gcaaaactaa aaaactgtat tataagtaaa tgcatgtata ctaaactcac    1260
aaattagagc ttcaatttaa ttatatcagt tattacccta tgcggtgtga aataccgcac    1320
agatgcgtaa ggagaaaata ccgcatcagg aaattgtaaa cgttaatatt ttgttaaaat    1380
tcgcgttaaa ttttgttaa  atcagctcat ttttttaacca ataggccgaa atcggcaaaa    1440
```

```
tcccttataa atcaaaagaa tagaccgaga tagggttgag tgttgttcca gtttggaaca    1500
agagtccact attaaagaac gtggactcca acgtcaaagg gcgaaaaacc gtctatcagg    1560
gcgatggccc actacgtgaa ccatcaccct aatcaagttt tttggggtcg aggtgccgta    1620
aagcactaaa tcggaaccct aaagggagcc cccgatttag agcttgacgg ggaaagccgg    1680
cgaacgtggc gagaaaggaa gggaagaaag cgaaaggagc gggcgctagg gcgctggcaa    1740
gtgtagcggt cacgctgcgc gtaaccacca cacccgccgc gcttaatgcg ccgctacagg    1800
gcgcgtcgcg ccattcgcca ttcaggctgc gcaactgttg ggaagggcga tcggtgcggg    1860
cctcttcgct attacgccag ctggcgaaag ggggatgtgc tgcaaggcga ttaagttggg    1920
taacgccagg gttttcccag tcacgacgtt gtaaaacgac ggccagtgag cgcgcgtaat    1980
acgactcact atagggcgaa ttgggtaccg ggccccccct cgaggtcgac tggccattaa    2040
tctttcccat attagatttc gccaagccat gaaagttcaa gaaaggtctt tagacgaatt    2100
acccttcatt tctcaaactg gcgtcaaggg atcctggtat ggttttatcg ttttatttct    2160
ggttcttata gcatcgtttt ggacttctct gttcccatta ggcggttcag gagccagcgc    2220
agaatcattc tttgaaggat acttatcctt tccaattttg attgtctgtt acgttggaca    2280
taaactgtat actagaaatt ggactttgat ggtgaaacta aagatatgg atcttgatac     2340 cggcagaaaa caagtagatt tgactcttcg tagggaagaa atgaggattg agcgagaaac    2400
attagcaaaa agatccttcg taacaagatt tttacatttc tggtgttgaa gggaaagata    2460
tgagctatac agcggaattt ccatatcact cagattttgt tatctaattt tttccttccc    2520
acgtccgcgg gaatctgtgt atattactgc atctagatat atgttatctt atcttggcgc    2580
gtacatttaa ttttcaacgt attctataag aaattgcggg agttttttc atgtagatga     2640 tactgactgc acgcaaatat aggcatgatt tataggcatg atttgatggc tgtaccgata    2700
ggaacgctaa gagtaacttc agaatcgtta tcctggcgga aaaaattcat ttgtaaactt    2760
taaaaaaaaa agccaatatc cccaaaatta ttaagagcgc ctccattatt aactaaaatt    2820
tcactcagca tccacaatgt atcaggtatc tactacagat attacatgtg gcgaaaaaga    2880
caagaacaat gcaatagcgc atcaagaaaa aacacaaagc tttcaatcaa tgaatcgaaa    2940
atgtcattaa aatagtatat aaattgaaac taagtcataa agctataaaa agaaaattta    3000
tttaaatgca agatttaaag taaattcacg gccctgcagg ccctaacctg ctaggacaca    3060
acgtctttgc ctggtaaagt ttctagctga cgtgattcct tcacctgtgg atccggcaat    3120
tgtaaaggtt gtgaaaccct cagcttcata accgacacct gcaaatgact ttgcattctt    3180
aacaaagata gttgtatcaa tttcacgttc gaatctatta aggttatcga tgttcttaga    3240
ataaatgtag gcgaatgtt ttctattctg ctcagctatc ttggcgtatt taatggcttc     3300
atcaatgtcc ttcactctaa ctataggcaa aattggcatc atcaactccg tcataacgaa    3360
cggatggttt gcgttgactt cacaaataat acactttaca ttacttggtg actctacatc    3420
tatttcatcc aaaaacagtt tagcgtcctt accaacccac ttcttattaa tgaaatattc    3480
ttgagtttca ttgttctttt gaagaacaag gtctatcagc ttggatactt ggtcttcatt    3540
gataatgacg cgttgttttt tcaacatgtt agagatcaga tcatctgcaa cgttttcaaa    3600
cacgaacact tcttttttccg cgatacaagg aagattgttg tcaaacgaac aaccttcaat    3660
aatgcttctg ccggccttct cgatatctgc tgtatcgtct acaataaccg gaggattacc    3720
cgcgccagct ccgatggcct ttttaccaga attaagaagg gttttaccat taccgggcc    3780
```

```
acccgtaccg cacaacaatt ttatggatgg atgtttgata atagcgtcta aactttccat    3840
agttgggttc tttatagtag tgacaaggtt ttcaggtcca ccacagctaa ttatggcttt    3900
gtttatcatt tctactgcga aagcgacaca ctttttggcg catgggtgac cattaaatac    3960
aactgcattc cccgcagcta tcatacctat agaattgcag ataacggttt ctgttggatt    4020
cgtgcttgga gttatagcgc cgataactcc gtatggactc atttcaacca ctgttagtcc    4080
attatcgccg gaccatgctg ttgttgtcag atcttcagtg cctggggtat acttggccac    4140
taattcatgt ttcaagattt tatcctcata ccttcccatg tgggtttcct ccaggatcat    4200
tgtggctaag acctctttat tctgtaatgc ggcttttctt atttcggtga ttattttctc    4260
tctttgttcc tttgtgtagt gtagggaaag aatcttttgt gcatgtactg cagaagaaat    4320
ggcattctca acatttcaa atactccaaa acatgaagag ttatcttgt aattctttaa       4380 gttgatgttt tcaccattag tcttcacttt caagtctttg gtggttggga ttaaggtatc    4440
tttatccatg tgtttgttt atgtgtgttt attcgaaact aagttcttgg tgttttaaaa     4500
ctaaaaaaaa gactaactat aaaagtagaa tttaagaagt ttaagaaata gatttacaga    4560
attacaatca atacctaccg tctttatata cttattagtc aagtagggga ataatttcag    4620
ggaactggtt tcaacctttt ttttcagctt tttccaaatc agagagagca gaaggtaata    4680
gaaggtgtaa gaaaatgaga tagatacatg cgtgggtcaa ttgccttgtg tcatcattta    4740
ctccaggcag gttgcatcac tccattgagg ttgtgcccgt ttttgcctg tttgtgcccc      4800 tgttctctgt agttgcgcta agagaatgga cctatgaact gatggttggt gaagaaaaca    4860
atattttggt gctgggattc ttttttttc tggatgccag cttaaaaagc gggctccatt      4920
atatttagtg gatgccagga ataaactgtt cacccagaca cctacgatgt tatatattct    4980
gtgtaacccg ccccctattt tgggcatgta cgggttacag cagaattaaa aggctaattt    5040
tttgactaaa taaagttagg aaaatcacta ctattaatta tttacgtatt ctttgaaatg    5100
gcagtattga taatgataaa ctcgaactga aaaagcgtgt ttttattca aaatgattct      5160 aactccctta cgtaatcaag gaatcttttt gccttggcct ccgcgtcatt aaacttcttg    5220
ttgttgacgc taacattcaa cgctagtata tattcgtttt tttcaggtaa gttcttttca    5280
acgggtctta ctgatgaggc agtcgcgtct gaacctgtta agaggtcaaa tatgtcttct    5340
tgaccgtacg tgtcttgcat gttattagct ttgggaattt gcatcaagtc ataggaaaat    5400
ttaaatcttg gctctcttgg gctcaaggtg acaaggtcct cgaaaatagg gcgcgcccca    5460
ccgcggtgga gctccagctt ttgttcccctt tagtgagggt taattgcgcg cttggcgtaa    5520
tcatggtcat agctgtttcc tgtgtgaaat tgttatccgc tcacaattcc acacaacata    5580
ggagccggaa gcataaagtg taaagcctgg ggtgcctaat gagtgaggta actcacatta    5640
attgcgttgc gctcactgcc cgcttttcag tcgggaaacc tgtcgtgcca gctgcattaa    5700
tgaatcggcc aacgcgcggg gagaggcggt ttgcgtattg ggcgctcttc cgcttcctcg    5760
ctcactgact cgctgcgctc ggtcgttcgg ctgcggcgag cggtatcagc tcactcaaag    5820
gcggtaatac ggttatccac agaatcaggg gataacgcag gaagaacat gtgagcaaaa     5880 ggccagcaaa aggccaggaa ccgtaaaaag gccgcgttgc tggcgttttt ccataggctc    5940
cgcccccctg acgagcatca caaaaatcga cgctcaagtc agaggtggcg aaacccgaca    6000
ggactataaa gataccaggc gtttccccct ggaagctccc tcgtgcgctc tcctgttccg    6060
accctgccgc ttaccggata cctgtccgcc tttctccctt cgggaagcgt ggcgctttct    6120
catagctcac gctgtaggta tctcagttcg gtgtaggtcg ttcgctccaa gctgggctgt    6180
```

```
gtgcacgaac cccccgttca gcccgaccgc tgcgccttat ccggtaacta tcgtcttgag    6240
tccaacccgg taagcacga cttatcgcca ctggcagcag ccactggtaa caggattagc     6300
agagcgaggt atgtaggcgg tgctacagag ttcttgaagt ggtggcctaa ctacggctac    6360
actagaagga cagtatttgg tatctgcgct ctgctgaagc cagttacctt cggaaaaaga    6420
gttggtagct cttgatccgg caaacaaacc accgctggta gcggtggttt ttttgtttgc    6480
aagcagcaga ttacgcgcag aaaaaaagga tctcaagaag atcctttgat cttttctacg    6540
gggtctgacg ctcagtggaa cgaaaactca cgttaaggga ttttggtcat gagattatca    6600
aaaaggatct tcacctagat ccttttaaat taaaaatgaa gttttaaatc aatctaaagt    6660
atatatgagt aaacttggtc tgacagttac caatgcttaa tcagtgaggc acctatctca    6720
gcgatctgtc tatttcgttc atccatagtt gcctgactcc ccgtcgtgta gataactacg    6780
atacgggagg gcttaccatc tggccccagt gctgcaatga taccgcgaga cccacgctca    6840
ccggctccag atttatcagc aataaaccag ccagccggaa gggccgagcg cagaagtggt    6900
cctgcaactt tatccgcctc catccagtct attaattgtt gccgggaagc tagagtaagt    6960
agttcgccag ttaatagttt gcgcaacgtt gttgccattg ctacaggcat cgtggtgtca    7020
cgctcgtcgt ttggtatggc ttcattcagc tccggttccc aacgatcaag gcgagttaca    7080
tgatccccca tgttgtgcaa aaaagcggtt agctccttcg gtcctccgat cgttgtcaga    7140
agtaagttgg ccgcagtgtt atcactcatg gttatggcag cactgcataa ttctcttact    7200
gtcatgccat ccgtaagatg cttttctgtg actggtgagt actcaaccaa gtcattctga    7260
gaatagtgta tgcggcgacc gagttgctct tgcccggcgt caatacggga taataccgcg    7320
ccacatagca gaactttaaa agtgctcatc attggaaaac gttcttcggg gcgaaaactc    7380
tcaaggatct taccgctgtt gagatccagt tcgatgtaac ccactcgtgc acccaactga    7440
tcttcagcat cttttacttt caccagcgtt tctgggtgag caaaaacagg aaggcaaaat    7500
gccgcaaaaa agggaataag ggcgacacgg aaatgttgaa tactcatact cttcctttt     7560 caatattatt gaagcattta tcagggttat tgtctcatga gcggatacat atttgaatgt    7620
atttagaaaa ataaacaaat aggggttccg cgcacatttc cccgaaaagt gccacctgaa    7680
cgaagcatct gtgcttcatt ttgtagaaca aaatgcaac gcgagagcgc taattttca      7740 aacaaagaat ctgagctgca ttttacaga acagaaatgc aacgcgaaag cgctatttta    7800
ccaacgaaga atctgtgctt cattttgta aaacaaaaat gcaacgcgag agcgctaatt     7860
tttcaaacaa agaatctgag ctgcatttt acagaacaga atgcaacgc gagagcgcta      7920 ttttaccaac aaagaatcta acttcttttt tgttctaca aaaatgcatc ccgagagcgc     7980
tatttttcta caaagcatc ttagattact ttttttctcc tttgtgcgct ctataatgca     8040
gtctcttgat aacttttgc actgtaggtc cgttaaggtt agaagaaggc tactttggtg     8100
tctattttct cttccataaa aaagcctga ctccacttcc cgcgtttact gattactagc     8160
gaagctgcgg gtgcattttt tcaagataaa ggcatccccg attatattct ataccgatgt    8220
ggattgcgca tactttgtga acagaaagtg atagcgttga tgattcttca ttggtcagaa    8280
aattatgaac ggtttcttct attttgtctc tatatactac gtataggaaa tgtttacatt    8340
ttcgtattgt tttcgattca ctctatgaat agttcttact acaattttt tgtctaaaga    8400 gtaatactag agataaacat aaaaaatgta gaggtcgagt ttagatgcaa gttcaaggag    8460
cgaaaggtgg atgggtaggt tatataggga tatagcacag agatatatag caaagagata    8520
```

```
cttttgagca atgtttgtgg aagcggtatt cgcaatattt tagtagctcg ttacagtccg    8580
gtgcgttttt ggttttttga aagtgcgtct tcagagcgct tttggttttc aaaagcgctc    8640
tgaagttcct atactttcta gagaatagga acttcggaat aggaacttca aagcgtttcc    8700
gaaaacgagc gcttccgaaa atgcaacgcg agctgcgcac atacagctca ctgttcacgt    8760
cgcacctata tctgcgtgtt gcctgtatat atatatacat gagaagaacg gcatagtgcg    8820
tgtttatgct taaatgcgta cttatatgcg tctatttatg taggatgaaa ggtagtctag    8880
tacctcctgt gatattatcc cattccatgc ggggtatcgt atgcttcctt cagcactacc    8940
ctttagctgt tctatatgct gccactcctc aattggatta gtctcatcct tcaatgctat    9000
catttccttt gatattggat catactaaga aaccattatt atcatgacat taacctataa    9060
aaataggcgt atcacgaggc cctttcgtc                                      9089

<210> SEQ ID NO 122
<211> LENGTH: 1023
<212> TYPE: DNA
<213> ORGANISM: Saccharomyces cerevisiae

<400> SEQUENCE: 122
caccgcggtg gggcgcgccc tattttcgag gaccttgtca ccttgagccc aagagagcca      60
agatttaaat ttttcctatga cttgatgcaa attcccaaag ctaataacat gcaagacacg     120
tacggtcaag aagacatatt tgacctctta acaggttcag acgcgactgc ctcatcagta     180
agacccgttg aaaagaactt acctgaaaaa aacgaatata tactagcgtt gaatgttagc     240
gtcaacaaca agaagtttaa tgacgcggag gccaaggcaa aaagattcct tgattacgta     300
agggagttag aatcattttg aataaaaaac acgcttttc agttcgagtt tatcattatc      360
aatactgcca tttcaaagaa tacgtaaata attaatagta gtgattttcc taactttatt     420
tagtcaaaaa attagccttt taattctgct gtaacccgta catgcccaaa ataggggggcg    480
ggttacacag aatatataac atcgtaggtg tctgggtgaa cagtttattc ctggcatcca     540
ctaaatataa tggagcccgc ttttttaagct ggcatccaga aaaaaaaaga atcccagcac    600
caaaatattg ttttcttcac caaccatcag ttcataggtc cattctctta gcgcaactac     660
agagaacagg ggcacaaaca ggcaaaaaac gggcacaacc tcaatggagt gatgcaacct    720
gcctggagta aatgatgaca caaggcaatt gacccacgca tgtatctatc tcattttctt     780
acaccttcta ttaccttctg ctctctctga tttggaaaaa gctgaaaaaa aaggttgaaa    840
ccagttccct gaaattattc ccctacttga ctaataagta tataaagacg gtaggtattg     900
attgtaattc tgtaaatcta tttcttaaac ttcttaaatt ctacttttat agttagtctt     960
ttttttagtt ttaaaacacc aagaacttag tttcgaataa acacacataa actagtaaac   1020
aaa                                                                 1023

<210> SEQ ID NO 123
<211> LENGTH: 21
<212> TYPE: DNA
<213> ORGANISM: Artificial Sequence
<220> FEATURE:
<223> OTHER INFORMATION: primer

<400> SEQUENCE: 123
caaaagctga gctccaccgc g                                                21

<210> SEQ ID NO 124
<211> LENGTH: 44
```

```
<212> TYPE: DNA
<213> ORGANISM: Artificial Sequence
<220> FEATURE:
<223> OTHER INFORMATION: primer

<400> SEQUENCE: 124
gtttactagt ttatgtgtgt ttattcgaaa ctaagttctt ggtg                           44

<210> SEQ ID NO 125

<400> SEQUENCE: 125

000

<210> SEQ ID NO 126
<211> LENGTH: 39
<212> TYPE: DNA
<213> ORGANISM: Artificial Sequence
<220> FEATURE:
<223> OTHER INFORMATION: primer

<400> SEQUENCE: 126
cacacatatt acaatagcta gctgaggatg aaagctctg                                 39

<210> SEQ ID NO 127
<211> LENGTH: 39
<212> TYPE: DNA
<213> ORGANISM: Artificial Sequence
<220> FEATURE:
<223> OTHER INFORMATION: primer

<400> SEQUENCE: 127
cagagctttc atcctcagct agctattgta atatgtgtg                                 39

<210> SEQ ID NO 128
<211> LENGTH: 9491
<212> TYPE: DNA
<213> ORGANISM: Artificial Sequence
<220> FEATURE:
<223> OTHER INFORMATION: constructed plasmid

<400> SEQUENCE: 128
tcgcgcgttt cggtgatgac ggtgaaaacc tctgacacat gcagctcccg gagacggtca          60
cagcttgtct gtaagcggat gccgggagca gacaagcccg tcaggcgcg tcagcgggtg         120 ttggcgggtg tcggggctgg cttaactatg cggcatcaga gcagattgta ctgagagtgc         180
accataaatt cccgttttaa gagcttggtg agcgctagga gtcactgcca ggtatcgttt         240
gaacacggca ttagtcaggg aagtcataac acagtccttt cccgcaattt tctttttcta         300
ttactcttgg cctcctctag tacactctat attttttat gcctcggtaa tgatttttcat         360 tttttttttt cccctagcgg atgactcttt ttttttctta gcgattggca ttatcacata         420
atgaattata cattatataa agtaatgtga tttcttcgaa gaatatacta aaaaatgagc         480
aggcaagata aacgaaggca aagatgacag agcagaaagc cctagtaaag cgtattacaa         540
atgaaaccaa gattcagatt gcgatctctt taaagggtgg tcccctagcg atagagcact         600
cgatcttccc agaaaaagag gcagaagcag tagcagaaca ggccacacaa tcgcaagtga         660
ttaacgtcca cacaggtata gggtttctgg accatatgat acatgctctg gccaagcatt         720
ccggctggtc gctaatcgtt gagtgcattg gtgacttaca catagacgac catcacacca         780
ctgaagactg cggattgct ctcggtcaag cttttaaaga ggccctactg gcgcgtggag          840
taaaaaggtt tggatcagga tttgcgcctt tggatgaggc actttccaga gcggtggtag         900
```

```
atctttcgaa caggccgtac gcagttgtcg aacttggttt gcaaagggag aaagtaggag    960
atctctcttg cgagatgatc ccgcatttct ttgaaagctt tgcagaggct agcagaatta   1020
ccctccacgt tgattgtctg cgaggcaaga atgatcatca ccgtagtgag agtgcgttca   1080
aggctcttgc ggttgccata agagaagcca cctcgcccaa tggtaccaac gatgttccct   1140
ccaccaaagg tgttcttatg tagtgacacc gattatttaa agctgcagca tacgatatat   1200
atacatgtgt atatatgtat acctatgaat gtcagtaagt atgtatacga acagtatgat   1260
actgaagatg acaaggtaat gcatcattct atacgtgtca ttctgaacga ggcgcgcttt   1320
ccttttttct ttttgctttt tctttttttt tctcttgaac tcgacggatc tatgcggtgt   1380
gaaataccgc acagatgcgt aaggagaaaa taccgcatca ggaaattgta acgttaata    1440
ttttgttaaa attcgcgtta aattttttgtt aaatcagctc attttttaac caataggccg   1500
aaatcggcaa aatcccttat aaatcaaaag aatagaccga gatagggttg agtgttgttc   1560
cagtttggaa caagagtcca ctattaaaga acgtggactc caacgtcaaa gggcgaaaaa   1620
ccgtctatca gggcgatggc ccactacgtg aaccatcacc ctaatcaagt ttttggggt    1680
cgaggtgccg taaagcacta aatcggaacc ctaaagggag cccccgattt agagcttgac   1740
ggggaaagcc ggcgaacgtg gcgagaaagg aagggaagaa agcgaaagga cgggcgcta    1800
gggcgctggc aagtgtagcg gtcacgctgc gcgtaaccac cacacccgcc gcgcttaatg   1860
cgccgctaca gggcgcgtcg cgccattcgc cattcaggct gcgcaactgt tgggaagggc   1920
gatcggtgcg ggcctcttcg ctattacgcc agctggcgaa aggggggatgt gctgcaaggc   1980
gattaagttg ggtaacgcca gggttttccc agtcacgacg ttgtaaaacg acggccagtg   2040
agcgcgcgta atacgactca ctatagggcg aattgggtac cgggccccc ctcgaggtcg    2100
acggcgcgcc actggtagag agcgactttg tatgccccaa ttgcgaaacc cgcgatatcc   2160
ttctcgattc tttagtaccc gaccaggaca aggaaaagga ggtcgaaacg ttttgaaga    2220
aacaagagga actacacgga agctctaaag atggcaacca gccagaaact aagaaaatga   2280
agttgatgga tccaactggc accgctggct gaacaacaa taccagcctt ccaacttctg   2340
taaataacgg cggtacgcca gtgccaccag taccgttacc tttcggtata cctcctttcc   2400
ccatgtttcc aatgcccttc atgcctccaa cggctactat cacaaatcct catcaagctg   2460
acgcaagccc taagaaatga ataacaatac tgacagtact aaataattgc ctacttggct   2520
tcacatacgt tgcatacgtc gatatagata ataatgataa tgacagcagg attatcgtaa   2580
tacgtaatag ttgaaaatct caaaaatgtg tgggtcatta cgtaaataat dataggaatg   2640
ggattcttct attttccctt tttccattct agcagccgtc gggaaaacgt ggcatcctct   2700
ctttcgggct caattggagt cacgctgccg tgagcatccc ctctttccat atctaacaac   2760
tgagcacgta accaatggaa aagcatgagc ttagcgttgc tccaaaaaag tattggatgg   2820
ttaataccat ttgtctgttc tcttctgact ttgactcctc aaaaaaaaaa aatctacaat   2880
caacagatcg cttcaattac gccctcacaa aaactttttt ccttcttctt cgcccacgtt   2940
aaattttatc cctcatgttg tctaacggat ttctgcactt gatttattat aaaaagacaa   3000
agacataata cttctctatc aatttcagtt attgttcttc cttgcgttat tcttctgttc   3060
ttctttttct tttgtcatat ataaccataa ccaagtaata catattcaaa ctagtatgac   3120
tgacaaaaaa actcttaaag acttaagaaa tcgtagttct gtttacgatt caatggttaa   3180
atcacctaat cgtgctatgt tgcgtgcaac tggtatgcaa gatgaagact ttgaaaaacc   3240
```

```
tatcgtcggt gtcatttcaa cttgggctga aaacacacct tgtaatatcc acttacatga    3300
ctttggtaaa ctagccaaag tcggtgttaa ggaagctggt gcttggccag ttcagttcgg    3360
aacaatcacg gtttctgatg gaatcgccat gggaacccaa ggaatgcgtt tctccttgac    3420
atctcgtgat attattgcag attctattga agcagccatg ggaggtcata atgcggatgc    3480
ttttgtagcc attggcggtt gtgataaaaa catgcccggt tctgttatcg ctatggctaa    3540
catggatatc ccagccattt ttgcttacgg cggaacaatt gcacctggta atttagacgg    3600
caaagatatc gatttagtct ctgtctttga aggtgtcggc cattggaacc acggcgatat    3660
gaccaaagaa gaagttaaag ctttggaatg taatgcttgt cccggtcctg gaggctgcgg    3720
tggtatgtat actgctaaca caatggcgac agctattgaa gttttgggac ttagccttcc    3780
gggttcatct tctcacccgg ctgaatccgc agaaaagaaa gcagatattg aagaagctgg    3840
tcgcgctgtt gtcaaaatgc tcgaaatggg cttaaaacct tctgacattt taacgcgtga    3900
agcttttgaa gatgctatta ctgtaactat ggctctggga ggttcaacca actcaacccct   3960
tcacctctta gctattgccc atgctgctaa tgtggaattg acacttgatg atttcaatac    4020
tttccaagaa aaagttcctc atttggctga tttgaaacct tctggtcaat atgtattcca    4080
agaccittac aaggtcggag gggtaccagc agttatgaaa tatctcctta aaaatggctt    4140
ccttcatggt gaccgtatca cttgtactgg caaacagtc gctgaaaatt tgaaggcttt    4200
tgatgattta acacctggtc aaaaggttat tatgccgctt gaaaatccta acgtgaaga    4260
tggtccgctc attattctcc atggtaactt ggctccagac ggtgccgttg ccaaagtttc    4320
tggtgtaaaa gtgcgtcgtc atgtcggtcc tgctaaggtc tttaattctg aagaagaagc    4380
cattgaagct gtcttgaatg atgatattgt tgatggtgat gttgttgtcg tacgttttgt    4440
aggaccaaag gcggtcctg gtatgcctga aatgcttcc ctttcatcaa tgattgttgg    4500
taaagggcaa ggtgaaaaag ttgccttct gacagatggc cgcttctcag gtggtactta    4560
tggtctgtc gtgggtcata tcgctcctga agcacaagat ggcggtccaa tcgcctacct    4620
gcaaacagga gacatagtca ctattgacca agacactaag gaattacact tgatatctc    4680
cgatgaagag ttaaaacatc gtcaagagac cattgaattg ccaccgctct attcacgcgg    4740
tatccttggt aaatatgctc acatcgtttc gtctgcttct aggggagccg taacagactt    4800
ttggaagcct gaagaaactg gcaaaaaatg ttgtcctggt tgctgtggtt aagcggccgc    4860
gttaattcaa attaattgat atagttttt aatgagtatt gaatctgttt agaaataatg    4920
gaatattatt tttatttatt tatttatatt attggtcggc tcttttcttc tgaaggtcaa    4980
tgacaaaatg atatgaagga ataatgatt tctaaaattt tacaacgtaa gatattttta   5040
caaaagccta gctcatcttt tgtcatgcac tattttactc acgcttgaaa ttaacggcca    5100
gtccactgcg gagtcatttc aaagtcatcc taatcgatct atcgttttg atagctcatt    5160
ttggagttcg cgattgtctt ctgttattca caactgtttt aatttttatt tcattctgga    5220
actcttcgag ttctttgtaa agtctttcat agtagcttac tttatcctcc aacatatta   5280
acttcatgtc aatttcggct cttaaatttt ccacatcatc aagttcaaca tcatctttta    5340
acttgaattt attctctagc tcttccaacc aagcctcatt gctccttgat ttactggtga    5400
aaagtgatac actttgcgcg caatccaggt caaaactttc ctgcaaagaa ttcaccaatt    5460
tctcgacatc atagtacaat ttgttttgtt ctcccatcac aatttaatat acctgatgga    5520
ttcttatgaa gcgctgggta atggacgtgt cactctactt cgccttttc cctactcctt    5580
ttagtacgga agacaatgct aataaataag agggtaataa taatattatt aatcggcaaa    5640
```

```
aaagattaaa cgccaagcgt ttaattatca gaaagcaaac gtcgtaccaa tccttgaatg   5700
cttcccaatt gtatattaag agtcatcaca gcaacatatt cttgttatta aattaattat   5760
tattgatttt tgatattgta taaaaaaacc aaatatgtat aaaaaaagtg aataaaaaat   5820
accaagtatg gagaaatata ttagaagtct atacgttaaa ccaccgcggt ggagctccag   5880
cttttgttcc ctttagtgag ggttaattgc gcgcttggcg taatcatggt catagctgtt   5940
tcctgtgtga aattgttatc cgctcacaat tccacacaac ataggagccg aagcataaa    6000 gtgtaaagcc tggggtgcct aatgagtgag gtaactcaca ttaattgcgt tgcgctcact   6060
gcccgctttc cagtcgggaa acctgtcgtg ccagctgcat taatgaatcg gccaacgcgc   6120
ggggagaggc ggtttgcgta ttgggcgctc ttccgcttcc tcgctcactg actcgctgcg   6180
ctcggtcgtt cggctgcggc gagcggtatc agctcactca aaggcggtaa tacgttatc    6240 cacagaatca ggggataacg caggaaagaa catgtgagca aaaggccagc aaaaggccag   6300
gaaccgtaaa aaggccgcgt tgctggcgtt tttccatagg ctccgccccc ctgacgagca   6360
tcacaaaaat cgacgctcaa gtcagaggtg gcgaaacccg acaggactat aaagatacca   6420
ggcgtttccc cctggaagct ccctcgtgcg ctctcctgtt ccgaccctgc cgcttaccgg   6480
atacctgtcc gcctttctcc cttcgggaag cgtggcgctt tctcatagct cacgctgtag   6540
gtatctcagt tcggtgtagg tcgttcgctc caagctgggc tgtgtgcacg aaccccccgt   6600
tcagcccgac cgctgcgcct tatccggtaa ctatcgtctt gagtccaacc cggtaagaca   6660
cgacttatcg ccactggcag cagccactgg taacaggatt agcagagcga ggtatgtagg   6720
cggtgctaca gagttcttga agtggtggcc taactacggc tacactagaa ggacagtatt   6780
tggtatctgc gctctgctga agccagttac cttcggaaaa agagttggta gctcttgatc   6840
cggcaaacaa accaccgctg gtagcggtgg tttttttgtt tgcaagcagc agattacgcg   6900
cagaaaaaaa ggatctcaag aagatccttt gatcttttct acggggtctg acgctcagtg   6960
gaacgaaaac tcacgttaag ggattttggt catgagatta tcaaaaagga tcttcaccta   7020 gatccttta aattaaaaat gaagttttaa atcaatctaa agtatatatg agtaaacttg   7080
gtctgacagt taccaatgct taatcagtga ggcacctatc tcagcgatct gtctatttcg   7140
ttcatccata gttgcctgac tccccgtcgt gtagataact acgatacggg agggcttacc   7200
atctggcccc agtgctgcaa tgataccgcg agacccacgc tcaccggctc agatttatc    7260 agcaataaac cagccagccg gaagggccga gcgcagaagt ggtcctgcaa ctttatccgc   7320
ctccatccag tctattaatt gttgccggga agctagagta agtagttcgc cagttaatag   7380
tttgcgcaac gttgttgcca ttgctacagg catcgtggtg tcacgctcgt cgtttggtat   7440
ggcttcattc agctccggtt cccaacgatc aaggcgagtt acatgatccc ccatgttgtg   7500
caaaaaagcg gttagctcct tcggtcctcc gatcgttgtc agaagtaagt tggccgcagt   7560
gttatcactc atggttatgg cagcactgca taattctctt actgtcatgc catccgtaag   7620
atgcttttct gtgactggtg agtactcaac caagtcattc tgagaatagt gtatgcggcg   7680
accgagttgc tcttgcccgg cgtcaatacg ggataatacc gcgccacata gcagaacttt   7740
aaaagtgctc atcattggaa aacgttcttc ggggcgaaaa ctctcaagga tcttaccgct   7800
gttgagatcc agttcgatgt aacccactcg tgcacccaac tgatcttcag catcttttac   7860
tttcaccagc gtttctgggt gagcaaaaac aggaaggcaa aatgccgcaa aaagggaat    7920 aagggcgaca cggaaatgtt gaatactcat actcttcctt tttcaatatt attgaagcat   7980
```

| | |
|---|---|
| ttatcagggt tattgtctca tgagcggata catatttgaa tgtatttaga aaaataaaca | 8040 |
| aatagggtt ccgcgcacat ttccccgaaa agtgccacct gaacgaagca tctgtgcttc | 8100 |
| attttgtaga acaaaaatgc aacgcgagag cgctaatttt tcaaacaaag aatctgagct | 8160 |
| gcattttac agaacagaaa tgcaacgcga aagcgctatt ttaccaacga agaatctgtg | 8220 |
| cttcattttt gtaaaacaaa aatgcaacgc gagagcgcta attttcaaa caaagaatct | 8280 |
| gagctgcatt tttacagaac agaaatgcaa cgcgagagcg ctattttacc aacaaagaat | 8340 |
| ctatacttct tttttgttct acaaaaatgc atcccgagag cgctattttt ctaacaaagc | 8400 |
| atcttagatt acttttttc tcctttgtgc gctctataat gcagtctctt gataaacttt | 8460 |
| tgcactgtag gtccgttaag gttagaagaa ggctactttg gtgtctattt tctcttccat | 8520 |
| aaaaaaagcc tgactccact tcccgcgttt actgattact agcgaagctg cgggtgcatt | 8580 |
| ttttcaagat aaaggcatcc ccgattatat tctataccga tgtggattgc gcatactttg | 8640 |
| tgaacagaaa gtgatagcgt tgatgattct tcattggtca gaaaattatg aacggtttct | 8700 |
| tctattttgt ctctatatac tacgtatagg aaatgtttac attttcgtat tgttttcgat | 8760 |
| tcactctatg aatagttctt actacaattt ttttgtctaa agagtaatac tagagataaa | 8820 |
| cataaaaaat gtagaggtcg agtttagatg caagttcaag gagcgaaagg tggatgggta | 8880 |
| ggttatatag ggatatagca cagagatata tagcaaagag atactttga gcaatgtttg | 8940 |
| tggaagcggt attcgcaata ttttagtagc tcgttacagt ccggtgcgtt tttggttttt | 9000 |
| tgaaagtgcg tcttcagagc gcttttggtt ttcaaaagcg ctctgaagtt cctatacttt | 9060 |
| ctagagaata ggaacttcgg aataggaact tcaaagcgtt tccgaaaacg agcgcttccg | 9120 |
| aaaatgcaac gcgagctgcg cacatacagc tcactgttca cgtcgcacct atatctgcgt | 9180 |
| gttgcctgta tatatatata catgagaaga acggcatagt gcgtgtttat gcttaaatgc | 9240 |
| gtacttatat gcgtctattt atgtaggatg aaaggtagtc tagtacctcc tgtgatatta | 9300 |
| tcccattcca tgcggggtat cgtatgcttc cttcagcact accctttagc tgttctatat | 9360 |
| gctgccactc ctcaattgga ttagtctcat ccttcaatgc tatcatttcc tttgatattg | 9420 |
| gatcatctaa gaaaccatta ttatcatgac attaacctat aaaaataggc gtatcacgag | 9480 |
| gccctttcgt c | 9491 |

<210> SEQ ID NO 129
<211> LENGTH: 1000
<212> TYPE: DNA
<213> ORGANISM: Saccharomyces cerevisiae

<400> SEQUENCE: 129

| | |
|---|---|
| gttaattcaa attaattgat atagtttttt aatgagtatt gaatctgttt agaaataatg | 60 |
| gaatattatt tttatttatt tatttatatt attggtcggc tcttttcttc tgaaggtcaa | 120 |
| tgacaaaatg atatgaagga aataatgatt tctaaaattt tacaacgtaa gatattttta | 180 |
| caaaagccta gctcatcttt tgtcatgcac tattttactc acgcttgaaa ttaacggcca | 240 |
| gtccactgcg gagtcatttc aaagtcatcc taatcgatct atcgttttg atagctcatt | 300 |
| ttggagttcg cgattgtctt ctgttattca caactgtttt aattttatt tcattctgga | 360 |
| actcttcgag ttctttgtaa agtctttcat agtagcttac tttatcctcc aacatatta | 420 |
| acttcatgtc aatttcggct cttaaatttt ccacatcatc aagttcaaca tcatctttta | 480 |
| acttgaattt attctctagc tcttccaacc aagcctcatt gctccttgat ttactggtga | 540 |
| aaagtgatac actttgcgcg caatccaggt caaaactttc ctgcaaagaa ttcaccaatt | 600 |

```
tctcgacatc atagtacaat ttgttttgtt ctcccatcac aatttaatat acctgatgga    660
ttcttatgaa gcgctgggta atggacgtgt cactctactt cgccttttc cctactcctt    720 ttagtacgga agacaatgct aataaataag agggtaataa taatattatt aatcggcaaa    780
aaagattaaa cgccaagcgt ttaattatca gaaagcaaac gtcgtaccaa tccttgaatg    840
cttcccaatt gtatattaag agtcatcaca gcaacatatt cttgttatta aattaattat    900
tattgatttt tgatattgta taaaaaaacc aaatatgtat aaaaaaagtg aataaaaaat    960
accaagtatg gagaaatata ttagaagtct atacgttaaa                         1000
```

<210> SEQ ID NO 130
<211> LENGTH: 16387
<212> TYPE: DNA
<213> ORGANISM: Artificial Sequence
<220> FEATURE:
<223> OTHER INFORMATION: Plasmid

<400> SEQUENCE: 130

```
gatcctctag tttctcggta ctatgcatat gatccaatat caaaggaaat gatagcattg     60
aaggatgaga ctaatccaat tgaggagtgg cagcatatag aacagctaaa gggtagtgct    120
gaaggaagca tacgataccc cgcatggaat gggataatat cacaggaggt actagactac    180
ctttcatcct acataaatag acgcataaa gtacgcattt aagcataaac acgcactatg     240
ccgttcttct catgtatata tatatacagg caacacgcag atataggtgc gacgtgaaca    300
gtgagctgta tgtgcgcagc tcgcgttgca ttttcggaag cgctcgtttt cggaaacgct    360
ttgaagttcc tattccgaag ttcctattct ctagaaagta taggaacttc agagcgcttt    420
tgaaaaccaa aagcgctctg aagacgcact tcaaaaaac caaaaacgca ccggactgta    480
acgagctact aaaatattgc gaataccgct tccacaaaca ttgctcaaaa gtatctcttt    540
gctatatatc tctgtgctat atccctatat aacctaccca tccacctttc gctccttgaa    600
cttgcatcta aactcgacct ctacatttt tatgtttatc tctagtatta ctctttagac    660
aaaaaaattg tagtaagaac tattcataga gtgaatcgaa acaatacga aaatgtaaac    720 atttcctata cgtagtatat agagacaaaa tagaagaaac cgttcataat tttctgacca    780
atgaagaatc atcaacgcta tcactttctg ttcacaaagt atgcgcaatc cacatcggta    840
tagaatataa tcggggatgc ctttatcttg aaaaaatgca cccgcagctt cgctagtaat    900
cagtaaacgc gggaagtgga gtcaggcttt ttttatggaa gagaaaatag acaccaaagt    960
agccttcttc taaccttaac ggacctacag tgcaaaagt tatcaagaga ctgcattata   1020
gagcgcacaa aggagaaaaa aagtaatcta agatgctttg ttagaaaaat agcgctctcg   1080
ggatgcattt ttgtagaaca aaaagaagt atagattctt tgttggtaaa atagcgctct   1140
cgcgttgcat ttctgttctg taaaaatgca gctcagattc tttgtttgaa aaattagcgc   1200
tctcgcgttg cattttttgtt ttacaaaaat gaagcacaga ttcttcgttg gtaaaatagc   1260
gctttcgcgt tgcattctg ttctgtaaaa atgcagctca gattctttgt tgaaaaatt    1320 agcgctctcg cgttgcattt tgttctaca aatgaagca cagatgcttc gttaacaaag   1380
atatgctatt gaagtgcaag atggaaacgc agaaaatgaa ccgggatgc gacgtgcaag   1440 attacctatg caatagatgc aatagttct ccaggaaccg aaatacatac attgtcttcc   1500
gtaaagcgct agactatata ttattataca ggttcaaata tactatctgt tcagggaaa    1560 actcccaggt tcggatgttc aaaattcaat gatgggtaac aagtacgatc gtaaatctgt   1620
```

-continued

```
aaaacagttt gtcggatatt aggctgtatc tcctcaaagc gtattcgaat atcattgaga    1680
agctgcattt tttttttttt tttttttttt ttttttata tatatttcaa ggatatacca    1740
ttgtaatgtc tgcccctaag aagatcgtcg ttttgccagg tgaccacgtt ggtcaagaaa    1800
tcacagccga agccattaag gttcttaaag ctatttctga tgttcgttcc aatgtcaagt    1860
tcgatttcga aaatcattta attggtggtg ctgctatcga tgctacaggt gttccacttc    1920
cagatgaggc gctggaagcc tccaagaagg ctgatgccgt tttgttaggt gctgtgggtg    1980
gtcctaaatg gggtaccggt agtgttagac ctgaacaagg tttactaaaa atccgtaaag    2040
aacttcaatt gtacgccaac ttaagaccat gtaactttgc atccgactct cttttagact    2100
tatctccaat caagccacaa tttgctaaag gtactgactt cgttgttgtt agagaattag    2160
tgggaggtat ttactttggt aagagaaagg aagacgatgg tgatggtgtc gcttgggata    2220
gtgaacaata caccgttcca gaagtgcaaa gaatcacaag aatggccgct ttcatggccc    2280
tacaacatga gccaccattg cctatttggt ccttggataa agctaatgtt ttggcctctt    2340
caagattatg gagaaaaact gtggaggaaa ccatcaagaa cgaattccct acattgaaag    2400
ttcaacatca attgattgat tctgccgcca tgatcctagt taagaaccca acccacctaa    2460
atggtattat aatcaccagc aacatgtttg gtgatatcat ctccgatgaa gcctccgtta    2520
tcccaggctc cttgggtttg ttgccatctg cgtccttggc ctctttgcca gacaagaaca    2580
ccgcatttgg tttgtacgaa ccatgccatg gttccgctcc agatttgcca aagaataagg    2640
tcaaccctat cgccactatc ttgtctgctg caatgatgtt gaaattgtca ttgaacttgc    2700
ctgaagaagg taaagccatt gaagatgcag ttaaaaaggt tttggatgca ggtatcagaa    2760
ctggtgattt aggtggttcc aacagtacca ccgaagtcgg tgatgctgtc gccgaagaag    2820
ttaagaaaat ccttgcttaa aaagattctc tttttttatg atatttgtac aaaaaaaaaa    2880
aaaaaaaaaa aaaaaaaaaa aaaaaaaaaa aaaaaaaaa aatgcagcgt cacatcggat    2940
aataatgatg gcagccattg tagaagtgcc ttttgcattt ctagtctctt tctcggtcta    3000
gctagtttta ctacatcgcg aagatagaat cttagatcac actgcctttg ctgagctgga    3060
tcaatagagt aacaaaagag tggtaaggcc tcgttaaagg acaaggacct gagcggaagt    3120
gtatcgtaca gtagacggag tatactagag tcgacctgca ggcatgcaag cttttcaatt    3180
catcattttt tttttattct tttttttgat ttcggtttcc ttgaaatttt tttgattcgg    3240
taatctccga acagaaggaa gaacgaagga aggagcacag acttagattg gtatatatac    3300
gcatatgtag tgttgaagaa acatgaaatt gcccagtatt cttaacccaa ctgcacagaa    3360
caaaaacctg caggaaacga agataaatca tgtcgaaagc tacatataag gaacgtgctg    3420
ctactcatcc tagtcctgtt gctgccaagc tatttaatat catgcacgaa aagcaaacaa    3480
acttgtgtgc ttcattggat gttcgtacca ccaaggaatt actggagtta gttgaagcat    3540
taggtcccaa aatttgttta ctaaaaacac atgtggatat cttgactgat ttttccatgg    3600
agggcacagt taagccgcta aaggcattat ccgccaagta caatttttta ctcttcgaag    3660
acagaaaatt tgctgacatt ggtaatacag tcaaattgca gtactctgcg ggtgtataca    3720
gaatagcaga atgggcagac attacgaatg cacacggtgt ggtgggccca ggtattgtta    3780
gcggtttgaa gcaggcggca gaagaagtaa caaaggaacc tagaggcctt ttgatgttag    3840
cagaattgtc atgcaagggc tccctatcta ctggagaata tactaagggt actgttgaca    3900
ttgcgaagag cgacaaagat tttgttatcg gctttattgc tcaaagagac atgggtggaa    3960
gagatgaagg ttacgattgg ttgattatga cacccggtgt gggtttagat gacaagggag    4020
```

```
acgcattggg tcaacagtat agaaccgtgg atgatgtggt ctctacagga tctgacatta    4080
ttattgttgg aagaggacta tttgcaaagg aagggatgc  taaggtagag ggtgaacgtt    4140
acagaaaagc aggctgggaa gcatatttga gaagatgcgg ccagcaaaac taaaaaactg    4200
tattataagt aaatgcatgt atactaaact cacaaattag agcttcaatt taattatatc    4260
agttattacc cgggaatctc ggtcgtaatg atttttataa tgacgaaaaa aaaaaaattg    4320
gaaagaaaaa gcttggcgta atcatggtca tagctgtttc ctgtgtgaaa ttgttatccg    4380
ctcacaattc cacacaacat acgagccgga agcataaagt gtaaagcctg gggtgcctaa    4440
tgagtgagct aactcacatt aattgcgttg cgctcactgc ccgctttcca gtcgggaaac    4500
ctgtcgtgcc agctgcatta atgaatcggc caacgcgcgg ggagaggcgg tttgcgtatt    4560
gggcgctctt ccgcttcctc gctcactgac tcgctgcgct cggtcgttcg gctgcggcga    4620
gcggtatcag ctcactcaaa ggcggtaata cggttatcca cagaatcagg ggataacgca    4680
ggaaagaaca tgtgagcaaa aggccagcaa aaggccagga accgtaaaaa ggccgcgttg    4740
ctggcgtttt tccataggct ccgcccccct gacgagcatc acaaaaatcg acgctcaagt    4800
cagaggtggc gaaacccgac aggactataa agataccagg cgtttccccc tggaagctcc    4860
ctcgtgcgct ctcctgttcc gaccctgccg cttaccggat acctgtccgc ctttctccct    4920
tcgggaagcg tggcgctttc tcatagctca cgctgtaggt atctcagttc ggtgtaggtc    4980
gttcgctcca agctgggctg tgtgcacgaa ccccccgttc agcccgaccg ctgcgcctta    5040
tccggtaact atcgtcttga gtccaacccg gtaagacacg acttatcgcc actggcagca    5100
gccactggta acaggattag cagagcgagg tatgtaggcg gtgctacaga gttcttgaag    5160
tggtggccta actacggcta cactagaaga acagtatttg gtatctgcgc tctgctgaag    5220
ccagttacct tcggaaaaag agttggtagc tcttgatccg gcaaacaaac caccgctggt    5280
agcggtggtt tttttgtttg caagcagcag attacgcgca gaaaaaaagg atctcaagaa    5340
gatcctttga tcttttctac ggggtctgac gctcagtgga acgaaaactc acgttaaggg    5400
attttggtca tgagattatc aaaaaggatc ttcacctaga tccttttaaa ttaaaaatga    5460
agttttaaat caatctaaag tatatatgag taaacttggt ctgacagtta ccaatgctta    5520
atcagtgagg cacctatctc agcgatctgt ctatttcgtt catccatagt tgcctgactc    5580
cccgtcgtgt agataactac gatacgggag ggcttaccat ctggccccag tgctgcaatg    5640
ataccgcgag acccacgctc accggctcca gatttatcag caataaacca gccagccgga    5700
agggccgagc gcagaagtgg tcctgcaact ttatccgcct ccatccagtc tattaattgt    5760
tgccgggaag ctagagtaag tagttcgcca gttaatagtt tgcgcaacgt tgttgccatt    5820
gctacaggca tcgtggtgtc acgctcgtcg tttggtatgg cttcattcag ctccggttcc    5880
caacgatcaa ggcgagttac atgatccccc atgttgtgca aaaaagcggt tagctccttc    5940
ggtcctccga tcgttgtcag aagtaagttg gccgcagtgt tatcactcat ggttatggca    6000
gcactgcata attctcttac tgtcatgcca tccgtaagat gcttttctgt gactggtgag    6060
tactcaacca agtcattctg agaatagtgt atgcggcgac cgagttgctc ttgcccggcg    6120
tcaatacggg ataataccgc gccacatagc agaactttaa aagtgctcat cattggaaaa    6180
cgttcttcgg ggcgaaaact ctcaaggatc ttaccgctgt tgagatccag ttcgatgtaa    6240
cccactcgtg cacccaactg atcttcagca tcttttactt tcaccagcgt ttctgggtga    6300
gcaaaaacag gaaggcaaaa tgccgcaaaa aagggaataa gggcgacacg gaaatgttga    6360
```

```
atactcatac tcttcctttt tcaatattat tgaagcattt atcagggtta ttgtctcatg   6420
agcggataca tatttgaatg tatttagaaa aataaacaaa tagggggttcc gcgcacattt   6480 ccccgaaaag tgccacctga cgtctaagaa accattatta tcatgacatt aacctataaa   6540
aataggcgta tcacgaggcc ctttcgtctc gcgcgtttcg gtgatgacgg tgaaaacctc   6600
tgacacatgc agctcccgga cggtcaca gcttgtctgt aagcggatgc cgggagcaga     6660
caagcccgtc agggcgcgtc agcgggtgtt ggcgggtgtc ggggctggct taactatgcg    6720
gcatcagagc agattgtact gagagtgcac cataaaattg taaacgttaa tattttgtta    6780
aaattcgcgt taaattttg ttaaatcagc tcatttttta accaatagac cgaaatcggc     6840
aaaatccctt ataaatcaaa agaatagccc gagatagagt tgagtgttgt tccagtttgg   6900
aacaagagtc cactattaaa gaacgtggac tccaacgtca aagggcgaaa aaccgtctat    6960
cagggcgatg gcccactacg tgaaccatca cccaaatcaa gttttttggg gtcgaggtgc   7020
cgtaaagcac taaatcggaa ccctaaaggg agccccgat ttagagcttg acggggaaag    7080
ccggcgaacg tggcgagaaa ggaagggaag aaagcgaaag gagcgggcgc taaggcgctg   7140
gcaagtgtag cggtcacgct gcgcgtaacc accacaccg ccgcgcttaa tgcgccgcta    7200
cagggcgcgt actatggttg ctttgacgta tgcggtgtga aataccgcac agatgcgtaa   7260
ggagaaaata ccgcatcagg cgccattcgc cattcaggct gcgcaactgt tgggaagggc   7320
gatcggtgcg ggcctcttcg ctattacgcc agctggcgaa aggggggatgt gctgcaaggc   7380 gattaagttg ggtaacgcca gggttttccc agtcacgacg ttgtaaaacg acggccagtg   7440
aattcgagct ccaccgcgga tagatctgaa atgaataaca atactgacag tactaaataa   7500
ttgcctactt ggcttcacat acgttgcata cgtcgatata gataataatg ataatgacag   7560
caggattatc gtaatacgta atagttgaaa atctcaaaaa tgtgtgggtc attacgtaaa   7620
taatgatagg aatgggattc ttctattttt cctttttcca ttctagcagc cgtcgggaaa   7680
acgtggcatc ctctctttcg ggctcaattg gagtcacgct gccgtgagca tcctctcttt   7740
ccatatctaa caactgagca cgtaaccaat ggaaaagcat gagcttagcg ttgctccaaa   7800
aaagtattgg atggttaata ccatttgtct gttctcttct gactttgact cctcaaaaaa   7860
aaaaaatcta caatcaacag atcgcttcaa ttacgccctc acaaaaactt ttttccttct   7920
tcttcgccca cgttaaattt tatccctcat gttgtctaac ggattctgc acttgattta    7980 ttataaaaag acaaagacat aatacttctc tatcaatttc agttattgtt cttccttgcg   8040
ttattcttct gttcttcttt ttcttttgtc atatataacc ataaccaagt aatacatatt   8100
caaatctaga gctgaggatg ttgaagcaaa tcaacttcgg tggtactgtt gaaaccgtct   8160
acgaaagagc tgactggcca agagaaaagt tgttggacta cttcaagaac gacactttg    8220 ctttgatcgg ttacggttcc caaggttacg gtcaaggttt gaacttgaga gacaacggtt   8280
tgaacgttat cattggtgtc cgtaaagatg gtgcttcttg gaaggctgcc atcgaagacg   8340
gttgggttcc aggcaagaac ttgttcactg ttgaagatgc tatcaagaga ggtagttacg   8400
ttatgaactt gttgtccgat gccgctcaat cagaaacctg gcctgctatc aagccattgt   8460
tgaccaaggg taagactttg tacttctccc acgtttctc cccagtcttc aaggacttga    8520
ctcacgttga accaccaaag gacttagatg ttatcttggt tgctccaaag ggttccggta   8580
gaactgtcag atctttgttc aaggaaggtc gtggtattaa ctcttcttac gccgtctgga   8640
acgatgtcac cggtaaggct cacgaaaagg cccaagcttt ggccgttgcc attggttccg   8700
gttacgttta ccaaaccact ttcgaaagag aagtcaactc tgacttgtac ggtgaaagag   8760
```

```
gttgtttaat gggtggtatc cacggtatgt tcttggctca atacgacgtc ttgagagaaa    8820
acggtcactc cccatctgaa gctttcaacg aaaccgtcga agaagctacc caatctctat    8880
acccattgat cggtaagtac ggtatggatt acatgtacga tgcttgttcc accaccgcca    8940
gaagaggtgc tttggactgg tacccaatct tcaagaatgc tttgaagcct gttttccaag    9000
acttgtacga atctaccaag aacggtaccg aaaccaagag atctttggaa ttcaactctc    9060
aacctgacta cagagaaaag ctagaaaagg aattagacac catcagaaac atggaaatct    9120
ggaaggttgg taaggaagtc agaaagttga gaccagaaaa ccaataatta attaatcatg    9180
taattagtta tgtcacgctt acattcacgc cctcccccca catccgctct aaccgaaaag    9240
gaaggagtta gacaacctga agtctaggtc cctatttatt tttttatagt tatgttagta    9300
ttaagaacgt tatttatatt tcaaattttt ctttttttc tgtacagacg cgtgtacgca    9360
tgtaacatta tactgaaaac cttgcttgag aaggttttgg gacgctcgaa ggctttaatt    9420
tgcgggcggc cgctctagag agttgttagc aaccttttgt ttcttttgag ctggttcaga    9480
cattatgtac acgtatatgt gacgagttcg agaagtattt tactatcgta ctaaatttta    9540
cctgaaaaat tatatactcg agaaagagga agccaagaat tgagaaaaaa gaaaaacccg    9600
cgagtaagga aattaaatac aggtgtacac atacacgcac acatatatat atatatatat    9660
atgtatatgt gtatataggaa agcgcgcgca tgttagtata tacgattcgt tggaaagggg    9720
ccgtccacca aacgtgactt gacgagttga caaattgacc tcaatatggc tcagtcagta    9780 attttagtt ccgctttatt cccgccatct ttcaggccac gagggtagct cataacgccg    9840
cgctaatgcc gctgcgtcac agcaaccagt agctcagcca aaaccgaaag agaaatcgta    9900
gctgtcccga tgaggactta tacacttgtc accatctaaa taaattattt attcgcgttt    9960
cggttcttgt tttcgattta attagattgt tcattgaatc ataataaata tgtaaaaaat   10020
atatatattt gaagctgctt cagaaaaaca gggcttccta gtgtacagat gtatgtcgga   10080
tgaaaaaaaa aaaatcttaa atgtgaaatt gggtcaattc aattgactat gacttgatgt   10140
tgcaaaaatt ccaagagaaa aagtttccag cacttgatat tattttcctc tttaattttt   10200
cgccttgtct acgatcttat tagcaccgat ccagggcatc atagacccta actgttcacc   10260
aataatttcg ataccatgtg ctgcattgtt tcttcttta gcagtcatac tcgggtaacc   10320
cgtagcgcct tcacttatga acatcttagc gtattcaccg tcctggatac gtttcaaggc   10380
atttctcatg gcttgtcttg attctgcgtt aatgacttca ggtccggtga catactcacc   10440
atattctgca ttatttgaaa tggaatagtt catattagct ataccacctt catacattaa   10500
gtctactatc aacttcaatt catgtagaca ttcgaagtat gccatttcgg gagcgtaccc   10560
tgcttcgaca agcgtctcaa agcctgcttt aaccaattca acagttcctc cgcacagaac   10620
cgcttgttct ccaaataaat ctgtctcagt ctcgtcttta aaagtggttt ctattatacc   10680
cgttctcccg ccaccaactc ctgctgcgta gcttaaagct acattcttag cgtttccgct   10740
tgcgtcttgg tatatagcga tcaaatctgg aataccacca cccttaacaa attcgctcct   10800
aacagtatgc cccggagcct taggtgcaat cataataacg tccaaatctg ccctggggac   10860
tacttgattg taatgaatgg caaatccatg actgaaggcc aaggtagcgc ccttcttaat   10920
gtttggttct atttcatttt tgtacaattg cgattgaaat tcatctggcg ttaaaatcat   10980
gactaaatca gcgccggcaa cagccgctgc aacatctgtg actttcaagc catgtgcttc   11040
agcctttgca acggtagcac tacctttttct cagacctact gtcacgtcga ccccagaatc   11100
```

-continued

```
tttcaagtta caggcttgtg cgtgtccttg ggaaccatat cctataatag caaccttctt    11160
tccctggatg atgctcagat cgcagtcttt atcgtaaaac accttcatgt tttatttttt    11220
acttatattg ctggtagggt aaaaaaatat aactcctagg aataggttgt ctatatgttt    11280
ttgtcttgct tctataattg taacaaacaa ggaaagggaa aatactgggt gtaaaagcca    11340
ttgagtcaag ttaggtcatc ccttttatac aaaattttc aattttttt ccaagattct      11400 tgtacgatta attatttttt ttttgcgtcc tacagcgtga tgaaaatttc cgcctgctgc    11460
aagatgagcg ggaacgggcg aaatgtgcac gcgcacaact tacgaaacgc ggatgagtca    11520
ctgacagcca ccgcagaggt tctgactcct actgagctct attggaggtg gcagaaccgg    11580
taccggagga gaccgctata accggtttga atttattgtc acagtgtcac atcagcggca    11640
actcagaagt ttgacagcaa gcaagttcat cattcgaact agccttattg ttttagttca    11700
gtgacagcga actgccgtac tcgatgcttt atttctcacg gtagagcgga agaacagata    11760
ggggcagcgt gagaagagtt agaaagtaaa tttttatcac gtctgaagta ttcttattca    11820
taggaaattt tgcaaggttt tttagctcaa taacgggcta agttatataa ggtgttcacg    11880
cgattttctt gttatgtata cctcttctct gaggaatggt actactgtcc tgatgtaggc    11940
tccttaaatt ggtgggcaag aataacttat cgatattttg tatattggtc ttggagttca    12000
ccacgtaatg cctgtttaag accatcagtt aactctagta ttatttggtc ttggctactg    12060
gccgtttgct attattcaag tcttttgtgc cttcccgtcg ggtaagggag ttatttaggg    12120
atacagaatc taacgaaaac taaatctcaa tgattaactc catttaatcc tttttttgaaa    12180 ggcaaaagag gtcccttgtt cacttacaac gttcttagcc aaattcgctt atcacttact    12240
acttcacgat atacagaagt aaaaacatat aaaaagatgt ctgtttgttt agccatcaca    12300
aaaggtatcg cagtttcttc tataggcctc tactctggtc ttttggcttc cgcttcattg    12360
attacatcta ctactccact agaggtttta acaggatctc taaaaacatc gatatcgtct    12420
ctgcgttcca atcctacggt gaatatattt ccaagcaatt cactgaagaa gaaagagaag    12480
atgttgtgga acatgcatgc ccaggtcctg gttcttgtgg tggtatgtat actgccaaca    12540
caatggcttc tgccgctgaa gtgctaggtt tgaccattcc aaaactcctct tccttcccag    12600 ccgtttccaa ggagaagtta gctgagtgtg acaacattgg tgaatacatc aagaagacaa    12660
tggaattggg tattttacct cgtgatatcc tcacaaaaga ggcttttgaa aacgccatta    12720
cttatgtcgt tgcaaccggt gggtccacta atgctgtttt gcatttggtg gctgttgctc    12780
actctgcggg tgtcaagttg tcaccagatg atttccaaag aatcagtgat actacaccat    12840
tgatcggtga cttcaaacct tctggtaaat acgtcatggc cgatttgatt aacgttggtg    12900
gtacccaatc tgtgattaag tatctatatg aaaacaacat gttgcacggt aacacaatga    12960
ctgttaccgg tgacactttg gcagaacgtg caaagaaagc accaagccta cctgaaggac    13020
aagagattat taagccactc tcccacccaa tcaggccaa cggtcacttg caaattctgt      13080
acggttcatt ggcaccaggt ggagctgtgg gtaaaattac cggtaaggaa ggtacttact    13140
tcaagggtag agcacgtgtg ttcgaagagg aaggtgcctt tattgaagcc ttggaaagag    13200
gtgaaatcaa gaagggtgaa aaaaccgttg ttgttatcag atatgaaggt ccaagaggtg    13260
caccaggtat gcctgaaatg ctaaagcctt cctctgctct gatgggttac ggtttgggta    13320
aagatgttgc attgttgact gatggtagat tctctggtgg ttctcacggg ttcttaatcg    13380
gccacattgt tcccgaagcc gctgaaggtg gtcctatcgg gttggtcaga gacggcgatg    13440
agattatcat tgatgctgat aataacaaga ttgacctatt agtctctgat aaggaaatgg    13500
```

```
ctcaacgtaa acaaagttgg gttgcacctc cacctcgtta cacaagaggt actctatcca    13560
agtatgctaa gttggtttcc aacgcttcca acggttgtgt tttagatgct tgattaatta    13620
agagtaagcg aatttcttat gatttatgat ttttattatt aaataagtta taaaaaaaat    13680
aagtgtatac aaattttaaa gtgactctta ggttttaaaa cgaaaattct tattcttgag    13740
taactctttc ctgtaggtca ggttgctttc tcaggtatag catgaggtcg ctcttattga    13800
ccacacctct accggcatgc cgagcaaatg cctgcaaatc gctccccatt tcacccaatt    13860
gtagatatgc taactccagc aatgagttga tgaatctcgg tgtgtatttt atgtcctcag    13920
aggacaacac ctgtggtact agttctagag cggccgccg caaattaaag ccttcgagcg     13980
tcccaaaacc ttctcaagca aggttttcag tataatgtta catgcgtaca cgcgtctgta    14040
cagaaaaaaa agaaaaattt gaaatataaa taacgttctt aatactaaca taactataaa    14100
aaaataaata gggacctaga cttcaggttg tctaactcct tccttttcgg ttagagcgga    14160
tgtgggggga gggcgtgaat gtaagcgtga cataactaat tacatgatta attaactaga    14220
gagctttcgt tttcatgagt tccccgaatt ctttcggaag cttgtcactt gctaaattaa    14280
tgttatcact gtagtcaacc gggacatcga tgatgacagg accttcagcg ttcatgcctt    14340
gacgcagaac atctgccagc tggtctggtg attctacgcg caagccagtt gctccgaagc    14400
tttccgcata tttcacgata tcgatatttc cgaaatcgac cgcagatgta cggttatatt    14460
ttttcaattg ctggaatgca accatgtcat atgtgctgtc gttccataca atgtgtacaa    14520
ttggtgcttt tagtcgaact gctgtctcta attccattgc tgagaataag aaaccgccgt    14580
caccagagac agaaaccact ttttctcccg gtttcaccaa tgaagcgccg attgcccaag    14640
gaagcgcaac gccgagtgtt tgcataccgt tactgatcat taatgttaac ggctcgtagc    14700
tgcggaaata acgtgacatc caaatggcgt gcgaaccgat atcgcaagtt actgtaacat    14760
gatcatcgac tgcattacgc aactctttaa cgatttcaag agggtgcgct ctgtctgatt    14820
tccaatctgc aggcacctgc tcaccttcat gcatatattg ttttaaatca gaaaggattt    14880
tctgctcacg ctctgcaaat tccactttca cagcatcgtg ttcgatatga ttgatcgtgg    14940
acggaatgtc accgatcaat tcaagatcag gctggtaagc atgatcaatg tcagcgataa    15000
tctcgtctaa atggataatt gtccggtctc cattgatatt ccagaatttc ggatcatatt    15060
caatcgggtc atagccgatc gtcagaacaa catctgcctg ctctagcagt aaatcgccag    15120
gctggttgcg gaacaaaccg atacggccaa aatattgatc ctctaaatct ctagaaaggg    15180
taccggcagc ttgatatgtt tcaacaaatg gaagctgaac cttttttcaaa agcttgcgaa    15240 ccgctttaat tgcttccggt cttccgcctt tcatgccgac caaaacgaca ggaagttttg    15300
ctgtttggat ttttgctatg gccgcactga ttgcatcatc tgctgcagga ccgagttttg    15360
gcgctgcaac agcacgcacg ttttttcgtat ttgtgacttc attcacaaca tcttgcggaa    15420
agctcacaaa agcggcccca gcctgccctg ctgacgctat cctaaatgca tttgtaacag    15480
cttccggtat attttttaca tcttgaactt ctacactgta ttttgtaatc ggctggaata    15540
gcgccgcatt atccaaagat tgatgtgtcc gttttaaacg atctgcacgg atcacgtttc    15600
cagcaagcgc aacgacaggg tctccttcag tgttcgctgt cagcaggcct gttgccaagt    15660
tagaggcacc cggtcctgat gtgactaaca cgactcccgg ttttccagtt aaacggccga    15720
ctgcttgggc catgaatgct gcgttttgtt cgtgccgggc aacgataatt tcaggtcctt    15780
tatcttgtaa agcgtcaaat accgcatcaa ttttgcacc tggaatgcca aatacatgtg     15840
```

| | |
|---|---:|
| tgacaccttg ctccactaag caatcaacaa caagctccgc ccctctgttt ttcacaaggg | 15900 |
| attttttgttc ttttgttgct tttgtcaaca tcctcagcga tgattgattg attgattgta | 15960 |
| cagtttgttt ttcttaatat ctatttcgat gacttctata tgatattgca ctaacaagaa | 16020 |
| gatattataa tgcaattgat acaagacaag gagttatttg cttctctttt atatgattct | 16080 |
| gacaatccat attgcgttgg tagtcttttt tgctggaacg gttcagcgga aaagacgcat | 16140 |
| cgctcttttt gcttctagaa gaaatgccag caaaagaatc tcttgacagt gactgacagc | 16200 |
| aaaaatgtct ttttctaact agtaacaagg ctaagatatc agcctgaaat aaagggtggt | 16260 |
| gaagtaataa ttaaatcatc cgtataaacc tatacacata tatgaggaaa ataatacaa | 16320 |
| aagtgtttta aatacagata catacatgaa catatgcacg tatagcgccc aaatgtcggt | 16380 |
| aatggga | 16387 |

<210> SEQ ID NO 131
<211> LENGTH: 1188
<212> TYPE: DNA
<213> ORGANISM: Saccharomyces cerevisiae

<400> SEQUENCE: 131

| | |
|---|---:|
| atgttgagaa ctcaagccgc cagattgatc tgcaactccc gtgtcatcac tgctaagaga | 60 |
| acctttgctt tggccacccg tgctgctgct tacagcagac cagctgcccg tttcgttaag | 120 |
| ccaatgatca ctacccgtgg tttgaagcaa atcaacttcg gtggtactgt tgaaaccgtc | 180 |
| tacgaaagag ctgactggcc aagagaaaag ttgttggact acttcaagaa cgacactttt | 240 |
| gctttgatcg gttacggttc ccaaggttac ggtcaaggtt tgaacttgag agacaacggt | 300 |
| ttgaacgtta tcattggtgt ccgtaaagat ggtgcttctt ggaaggctgc catcgaagac | 360 |
| ggttgggttc caggcaagaa cttgttcact gttgaagatg ctatcaagag aggtagttac | 420 |
| gttatgaact tgttgtccga tgccgctcaa tcagaaacct ggcctgctat caagccattg | 480 |
| ttgaccaagg gtaagacttt gtacttctcc cacggttct ccccagtctt caaggacttg | 540 |
| actcacgttg aaccaccaaa ggacttagat gttatcttgg ttgctccaaa gggttccggt | 600 |
| agaactgtca gatctttgtt caaggaaggt cgtggtatta ctcttcttta cgccgtctgg | 660 |
| aacgatgtca ccggtaaggc tcacgaaaag gcccaagctt tggccgttgc cattggttcc | 720 |
| ggttacgttt accaaaccac tttcgaaaga gaagtcaact ctgacttgta cggtgaaaga | 780 |
| ggttgtttaa tgggtggtat ccacggtatg ttcttggctc aatacgacgt cttgagagaa | 840 |
| aacggtcact cccatctga agctttcaac gaaaccgtcg aagaagctac ccaatctcta | 900 |
| tacccattga tcggtaagta cggtatggat tacatgtacg atgcttgttc caccaccgcc | 960 |
| agaagaggtg ctttgactg gtacccaatc ttcaagaatg ctttgaagcc tgttttccaa | 1020 |
| gacttgtacg aatctaccaa gaacggtacc gaaaccaaga gatctttgga attcaactct | 1080 |
| caacctgact acagagaaaa gctagaaaag gaattagaca ccatcagaaa catggaaatc | 1140 |
| tggaaggttg gtaaggaagt cagaaagttg agaccagaaa accaataa | 1188 |

<210> SEQ ID NO 132
<211> LENGTH: 1014
<212> TYPE: DNA
<213> ORGANISM: Pseudomonas fluorescens

<400> SEQUENCE: 132

| | |
|---|---:|
| atgaaagttt tctacgataa agactgcgac ctgtcgatca tccaaggtaa gaaagttgcc | 60 |
| atcatcggct acggttccca gggccacgct caagcatgca acctgaagga ttccggcgta | 120 |

```
gacgtgactg ttggcctgcg taaaggctcg gctaccgttg ccaaggctga agcccacggc    180
ttgaaagtga ccgacgttgc tgcagccgtt gccggtgccg acttggtcat gatcctgacc    240
ccggacgagt tccagtccca gctgtacaag aacgaaatcg agccgaacat caagaagggc    300
gccactctgg ccttctccca cggcttcgcg atccactaca accaggttgt gcctcgtgcc    360
gacctcgacg tgatcatgat cgcgccgaag gctccaggcc acaccgtacg ttccgagttc    420
gtcaagggcg gtggtattcc tgacctgatc gcgatctacc aggacgcttc cggcaacgcc    480
aagaacgttg ccctgtccta cgccgcaggc gtgggcggcg gccgtaccgg catcatcgaa    540
accaccttca aggacgagac tgaaaccgac ctgttcggtg agcaggctgt tctgtgtggc    600
ggtaccgtcg agctggtcaa gccggtttc gaaaccctgg ttgaagctgg ctacgctcca    660
gaaatggcct acttcgagtg cctgcacgaa ctgaagctga tcgttgacct catgtacgaa    720
ggcggtatcg ccaacatgaa ctactcgatc tccaacaacg ctgaatacgg cgagtacgtg    780
actggtccag aagtcatcaa cgccgaatcc cgtcaggcca tgcgcaatgc tctgaagcgc    840
atccaggacg gcgaatacgc gaagatgttc atcagcgaag gcgctaccgg ctacccatcg    900
atgaccgcca agcgtcgtaa caacgctgct cacggtatcg aaatcatcgg cgagcaactg    960
cgctcgatga tgccttggat cggtgccaac aaaatcgtcg acaaagccaa gaac         1014

<210> SEQ ID NO 133
<211> LENGTH: 250
<212> TYPE: DNA
<213> ORGANISM: Saccharomyces cerevisiae

<400> SEQUENCE: 133
ccgcaaatta aagccttcga gcgtcccaaa accttctcaa gcaaggtttt cagtataatg     60
ttacatgcgt acacgcgtct gtacagaaaa aaaagaaaaa tttgaaatat aaataacgtt    120
cttaatacta acataactat aaaaaaataa atagggacct agacttcagg ttgtctaact    180
ccttcctttt cggttagagc ggatgtgggg ggagggcgtg aatgtaagcg tgacataact    240
aattacatga                                                          250

<210> SEQ ID NO 134
<211> LENGTH: 1181
<212> TYPE: DNA
<213> ORGANISM: Saccharomyces cerevisiae

<400> SEQUENCE: 134
taaaacctct agtggagtag tagatgtaat caatgaagcg gaagccaaaa gaccagagta     60
gaggcctata gaagaaactg cgatacctt tgtgatggct aaacaaacag acatcttttt    120
atatgttttt acttctgtat atcgtgaagt agtaagtgat aagcgaattt ggctaagaac    180
gttgtaagtg aacaagggac ctctttgcc tttcaaaaaa ggattaaatg gagttaatca    240
ttgagattta gttttcgtta gattctgtat ccctaaataa ctcccttacc cgacgggaag    300
gcacaaaaga cttgaataat agcaaacggc cagtagccaa gaccaaataa tactagagtt    360
aactgatggt cttaaacagg cattacgtgg tgaactccaa gaccaatata caaaatatcg    420
ataagttatt cttgcccacc aatttaagga gcctacatca ggacagtagt accattcctc    480
agagaagagg tatacataac aagaaaatcg cgtgaacacc ttatataact tagcccgtta    540
ttgagctaaa aaaccttgca aaatttccta tgaataagaa tacttcagac gtgataaaaa    600 tttacttct aactcttctc acgctgcccc tatctgttct tccgctctac cgtgagaaat    660
```

| | |
|---|---|
| aaagcatcga gtacggcagt tcgctgtcac tgaactaaaa caataaggct agttcgaatg | 720 |
| atgaacttgc ttgctgtcaa acttctgagt tgccgctgat gtgacactgt gacaataaat | 780 |
| tcaaaccggt tatagcggtc tcctccggta ccggttctgc cacctccaat agagctcagt | 840 |
| aggagtcaga acctctgcgg tggctgtcag tgactcatcc gcgtttcgta agttgtgcgc | 900 |
| gtgcacattt cgcccgttcc cgctcatctt gcagcaggcg gaaattttca tcacgctgta | 960 |
| ggacgcaaaa aaaaataat taatcgtaca agaatcttgg aaaaaaaatt gaaaattttt | 1020 |
| gtataaaagg gatgacctaa cttgactcaa tggcttttac acccagtatt ttcccttcc | 1080 |
| ttgtttgtta caattataga agcaagacaa aaacatatag acaacctatt cctaggagtt | 1140 |
| atattttttt accctaccag caatataagt aaaaaactag t | 1181 |

<210> SEQ ID NO 135
<211> LENGTH: 759
<212> TYPE: DNA
<213> ORGANISM: Saccharomyces cerevisiae

<400> SEQUENCE: 135

| | |
|---|---|
| ggccctgcag gcctatcaag tgctggaaac ttttctctt ggaattttg caacatcaag | 60 |
| tcatagtcaa ttgaattgac ccaatttcac atttaagatt ttttttttt catccgacat | 120 |
| acatctgtac actaggaagc cctgtttttc tgaagcagct tcaaatatat atatttttta | 180 |
| catatttatt atgattcaat gaacaatcta attaaatcga aaacaagaac cgaaacgcga | 240 |
| ataaataatt tatttagatg gtgacaagtg tataagtcct catcgggaca gctacgattt | 300 |
| ctctttcggt tttggctgag ctactggttg ctgtgacgca gcggcattag cgcggcgtta | 360 |
| tgagctaccc tcgtggcctg aaagatggcg ggaataaagc ggaactaaaa attactgact | 420 |
| gagccatatt gaggtcaatt tgtcaactcg tcaagtcacg tttggtggac ggccccttc | 480 |
| caacgaatcg tatatactaa catgcgcgcg cttcctatat acacatatac atatatatat | 540 |
| atatatatat gtgtgcgtgt atgtgtacac ctgtatttaa tttccttact cgcgggtttt | 600 |
| tcttttttct caattcttgg cttcctcttt ctcgagtata aattttttca ggtaaaattt | 660 |
| agtacgatag taaaatactt ctcgaactcg tcacatatac gtgtacataa tgtctgaacc | 720 |
| agctcaaaag aaacaaaagg ttgctaacaa ctctctaga | 759 |

<210> SEQ ID NO 136
<211> LENGTH: 643
<212> TYPE: DNA
<213> ORGANISM: Saccharomyces cerevisiae

<400> SEQUENCE: 136

| | |
|---|---|
| gaaatgaata acaatactga cagtactaaa taattgccta cttggcttca catacgttgc | 60 |
| atacgtcgat atagataata atgataatga cagcaggatt atcgtaatac gtaatagttg | 120 |
| aaaatctcaa aaatgtgtgg gtcattacgt aaataatgat aggaatggga ttcttctatt | 180 |
| tttccttttt ccattctagc agccgtcggg aaaacgtggc atcctctctt tcgggctcaa | 240 |
| ttggagtcac gctgccgtga gcatcctctc tttccatatc taacaactga gcacgtaacc | 300 |
| aatgaaaag catgagctta gcgttgctcc aaaaagtat tggatggtta ataccatttg | 360 |
| tctgttctct tctgactttg actcctcaaa aaaaaaaat ctacaatcaa cagatcgctt | 420 |
| caattacgcc ctcacaaaaa cttttttcct tcttcttcgc ccacgttaaa tttatccct | 480 |
| catgttgtct aacggattc tgcacttgat ttattataaa aagacaaaga cataatactt | 540 |
| ctctatcaat ttcagttatt gttcttcctt gcgttattct tctgttcttc ttttcttt | 600 |

```
gtcatatata accataacca agtaatacat attcaaatct aga              643
```

<210> SEQ ID NO 137
<211> LENGTH: 1716
<212> TYPE: DNA
<213> ORGANISM: Bacillus subtilis

<400> SEQUENCE: 137

```
atgttgacaa aagcaacaaa agaacaaaaa tcccttgtga aaaacagagg ggcggagctt    60
gttgttgatt gcttagtgga gcaaggtgtc acacatgtat ttggcattcc aggtgcaaaa   120
attgatgcgg tatttgacgc tttacaagat aaaggacctg aaattatcgt tgcccggcac   180
gaacaaaacg cagcattcat ggcccaagca gtcggccgtt taactggaaa accgggagtc   240
gtgttagtca catcaggacc gggtgcctct aacttggcaa caggcctgct gacagcgaac   300
actgaaggag accctgtcgt tgcgcttgct ggaaacgtga tccgtgcaga tcgtttaaaa   360
cggacacatc aatctttgga taatgcggcg ctattccagc cgattacaaa atacagtgta   420
gaagttcaag atgtaaaaaa tataccggaa gctgttacaa atgcatttag gatagcgtca   480
gcagggcagg ctgggccgc ttttgtgagc tttccgcaag atgttgtgaa tgaagtcaca   540
aatacgaaaa acgtgcgtgc tgttgcagcg ccaaaactcg gtcctgcagc agatgatgca   600
atcagtgcgg ccatagcaaa aatccaaaca gcaaaacttc ctgtcgtttt ggtcggcatg   660
aaaggcggaa gaccggaagc aattaaagcg gttcgcaagc ttttgaaaaa ggttcagctt   720
ccatttgttg aaacatatca agctgccggt accctttcta gagatttaga ggatcaatat   780
tttggccgta tcggtttgtt ccgcaaccag cctggcgatt tactgctaga gcaggcagat   840
gttgttctga cgatcggcta tgacccgatt gaatatgatc cgaaattctg gaatatcaat   900
ggagaccgga caattatcca tttagacgag attatcgctg acattgatca tgcttaccag   960
cctgatcttg aattgatcgg tgacattccg tccacgatca atcatatcga acacgatgct  1020
gtgaaagtgg aatttgcaga gcgtgagcag aaaatccttt ctgatttaaa acaatatatg  1080
catgaaggtg agcaggtgcc tgcagattgg aaatcagaca gagcgcaccc tcttgaaatc  1140
gttaaagagt tgcgtaatgc agtcgatgat catgttacag taacttgcga tatcggttcg  1200
cacgccattt ggatgtcacg ttatttccgc agctacgagc cgttaacatt aatgatcagt  1260
aacggtatgc aaacactcgg cgttgcgctt ccttgggcaa tcggcgcttc attggtgaaa  1320
ccgggagaaa aagtggtttc tgtctctggt gacggcggtt tcttattctc agcaatggaa  1380
ttagagacag cagttcgact aaaagcacca attgtacaca ttgtatggaa cgacagcaca  1440
tatgacatgg ttgcattcca gcaattgaaa aaatataacc gtacatctgc ggtcgatttc  1500
ggaaatatcg atatcgtgaa atatgcggaa agcttcggag caactggctt gcgcgtagaa  1560
tcaccagacc agctggcaga tgttctgcgt caaggcatga acgctgaagg tcctgtcatc  1620
atcgatgtcc cggttgacta cagtgataac attaatttag caagtgacaa gcttccgaaa  1680
gaattcgggg aactcatgaa aacgaaagct ctctag                            1716
```

<210> SEQ ID NO 138
<211> LENGTH: 571
<212> TYPE: PRT
<213> ORGANISM: Bacillus subtilis

<400> SEQUENCE: 138

```
Met Leu Thr Lys Ala Thr Lys Glu Gln Lys Ser Leu Val Lys Asn Arg
1               5                   10                  15
```

-continued

```
Gly Ala Glu Leu Val Val Asp Cys Leu Val Glu Gln Gly Val Thr His
            20                  25                  30

Val Phe Gly Ile Pro Gly Ala Lys Ile Asp Ala Val Phe Asp Ala Leu
            35                  40                  45

Gln Asp Lys Gly Pro Glu Ile Ile Val Ala Arg His Glu Gln Asn Ala
 50                  55                  60

Ala Phe Met Ala Gln Ala Val Gly Arg Leu Thr Gly Lys Pro Gly Val
 65                  70                  75                  80

Val Leu Val Thr Ser Gly Pro Gly Ala Ser Asn Leu Ala Thr Gly Leu
                85                  90                  95

Leu Thr Ala Asn Thr Glu Gly Asp Pro Val Val Ala Leu Ala Gly Asn
            100                 105                 110

Val Ile Arg Ala Asp Arg Leu Lys Arg Thr His Gln Ser Leu Asp Asn
            115                 120                 125

Ala Ala Leu Phe Gln Pro Ile Thr Lys Tyr Ser Val Glu Val Gln Asp
130                 135                 140

Val Lys Asn Ile Pro Glu Ala Val Thr Asn Ala Phe Arg Ile Ala Ser
145                 150                 155                 160

Ala Gly Gln Ala Gly Ala Ala Phe Val Ser Phe Pro Gln Asp Val Val
                165                 170                 175

Asn Glu Val Thr Asn Thr Lys Asn Val Arg Ala Val Ala Ala Pro Lys
            180                 185                 190

Leu Gly Pro Ala Ala Asp Asp Ala Ile Ser Ala Ala Ile Ala Lys Ile
            195                 200                 205

Gln Thr Ala Lys Leu Pro Val Val Leu Val Gly Met Lys Gly Gly Arg
210                 215                 220

Pro Glu Ala Ile Lys Ala Val Arg Lys Leu Leu Lys Lys Val Gln Leu
225                 230                 235                 240

Pro Phe Val Glu Thr Tyr Gln Ala Ala Gly Thr Leu Ser Arg Asp Leu
                245                 250                 255

Glu Asp Gln Tyr Phe Gly Arg Ile Gly Leu Phe Arg Asn Gln Pro Gly
            260                 265                 270

Asp Leu Leu Leu Glu Gln Ala Asp Val Val Leu Thr Ile Gly Tyr Asp
            275                 280                 285

Pro Ile Glu Tyr Asp Pro Lys Phe Trp Asn Ile Asn Gly Asp Arg Thr
290                 295                 300

Ile Ile His Leu Asp Glu Ile Ile Ala Asp Ile Asp His Ala Tyr Gln
305                 310                 315                 320

Pro Asp Leu Glu Leu Ile Gly Asp Ile Pro Ser Thr Ile Asn His Ile
                325                 330                 335

Glu His Asp Ala Val Lys Val Glu Phe Ala Glu Arg Gly Gln Lys Ile
            340                 345                 350

Leu Ser Asp Leu Lys Gln Tyr Met His Glu Gly Glu Gln Val Pro Ala
            355                 360                 365

Asp Trp Lys Ser Asp Arg Ala His Pro Leu Glu Ile Val Lys Glu Leu
            370                 375                 380

Arg Asn Ala Val Asp Asp His Val Thr Val Thr Cys Asp Ile Gly Ser
385                 390                 395                 400

His Ala Ile Trp Met Ser Arg Tyr Phe Arg Ser Tyr Glu Pro Leu Thr
                405                 410                 415

Leu Met Ile Ser Asn Gly Met Gln Thr Leu Gly Val Ala Leu Pro Trp
            420                 425                 430
```

```
Ala Ile Gly Ala Ser Leu Val Lys Pro Gly Glu Lys Val Ser Val
        435                 440                 445

Ser Gly Asp Gly Gly Phe Leu Phe Ser Ala Met Glu Leu Glu Thr Ala
450                 455                 460

Val Arg Leu Lys Ala Pro Ile Val His Ile Val Trp Asn Asp Ser Thr
465                 470                 475                 480

Tyr Asp Met Val Ala Phe Gln Gln Leu Lys Lys Tyr Asn Arg Thr Ser
                485                 490                 495

Ala Val Asp Phe Gly Asn Ile Asp Ile Val Lys Tyr Ala Glu Ser Phe
                500                 505                 510

Gly Ala Thr Gly Leu Arg Val Glu Ser Pro Asp Gln Leu Ala Asp Val
            515                 520                 525

Leu Arg Gln Gly Met Asn Ala Glu Gly Pro Val Ile Ile Asp Val Pro
530                 535                 540

Val Asp Tyr Ser Asp Asn Ile Asn Leu Ala Ser Asp Lys Leu Pro Lys
545                 550                 555                 560

Glu Phe Gly Glu Leu Met Lys Thr Lys Ala Leu
                565                 570

<210> SEQ ID NO 139
<211> LENGTH: 448
<212> TYPE: DNA
<213> ORGANISM: Saccharomyces cerevisiae

<400> SEQUENCE: 139
cccattaccg acatttgggc gctatacgtg catatgttca tgtatgtatc tgtatttaaa      60
acacttttgt attattttc ctcatatatg tgtataggtt tatacggatg atttaattat     120
tacttcacca cccttatt caggctgata tcttagcctt gttactagtt agaaaaagac     180 attttgctg tcagtcactg tcaagagatt cttttgctgg catttcttct agaagcaaaa     240
agagcgatgc gtcttttccg ctgaaccgtt ccagcaaaaa agactaccaa cgcaatatgg     300
attgtcagaa tcatataaaa gagaagcaaa taactccttg tcttgtatca attgcattat     360
aatatcttct tgttagtgca atatcatata gaagtcatcg aaatagatat taagaaaaac     420
aaactgtaca atcaatcaat caatcatc                                        448

<210> SEQ ID NO 140
<211> LENGTH: 16387
<212> TYPE: DNA
<213> ORGANISM: Artificial Sequence
<220> FEATURE:
<223> OTHER INFORMATION: plasmid construct

<400> SEQUENCE: 140
tcccattacc gacatttggg cgctatacgt gcatatgttc atgtatgtat ctgtatttaa      60 acactttg tattatttt cctcatatat gtgtataggt ttatacggat gatttaatta     120
ttacttcacc acccttatt tcaggctgat atcttagcct tgttactagt tagaaaaga     180 catttttgct gtcagtcact gtcaagagat tcttttgctg gcatttcttc tagaagcaaa     240
aagagcgatg cgtcttttcc gctgaaccgt tccagcaaaa aagactacca acgcaatatg     300
gattgtcaga atcatataaa agagaagcaa ataactcctt gtcttgtatc aattgcatta     360
taatatcttc ttgttagtgc aatatcatat agaagtcatc gaaatagata ttaagaaaaa     420
caaactgtac aatcaatcaa tcaatcatcg ctgaggatgt tgacaaaagc aacaaaagaa     480
caaaaatccc ttgtgaaaaa cagaggggcg gagcttgttg ttgattgctt agtggagcaa     540
```

```
ggtgtcacac atgtatttgg cattccaggt gcaaaaattg atgcggtatt tgacgcttta    600
caagataaag gacctgaaat tatcgttgcc cggcacgaac aaaacgcagc attcatggcc    660
caagcagtcg gccgtttaac tggaaaaccg ggagtcgtgt tagtcacatc aggaccgggt    720
gcctctaact tggcaacagg cctgctgaca gcgaacactg aaggagaccc tgtcgttgcg    780
cttgctggaa acgtgatccg tgcagatcgt ttaaaacgga cacatcaatc tttggataat    840
gcggcgctat tccagccgat tacaaaatac agtgtagaag ttcaagatgt aaaaaatata    900
ccggaagctg ttacaaatgc atttaggata gcgtcagcag ggcaggctgg ggccgctttt    960
gtgagctttc gcaagatgt tgtgaatgaa gtcacaaata cgaaaaacgt gcgtgctgtt    1020
gcagcgccaa aactcggtcc tgcagcagat gatgcaatca gtgcggccat agcaaaaatc    1080
caaacagcaa aacttcctgt cgttttggtc ggcatgaaag gcggaagacc ggaagcaatt    1140
aaagcggttc gcaagctttt gaaaaaggtt cagcttccat tgttgaaac atatcaagct    1200
gccggtaccc tttctagaga tttagaggat caatattttg gccgtatcgg tttgttccgc    1260
aaccagcctg gcgatttact gctagagcag gcagatgttg ttctgacgat cggctatgac    1320
ccgattgaat atgatccgaa attctggaat atcaatggag accggacaat tatccattta    1380
gacgagatta tcgctgacat tgatcatgct taccagcctg atcttgaatt gatcggtgac    1440
attccgtcca cgatcaatca tatcgaacac gatgctgtga agtggaatt tgcagagcgt    1500
gagcagaaaa tccttttctga tttaaaacaa tatatgcatg aaggtgagca ggtgcctgca    1560
gattggaaat cagacagagc gcaccctctt gaaatcgtta agagttgcg taatgcagtc    1620
gatgatcatg ttacagtaac ttgcgatatc ggttcgcacg ccatttggat gtcacgttat    1680
ttccgcagct acgagccgtt aacattaatg atcagtaacg gtatgcaaac actcggcgtt    1740
gcgcttcctt gggcaatcgg cgcttcattg gtgaaaccgg gagaaaaagt ggtttctgtc    1800
tctggtgacg gcggtttctt attctcagca atggaattag agacagcagt tcgactaaaa    1860
gcaccaattg tacacattgt atggaacgac agcacatatg acatggttgc attccagcaa    1920
ttgaaaaaat ataaccgtac atctgcggtc gatttcggaa atatcgatat cgtgaaatat    1980
gcggaaagct tcggagcaac tggcttgcgc gtagaatcac cagaccagct ggcagatgtt    2040
ctgcgtcaag gcatgaacgc tgaaggtcct gtcatcatcg atgtcccggt tgactacagt    2100
gataacatta atttagcaag tgacaagctt ccgaaagaat tcggggaact catgaaaacg    2160
aaagctctct agttaattaa tcatgtaatt agttatgtca cgcttacatt cacgccctcc    2220
ccccacatcc gctctaaccg aaaaggaagg agttagacaa cctgaagtct aggtccctat    2280
ttattttttt atagttatgt tagtattaag aacgttattt atatttcaaa ttttttcttt    2340
ttttctgtac agacgcgtgt acgcatgtaa cattatactg aaaaccttgc ttgagaaggt    2400
tttgggacgc tcgaaggctt taatttgcgg gcggccgctc tagaactagt accacaggtg    2460
ttgtcctctg aggacataaa atacacaccg agattcatca actcattgct ggagttagca    2520
tatctacaat tgggtgaaat ggggagcgat ttgcaggcat ttgctcggca tgccggtaga    2580
ggtgtggtca ataagagcga cctcatgcta tacctgagaa agcaacctga cctacaggaa    2640
agagttactc aagaataaga attttcgttt taaaacctaa gagtcacttt aaaatttgta    2700
tacacttatt ttttttataa cttatttaat aataaaaatc ataaatcata agaaattcgc    2760
ttactcttaa ttaatcaagc atctaaaaca caaccgttgg aagcgttgga accaacttaa    2820
gcatacttgg atagagtacc tcttgtgtaa cgaggtggag gtgcaaccca actttgttta    2880
cgttgagcca tttccttatc agagactaat aggtcaatct tgttattatc agcatcaatg    2940
```

```
ataatctcat cgccgtctct gaccaacccg ataggaccac cttcagcggc ttcgggaaca   3000
atgtggccga ttaagaaccc gtgagaacca ccagagaatc taccatcagt caacaatgca   3060
acatctttac ccaaaccgta acccatcaga gcagaggaag ctttagcat ttcaggcata    3120 cctggtgcac ctcttggacc ttcatatctg ataacaacaa cggttttttc acccttcttg   3180
atttcacctc tttccaaggc ttcaataaag gcaccttcct cttcgaacac acgtgctcta   3240
cccttgaagt aagtaccttc cttaccggta attttaccca cagctccacc tggtgccaat   3300
gaaccgtaca gaatttgcaa gtgaccgttg gccttgattg ggtgggagag tggcttaata   3360
atctcttgtc cttcaggtag gcttggtgct ttctttgcac gttctgccaa agtgtcaccg   3420
gtaacagtca ttgtgttacc gtgcaacatg ttgttttcat atagatactt aatcacagat   3480
tgggtaccac caacgttaat caaatcggcc atgacgtatt taccagaagg tttgaagtca   3540
ccgatcaatg gtgtagtatc actgattctt tggaaatcat ctggtgacaa cttgacaccc   3600
gcagagtgag caacagccac caaatgcaaa acagcattag tggacccacc ggttgcaacg   3660
acataagtaa tggcgttttc aaaagcctct tttgtgagga tatcacgagg taaaataccc   3720
aattccattg tcttcttgat gtattcacca atgttgtcac actcagctaa cttctccttg   3780
gaaacggctg ggaaggaaga ggagtttgga atggtcaaac ctagcacttc agcggcagaa   3840
gccattgtgt tggcagtata cataccacca caagaaccag gacctgggca tgcatgttcc   3900
acaacatctt ctctttcttc ttcagtgaat tgcttggaaa tatattcacc gtaggattgg   3960
aacgcagaga cgatatcgat gttttttagag atcctgttaa aacctctagt ggagtagtag   4020
atgtaatcaa tgaagcggaa gccaaaagac cagagtagag gcctatagaa gaaactgcga   4080 tacctttgt gatggctaaa caaacagaca tcttttttata tgtttttact tctgtatatc    4140
gtgaagtagt aagtgataag cgaatttggc taagaacgtt gtaagtgaac aagggacctc   4200
ttttgccttt caaaaaagga ttaaatggag ttaatcattg agatttagtt ttcgttagat   4260
tctgtatccc taaataactc ccttacccga cgggaaggca caaagacttt gaataatagc   4320
aaacggccag tagccaagac caaataatac tagagttaac tgatggtctt aaacaggcat   4380
tacgtggtga actccaagac caatatacaa aatatcgata agttattctt gcccaccaat   4440
ttaaggagcc tacatcagga cagtagtacc attcctcaga gaagaggtat acataacaag   4500
aaaatcgcgt gaacaccta tataacttag cccgttattg agctaaaaaa ccttgcaaaa     4560
tttcctatga ataagaatac ttcagacgtg ataaaaattt actttctaac tcttctcacg   4620
ctgcccctat ctgttcttcc gctctaccgt gagaaataaa gcatcgagta cggcagttcg   4680
ctgtcactga actaaaacaa taaggctagt tcgaatgatg aacttgcttg ctgtcaaact   4740
tctgagttgc cgctgatgtg acactgtgac aataaattca aaccggttat agcggtctcc   4800
tccggtaccg gttctgccac ctccaataga gctcagtagg agtcagaacc tctgcggtgg   4860
ctgtcagtga ctcatccgcg tttcgtaagt tgtgcgcgtg cacatttcgc ccgttcccgc   4920
tcatcttgca gcaggcggaa attttcatca cgctgtagga cgcaaaaaaa aaataattaa   4980
tcgtacaaga atcttggaaa aaaaattgaa aaatttttgta taaaagggat gacctaactt   5040
gactcaatgg cttttacacc cagtattttc cctttccttg tttgttacaa ttatagaagc   5100
aagacaaaaa catatagaca acctattcct aggagttata ttttttttacc ctaccagcaa   5160 tataagtaaa aaactagtat gaaggtgttt tacgataaag actgcgatct gagcatcatc   5220
cagggaaaga aggttgctat tataggatat ggttcccaag gacacgcaca agccttgaac   5280
```

```
ttgaaagatt ctggggtcga cgtgacagta ggtctgtata aaggtgctgc tgatgcagca    5340
aaggctgaag cacatggctt taaagtcaca gatgttgcag cggctgttgc tggcgctgat    5400
ttagtcatga ttttaattcc agatgaattt caatcgcaat tgtacaaaaa tgaaatagaa    5460
ccaaacatta agaagggcgc taccttggcc ttcagtcatg gatttgccat tcattacaat    5520
caagtagtcc ccagggcaga tttggacgtt attatgattg cacctaaggc tccggggcat    5580
actgttagga gcgaatttgt taagggtggt ggtattccag atttgatcgc tatataccaa    5640
gacgttagcg gaaacgctaa gaatgtagct ttaagctacg cagcaggagt tggtggcggg    5700
agaacgggta taatagaaac cacttttaaa gacgagactg agacagattt atttggagaa    5760
caagcggttc tgtgcggagg aactgttgaa ttggttaaag caggctttga gacgcttgtc    5820
gaagcagggt acgctcccga aatggcatac ttcgaatgtc tacatgaatt gaagttgata    5880
gtagacttaa tgtatgaagg tggtatagct aaatgaact attccatttc aaataatgca    5940
gaatatggtg agtatgtcac cggacctgaa gtcattaacg cagaatcaag acaagccatg    6000
agaaatgcct tgaaacgtat ccaggacggt gaatacgcta gatgttcat aagtgaaggc    6060
gctacgggtt acccgagtat gactgctaaa agaagaaaca atgcagcaca tggtatcgaa    6120
attattggtg aacagttaag gtctatgatg ccctggatcg gtgctaataa gatcgtagac    6180
aaggcgaaaa attaaggccc tgcaggccta tcaagtgctg gaaacttttt ctcttggaat    6240
ttttgcaaca tcaagtcata gtcaattgaa ttgacccaat ttcacattta agattttttt    6300
tttttcatcc gacatacatc tgtacactag gaagccctgt ttttctgaag cagcttcaaa    6360
tatatatatt ttttacatat ttattatgat tcaatgaaca atctaattaa atcgaaaaca    6420
agaaccgaaa cgcgaataaa taatttattt agatggtgac aagtgtataa gtcctcatcg    6480
ggacagctac gatttctctt tcggttttgg ctgagctact ggttgctgtg acgcagcggc    6540
attagcgcgg cgttatgagc taccctcgtg gcctgaaaga tggcgggaat aaagcggaac    6600
taaaaattac tgactgagcc atattgaggt caatttgtca actcgtcaag tcacgtttgg    6660
tggacggccc ctttccaacg aatcgtatat actaacatgc gcgcgcttcc tatatacaca    6720
tatacatata tatatatata tatatgtgtg cgtgtatgtg tacacctgta tttaatttcc    6780
ttactcgcgg gttttctttt tttctcaatt cttggcttcc tctttctcga gtatataatt    6840
tttcaggtaa aatttagtac gatagtaaaa tacttctcga actcgtcaca tatacgtgta    6900
cataatgtct gaaccagctc aaaagaaaca aaaggttgct aacaactctc tagagcggcc    6960
gcccgcaaat taaagccttc gagcgtccca aaaccttctc aagcaaggtt ttcagtataa    7020
tgttacatgc gtacacgcgt ctgtacagaa aaaaagaaa aatttgaaat ataaataacg    7080
ttcttaatac taacataact ataaaaaaat aaatagggac ctagacttca ggttgtctaa    7140
ctccttcctt ttcggttaga gcggatgtgg ggggagggcg tgaatgtaag cgtgacataa    7200
ctaattacat gattaattaa ttattggttt tctggtctca actttctgac ttccttacca    7260
accttccaga tttccatgtt tctgatggtg tctaattcct tttctagctt ttctctgtag    7320
tcaggttgag agttgaattc caaagatctc ttggtttcgg taccgttctt ggtagattcg    7380
tacaagtctt ggaaaacagg cttcaaagca ttcttgaaga ttgggtacca gtccaaagca    7440
cctcttctgg cggtggtgga acaagcatcg tacatgtaat ccataccgta cttaccgatc    7500
aatgggtata gagattgggt agcttccttc acggtttcgt tgaaagcttc agatggggag    7560
tgaccgtttt ctctcaagac gtcgtattga gccaagaaca taccgtggat accacccatt    7620
aaacaacctc tttcaccgta caagtcagag ttgacttctc tttcgaaagt ggtttggtaa    7680
```

```
acgtaaccgg aaccaatggc aacggccaaa gcttgggcct tttcgtgagc cttaccggtg   7740
acatcgttcc agacggcgta agaagagtta ataccacgac cttccttgaa caaagatctg   7800
acagttctac cggaacccct tggagcaacc aagataacat ctaagtcctt tggtggttca   7860
acgtgagtca agtccttgaa gactggggag aaaccgtggg agaagtacaa agtcttaccc   7920
ttggtcaaca atggcttgat agcaggccag gtttctgatt gagcggcatc ggacaacaag   7980
ttcataacgt aactacctct cttgatagca tcttcaacag tgaacaagtt cttgcctgga   8040
acccaaccgt cttcgatggc agccttccaa gaagcaccat ctttacggac accaatgata   8100
acgttcaaac cgttgtctct caagttcaaa ccttgaccgt aaccttggga accgtaaccg   8160
atcaaagcaa aagtgtcgtt cttgaagtag tccaacaact tttctcttgg ccagtcagct   8220
ctttcgtaga cggtttcaac agtaccaccg aagttgattt gcttcaacat cctcagctct   8280
agatttgaat atgtattact tggttatggt tatatatgac aaaagaaaaa gaagaacaga   8340
agaataacgc aaggaagaac aataactgaa attgatagag aagtattatg tctttgtctt   8400
tttataataa atcaagtgca gaaatccgtt agacaacatg agggataaaa tttaacgtgg   8460
gcgaagaaga aggaaaaaag tttttgtgag ggcgtaattg aagcgatctg ttgattgtag   8520 atttttttt tttgaggagt caaagtcaga agagaacaga caaatggtat taaccatcca   8580
atactttttt ggagcaacgc taagctcatg cttttccatt ggttacgtgc tcagttgtta   8640
gatatggaaa gagaggatgc tcacggcagc gtgactccaa ttgagcccga aagagaggat   8700
gccacgtttt cccgacggct gctagaatgg aaaaagaaa aatagaagaa tcccattcct   8760
atcattattt acgtaatgac ccacacattt ttgagatttt caactattac gtattacgat   8820
aatcctgctg tcattatcat tattatctat atcgacgtat gcaacgtatg tgaagccaag   8880
taggcaatta tttagtactg tcagtattgt tattcatttc agatctatcc gcggtggagc   8940
tcgaattcac tggccgtcgt tttacaacgt cgtgactggg aaaaccctgg cgttacccaa   9000
cttaatcgcc ttgcagcaca tccccctttc gccagctggc gtaatagcga agaggcccgc   9060
accgatcgcc cttcccaaca gttgcgcagc ctgaatggcg aatggcgcct gatgcggtat   9120
tttctcctta cgcatctgtg cggtatttca caccgcatac gtcaaagcaa ccatagtacg   9180
cgccctgtag cggcgcatta agcgcggcgg gtgtggtggt tacgcgcagc gtgaccgcta   9240
cacttgccag cgccttagcg cccgctcctt tcgctttctt cccttccttt ctcgccacgt   9300
tcgccggctt tccccgtcaa gctctaaatc ggggggctccc tttagggttc gatttagtg   9360 ctttacggca cctcgacccc aaaaaacttg atttgggtga tggttcacgt agtgggccat   9420
cgccctgata cggttttt cgcccttga cgttggagtc cacgttcttt aatagtggac   9480
tcttgttcca aactgaacaa cactcaact ctatctcggg ctattctttt gatttataag   9540
ggattttgcc gatttcggtc tattggttaa aaaatgagct gatttaacaa aaatttaacg   9600
cgaattttaa caaaatatta acgtttacaa ttttatggtg cactctcagt acaatctgct   9660
ctgatgccgc atagttaagc cagccccgac acccgccaac acccgctgac gcgccctgac   9720
gggcttgtct gctcccggca tccgcttaca gacaagctgt gaccgtctcc gggagctgca   9780
tgtgtcagag gttttcaccg tcatcaccga aacgcgcgag acgaaagggc ctcgtgatac   9840
gcctattttt ataggttaat gtcatgataa taatggtttc ttagacgtca ggtggcactt   9900
ttcggggaaa tgtgcgcgga acccctattt gtttattttt ctaaatacat tcaaatatgt   9960
atccgctcat gagacaataa ccctgataaa tgcttcaata atattgaaaa aggaagagta  10020
```

```
tgagtattca acatttccgt gtcgcccta ttcccttttt tgcggcattt tgccttcctg   10080 ttttttgctca cccagaaacg ctggtgaaag taaaagatgc tgaagatcag ttgggtgcac  10140
gagtgggtta catcgaactg gatctcaaca gcggtaagat ccttgagagt tttcgccccg  10200
aagaacgttt tccaatgatg agcactttta aagttctgct atgtggcgcg gtattatccc  10260
gtattgacgc cgggcaagag caactcggtc gccgcataca ctattctcag aatgacttgg  10320
ttgagtactc accagtcaca gaaaagcatc ttacggatgg catgacagta agagaattat  10380
gcagtgctgc cataaccatg agtgataaca ctgcggccaa cttacttctg acaacgatcg  10440
gaggaccgaa ggagctaacc gcttttttgc acaacatggg gatcatgta actcgccttg  10500 atcgttggga accggagctg aatgaagcca taccaaacga cgagcgtgac accacgatgc  10560
ctgtagcaat ggcaacaacg ttgcgcaaac tattaactgg cgaactactt actctagctt  10620
cccggcaaca attaatagac tggatggagg cggataaagt tgcaggacca cttctgcgct  10680
cggcccttcc ggctggctgg tttattgctg ataaatctgg agccggtgag cgtgggtctc  10740
gcggtatcat tgcagcactg gggccagatg gtaagccctc ccgtatcgta gttatctaca  10800
cgacggggag tcaggcaact atggatgaac gaaatagaca gatcgctgag ataggtgcct  10860
cactgattaa gcattggtaa ctgtcagacc aagtttactc atatatactt tagattgatt  10920
taaaacttca ttttttaattt aaaaggatct aggtgaagat cctttttgat aatctcatga  10980
ccaaaatccc ttaacgtgag ttttcgttcc actgagcgtc agaccccgta gaaaagatca  11040
aaggatcttc ttgagatcct ttttttctgc gcgtaatctg ctgcttgcaa acaaaaaaac  11100
caccgctacc agcggtggtt tgtttgccgg atcaagagct accaactctt tttccgaagg  11160
taactggctt cagcagagcg cagataccaa atactgttct tctagtgtag ccgtagttag  11220
gccaccactt caagaactct gtagcaccgc ctacatacct cgctctgcta atcctgttac  11280
cagtggctgc tgccagtggc gataagtcgt gtcttaccgg gttggactca agacgatagt  11340
taccggataa ggcgcagcgg tcgggctgaa cggggggttc gtgcacacag cccagcttgg  11400
agcgaacgac ctacaccgaa ctgagatacc tacagcgtga gctatgagaa agcgccacgc  11460
ttcccgaagg gagaaaggcg gacaggtatc cggtaagcgg cagggtcgga acaggagagc  11520
gcacgaggga gcttccaggg ggaaacgcct ggtatcttta tagtcctgtc gggtttcgcc  11580
acctctgact tgagcgtcga tttttgtgat gctcgtcagg ggggcggagc ctatggaaaa  11640
acgccagcaa cgcggccttt ttacggttcc tggccttttg ctggcctttt gctcacatgt  11700
tctttcctgc gttatcccct gattctgtgg ataaccgtat taccgccttt gagtgagctg  11760
ataccgctcg ccgcagccga acgaccgagc gcagcgagtc agtgagcgag gaagcggaag  11820
agcgcccaat acgcaaaccg cctctccccg cgcgttggcc gattcattaa tgcagctggc  11880
acgacaggtt cccgactgga aaagcgggca gtgagcgcaa cgcaattaat gtgagttagc  11940
tcactcatta ggcaccccag gctttacact ttatgcttcc ggctcgtatg ttgtgtggaa  12000
ttgtgagcgg ataacaattt cacacaggaa acagctatga ccatgattac gccaagcttt  12060
ttctttccaa tttttttttt ttcgtcatta taaaaatcat tacgaccgag attcccgggt  12120
aataactgat ataattaaat tgaagctcta atttgtgagt ttagtataca tgcatttact  12180
tataatacag ttttttagtt ttgctggccg catcttctca aatatgcttc ccagcctgct  12240
tttctgtaac gttcaccctc taccttagca tccctccct ttgcaaatag tcctcttcca  12300
acaataataa tgtcagatcc tgtagagacc acatcatcca cggttctata ctgttgaccc  12360
aatgcgtctc ccttgtcatc taaacccaca ccgggtgtca taatcaacca atcgtaacct  12420
```

```
tcatctcttc cacccatgtc tctttgagca ataaagccga taacaaaatc tttgtcgctc   12480
ttcgcaatgt caacagtacc cttagtatat tctccagtag ataggggagcc cttgcatgac   12540 aattctgcta acatcaaaag gcctctaggt tcctttgtta cttcttctgc cgcctgcttc   12600
aaaccgctaa caataccctgg gcccaccaca ccgtgtgcat tcgtaatgtc tgcccattct   12660
gctattctgt atacacccgc agagtactgc aatttgactg tattaccaat gtcagcaaat   12720
tttctgtctt cgaagagtaa aaaattgtac ttggcggata atgcctttag cggcttaact   12780
gtgccctcca tggaaaaatc agtcaagata tccacatgtg tttttagtaa acaaattttg   12840
ggacctaatg cttcaactaa ctccagtaat tccttggtgg tacgaacatc caatgaagca   12900
cacaagtttg tttgcttttc gtgcatgata ttaaatagct tggcagcaac aggactagga   12960
tgagtagcag cacgttcctt atatgtagct ttcgacatga tttatcttcg tttcctgcag   13020 gttttttgttc tgtgcagttg ggttaagaat actgggcaat ttcatgtttc ttcaacacta   13080
catatgcgta tataccaa tctaagtctg tgctccttcc ttcgttcttc cttctgttcg   13140
gagattaccg aatcaaaaaa atttcaagga aaccgaaatc aaaaaaaaga ataaaaaaaa   13200
aatgatgaat tgaaaagctt gcatgcctgc aggtcgactc tagtatactc cgtctactgt   13260
acgatacact tccgctcagg tccttgtcct ttaacgaggc cttaccactc ttttgttact   13320
ctattgatcc agctcagcaa aggcagtgtg atctaagatt ctatcttcgc gatgtagtaa   13380
aactagctag accgagaaag agactagaaa tgcaaaaggc acttctacaa tggctgccat   13440
cattattatc cgatgtgacg ctgcattttt tttttttttt tttttttttt tttttttttt   13500
tttttttttt tttttttgta caaatatcat aaaaaaagag aatcttttta agcaaggatt   13560
ttcttaactt cttcggcgac agcatcaccg acttcggtgg tactgttgga accacctaaa   13620
tcaccagttc tgatacctgc atccaaaacc tttttaactg catcttcaat ggctttacct   13680
tcttcaggca agttcaatga caatttcaac atcattgcag cagacaagat agtggcgata   13740
gggttgacct tattctttgg caaatctgga gcggaaccat ggcatggttc gtacaaacca   13800
aatgcggtgt tcttgtctgg caaagaggcc aaggacgcag atggcaacaa acccaaggag   13860
cctgggataa cggaggcttc atcggagatg atatcaccaa acatgttgct ggtgattata   13920
ataccattta ggtgggttgg gttcttaact aggatcatgg cggcagaatc aatcaattga   13980
tgttgaactt tcaatgtagg gaattcgttc ttgatggttt cctccacagt ttttctccat   14040
aatcttgaag aggccaaaac attagcttta tccaaggacc aaataggcaa tggtggctca   14100
tgttgtaggg ccatgaaagc ggccattctt gtgattcttt gcacttctgg aacggtgtat   14160
tgttcactat cccaagcgac accatcacca tcgtcttcct ttctcttacc aaagtaaata   14220
cctcccacta attctctaac aacaacgaag tcagtacctt tagcaaattg tggcttgatt   14280
ggagataagt ctaaaagaga gtcggatgca aagttacatg gtcttaagtt ggcgtacaat   14340
tgaagttctt tacggatttt tagtaaacct tgttcaggtc taacactacc ggtaccccat   14400
ttaggaccac ccacagcacc taacaaaacg gcatcagcct tcttggaggc ttccagcgcc   14460
tcatctggaa gtggaacacc tgtagcatcg atagcagcac caccaattaa atgattttcg   14520
aaatcgaact tgacattgga acgaacatca gaaatagctt taagaaccttt aatggcttcg   14580 gctgtgattt cttgaccaac gtggtcacct ggcaaaacga cgatcttctt aggggcagac   14640
attacaatgg tatatccttg aaatatatat aaaaaaaaaa aaaaaaaaaa aaaaaaaaaa   14700
tgcagcttct caatgatatt cgaatacgct ttgaggagat acagcctaat atccgacaaa   14760
```

```
ctgttttaca gatttacgat cgtacttgtt acccatcatt gaattttgaa catccgaacc    14820
tgggagtttt ccctgaaaca gatagtatat ttgaacctgt ataataatat atagtctagc    14880
gctttacgga agacaatgta tgtatttcgg ttcctggaga aactattgca tctattgcat    14940
aggtaatctt gcacgtcgca tccccggttc attttctgcg tttccatctt gcacttcaat    15000
agcatatctt tgttaacgaa gcatctgtgc ttcattttgt agaacaaaaa tgcaacgcga    15060
gagcgctaat ttttcaaaca aagaatctga gctgcatttt tacagaacag aaatgcaacg    15120
cgaaagcgct attttaccaa cgaagaatct gtgcttcatt tttgtaaaac aaaaatgcaa    15180
cgcgagagcg ctaattttc aaacaaagaa tctgagctgc attttacag aacagaaatg    15240 caacgcgaga gcgctatttt accaacaaag aatctatact tcttttttgt tctacaaaaa    15300
tgcatcccga gagcgctatt tttctaacaa agcatcttag attactttt ttctcctttg    15360 tgcgctctat aatgcagtct cttgataact ttttgcactg taggtccgtt aaggttagaa    15420
gaaggctact ttggtgtcta ttttctcttc cataaaaaaa gcctgactcc acttcccgcg    15480
tttactgatt actagcgaag ctgcgggtgc attttttcaa gataaaggca tccccgatta    15540
tattctatac cgatgtggat tgcgcatact ttgtgaacag aaagtgatag cgttgatgat    15600
tcttcattgg tcagaaaatt atgaacggtt tcttctattt tgtctctata tactacgtat    15660
aggaaatgtt tacattttcg tattgttttc gattcactct atgaatagtt cttactacaa    15720 ttttttttgtc taaagagtaa tactagagat aaacataaaa aatgtagagg tcgagtttag    15780
atgcaagttc aaggagcgaa aggtggatgg gtaggttata tagggatata gcacagagat    15840
atatagcaaa gagatacttt tgagcaatgt ttgtggaagc ggtattcgca atattttagt    15900
agctcgttac agtccggtgc gttttggtt ttttgaaagt gcgtcttcag agcgcttttg    15960
gttttcaaaa gcgctctgaa gttcctatac tttctagaga ataggaactt cggaatagga    16020
acttcaaagc gtttccgaaa acgagcgctt ccgaaaatgc aacgcgagct gcgcacatac    16080
agctcactgt tcacgtcgca cctatatctg cgtgttgcct gtatatatat atacatgaga    16140
agaacggcat agtgcgtgtt tatgcttaaa tgcgtactta tatgcgtcta tttatgtagg    16200
atgaaaggta gtctagtacc tcctgtgata ttatcccatt ccatgcgggg tatcgtatgc    16260
ttccttcagc actaccctt agctgttcta tatgctgcca ctcctcaatt ggattagtct    16320
catccttcaa tgctatcatt tcctttgata ttggatcata tgcatagtac cgagaaacta    16380
gaggatc                                                             16387
```

<210> SEQ ID NO 141
<211> LENGTH: 2237
<212> TYPE: DNA
<213> ORGANISM: Artificial Sequence
<220> FEATURE:
<223> OTHER INFORMATION: PDC1 Fragment A-ilvDSm

<400> SEQUENCE: 141

```
ttatgtatgc tcttctgact tttcgtgtga tgaggctcgt ggaaaaaatg aataatttat      60
gaatttgaga acaattttgt gttgttacgg tattttacta tggaataatc aatcaattga     120 ggatttatg caaatatcgt ttgaatattt ttccgaccct ttgagtactt ttcttcataa     180
ttgcataata ttgtccgctg ccccttttc tgttagacgg tgtcttgatc tacttgctat     240
cgttcaacac caccttattt tctaactatt tttttttag ctcatttgaa tcagcttatg     300
gtgatggcac atttttgcat aaacctagct gtcctcgttg aacataggaa aaaaaatat     360 ataaacaagg ctctttcact ctccttgcaa tcagatttgg gtttgttccc tttatttca     420
```

```
tatttcttgt catattcctt tctcaattat tattttctac tcataacctc acgcaaaata    480
acacagtcaa atcaatcaaa atgactgaca aaaaaactct taaagactta agaaatcgta    540
gttctgttta cgattcaatg gttaaatcac ctaatcgtgc tatgttgcgt gcaactggta    600
tgcaagatga agactttgaa aaacctatcg tcggtgtcat ttcaacttgg gctgaaaaca    660
caccttgtaa tatccactta catgactttg gtaaactagc caaagtcggt gttaaggaag    720
ctggtgcttg gccagttcag ttcggaacaa tcacggtttc tgatggaatc gccatgggaa    780
cccaaggaat gcgtttctcc ttgacatctc gtgatattat tgcagattct attgaagcag    840
ccatgggagg tcataatgcg gatgcttttg tagccattgg cggttgtgat aaaaacatgc    900
ccggttctgt tatcgctatg gctaacatgg atatcccagc catttttgct tacggcggaa    960
caattgcacc tggtaattta dacggcaaag atatcgattt agtctctgtc tttgaaggtg   1020
tcggccattg gaaccacggc gatatgacca agaagaagt taaagctttg gaatgtaatg    1080
cttgtcccgg tcctggaggc tgcggtggta tgtatactgc taacacaatg gcgacagcta   1140
ttgaagtttt gggacttagc cttccgggtt catcttctca cccggctgaa tccgcagaaa   1200
agaaagcaga tattgaagaa gctggtcgcg ctgttgtcaa aatgctcgaa atgggcttaa   1260
aaccttctga cattttaacg cgtgaagctt ttgaagatgc tattactgta actatggctc   1320
tgggaggttc aaccaactca acccttcacc tcttagctat tgcccatgct gctaatgtgg   1380
aattgacact tgatgatttc aatactttcc aagaaaaagt tcctcatttg gctgatttga   1440
aaccttctgg tcaatatgta ttccaagacc tttacaaggt cggaggggta ccagcagtta   1500
tgaaatatct ccttaaaaat ggcttccttc atggtgaccg tatcacttgt actggcaaaa   1560
cagtcgctga aaatttgaag gcttttgatg atttaacacc tggtcaaaag gttattatgc   1620
cgcttgaaaa tcctaaacgt gaagatggtc cgctcattat tctccatggt aacttggctc   1680
cagacggtgc cgttgccaaa gtttctggtg taaaagtgcg tcgtcatgtc ggtcctgcta   1740
aggtctttaa ttctgaagaa gaagccattg aagctgtctt gaatgatgat attgttgatg   1800
gtgatgttgt tgtcgtacgt tttgtaggac caaagggcgg tcctggtatg cctgaaatgc   1860 tttcccttc atcaatgatt gttggtaaag ggcaaggtga aaaagttgcc cttctgacag   1920
atggccgctt ctcaggtggt acttatggtc ttgtcgtggg tcatatcgct cctgaagcac   1980
aagatggcgg tccaatcgcc tacctgcaaa caggagacat agtcactatt gaccaagaca   2040
ctaaggaatt acactttgat atctccgatg aagagttaaa acatcgtcaa gagaccattg   2100
aattgccacc gctctattca cgcggtatcc ttggtaaata tgctcacatc gtttcgtctg   2160
cttctagggg agccgtaaca gacttttgga agcctgaaga aactggcaaa aaatgagcga   2220
tttaatctct aattatt                                                  2237
```

<210> SEQ ID NO 142  
<211> LENGTH: 4420  
<212> TYPE: DNA  
<213> ORGANISM: Artificial Sequence  
<220> FEATURE:  
<223> OTHER INFORMATION: PDC1 A-ilvDSm-BUC cassette

<400> SEQUENCE: 142

```
ttatgtatgc tcttctgact tttcgtgtga tgaggctcgt ggaaaaaatg aataaatttat    60 gaatttgaga acaattttgt gttgttacgg tattttacta tggaataatc aatcaattga    120
ggattttatg caaatatcgt ttgaatattt ttccgaccct ttgagtactt ttcttcataa    180
```

```
ttgcataata ttgtccgctg cccctttttc tgttagacgg tgtcttgatc tacttgctat    240
cgttcaacac caccttattt tctaactatt ttttttttag ctcatttgaa tcagcttatg    300
gtgatggcac attttttgcat aaacctagct gtcctcgttg aacataggaa aaaaaaatat  360
ataaacaagg ctcttttcact ctccttgcaa tcagatttgg gtttgttccc tttattttca  420
tatttcttgt catattcctt tctcaattat tattttctac tcataacctc acgcaaaata   480
acacagtcaa atcaatcaaa atgactgaca aaaaaactct taaagactta agaaatcgta   540
gttctgttta cgattcaatg gttaaatcac ctaatcgtgc tatgttgcgt gcaactggta   600
tgcaagatga agactttgaa aaacctatcg tcggtgtcat ttcaacttgg gctgaaaaca   660
caccttgtaa tatccactta catgactttg gtaaactagc caaagtcggt gttaaggaag   720
ctggtgcttg gccagttcag ttcggaacaa tcacggtttc tgatggaatc gccatgggaa   780
cccaaggaat gcgtttctcc ttgacatctc gtgatattat tgcagattct attgaagcag   840
ccatgggagg tcataatgcg gatgcttttg tagccattgg cggttgtgat aaaaacatgc   900
ccggttctgt tatcgctatg gctaacatgg atatcccagc catttttgct tacggcggaa   960
caattgcacc tggtaattta gacggcaaag atatcgattt agtctctgtc tttgaaggtg  1020
tcggccattg gaaccacggc gatatgacca agaagaagt taaagctttg gaatgtaatg   1080
cttgtcccgg tcctggaggc tgcggtggta tgtatactgc taacacaatg gcgacagcta  1140
ttgaagtttt gggacttagc cttccgggtt catcttctca cccggctgaa tccgcagaaa  1200
agaaagcaga tattgaagaa gctggtcgcg ctgttgtcaa aatgctcgaa atgggcttaa   1260
aaccttctga cattttaacg cgtgaagctt ttgaagatgc tattactgta actatggctc  1320
tgggaggttc aaccaactca acccttcacc tcttagctat tgcccatgct gctaatgtgg   1380
aattgacact tgatgatttc aatactttcc aagaaaaagt tcctcatttg gctgatttga  1440
aaccttctgg tcaatatgta ttccaagacc tttacaaggt cggaggggta ccagcagtta   1500
tgaaatatct ccttaaaaat ggcttccttc atggtgaccg tatcacttgt actggcaaaa   1560
cagtcgctga aaatttgaag gcttttgatg atttaacacc tggtcaaaag gttattatgc   1620
cgcttgaaaa tcctaaacgt gaagatggtc cgctcattat tctccatggt aacttggctc   1680
cagacggtgc cgttgccaaa gtttctggtg taaaagtgcg tcgtcatgtc ggtcctgcta   1740
aggtctttaa ttctgaagaa gaagccattg aagctgtctt gaatgatgat attgttgatg   1800
gtgatgttgt tgtcgtacgt tttgtaggac caaagggcgg tcctggtatg cctgaaatgc   1860
tttcccttc atcaatgatt gttggtaaag ggcaaggtga aaaagttgcc cttctgacag   1920
atggccgctt ctcaggtggt acttatggtc ttgtcgtggg tcatatcgct cctgaagcac   1980
aagatgcgg tccaatcgcc tacctgcaaa caggagacat agtcactatt gaccaagaca   2040
ctaaggaatt acactttgat atctccgatg aagagttaaa acatcgtcaa gagaccattg   2100
aattgccacc gctctattca cgcggtatcc ttggtaaata tgctcacatc gtttcgtctg   2160
cttctagggg agccgtaaca gacttttgga agcctgaaga aactggcaaa aaatgagcga   2220
tttaatctct aattattagt taaagtttta taagcatttt tatgtaacga aaaataaatt   2280
ggttcatatt attactgcac tgtcacttac catggaaaga ccagacaaga agttgccgac   2340
agtctgttga attggcctgg ttaggcttaa gtctgggtcc gcttctttac aaatttggag   2400
aatttctctt aaacgatatg tatattcttt tcgttggaaa agatgtcttc caaaaaaaaa  2460
accgatgaat tagtggaacc aaggaaaaaa aaagaggtat ccttgattaa ggaacactgt   2520
ttaaacagtg tggttccaa aaccctgaaa ctgcattagt gtaatagaag actagacacc    2580
```

```
tcgatacaaa taatggttac tcaattcaaa actgccagcg aattcgactc tgcaattgct   2640
caagacaagc tagttgtcgt agatttctac gccacttggt gcggtccatg taaaatgatt   2700
gctccaatga ttgaaaaatg tggctgtggt ttcagggtcc ataaagcttt tcaattcatc   2760
tttttttttt ttgttcttt ttttgattcc ggtttctttg aaatttttt gattcggtaa     2820 tctccgagca gaaggaagaa cgaaggaagg agcacagact tagattggta tatatacgca   2880
tatgtggtgt tgaagaaaca tgaaattgcc cagtattctt aacccaactg cacagaacaa   2940
aaacctgcag gaaacgaaga taaatcatgt cgaaagctac atataaggaa cgtgctgcta   3000
ctcatcctag tcctgttgct gccaagctat ttaatatcat gcacgaaaag caaacaaact   3060
tgtgtgcttc attggatgtt cgtaccacca aggaattact ggagttagtt gaagcattag   3120
gtcccaaaat tgtttacta aaaacacatg tggatatctt gactgatttt tccatggagg    3180
gcacagttaa gccgctaaag gcattatccg ccaagtacaa ttttttactc ttcgaagaca   3240
gaaaatttgc tgacattggt aatacagtca aattgcagta ctctgcgggt gtatacagaa   3300
tagcagaatg ggcagacatt acgaatgcac acggtgtggt gggcccaggt attgttagcg   3360
gtttgaagca ggcggcggaa gaagtaacaa aggaacctag aggcccttttg atgttagcag   3420 aattgtcatg caagggctcc ctagctactg gagaatatac taagggtact gttgacattg   3480
cgaagagcga caaagatttt gttatcggct ttattgctca aagagacatg ggtgaagag    3540 atgaaggtta cgattggttg attatgacac ccggtgtggg tttagatgac aagggagacg   3600
cattgggtca acagtataga accgtggatg atgtggtctc tacaggatct gacattatta   3660
ttgttggaag aggactattt gcaaagggaa gggatgctaa ggtagagggt gaacgttaca   3720
gaaaagcagg ctgggaagca tatttgagaa gatgcggcca gcaaaactaa aaaactgtat   3780
tataagtaaa tgcatgtata ctaaactcac aaattagagc ttcaatttaa ttatatcagt    3840
tattacccgg gaatctcggt cgtaatgatt tctataatga cgaaaaaaa aaaattggaa    3900 agaaaaagct tcatggcctt ccactttccc aaacaacacc tacggtatct ctcaagtctt   3960
atggggttcc attggtttca ccactggtgc taccttgggt gctgctttcg ctgctgaaga   4020
aattgatcca agaagagag ttatcttatt cattggtgac ggttctttgc aattgactgt   4080
tcaagaaatc tccaccatga tcagatgggg cttgaagcca tacttgttcg tcttgaacaa   4140
cgatggttac accattgaaa agttgattca cggtccaaag gctcaataca acgaaattca   4200
aggttgggac cacctatcct tgttgccaac tttcggtgct aaggactatg aaacccacag   4260
agtcgctacc accggtgaat gggacaagtt gacccaagac aagtctttca cgacaactc    4320 taagatcaga atgattgaaa tcatgttgcc agtcttcgat gctccacaaa acttggttga   4380
acaagctaag ttgactgctg ctaccaacgc taagcaataa                          4420
```

<210> SEQ ID NO 143
<211> LENGTH: 2686
<212> TYPE: DNA
<213> ORGANISM: Artificial Sequence
<220> FEATURE:
<223> OTHER INFORMATION: pUC19

<400> SEQUENCE: 143

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
```

| | |
|---|---|
| accatatgcg gtgtgaaata ccgcacagat gcgtaaggag aaaataccgc atcaggcgcc | 240 |
| attcgccatt caggctgcgc aactgttggg aagggcgatc ggtgcgggcc tcttcgctat | 300 |
| tacgccagct ggcgaaaggg ggatgtgctg caaggcgatt aagttgggta acgccagggt | 360 |
| tttcccagtc acgacgttgt aaaacgacgg ccagtgaatt cgagctcggt acccggggat | 420 |
| cctctagagt cgacctgcag gcatgcaagc ttggcgtaat catggtcata gctgtttcct | 480 |
| gtgtgaaatt gttatccgct cacaattcca caacatac gagccggaag cataaagtgt | 540 |
| aaagcctggg gtgcctaatg agtgagctaa ctcacattaa ttgcgttgcg ctcactgccc | 600 |
| gctttccagt cgggaaacct gtcgtgccag ctgcattaat gaatcggcca acgcgcgggg | 660 |
| agaggcggtt tgcgtattgg gcgctcttcc gcttcctcgc tcactgactc gctgcgctcg | 720 |
| gtcgttcggc tgcggcgagc ggtatcagct cactcaaagg cggtaatacg gttatccaca | 780 |
| gaatcagggg ataacgcagg aaagaacatg tgagcaaaag gccagcaaaa ggccaggaac | 840 |
| cgtaaaaagg ccgcgttgct ggcgtttttc cataggctcc gcccccctga cgagcatcac | 900 |
| aaaaatcgac gctcaagtca gaggtggcga acccgacag gactataaag ataccaggcg | 960 |
| tttccccctg gaagctccct cgtgcgctct cctgttccga ccctgccgct taccggatac | 1020 |
| ctgtccgcct ttctcccttc gggaagcgtg gcgctttctc atagctcacg ctgtaggtat | 1080 |
| ctcagttcgg tgtaggtcgt tcgctccaag ctgggctgtg tgcacgaacc ccccgttcag | 1140 |
| cccgaccgct gcgccttatc cggtaactat cgtcttgagt ccaacccggt aagacacgac | 1200 |
| ttatcgccac tggcagcagc cactggtaac aggattagca gagcgaggta tgtaggcggt | 1260 |
| gctacagagt tcttgaagtg gtggcctaac tacggctaca ctagaaggac agtatttggt | 1320 |
| atctgcgctc tgctgaagcc agttaccttc ggaaaaagag ttggtagctc ttgatccggc | 1380 |
| aaacaaacca ccgctggtag cggtggtttt tttgtttgca agcagcagat tacgcgcaga | 1440 |
| aaaaaaggat ctcaagaaga tcctttgatc ttttctacgg ggtctgacgc tcagtggaac | 1500 |
| gaaaactcac gttaagggat tttggtcatg agattatcaa aaaggatctt cacctagatc | 1560 |
| cttttaaatt aaaaatgaag ttttaaatca atctaaagta tatatgagta aacttggtct | 1620 |
| gacagttacc aatgcttaat cagtgaggca cctatctcag cgatctgtct atttcgttca | 1680 |
| tccatagttg cctgactccc cgtcgtgtag ataactacga tacgggaggg cttaccatct | 1740 |
| ggccccagtg ctgcaatgat accgcgagac ccacgctcac cggctccaga tttatcagca | 1800 |
| ataaaccagc cagccggaag ggccgagcgc agaagtggtc ctgcaacttt atccgcctcc | 1860 |
| atccagtcta ttaattgttg ccgggaagct agagtaagta gttcgccagt taatagtttg | 1920 |
| cgcaacgttg ttgccattgc tacaggcatc gtggtgtcac gctcgtcgtt tggtatggct | 1980 |
| tcattcagct ccggttccca acgatcaagg cgagttacat gatcccccat gttgtgcaaa | 2040 |
| aaagcggtta gctccttcgg tcctccgatc gttgtcagaa gtaagttggc cgcagtgtta | 2100 |
| tcactcatgg ttatggcagc actgcataat tctcttactg tcatgccatc cgtaagatgc | 2160 |
| ttttctgtga ctggtgagta ctcaaccaag tcattctgag aatagtgtat gcggcgaccg | 2220 |
| agttgctctt gcccggcgtc aatacgggat aataccgcgc cacatagcag aactttaaaa | 2280 |
| gtgctcatca ttggaaaacg ttcttcgggg cgaaaactct caaggatctt accgctgttg | 2340 |
| agatccagtt cgatgtaacc cactcgtgca cccaactgat cttcagcatc ttttactttc | 2400 |
| accagcgttt ctgggtgagc aaaaacagga aggcaaaatg ccgcaaaaaa gggaataagg | 2460 |
| gcgacacgga aatgttgaat actcatactc ttcctttttc aatattattg aagcatttat | 2520 |
| cagggttatt gtctcatgag cggatacata tttgaatgta tttagaaaaa taaacaaata | 2580 |

```
ggggttccgc gcacatttcc ccgaaaagtg ccacctgacg tctaagaaac cattattatc    2640
atgacattaa cctataaaaa taggcgtatc acgaggccct ttcgtc                   2686

<210> SEQ ID NO 144
<211> LENGTH: 3521
<212> TYPE: DNA
<213> ORGANISM: Artificial Sequence
<220> FEATURE:
<223> OTHER INFORMATION: PDC5 A-sadB-BUC cassette

<400> SEQUENCE: 144
aaggaaataa agcaaataac aataacacca ttattttaat tttttttcta ttactgtcgc      60
taacacctgt atggttgcaa ccaggtgaga atccttctga tgcatacttt atgcgtttat    120
gcgttttgcg ccccttggaa aaaaattgat tctcatcgta aatgcatact acatgcgttt    180
atgggaaaag cctccatatc caaggtcgc gtttcttttta gaaaaactaa tacgtaaacc    240
tgcattaagg taagattata tcagaaaatg tgttgcaaga aatgcattat gcaatttttt    300
gattatgaca atctctcgaa agaaatttca tatgatgaga cttgaataat gcagcggcgc    360
ttgctaaaag aacttgtata taagagctgc cattctcgat caatatactg tagtaagtcc    420
tttcctctct ttcttattac acttatttca cataatcaat ctcaaagaga acaacacaat    480
acaataacaa gaagaacaaa atgaaagctc tggtttatca cggtgaccac aagatctcgc    540
ttgaagacaa gcccaagccc acccttcaaa agcccacgga tgtagtagta cgggttttga    600
agaccacgat ctgcggcacg gatctcggca tctacaaagg caagaatcca gaggtcgccg    660 acggcgcat cctgggccat gaaggggtag gcgtcatcga ggaagtgggc gagagtgtca    720
cgcagttcaa gaaaggcgac aaggtcctga tttcctgcgt cacttcttgc ggctcgtgcg    780
actactgcaa gaagcagctt tactcccatt gccgcgacgg cgggtggatc ctgggttaca    840
tgatcgatgg cgtgcaggcc gaatacgtcc gcatcccgca tgccgacaac agcctctaca    900
agatccccca gacaattgac gacgaaatcg ccgtcctgct gagcgacatc ctgcccaccg    960
gccacgaaat cggcgtccag tatgggaatg tccagccggg cgatgcggtg gctattgtcg   1020
gcgcgggccc cgtcggcatg tccgtactgt tgaccgccca gttctactcc cctcgacca   1080 tcatcgtgat cgacatggac gagaatcgcc tccagctcgc caaggagctc ggggcaacgc   1140
acaccatcaa ctccggcacg gagaacgttg tcgaagccgt gcataggatt gcggcagagg   1200
gagtcgatgt tgcgatcgag gcggtgggca taccggcgac ttgggacatc tgccaggaga   1260
tcgtcaagcc cggcgcgcac atcgccaacg tcggcgtgca tggcgtcaag gttgacttcg   1320
agattcagaa gctctggatc aagaacctga cgatcaccac gggactggtg aacacgaaca   1380
cgacgcccat gctgatgaag gtcgcctcga ccgacaagct tccgttgaag aagatgatta   1440
cccatcgctt cgagctggcc gagatcgagc acgcctatca ggtattcctc aatggcgcca   1500
aggagaaggc gatgaagatc atcctctcga acgcaggcgc tgcctgagct aattaacata   1560
aaactcatga ttcaacgttt gtgtattttt ttactttttga aggttataga tgtttaggta   1620
aataattggc atagatatag ttttagtata ataaatttct gatttggttt aaaatatcaa   1680 ctatttttt tcacatatgt tcttgtaatt acttttctgt cctgtcttcc aggttaaaga   1740
ttagcttcta atattttagg tggtttatta tttaatttta tgctgattaa tttatttact   1800
tgtttaaacg gccggccaat gtggctgtgg tttcagggtc cataaagctt ttcaattcat   1860
cttttttttt tttgttcttt ttttgattc cggtttcttt gaaattttt tgattcggta    1920
```

| | |
|---|---|
| atctccgagc agaaggaaga acgaaggaag gagcacagac ttagattggt atatatacgc | 1980 |
| atatgtggtg ttgaagaaac atgaaattgc ccagtattct taacccaact gcacagaaca | 2040 |
| aaaacctgca ggaaacgaag ataaatcatg tcgaaagcta catataagga acgtgctgct | 2100 |
| actcatccta gtcctgttgc tgccaagcta tttaatatca tgcacgaaaa gcaaacaaac | 2160 |
| ttgtgtgctt cattggatgt tcgtaccacc aaggaattac tggagttagt tgaagcatta | 2220 |
| ggtcccaaaa tttgtttact aaaaacacat gtggatatct tgactgattt ttccatggag | 2280 |
| ggcacagtta agccgctaaa ggcattatcc gccaagtaca atttttact cttcgaagac | 2340 |
| agaaaatttg ctgacattgg taatacagtc aaattgcagt actctgcggg tgtatacaga | 2400 |
| atagcagaat gggcagacat tacgaatgca cacggtgtgg tgggcccagg tattgttagc | 2460 |
| ggtttgaagc aggcggcgga agaagtaaca aggaaccta gaggcctttt gatgttagca | 2520 |
| gaattgtcat gcaagggctc cctagctact ggagaatata ctaagggtac tgttgacatt | 2580 |
| gcgaagagcg acaaagattt tgttatcggc tttattgctc aaagagacat gggtggaaga | 2640 |
| gatgaaggtt acgattggtt gattatgaca cccggtgtgg gtttagatga caagggagac | 2700 |
| gcattgggtc aacagtatag aaccgtggat gatgtggtct ctacaggatc tgacattatt | 2760 |
| attgttggaa gaggactatt tgcaaaggga agggatgcta aggtagaggg tgaacgttac | 2820 |
| agaaaagcag gctgggaagc atatttgaga agatgcggcc agcaaaacta aaaaactgta | 2880 |
| ttataagtaa atgcatgtat actaaactca caaattagag cttcaattta attatatcag | 2940 |
| ttattacccg ggaatctcgg tcgtaatgat ttctataatg acgaaaaaaa aaaaattgga | 3000 |
| aagaaaaagc ttcatggcct tctactttcc caacagatgt atacgctatc gtccaagtct | 3060 |
| tgtgggttc cattggtttc acagtcggcg ctctattggg tgctactatg gccgctgaag | 3120 |
| aacttgatcc aaagaagaga gttatttat tcattggtga cggttctcta caattgactg | 3180 |
| ttcaagaaat ctctaccatg attagatggg gtttgaagcc atcattttt gtcttgaata | 3240 |
| acaacggtta caccattgaa aaattgattc acgtcctca tgccaatat aatgaaattc | 3300 |
| aaggttggga ccacttggcc ttattgccaa cttttggtgc tagaaactac gaaacccaca | 3360 |
| gagttgctac cactggtgaa tgggaaaagt tgactcaaga caaggacttc caagacaact | 3420 |
| ctaagattag aatgattgaa gttatgttgc cagtctttga tgctccacaa aacttggtta | 3480 |
| aacaagctca attgactgcc gctactaacg ctaaacaata a | 3521 |

<210> SEQ ID NO 145
<211> LENGTH: 1685
<212> TYPE: DNA
<213> ORGANISM: Artificial Sequence
<220> FEATURE:
<223> OTHER INFORMATION: gpd2::loxP-URA3-loxP cassette

<400> SEQUENCE: 145

| | |
|---|---|
| gtatttggt agattcaatt ctctttccct ttccttttcc ttcgctcccc ttccttatca | 60 |
| gcattgcgga ttacgtattc taatgttcag ataacttcgt atagcataca ttatacgaag | 120 |
| ttatgcagat tgtactgaga gtgcaccata ccacagcttt tcaattcaat tcatcatttt | 180 |
| ttttttattc tttttttga tttcggtttc tttgaaattt ttttgattcg gtaatctccg | 240 |
| aacagaagga agaacgaagg aaggagcaca gacttagatt ggtatatata cgcatatgta | 300 |
| gtgttgaaga aacatgaaat tgcccagtat tcttaaccca actgcacaga acaaaaacct | 360 |
| gcaggaaacg aagataaatc atgtcgaaag ctacatataa ggaacgtgct gctactcatc | 420 |
| ctagtcctgt tgctgccaag ctatttaata tcatgcacga aaagcaaaca aacttgtgtg | 480 |

```
cttcattgga tgttcgtacc accaaggaat tactggagtt agttgaagca ttaggtccca      540
aaatttgttt actaaaaaca catgtggata tcttgactga tttttccatg gagggcacag      600
ttaagccgct aaaggcatta tccgccaagt acaatttttt actcttcgaa gacagaaaat      660
ttgctgacat tggtaataca gtcaaattgc agtactctgc gggtgtatac agaatagcag      720
aatgggcaga cattacgaat gcacacggtg tggtgggccc aggtattgtt agcggtttga      780
agcaggcggc agaagaagta acaaaggaac ctagaggcct tttgatgtta gcagaattgt      840
catgcaaggg ctccctatct actggagaat atactaaggg tactgttgac attgcgaaga      900
gcgacaaaga ttttgttatc ggctttattg ctcaaagaga catgggtgga agagatgaag      960
gttacgattg gttgattatg acacccggtg tgggtttaga tgacaaggga gacgcattgg     1020
gtcaacagta tagaaccgtg gatgatgtgg tctctacagg atctgacatt attattgttg     1080
gaagaggact atttgcaaag ggaagggatg ctaaggtaga gggtgaacgt tacagaaaag     1140
caggctggga agcatatttg agaagatgcg gccagcaaaa ctaaaaaact gtattataag     1200
taaatgcatg tatactaaac tcacaaatta gagcttcaat ttaattatat cagttattac     1260
cctatgcggt gtgaaatacc gcacagatgc gtaaggagaa aataccgcat caggaaattg     1320
taaacgttaa tattttgtta aaattcgcgt taaattttg ttaaatcagc tcattttta      1380 accaataggc cgaaatcggc aaaatccctt ataaatcaaa agaatagacc gagatagggt     1440
tgagtgttgt tccagtttgg aacaagagtc cactattaaa gaacgtggac tccaacgtca     1500
aagggcgaaa aaccgtctat cagggcgatg gcccactacg tgaaccatca ccctaatcaa     1560
gataacttcg tatagcatac attatacgaa gttatccagt gatgatacaa cgagttagcc     1620
aaggtgacac tctccccccc cctcccccte tgatctttcc tgttgcctct ttttccccca     1680
accaa                                                                 1685
```